US009952221B2

(12) United States Patent
Guyon

(10) Patent No.: US 9,952,221 B2
(45) Date of Patent: Apr. 24, 2018

(54) METHODS FOR SCREENING, PREDICTING AND MONITORING PROSTATE CANCER

(71) Applicant: Health Discovery Corporation, Atlanta, GA (US)

(72) Inventor: Isabelle Guyon, Berkeley, CA (US)

(73) Assignee: Health Discovery Corporation, Atlanta, GA (US)

( * ) Notice: Subject to any disclaimer, the term of this patent is extended or adjusted under 35 U.S.C. 154(b) by 0 days.

(21) Appl. No.: 14/754,434

(22) Filed: Jun. 29, 2015

(65) Prior Publication Data

US 2015/0339448 A1 Nov. 26, 2015

Related U.S. Application Data

(63) Continuation of application No. 12/349,437, filed on Jan. 6, 2009, now abandoned, which is a continuation-in-part of application No. 12/025,724, filed on Feb. 4, 2008, now abandoned, which is a continuation-in-part of application No. 11/274,931, filed on Nov. 14, 2005, now abandoned.

(60) Provisional application No. 60/888,070, filed on Feb. 2, 2007, provisional application No. 60/627,626, filed on Nov. 12, 2004, provisional application No. 60/651,340, filed on Feb. 9, 2005.

(51) Int. Cl.
*G01N 33/574* (2006.01)
*C12Q 1/68* (2006.01)

(52) U.S. Cl.
CPC ..... *G01N 33/57434* (2013.01); *C12Q 1/6886* (2013.01); *C12Q 2600/112* (2013.01); *C12Q 2600/118* (2013.01); *C12Q 2600/158* (2013.01); *C12Q 2600/16* (2013.01); *G01N 2800/52* (2013.01)

(58) Field of Classification Search
None
See application file for complete search history.

(56) References Cited

U.S. PATENT DOCUMENTS 5,143,854 A 9/1992 Pirrung et al.
5,552,277 A 9/1996 Nelson et al.
5,837,832 A 11/1998 Chee et al.
5,972,615 A 10/1999 An et al.
6,107,103 A 8/2000 Xuan et al.
6,128,608 A 10/2000 Barnhill
6,171,796 B1 1/2001 An et al.
6,258,540 B1 * 7/2001 Lo ........................ C12Q 1/6879 435/440
6,355,623 B2 * 3/2002 Seidman ................ A61K 31/52 514/263.4
6,395,479 B1 5/2002 Reichardt et al.
6,427,141 B1 7/2002 Barnhill
6,566,130 B1 5/2003 Srivastava et al.
6,685,395 B1 2/2004 Busby
6,692,916 B2 2/2004 Bevilacqua et al.
6,714,925 B1 3/2004 Barnhill et al.
6,760,715 B1 7/2004 Barnhill et al.
6,789,069 B1 9/2004 Barnhill et al.
6,882,990 B1 4/2005 Barnhill et al.
6,949,342 B2 9/2005 Golub et al.
6,960,439 B2 11/2005 Bevilacqua et al.
7,117,188 B2 10/2006 Guyon et al.
7,252,935 B2 8/2007 Sidransky
2001/0007748 A1 7/2001 An et al.
2002/0081659 A1 6/2002 Rosen et al.
2002/0151681 A1 10/2002 Rosen
2002/0168638 A1 11/2002 Schlegel et al.
2003/0049645 A1 3/2003 Mu et al.
2003/0087818 A1 5/2003 Jiang
2003/0108963 A1 6/2003 Schlegel
2003/0113762 A1 6/2003 Warrington
2003/0138793 A1 7/2003 Su et al.
2003/0172043 A1 9/2003 Guyon et al.
2003/0175736 A1 9/2003 Chinnaiyan et al.
2003/0180738 A1 9/2003 Rees et al.
2003/0215835 A1 11/2003 Sun et al.
2004/0009481 A1 1/2004 Schlegel et al.
2004/0029151 A1 2/2004 Mahadevappa et al.
2004/0110221 A1 6/2004 Twine et al.
2004/0121413 A1 6/2004 Aebersold et al.
2004/0133352 A1 7/2004 Bevilacqua et al.
2004/0235071 A1 7/2004 Dong et al.
2004/0203012 A1 10/2004 Diamandis
2004/0225449 A1 11/2004 Bevilacqua et al.
2004/0259086 A1 12/2004 Schlegel et al.
2005/0009771 A1 1/2005 Levanon et al.
2005/0032065 A1 2/2005 Afar et al.
2005/0112134 A1 5/2005 Graddis et al.
2005/0119210 A1 6/2005 Be et al.
2005/0136493 A1 6/2005 Rubin et al.
2005/0191673 A1 9/2005 Schlegel et al.
2005/0227917 A1 10/2005 Williams
2005/0244843 A1 11/2005 Chen et al.
2005/0244973 A1 11/2005 Andel et al.
2005/0259483 A1 11/2005 Nakamura et al.
2006/0134688 A1 6/2006 Welsh
2006/0211025 A1 9/2006 Su et al.
2007/0014801 A1 1/2007 Gish
2007/0041944 A1 2/2007 Iavarone
2007/0048738 A1 3/2007 Donkena et al.

(Continued)

FOREIGN PATENT DOCUMENTS

EP 2373816 B1 5/2014
WO 2005015236 A2 2/2005

OTHER PUBLICATIONS

Vandesompele et al. (Genome Biology 2002 3(7)/ research/0034. 1).*

(Continued)

*Primary Examiner* — Peter J Reddig
(74) *Attorney, Agent, or Firm* — Eleanor Musick; Musick Davison LLP

(57) ABSTRACT

Biomarkers are identified by analyzing gene expression data using support vector machines (SVM) to rank genes according to their ability to separate prostate cancer from normal tissue. Expression products of identified genes are detected in patient samples, including prostate tissue, serum, semen and urine, to screen, predict and monitor prostate cancer.

13 Claims, 35 Drawing Sheets

(56) References Cited

U.S. PATENT DOCUMENTS

| | | | |
|---|---|---|---|
| 2007/0059712 A1 | 3/2007 | Gish | |
| 2007/0292423 A1 | 12/2007 | Oka et al. | |
| 2008/0254455 A1 | 10/2008 | Wang et al. | |
| 2009/0170075 A1 * | 7/2009 | Petrovics ............. | C12Q 1/6886 435/6.14 |
| 2009/0215058 A1 * | 8/2009 | Guyon ................. | C12Q 1/6886 435/6.12 |

OTHER PUBLICATIONS

Bhaskar et al., "E-selectin up-regulation allows for targeted drug delivery in prostate cancer", Cancer Research, Oct. 2003, 63:6387-6394.

Bhandari, et al., "Prostate cancer therapeutic target identification via meta analysis of prostate cancer microarray data using ONCOMINE", 2005 Prostate Cancer Symposium, American Society of Clinical Oncology, Abstract No. 195.

Rhodes, et al., Oncomine 3.0: Genes, Pathways, and Networks in a Collection of 18,000 Cancer Gene Expression Profiles, Neoplasia, 2007, 9(2):166-180.

Guyon, I., et al, "A Four-Gene Expression Signature for Prostate Cancer Cells Consisting of UAP1, PDLIM5, IMPDH2, and HSPD1", UroToday Int'l Journal, 2(4), Aug. 6, 2009 (on-line) 10 pages.

Luo, J-H, et al., "Gene Expression analysis of Prostate Cancers", Molecular Carcinogenesis, 2002, 33:25-25.

Lai, Y., et al, "A statistical method for identifying differential gene-gene co-expression patterns", Bioinformatics 2004, 20(17): 3146-3155.

Kiessling, F., et al., "Simple models improve the discrimination of prostate cancers from the peripheral gland by T1-weighted dynamic MRI", Eur. Radiol. Oct. 2004, 14(10): 1793-1801 (Abstract).

Hsiao, L-L, et al, "A compendium of gene expression in normal human tissues", Physiol. Genomics, 2001 7:97-104.

* cited by examiner

| Rank | Gene ID | Unigene ID | Under Expr. In tumor | AUC | Pval | FDR | Ave. rank |
|---|---|---|---|---|---|---|---|
| 1 | 9459 | Hs.128749 | -1 | 0.9458 | 0.02 | 0.025 | 1.16 |
| 2 | 9458 | Hs.128749 | -1 | 0.9425 | 0.02 | 0.012 | 2.48 |
| 3 | 9457 | Hs.128749 | -1 | 0.9423 | 0.02 | 0.0083 | 2.51 |
| 4 | 11911 | Hs.279009 | 1 | 0.9253 | 0.02 | 0.0062 | 4.31 |
| 5 | 12337 | Hs.7780 | -1 | 0.9125 | 0.02 | 0.005 | 7.23 |
| 6 | 983 | Hs.226795 | 1 | 0.9076 | 0.02 | 0.0042 | 8.42 |
| 7 | 18792 | Hs.6823 | -1 | 0.9047 | 0.02 | 0.0036 | 10.04 |
| 8 | 1908 | Hs.692 | -1 | 0.9044 | 0.02 | 0.0031 | 10.03 |
| 9 | 19589 | Hs.45140 | 1 | 0.9033 | 0.02 | 0.0028 | 10.47 |
| 10 | 6519 | Hs.243960 | 1 | 0.8996 | 0.02 | 0.0025 | 12.67 |
| 11 | 17714 | Hs.5216 | -1 | 0.8985 | 0.02 | 0.0023 | 13.93 |
| 12 | 18122 | Hs.106747 | 1 | 0.8985 | 0.02 | 0.0021 | 13.86 |
| 13 | 18237 | Hs.283719 | 1 | 0.8961 | 0.02 | 0.0019 | 16.61 |
| 14 | 3059 | Hs.771 | 1 | 0.8942 | 0.02 | 0.0018 | 17.86 |
| 15 | 16533 | Hs.110826 | -1 | 0.8921 | 0.02 | 0.0017 | 19.44 |
| 16 | 18598 | Hs.9728 | 1 | 0.8904 | 0.02 | 0.0016 | 19.43 |
| 17 | 12434 | Hs.250723 | 1 | 0.8899 | 0.02 | 0.0015 | 20.19 |
| 18 | 4922 | Hs.55279 | 1 | 0.884 | 0.02 | 0.0014 | 27.23 |
| 19 | 13862 | Hs.66744 | -1 | 0.8832 | 0.02 | 0.0013 | 30.59 |
| 20 | 9976 | Hs.103665 | 1 | 0.8824 | 0.02 | 0.0012 | 30.49 |
| 21 | 18835 | Hs.44278 | -1 | 0.8824 | 0.02 | 0.0012 | 30.94 |
| 22 | 3331 | Hs.54697 | 1 | 0.8802 | 0.02 | 0.0011 | 32.35 |
| 23 | 18969 | Hs.20814 | -1 | 0.8797 | 0.02 | 0.0011 | 35.89 |
| 24 | 9373 | Hs.21293 | -1 | 0.8786 | 0.02 | 0.001 | 35.52 |
| 25 | 15294 | Hs.288649 | -1 | 0.8786 | 0.02 | 0.001 | 35.69 |
| 26 | 4497 | Hs.33084 | 1 | 0.8776 | 0.02 | 0.00096 | 37.77 |
| 27 | 5001 | Hs.823 | -1 | 0.8765 | 0.02 | 0.00093 | 40.25 |
| 28 | 9765 | Hs.22599 | 1 | 0.8765 | 0.02 | 0.00089 | 39.32 |
| 29 | 4479 | Hs.198760 | 1 | 0.8759 | 0.02 | 0.00086 | 40.82 |
| 30 | 239 | Hs.198760 | 1 | 0.8749 | 0.02 | 0.00083 | 43.04 |
| 31 | 6666 | Hs.90911 | 1 | 0.8749 | 0.02 | 0.00081 | 42.53 |
| 32 | 12655 | Hs.10587 | 1 | 0.8749 | 0.02 | 0.00078 | 41.56 |
| 33 | 19264 | Hs.31608 | -1 | 0.8743 | 0.02 | 0.00076 | 44.66 |
| 34 | 5923 | Hs.171731 | 1 | 0.8738 | 0.02 | 0.00074 | 44.3 |
| 35 | 1889 | Hs.195850 | 1 | 0.8727 | 0.02 | 0.00071 | 46.1 |
| 36 | 21568 | Hs.111676 | 1 | 0.8716 | 0.02 | 0.00069 | 48.3 |
| 37 | 3264 | Hs.139336 | -1 | 0.8714 | 0.02 | 0.00068 | 51.17 |
| 38 | 14738 | Hs.8198 | 1 | 0.8706 | 0.02 | 0.00066 | 52.7 |
| 39 | 1867 | Hs.234680 | 1 | 0.8695 | 0.02 | 0.00064 | 52.99 |
| 40 | 4467 | Hs.24587 | 1 | 0.8695 | 0.02 | 0.00062 | 52.25 |
| 41 | 9614 | Hs.8583 | 1 | 0.8695 | 0.02 | 0.00061 | 53.62 |
| 42 | 18659 | Hs.73625 | -1 | 0.8692 | 0.02 | 0.0006 | 56.86 |
| 43 | 20137 | Hs.249727 | 1 | 0.8692 | 0.02 | 0.00058 | 55.2 |
| 44 | 12023 | Hs.74034 | 1 | 0.869 | 0.02 | 0.00057 | 55.69 |
| 45 | 12435 | Hs.82432 | 1 | 0.869 | 0.02 | 0.00056 | 56.63 |
| 46 | 14626 | Hs.23960 | -1 | 0.8687 | 0.02 | 0.00054 | 58.95 |
| 47 | 7082 | Hs.95197 | 1 | 0.8684 | 0.02 | 0.00053 | 56.27 |
| 48 | 15022 | Hs.110826 | -1 | 0.8679 | 0.02 | 0.00052 | 59.51 |
| 49 | 20922 | Hs.0 | -1 | 0.8679 | 0.02 | 0.00051 | 59.93 |

FIG. 4a

| Rank | Gene ID | Unigene ID | Under Expr. In tumor | AUC | Pval | FDR | Ave. rank |
|---|---|---|---|---|---|---|---|
| 50 | 4361 | Hs.102 | 1 | 0.8673 | 0.02 | 0.0005 | 60.94 |
| 51 | 18392 | Hs.1227 | 1 | 0.8671 | 0.02 | 0.00049 | 59.16 |
| 52 | 5199 | Hs.118127 | 1 | 0.8657 | 0.02 | 0.00048 | 62.89 |
| 53 | 4781 | Hs.30054 | -1 | 0.8652 | 0.02 | 0.00047 | 66.67 |
| 54 | 19167 | Hs.9238 | 1 | 0.8652 | 0.02 | 0.00046 | 67.82 |
| 55 | 19573 | Hs.232165 | 1 | 0.8652 | 0.02 | 0.00045 | 66.61 |
| 56 | 4524 | Hs.65029 | 1 | 0.8641 | 0.02 | 0.00045 | 68.12 |
| 57 | 21444 | Hs.262958 | 1 | 0.8641 | 0.02 | 0.00044 | 68.16 |
| 58 | 13307 | Hs.7000 | 1 | 0.8639 | 0.02 | 0.00043 | 69.32 |
| 59 | 17019 | Hs.128749 | -1 | 0.8639 | 0.02 | 0.00042 | 70.9 |
| 60 | 3699 | Hs.242407 | 1 | 0.8636 | 0.02 | 0.00042 | 68.07 |
| 61 | 14522 | Hs.285508 | 1 | 0.8636 | 0.02 | 0.00041 | 69.6 |
| 62 | 1190 | Hs.90061 | 1 | 0.8631 | 0.02 | 0.0004 | 69.94 |
| 63 | 876 | Hs.79037 | -1 | 0.8625 | 0.02 | 0.0004 | 70.66 |
| 64 | 1051 | Hs.118796 | 1 | 0.862 | 0.02 | 0.00039 | 73.7 |
| 65 | 5040 | Hs.2679 | -1 | 0.8617 | 0.02 | 0.00038 | 75.75 |
| 66 | 7460 | Hs.158309 | 1 | 0.8617 | 0.02 | 0.00038 | 76.42 |
| 67 | 4860 | Hs.113082 | 1 | 0.8614 | 0.02 | 0.00037 | 75.84 |
| 68 | 12042 | Hs.142653 | -1 | 0.8612 | 0.02 | 0.00037 | 75.69 |
| 69 | 12046 | Hs.166982 | 1 | 0.8609 | 0.02 | 0.00036 | 80.61 |
| 70 | 10874 | Hs.24587 | 1 | 0.8604 | 0.02 | 0.00036 | 80.34 |
| 71 | 1500 | Hs.74566 | 1 | 0.8598 | 0.02 | 0.00035 | 79.91 |
| 72 | 7822 | Hs.288771 | 1 | 0.8598 | 0.02 | 0.00035 | 81.65 |
| 73 | 8824 | Hs.29759 | 1 | 0.8598 | 0.02 | 0.00034 | 78.78 |
| 74 | 5022 | Hs.15154 | 1 | 0.8593 | 0.02 | 0.00034 | 81.05 |
| 75 | 19501 | Hs.272813 | 1 | 0.8593 | 0.02 | 0.00033 | 82.64 |
| 76 | 1959 | Hs.75319 | -1 | 0.8585 | 0.02 | 0.00033 | 86.9 |
| 77 | 2573 | Hs.82237 | 1 | 0.8577 | 0.02 | 0.00032 | 85.87 |
| 78 | 5150 | Hs.174151 | 1 | 0.8571 | 0.02 | 0.00032 | 89.59 |
| 79 | 5894 | Hs.80247 | 1 | 0.8566 | 0.02 | 0.00032 | 90.53 |
| 80 | 6665 | Hs.90911 | 1 | 0.8563 | 0.02 | 0.00031 | 93.17 |
| 81 | 12572 | Hs.9651 | 1 | 0.8561 | 0.02 | 0.00031 | 93.92 |
| 82 | 6924 | Hs.820 | -1 | 0.8555 | 0.02 | 0.0003 | 94.63 |
| 83 | 1919 | Hs.82422 | 1 | 0.8555 | 0.02 | 0.0003 | 95.13 |
| 84 | 3705 | Hs.278581 | 1 | 0.8555 | 0.02 | 0.0003 | 94.75 |
| 85 | 6131 | Hs.10755 | 1 | 0.8555 | 0.02 | 0.00029 | 93.85 |
| 86 | 11248 | Hs.17481 | 1 | 0.855 | 0.02 | 0.00029 | 97.22 |
| 87 | 17884 | Hs.284243 | -1 | 0.8545 | 0.02 | 0.00029 | 96.85 |
| 88 | 9813 | Hs.18858 | -1 | 0.8542 | 0.02 | 0.00028 | 99.37 |
| 89 | 9336 | Hs.3128 | -1 | 0.8539 | 0.02 | 0.00028 | 99.26 |
| 90 | 19488 | Hs.17752 | -1 | 0.8539 | 0.02 | 0.00028 | 103.94 |
| 91 | 21484 | Hs.28777 | -1 | 0.8539 | 0.02 | 0.00027 | 101.18 |
| 92 | 2624 | Hs.211582 | 1 | 0.8534 | 0.02 | 0.00027 | 100.15 |
| 93 | 5038 | Hs.2621 | 1 | 0.8534 | 0.02 | 0.00027 | 102.73 |
| 94 | 12168 | Hs.75318 | 1 | 0.8528 | 0.02 | 0.00027 | 103.59 |
| 95 | 3425 | Hs.77256 | -1 | 0.8518 | 0.02 | 0.00026 | 107.11 |
| 96 | 5712 | Hs.80667 | -1 | 0.8518 | 0.02 | 0.00026 | 107.92 |
| 97 | 9889 | Hs.137569 | 1 | 0.8518 | 0.02 | 0.00026 | 108.05 |
| 98 | 9851 | Hs.75939 | -1 | 0.8515 | 0.02 | 0.00026 | 110.7 |
| 99 | 1646 | Hs.118638 | -1 | 0.8512 | 0.02 | 0.00025 | 108.38 |

FIG. 4b

| Rank | Gene ID | Unigene ID | Under Expr. In tumor | AUC | Pval | FDR | Ave. rank |
|---|---|---|---|---|---|---|---|
| 100 | 18630 | Hs.104859 | -1 | 0.8507 | 0.02 | 0.00025 | 111.66 |
| 101 | 19422 | Hs.296178 | -1 | 0.8507 | 0.02 | 0.00025 | 112.71 |
| 102 | 979 | Hs.1708 | -1 | 0.8502 | 0.02 | 0.00025 | 111.48 |
| 103 | 2300 | Hs.69469 | -1 | 0.8502 | 0.02 | 0.00024 | 113.24 |
| 104 | 13066 | Hs.12520 | -1 | 0.8502 | 0.02 | 0.00024 | 114.1 |
| 105 | 19840 | Hs.58561 | 1 | 0.8496 | 0.02 | 0.00024 | 116.23 |
| 106 | 13510 | Hs.90911 | 1 | 0.8488 | 0.02 | 0.00024 | 118.16 |
| 107 | 1127 | Hs.9615 | 1 | 0.8485 | 0.02 | 0.00023 | 117.57 |
| 108 | 14690 | Hs.110826 | -1 | 0.848 | 0.02 | 0.00023 | 121.93 |
| 109 | 9499 | Hs.44 | 1 | 0.8475 | 0.02 | 0.00023 | 124.73 |
| 110 | 11793 | Hs.234680 | 1 | 0.8464 | 0.02 | 0.00023 | 127.61 |
| 111 | 12113 | Hs.8272 | 1 | 0.8464 | 0.02 | 0.00023 | 127.01 |
| 112 | 17891 | Hs.8858 | -1 | 0.8464 | 0.02 | 0.00022 | 128 |
| 113 | 22021 | Hs.240845 | -1 | 0.8464 | 0.02 | 0.00022 | 129.22 |
| 114 | 17944 | Hs.279905 | -1 | 0.8459 | 0.02 | 0.00022 | 129.62 |
| 115 | 3310 | Hs.154103 | -1 | 0.8456 | 0.02 | 0.00022 | 129.99 |
| 116 | 12809 | Hs.169401 | -1 | 0.8456 | 0.02 | 0.00022 | 133.01 |
| 117 | 9304 | Hs.75517 | 1 | 0.8453 | 0.02 | 0.00021 | 130.63 |
| 118 | 2123 | Hs.159608 | 1 | 0.8448 | 0.02 | 0.00021 | 136.05 |
| 119 | 21442 | Hs.71819 | -1 | 0.8448 | 0.02 | 0.00021 | 138.01 |
| 120 | 4523 | Hs.65029 | 1 | 0.8445 | 0.02 | 0.00021 | 135.36 |
| 121 | 1690 | Hs.76307 | 1 | 0.8443 | 0.02 | 0.00021 | 135.4 |
| 122 | 3652 | Hs.16622 | 1 | 0.8443 | 0.02 | 0.0002 | 133.49 |
| 123 | 4801 | Hs.80342 | 1 | 0.8443 | 0.02 | 0.0002 | 135.8 |
| 124 | 11607 | Hs.0 | 1 | 0.8437 | 0.02 | 0.0002 | 137.48 |
| 125 | 5149 | Hs.174151 | 1 | 0.8432 | 0.02 | 0.0002 | 140.08 |
| 126 | 966 | Hs.194431 | 1 | 0.8426 | 0.02 | 0.0002 | 140.95 |
| 127 | 9180 | Hs.239926 | 1 | 0.8426 | 0.02 | 0.0002 | 142.19 |
| 128 | 9317 | Hs.1940 | 1 | 0.8426 | 0.02 | 0.0002 | 141.86 |
| 129 | 12605 | Hs.100623 | -1 | 0.8426 | 0.02 | 0.00019 | 144.57 |
| 130 | 21482 | Hs.301732 | -1 | 0.8426 | 0.02 | 0.00019 | 143.39 |
| 131 | 724 | Hs.177656 | 1 | 0.8421 | 0.02 | 0.00019 | 144.91 |
| 132 | 4018 | Hs.21223 | 1 | 0.8421 | 0.02 | 0.00019 | 144.14 |
| 133 | 3390 | Hs.139851 | 1 | 0.8416 | 0.02 | 0.00019 | 148.37 |
| 134 | 7327 | Hs.2388 | -1 | 0.8416 | 0.02 | 0.00019 | 148.06 |
| 135 | 13911 | Hs.408 | 1 | 0.8413 | 0.02 | 0.00019 | 146.81 |
| 136 | 4351 | Hs.303090 | 1 | 0.841 | 0.02 | 0.00018 | 149.01 |
| 137 | 11912 | Hs.279009 | 1 | 0.841 | 0.02 | 0.00018 | 149.29 |
| 138 | 18968 | Hs.207443 | 1 | 0.841 | 0.02 | 0.00018 | 150.77 |
| 139 | 1082 | Hs.117950 | -1 | 0.8405 | 0.02 | 0.00018 | 148.4 |
| 140 | 1961 | Hs.75432 | -1 | 0.8405 | 0.02 | 0.00018 | 153.15 |
| 141 | 2217 | Hs.79217 | -1 | 0.8405 | 0.02 | 0.00018 | 151.68 |
| 142 | 1935 | Hs.75772 | 1 | 0.8402 | 0.02 | 0.00018 | 154.34 |
| 143 | 1912 | Hs.76224 | 1 | 0.84 | 0.02 | 0.00017 | 153.7 |
| 144 | 2343 | Hs.78045 | 1 | 0.84 | 0.02 | 0.00017 | 152.02 |
| 145 | 4754 | Hs.105460 | 1 | 0.84 | 0.02 | 0.00017 | 152.61 |
| 146 | 5832 | Hs.104117 | 1 | 0.84 | 0.02 | 0.00017 | 154.17 |
| 147 | 9325 | Hs.34853 | 1 | 0.84 | 0.02 | 0.00017 | 153.72 |
| 148 | 13843 | Hs.154145 | 1 | 0.84 | 0.02 | 0.00017 | 154.54 |
| 149 | 4386 | Hs.82280 | -1 | 0.8394 | 0.02 | 0.00017 | 155.7 |
| 150 | 10974 | Hs.77899 | 1 | 0.8394 | 0.02 | 0.00017 | 153.76 |

FIG. 4c

| Rank | Gene ID | Unigene ID | Under Expr. In tumor | AUC | Pval | FDR | Ave. rank |
|---|---|---|---|---|---|---|---|
| 151 | 11688 | Hs.0 | 1 | 0.8394 | 0.02 | 0.00017 | 156.4 |
| 152 | 1036 | Hs.699 | -1 | 0.8389 | 0.02 | 0.00016 | 158.14 |
| 153 | 2291 | Hs.279604 | 1 | 0.8389 | 0.02 | 0.00016 | 155.21 |
| 154 | 15260 | Hs.25648 | 1 | 0.8386 | 0.02 | 0.00016 | 157.48 |
| 155 | 1405 | Hs.66708 | 1 | 0.8373 | 0.02 | 0.00016 | 165.04 |
| 156 | 3978 | Hs.75151 | -1 | 0.8373 | 0.02 | 0.00016 | 167.79 |
| 157 | 8821 | Hs.121849 | 1 | 0.8362 | 0.02 | 0.00016 | 169.79 |
| 158 | 8999 | Hs.132898 | 1 | 0.8362 | 0.02 | 0.00016 | 167.99 |
| 159 | 18579 | Hs.283404 | 1 | 0.8359 | 0.02 | 0.00016 | 169.99 |
| 160 | 21798 | Hs.135150 | 1 | 0.8354 | 0.02 | 0.00016 | 176.72 |
| 161 | 4802 | Hs.89901 | 1 | 0.8351 | 0.02 | 0.00016 | 172.85 |
| 162 | 7542 | Hs.283312 | 1 | 0.8351 | 0.02 | 0.00015 | 178.51 |
| 163 | 11677 | Hs.0 | 1 | 0.8351 | 0.02 | 0.00015 | 174.71 |
| 164 | 22117 | Hs.109274 | 1 | 0.8351 | 0.02 | 0.00015 | 176.32 |
| 165 | 308 | Hs.76307 | 1 | 0.8346 | 0.02 | 0.00015 | 175.35 |
| 166 | 1410 | Hs.104925 | -1 | 0.8346 | 0.02 | 0.00015 | 177.73 |
| 167 | 6568 | Hs.89584 | -1 | 0.8346 | 0.02 | 0.00015 | 176.11 |
| 168 | 3363 | Hs.34114 | 1 | 0.834 | 0.02 | 0.00015 | 178.85 |
| 169 | 14542 | Hs.159309 | 1 | 0.8335 | 0.02 | 0.00015 | 183.16 |
| 170 | 9791 | Hs.82223 | 1 | 0.833 | 0.02 | 0.00015 | 182.87 |
| 171 | 18786 | Hs.33085 | -1 | 0.833 | 0.02 | 0.00015 | 184.64 |
| 172 | 6722 | Hs.284203 | -1 | 0.8327 | 0.02 | 0.00015 | 184.85 |
| 173 | 3638 | Hs.74120 | 1 | 0.8324 | 0.02 | 0.00014 | 186.98 |
| 174 | 4109 | Hs.82318 | -1 | 0.8324 | 0.02 | 0.00014 | 188.63 |
| 175 | 14497 | Hs.13804 | 1 | 0.8324 | 0.02 | 0.00014 | 186.08 |
| 176 | 9860 | Hs.158304 | 1 | 0.8319 | 0.02 | 0.00014 | 190.19 |
| 177 | 12838 | Hs.152151 | 1 | 0.8319 | 0.02 | 0.00014 | 189.73 |
| 178 | 4268 | Hs.211595 | -1 | 0.8316 | 0.02 | 0.00014 | 192.31 |
| 179 | 5572 | Hs.159642 | -1 | 0.8314 | 0.02 | 0.00014 | 194.58 |
| 180 | 9467 | Hs.311 | -1 | 0.8311 | 0.02 | 0.00014 | 194.53 |
| 181 | 4779 | Hs.284122 | 1 | 0.8303 | 0.02 | 0.00014 | 197.06 |
| 182 | 374 | Hs.234642 | 1 | 0.8298 | 0.02 | 0.00014 | 198.85 |
| 183 | 3134 | Hs.323469 | 1 | 0.8298 | 0.02 | 0.00014 | 200.94 |
| 184 | 3391 | Hs.139851 | 1 | 0.8292 | 0.02 | 0.00014 | 202.25 |
| 185 | 3822 | Hs.36708 | -1 | 0.8292 | 0.02 | 0.00014 | 200.4 |
| 186 | 3999 | Hs.1162 | -1 | 0.8292 | 0.02 | 0.00013 | 201.46 |
| 187 | 5924 | Hs.1813 | 1 | 0.8292 | 0.02 | 0.00013 | 201.77 |
| 188 | 19025 | Hs.24743 | -1 | 0.8292 | 0.02 | 0.00013 | 203.7 |
| 189 | 12811 | Hs.209100 | 1 | 0.8289 | 0.02 | 0.00013 | 203.54 |
| 190 | 9326 | Hs.34853 | 1 | 0.8287 | 0.02 | 0.00013 | 207.16 |
| 191 | 14516 | Hs.162209 | -1 | 0.8284 | 0.02 | 0.00013 | 206.26 |
| 192 | 167 | Hs.7101 | -1 | 0.8276 | 0.02 | 0.00013 | 209.05 |
| 193 | 231 | Hs.184510 | 1 | 0.8276 | 0.02 | 0.00013 | 209 |
| 194 | 9903 | Hs.63236 | 1 | 0.8273 | 0.02 | 0.00013 | 216.07 |
| 195 | 18867 | Hs.9029 | 1 | 0.8268 | 0.02 | 0.00013 | 216.86 |
| 196 | 9401 | Hs.113 | 1 | 0.8265 | 0.02 | 0.00013 | 216.66 |
| 197 | 14166 | Hs.278503 | 1 | 0.8265 | 0.02 | 0.00013 | 220.19 |
| 198 | 1830 | Hs.154672 | -1 | 0.826 | 0.02 | 0.00013 | 216.11 |
| 199 | 2623 | Hs.2006 | 1 | 0.826 | 0.02 | 0.00013 | 220.9 |
| 200 | 5676 | Hs.2463 | 1 | 0.8255 | 0.02 | 0.00012 | 225.42 |

FIG. 4d

G4 Tumor vs. Others Table Legend:
Rkn=rank in study n; OE=+1 if overexpressed in tumor, -1 otherwise; Score n=AUC score in study n; Pvaln=Bonfenoni corrected value in study n; FRDn=False discovery rate in study n.

2001 Study

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 1 | Hs.171731 | -1 | 0.9495 | 0.025 | 0.025 | 3 | 0.8754 | 0.025 | 0.0083 | Human RACH1 (RACH1) mRNA |
| 2 | Hs.3128 | 1 | 0.9081 | 0.025 | 0.012 | 15 | 0.841 | 0.025 | 0.0017 | Human RNA polymerase II subunit (hsRPB8) mRNA |
| 3 | Hs.2025 | -1 | 0.9027 | 0.025 | 0.0083 | 73 | 0.7744 | 0.025 | 0.00034 | Human transforming growth factor-beta 3 (TGF-beta3) mRNA |
| 4 | Hs.174151 | -1 | 0.8892 | 0.025 | 0.0062 | 10 | 0.8448 | 0.025 | 0.0025 | Human aldehyde oxidase (hAOX) mRNA |
| 5 | Hs.34853 | -1 | 0.8892 | 0.025 | 0.005 | 20 | 0.8314 | 0.025 | 0.0012 | Human Id-related helix-loop-helix protein Id4 mRNA |
| 6 | Hs.155585 | -1 | 0.8838 | 0.025 | 0.0042 | 94 | 0.7626 | 0.025 | 0.00027 | Human transmembrane receptor (ror2) mRNA |
| 7 | Hs.195850 | -1 | 0.8811 | 0.025 | 0.0036 | 2 | 0.8813 | 0.025 | 0.012 | Human keratin type 11(58 kD)mRNA |
| 8 | Hs.65029 | -1 | 0.8802 | 0.025 | 0.0031 | 5 | 0.8647 | 0.025 | 0.005 | Human gas1 gene |
| 9 | Hs.172323 | -1 | 0.8766 | 0.025 | 0.0028 | 2260 | 0.5048 | 1 | 0.97 | Human fetal liver cytochrome P-450 (P450 HFLa) |
| 10 | Hs.85302 | -1 | 0.873 | 0.025 | 0.0025 | 268 | 0.689 | 1 | 0.022 | Human dsRNA adenosine deaminase DRADA2b (DRADA2b) mRNA |
| 11 | Hs.27311 | 1 | 0.8694 | 0.025 | 0.0023 | 42 | 0.8056 | 0.025 | 0.0006 | Human transcription factor SIM2 long form mRNA |
| 12 | Hs.44 | -1 | 0.8685 | 0.025 | 0.0021 | 14 | 0.841 | 0.025 | 0.0018 | Human nerve growth factor (HBNF-1)mRNA |
| 13 | Hs.113 | -1 | 0.8658 | 0.025 | 0.0019 | 24 | 0.8217 | 0.025 | 0.001 | Human cytosolic epoxide hydrolase mRNA |
| 14 | Hs.77546 | -1 | 0.8649 | 0.025 | 0.0018 | 46 | 0.8008 | 0.025 | 0.00054 | Human mRNA for KIAA0172 gene |
| 15 | Hs.771 | -1 | 0.8532 | 0.025 | 0.0017 | 1 | 0.8953 | 0.025 | 0.025 | Human liver glycogen phosphorylase mRNA |
| 16 | Hs.79217 | 1 | 0.8532 | 0.025 | 0.0016 | 7 | 0.855 | 0.025 | 0.0036 | Human pyrroline 5-carboxylate reductase mRNA |
| 17 | Hs.10526 | -1 | 0.8532 | 0.025 | 0.0015 | 105 | 0.7556 | 0.075 | 0.00071 | Human smooth muscl LIM protein (h-SmLIM)mRNA |
| 18 | Hs.620 | -1 | 0.8523 | 0.025 | 0.0014 | 115 | 0.7497 | 0.075 | 0.00065 | Human bullous pemphigoid antigen (BPAG1) mRNA |
| 19 | Hs.198760 | -1 | 0.8495 | 0.025 | 0.0013 | 4 | 0.869 | 0.025 | 0.0062 | H.sapiens NF-H gene |
| 20 | Hs.85146 | -1 | 0.8459 | 0.025 | 0.0012 | 103 | 0.7552 | 0.075 | 0.00073 | Human erythroblastosis virus oncogene homolog 2 (ets-2) mRNA |
| 21 | Hs.75111 | -1 | 0.8432 | 0.025 | 0.0012 | 85 | 0.7669 | 0.025 | 0.00028 | Human cancellous bone osteoblast mRNA for serin protease with IG |
| 22 | Hs.33084 | -1 | 0.8432 | 0.025 | 0.0011 | 151 | 0.7304 | 0.38 | 0.0025 | Human glucose transport-likes (GLUT5) mRNA |
| 23 | Hs.78909 | -1 | 0.8423 | 0.025 | 0.0011 | 234 | 0.7009 | 1 | 0.011 | Human Tis11d gene |

FIG. 5a

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 24 | Hs.2785 | -1 | 0.8414 | 0.025 | 0.001 | 51 | 0.7911 | 0.025 | 0.00049 | H.sapiens gene for cytokeratin 17 |
| 25 | Hs.77840 | -1 | 0.8378 | 0.025 | 0.001 | 446 | 0.6498 | 1 | 0.086 | Human annexin IV (ANX4) mRNA |
| 26 | Hs.74566 | -1 | 0.8369 | 0.025 | 0.00096 | 125 | 0.7433 | 0.1 | 0.0008 | Human mRNA for dihydropyrimidinase related protein-3 |
| 27 | Hs.1869 | -1 | 0.836 | 0.025 | 0.00093 | 284 | 0.6821 | 1 | 0.028 | Human phosphoglucomutase 1 (PGM1) mRNA |
| 28 | Hs.76224 | -1 | 0.836 | 0.025 | 0.00089 | 39 | 0.8083 | 0.025 | 0.00064 | Human extracellular protein (S1-5) mRNA |
| 29 | Hs.76688 | -1 | 0.8342 | 0.025 | 0.00086 | 325 | 0.6735 | 1 | 0.038 | Human carboxylesterase mRNA |
| 30 | Hs.78089 | 1 | 0.8315 | 0.05 | 0.0017 | 564 | 0.6327 | 1 | 0.14 | Human fetus brain mRNA for vacuolar ATPase |
| 31 | Hs.1813 | -1 | 0.827 | 0.05 | 0.0016 | 25 | 0.8201 | 0.025 | 0.001 | Homo sapiens synaptic vesicle amine transporter (SVAT) mRNA |
| 32 | Hs.76194 | 1 | 0.8216 | 0.05 | 0.0016 | 391 | 0.6606 | 1 | 0.6 | Human ribosomal protein S5 mRNA |
| 33 | Hs.0 | -1 | 0.8171 | 0.075 | 0.0023 | 148 | 0.7315 | 0.38 | 0.0025 | Human CX3C chemokine precursor |
| 34 | Hs.155418 | -1 | 0.8153 | 0.075 | 0.0022 | 329 | 0.6729 | 1 | 0.039 | Human cancellous bone osteoblast mRNA for GS3955 |
| 35 | Hs.153322 | -1 | 0.8126 | 0.075 | 0.0021 | 98 | 0.7589 | 0.025 | 0.00026 | Human mRNA for phospholipase C |
| 36 | Hs.1440 | 1 | 0.8108 | 0.075 | 0.0021 | 92 | 0.7632 | 0.025 | 0.00027 | Human gamma amino butyric acid (GABAA) receptor beta-3 subunit |
| 37 | Hs.75137 | -1 | 0.8108 | 0.075 | 0.002 | 86 | 0.7664 | 0.025 | 0.00029 | Human mRNA for KIAA0193 gene |
| 38 | Hs.1298 | -1 | 0.8108 | 0.075 | 0.002 | 126 | 0.7433 | 0.1 | 0.00079 | Human common acute lymphoblastic leukemia antigen (CALLA) mRNA |
| 39 | Hs.164568 | -1 | 0.8108 | 0.075 | 0.0019 | 456 | 0.6493 | 1 | 0.087 | Human keratinocyte growth factor mRNA |
| 40 | Hs.2006 | -1 | 0.8099 | 0.075 | 0.0019 | 23 | 0.8255 | 0.025 | 0.0011 | Human glutathione transferase M3 (GSTM3)mRNA |
| 41 | Hs.250692 | -1 | 0.8099 | 0.075 | 0.0018 | 133 | 0.738 | 0.23 | 0.0017 | Human hepatic leukemia factor (HLF) mRNA |
| 42 | Hs.89591 | -1 | 0.809 | 0.075 | 0.0018 | 219 | 0.7052 | 1 | 0.0096 | Homo sapiens Kallmann syndrome (KAL) mRNA |
| 43 | Hs.81874 | 1 | 0.8072 | 0.075 | 0.0017 | 646 | 0.6219 | 1 | 0.18 | Human microsomal glutathione S-transferase (GST-II)mRNA |
| 44 | Hs.79059 | -1 | 0.8063 | 0.075 | 0.0017 | 87 | 0.7653 | 0.025 | 0.00029 | Human transforming growth factor-beta type III receptor (TGF-beta) |
| 45 | Hs.30054 | 1 | 0.8054 | 0.1 | 0.0022 | 74 | 0.7734 | 0.025 | 0.00034 | Human coagulation factor V mRNA |
| 46 | Hs.180015 | 1 | 0.8054 | 0.1 | 0.0022 | 470 | 0.6466 | 1 | 0.095 | Human D-dopachrome tautomerase mRNA |
| 47 | Hs.111334 | 1 | 0.8009 | 0.1 | 0.0021 | 1887 | 0.5269 | 1 | 0.83 | Human ferritin L chain mRNA |
| 48 | Hs.172851 | -1 | 0.8 | 0.1 | 0.0021 | 101 | 0.7567 | 0.075 | 0.00074 | Human arginase type II mRNA |
| 49 | Hs.76244 | 1 | 0.8 | 0.1 | 0.002 | 236 | 0.7009 | 1 | 0.012 | Human spermidine synthase mRNA |
| 50 | Hs.23838 | 1 | 0.7982 | 0.1 | 0.002 | 22 | 0.8287 | 0.025 | 0.0011 | Human neuronal DHP-sensitive |
| 51 | Hs.1342 | 1 | 0.7973 | 0.1 | 0.002 | 948 | 0.5908 | 1 | 0.37 | Human cytochrome c oxidase subunit Vb (coxVb) mRNA |
| 52 | Hs.155591 | -1 | 0.7973 | 0.1 | 0.0019 | 76 | 0.7723 | 0.025 | 0.00033 | Human forkhead protein FREAC-1 mRNA |

FIG. 5b

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 53 | Hs.10755 | -1 | 0.7955 | 0.1 | 0.0019 | 17 | 0.8373 | 0.025 | 0.0015 | Human mRNA for dihydropyrimidinase |
| 54 | Hs.83383 | 1 | 0.7955 | 0.1 | 0.0019 | 235 | 0.7009 | 1 | 0.012 | Human antioxidant enzyme AOE37-2 mRNA |
| 55 | Hs.56145 | 1 | 0.7946 | 0.1 | 0.0018 | 114 | 0.7508 | 0.075 | 0.00066 | Human mRNA for NB thymosin beta |
| 56 | Hs.245188 | -1 | 0.7937 | 0.1 | 0.0018 | 113 | 0.7519 | 0.075 | 0.00066 | Human tissue inhibitor of metalloproteinases-3mRNA |
| 57 | Hs.79345 | -1 | 0.7928 | 0.13 | 0.0022 | 724 | 0.6117 | 1 | 0.24 | Human coagulation factor VIII:C mRNA |
| 58 | Hs.79876 | -1 | 0.7928 | 0.13 | 0.0022 | 597 | 0.6284 | 1 | 0.16 | Human steroid sulfatase (STS) mRNA |
| 59 | Hs.0 | 1 | 0.7892 | 0.15 | 0.0025 | 195 | 0.7143 | 1 | 0.0073 | M17390 Human erg protein (ets-related gene) mRNA |
| 60 | Hs.66052 | -1 | 0.7883 | 0.15 | 0.0025 | 93 | 0.7626 | 0.025 | 0.00027 | 1299-1305 |
| 61 | Hs.81412 | -1 | 0.7865 | 0.18 | 0.0029 | 106 | 0.7551 | 0.075 | 0.00071 | Human mRNA for KIAA0188 gene |
| 62 | Hs.87539 | 1 | 0.7838 | 0.18 | 0.0028 | 465 | 0.6472 | 1 | 0.093 | Human aldehyde dehydrogenase (ALDH8) mRNA |
| 63 | Hs.180911 | 1 | 0.7829 | 0.18 | 0.0028 | 579 | 0.6305 | 1 | 0.15 | Human ribosomal protein (RPS4Y) isoform mRNA |
| 64 | Hs.171900 | 1 | 0.7829 | 0.18 | 0.0027 | 1910 | 0.5258 | 1 | 0.84 | Human armadillo repeat protein mRNA |
| 65 | Hs.0 | -1 | 0.7811 | 0.18 | 0.0027 | 659 | 0.6208 | 1 | 0.19 | Homo sapiens growth-arrest-specific protein (gas) mRNA |
| 66 | Hs.4437 | 1 | 0.7811 | 0.18 | 0.0027 | 188 | 0.7159 | 1 | 0.0068 | Human ribosomal protein L28 mRNA |
| 67 | Hs.32500 | -1 | 0.7793 | 0.18 | 0.0026 | 1729 | 0.5354 | 1 | 0.78 | Human mRNA for mitochondrial 3-oxoacyl-CoA thiolase |
| 68 | Hs.118065 | 1 | 0.7793 | 0.18 | 0.0026 | 467 | 0.6466 | 1 | 0.096 | Human mRNA for proteasome subunitz |
| 69 | Hs.56937 | 1 | 0.7793 | 0.18 | 0.0025 | 2391 | 0.6987 | 1 | 0.013 | Human SNC19 mRNA sequence |
| 70 | Hs.211933 | -1 | 0.7784 | 0.18 | 0.0025 | 80 | 0.7707 | 0.025 | 0.00031 | Human (clones HT-[125 |
| 71 | Hs.738 | 1 | 0.7766 | 0.23 | 0.0032 | 1145 | 0.5752 | 1 | 0.47 | Human mRNA for ribosomal protein L14 |
| 72 | Hs.69360 | 1 | 0.7766 | 0.23 | 0.0031 | 159 | 0.7277 | 0.55 | 0.0035 | Human mitotic centromere-associated kinesin mRNA |
| 73 | Hs.80986 | 1 | 0.7757 | 0.25 | 0.0034 | 343 | 0.6702 | 1 | 0.043 | |
| 74 | Hs.75260 | -1 | 0.7757 | 0.25 | 0.0034 | 139 | 0.7358 | 0.27 | 0.002 | H.sapiens mitogen inducible gene mig-2 |
| 75 | Hs.86978 | 1 | 0.7748 | 0.25 | 0.0033 | 70 | 0.7777 | 0.025 | 0.00036 | H.sapiens mRNA for prolyl oligopeptidase |
| 76 | Hs.78894 | 1 | 0.773 | 0.27 | 0.0036 | 199 | 0.7127 | 1 | 0.0074 | Human mRNA for KIAA0161 gene |
| 77 | Hs.1050 | -1 | 0.773 | 0.27 | 0.0036 | 676 | 0.6187 | 1 | 0.2 | Human homologue of yeast sec7 mRNA |
| 78 | Hs.75746 | 1 | 0.7721 | 0.27 | 0.0035 | 81 | 0.7691 | 0.025 | 0.00031 | Human aldehyde dehydrogenase 6 mRNA |
| 79 | Hs.211578 | -1 | 0.7721 | 0.27 | 0.0035 | 1053 | 0.5822 | 1 | 0.42 | Human mad protein homolog (hMAD-3)mRNA |
| 80 | Hs.78864 | 1 | 0.7721 | 0.27 | 0.0034 | 351 | 0.6692 | 1 | 0.045 | Human IgG low affinity Fc fragment receptor (FcRIIa) mRNA |
| 81 | Hs.237356 | -1 | 0.7712 | 0.3 | 0.0037 | 61 | 0.7846 | 0.025 | 0.00041 | Human intercrine-alpha (hIRH) mRNA |
| 82 | Hs.286 | 1 | 0.7694 | 0.33 | 0.004 | 134 | 0.7374 | 0.27 | 0.0021 | Human mRNA for ribosomal protein |
| 83 | Hs.155560 | 1 | 0.7676 | 0.35 | 0.0042 | 238 | 0.6987 | 1 | 0.013 | Homo sapiens integral membrane protein |
| 84 | Hs.81875 | -1 | 0.7676 | 0.38 | 0.0045 | 341 | 0.6713 | 1 | 0.042 | Human mRNA for KIA0207 gene |

FIG. 5c

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 85 | Hs.155597 | -1 | 0.7676 | 0.38 | 0.0044 | 78 | 0.7712 | 0.025 | 0.00032 | Human adipsin/complement factor D mRNA |
| 86 | Hs.76307 | -1 | 0.7658 | 0.38 | 0.0044 | 12 | 0.841 | 0.025 | 0.0021 | Human mRNA for unknown product |
| 87 | Hs.77448 | -1 | 0.7658 | 0.38 | 0.0043 | 99 | 0.7583 | 0.025 | 0.00025 | Human pyrroline-5-carboxylate dehydrogenase (P5CDh) mRNA |
| 88 | Hs.188 | -1 | 0.764 | 0.38 | 0.0043 | 295 | 0.6794 | 1 | 0.031 | Human phosphodiesterase mRNA |
| 89 | Hs.75244 | -1 | 0.7586 | 0.45 | 0.0051 | 209 | 0.71 | 1 | 0.0077 | Human mRNA for KIAA0271 gene |
| 90 | Hs.89529 | 1 | 0.7577 | 0.47 | 0.0053 | 762 | 0.6069 | 1 | 0.27 | Human aldehyde reductase mRNA |
| 91 | Hs.170328 | -1 | 0.7577 | 0.47 | 0.0052 | 227 | 0.703 | 1 | 0.011 | Human moesin mRNA |
| 92 | Hs.51299 | 1 | 0.7568 | 0.47 | 0.0052 | 161 | 0.7272 | 0.6 | 0.0037 | Human nuclear-encoded mitochondrial NADH-ubiquinone reductase |
| 93 | Hs.50130 | -1 | 0.7568 | 0.47 | 0.0051 | 155 | 0.7293 | 0.42 | 0.0027 | Human NECDIN related protein mRNA |
| 94 | Hs.190787 | -1 | 0.7568 | 0.47 | 0.0051 | 69 | 0.7782 | 0.025 | 0.00036 | Human tissue inhibitor of metalloproteinase4 mRNA |
| 95 | Hs.171862 | -1 | 0.755 | 0.5 | 0.0053 | 280 | 0.6831 | 1 | 0.027 | Human guanylate binding protein isoform II (GBP-2)mRNA |
| 96 | Hs.180107 | 1 | 0.7541 | 0.57 | 0.006 | 44 | 0.8024 | 0.025 | 0.00057 | Human mRNA for DNA polymerase beta |
| 97 | Hs.2090 | -1 | 0.7532 | 0.63 | 0.0064 | 745 | 0.609 | 1 | 0.26 | Human prostaglandin E2 receptor mRNA |
| 98 | Hs.29117 | -1 | 0.7514 | 0.75 | 0.0077 | 848 | 0.5999 | 1 | 0.31 | H.sapiens Pur (pur-alpha) mRNA |
| 99 | Hs.26776 | -1 | 0.7514 | 0.75 | 0.0076 | 2264 | 0.5043 | 1 | 0.98 | trkC [human |
| 100 | Hs.750 | -1 | 0.7495 | 0.88 | 0.0087 | 855 | 0.5988 | 1 | 0.32 | Homo sapiens fibrillin mRNA |
| 101 | Hs.83450 | -1 | 0.7495 | 0.88 | 0.0087 | 67 | 0.7803 | 0.025 | 0.00037 | Homo sapiens laminin-related protein (LamA3) mRNA |
| 102 | Hs.687 | -1 | 0.7495 | 0.88 | 0.0086 | 26 | 0.8195 | 0.025 | 0.00096 | Human lung cytochrome P450 (IV subfamily) BI protein |
| 103 | Hs.179774 | 1 | 0.7486 | 0.88 | 0.0085 | 739 | 0.6101 | 1 | 0.25 | Human mRNA for proteasome activator hPA28 subunit beta |
| 104 | Hs.75151 | 1 | 0.7486 | 0.88 | 0.0084 | 8 | 0.8545 | 0.025 | 0.0031 | Human GTPase activating protein (rap1GAP) mRNA |
| 105 | Hs.62661 | -1 | 0.7477 | 0.98 | 0.0093 | 319 | 0.6751 | 1 | 0.036 | Human guanylate binding protein isoform I (GBP-2) mRNA |
| 106 | Hs.283749 | -1 | 0.7468 | 1 | 0.01 | 110 | 0.7524 | 0.075 | 0.00068 | Human mRNA for RNase 4 |
| 107 | Hs.77311 | -1 | 0.7468 | 1 | 0.01 | 384 | 0.6622 | 1 | 0.057 | Human mRNA for tob family |
| 108 | Hs.71622 | -1 | 0.7468 | 1 | 0.01 | 149 | 0.7309 | 0.38 | 0.0025 | Human SWI/SNF complex 60 KDa subunit (BAF60c) mRNA |
| 109 | Hs.83656 | 1 | 0.7459 | 1 | 0.01 | 176 | 0.7191 | 1 | 0.0057 | Human GDP-dissociation inhibitor protein (Ly-GDI) mRNA |
| 110 | Hs.169718 | -1 | 0.7459 | 1 | 0.01 | 890 | 0.5956 | 1 | 0.34 | Human adult heart mRNA for neutral calponin |
| 111 | Hs.76780 | -1 | 0.7459 | 1 | 0.01 | 146 | 0.732 | 0.38 | 0.0026 | Human protein phosphatase-1 inhibitor mRNA |

FIG. 5d

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 112 | Hs.155606 | -1 | 0.745 | 1 | 0.01 | 132 | 0.7406 | 0.15 | 0.0011 | Human homeobox protein (PHOX1)mRNA |
| 113 | Hs.102497 | 1 | 0.7432 | 1 | 0.011 | 577 | 0.631 | 1 | 0.14 | Human paxillin mRNA |
| 114 | Hs.249495 | 1 | 0.7432 | 1 | 0.011 | 358 | 0.6681 | 1 | 0.046 | H.sapiens mRNA for hnRNPcore protein Al. |
| 115 | Hs.79172 | 1 | 0.7432 | 1 | 0.011 | 581 | 0.6305 | 1 | 0.15 | Human ADP/ATP carrier protein mRNA |
| 116 | Hs.250655 | 1 | 0.7432 | 1 | 0.011 | 708 | 0.6139 | 1 | 0.23 | Human prothymosin alpha mRNA(ProT-alpha) |
| 117 | Hs.323032 | 1 | 0.7423 | 1 | 0.012 | 32 | 0.8163 | 0.025 | 0.00078 | Human SIL mRNA |
| 118 | Hs.112396 | 1 | 0.7414 | 1 | 0.012 | 632 | 0.623 | 1 | 0.18 | Human mRNA for KIAA0077 gene |
| 119 | Hs.737 | 1 | 0.7414 | 1 | 0.012 | 551 | 0.6348 | 1 | 0.13 | Human transcription factor ETR101 mRNA |
| 120 | Hs.211569 | -1 | 0.7405 | 1 | 0.012 | 1184 | 0.5725 | 1 | 0.49 | Human G protein-coupled receptor kinase (GRK5) mRNA |
| 121 | Hs.177543 | -1 | 0.7396 | 1 | 0.013 | 999 | 0.5865 | 1 | 0.4 | Human MIC2 mRNA |
| 122 | Hs.47860 | 1 | 0.7396 | 1 | 0.013 | 1443 | 0.5526 | 1 | 0.65 | Human tyrosine kinase receptor pl45TRK-B (TRK-B) mRNA |
| 123 | Hs.81892 | 1 | 0.7387 | 1 | 0.013 | 27 | 0.819 | 0.025 | 0.00093 | Human mRNA for KIAA0101 gene |
| 124 | Hs.262476 | 1 | 0.7387 | 1 | 0.013 | 1079 | 0.58 | 1 | .0.44 | Human S-adenosylmethionine decarboxylase mRNA |
| 125 | Hs.154210 | -1 | 0.7387 | 1 | 0.013 | 852 | 0.5994 | 1 | 0.31 | Human endothelial differentiation protein (edg-1)gene mRNA |
| 126 | Hs.182825 | 1 | 0.7387 | 1 | 0.013 | 379 | 0.6638 | 1 | 0.053 | Human ribosomal protein L35 mRNA |
| 127 | Hs.149923 | 1 | 0.736 | 1 | 0.015 | 294 | 0.6794 | 1 | 0.03 | Human X box binding protein-1 (XBP-1) mRNA |
| 128 | Hs.211600 | -1 | 0.7351 | 1 | 0.015 | 1708 | 0.5365 | 1 | 0.77 | Human tumor necrosis factor alpha inducible protein A20 mRNA |
| 129 | Hs.78913 | -1 | 0.7351 | 1 | 0.015 | 252 | 0.6933 | 1 | 0.018 | Human G protein-coupled receptor V28 mRNA |
| 130 | Hs.301613 | 1 | 0.7351 | 1 | 0.015 | 104 | 0.7562 | 0.075 | 0.00072 | Human JTV-1 (JTV-1)mRNA |
| 131 | Hs.82109 | -1 | 0.7351 | 1 | 0.015 | 186 | 0.7164 | 1 | 0.0067 | H.sapiens syndecan-1 gene (exons 2-5) |
| 132 | Hs.254105 | 1 | 0.7351 | 1 | 0.015 | 224 | 0.7035 | 1 | 0.011 | Human alpha enolase mRNA |
| 133 | Hs.172471 | -1 | 0.7342 | 1 | 0.016 | 55 | 0.7889 | 0.025 | 0.0004 | Homo sapiens (done hKvBeta3) K+ channel beta subunit mRNA |
| 134 | Hs.211579 | -1 | 0.7342 | 1 | 0.016 | 129 | 0.7427 | 0.1 | 0.00078 | Human MUCl8 glycoprotein mRNA |
| 135 | Hs.1239 | -1 | 0.7333 | 1 | 0.017 | 181 | 0.7175 | 1 | 0.0064 | Human aminopeptidase N/CD13 mRNA encoding aminopeptidase N |
| 136 | Hs.75741 | -1 | 0.7333 | 1 | 0.017 | 50 | 0.7932 | 0.025 | 00005 | Human done HP-DAO1 diamine oxidase |
| 137 | Hs.82793 | 1 | 07333 | 1 | 0.017 | 861 | 0.5977 | 1 | 0.32 | Human mRNA for proteasome subunit HsC10-11 |
| 138 | Hs.75458 | 1 | 0.7333 | 1 | 0.017 | 1094 | 0.5789 | 1 | 0.45 | Homo sapiens ribosomal protein L18 (RPL18) mRNA |
| 139 | Hs.505 | -1 | 0.7324 | 1 | 0.017 | 144 | 0.7336 | 0.33 | 0.0023 | Human ISL-1 (Islet-1)mRNA |
| 140 | Hs.75400 | -1 | 0.7315 | 1 | 0.018 | 1895 | 0.5263 | 1 | 0.84 | Human mRNA for KIA0280 gene |

FIG. 5e

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 141 | Hs.1989 | -1 | 0.7315 | 1 | 0.018 | 107 | 0.7551 | 0.075 | 0.0007 | Human steroid 5-alpha-reductase 2 (SRD5A2) mRNA |
| 142 | Hs.180920 | 1 | 0.7315 | 1 | 0.018 | 686 | 0.6176 | 1 | 0.2 | Human ribosomal protein S9 mRNA |
| 143 | Hs.180034 | 1 | 0.7315 | 1 | 0.018 | 772 | 0.6063 | 1 | 0.27 | Human cleavage stimulation factor 77kDa subunit mRNA |
| 144 | Hs.82124 | -1 | 0.7306 | 1 | 0.018 | 1089 | 0.5795 | 1 | 0.44 | Human laminin B1 chain mRNA |
| 145 | Hs.90408 | -1 | 0.7306 | 1 | 0.018 | 2150 | 0.5118 | 1 | 0.93 | Human neogenin mRNA |
| 146 | Hs.1602 | -1 | 0.7306 | 1 | 0.018 | 522 | 0.638 | 1 | 0.12 | Human lymphocyte dihydropynmidine dehydrogenase mRNA |
| 147 | Hs.75139 | 1 | 0.7297 | 1 | 0.018 | 1062 | 0.5811 | 1 | 0.43 | Human arfaptin 2 |
| 148 | Hs.119 | -1 | 0.7288 | 1 | 0.018 | 661 | 0.6203 | 1 | 0.19 | Human mRNA for KIAA0l05 gene |
| 149 | Hs.278027 | -1 | 0.7288 | 1 | 0.018 | 657 | 0.6208 | 1 | 0.19 | Human mRNA for LIMK-2 |
| 150 | Hs.85050 | -1 | 0.7279 | 1 | 0.019 | 296 | 0.6794 | 1 | 0.03 | Human phospholamban mRNA |
| 151 | Hs.159525 | 1 | 0.7279 | 1 | 0.019 | 54 | 0.7895 | 0.025 | 0.00046 | Human cell growth regulator CGR11 mRNA |
| 152 | Hs.94581 | -1 | 0.7279 | 1 | 0.019 | 138 | 0.7363 | 027 | 0.002 | Homo sapiens hydroxysteroid sulfotransferase SULT2B1a (HSST2) |
| 153 | Hs.75618 | 1 | 0.727 | 1 | 0.019 | 237 | 0.6998 | 1 | 0.013 | Homo sapiens rab11a GTPase mRNA |
| 154 | Hs.298262 | 1 | 0.727 | 1 | 0.019 | 729 | 0.6112 | 1 | 0.24 | H.sapiens S19 ribosomal protein mRNA |
| 155 | Hs.27747 | 1 | 0.727 | 1 | 0.019 | 797 | 0.6037 | 1 | 0.29 | Human putative endothelin receptor type B-like protein mRNA |
| 156 | Hs.56045 | -1 | 0.7261 | 1 | 0.02 | 36 | 0.8099 | 0.025 | 0.00069 | Human mRNA for stac |
| 157 | Hs.75655 | 1 | 0.7243 | 1 | 0.021 | 225 | 0.703 | 1 | 0.011 | Human thyroid hormone binding protein (p55) mRNA |
| 158 | Hs.80712 | -1 | 0.7243 | 1 | 0.022 | 260 | 0.6896 | 1 | 0.021 | Human mRNA for KIAA0202 gene |
| 159 | Hs.23111 | 1 | 0.7234 | 1 | 0.022 | 293 | 0.6799 | 1 | 0.03 | Human putative tRNA synthetase-like protein mRNA |
| 160 | Hs.2388 | 1 | 0.7225 | 1 | 0.023 | 19 | 0.8362 | 0.025 | 0.0013 | Human apolipoprotein F (APOF) mRNA |
| 161 | Hs.307164 | -1 | 0.7226 | 1 | 0.023 | 428 | 0.6547 | 1 | 0.072 | Human 3' |
| 162 | Hs.3852 | -1 | 0.7207 | 1 | 0.026 | 776 | 0.6053 | 1 | 0.28 | Human mRNA for KIAA0368 gene |
| 163 | Hs.153179 | 1 | 0.7207 | 1 | 0.026 | 1080 | 0.58 | 1 | 0.44 | Human fatty acid binding protein homologue(PA-FABP)mRNA |
| 164 | Hs.26403 | 1 | 0.7207 | 1 | 0.026 | 2113 | 0.514 | 1 | 0.91 | Human glutathione transferase Zeta 1 (GSTZ1)mRNA |
| 165 | Hs.50964 | -1 | 0.7198 | 1 | 0.027 | 421 | 0.6563 | 1 | 0.068 | Human mRNA for transmembrane cardnoembryonic antigen BGPa (f |
| 166 | Hs.92002 | -1 | 0.7198 | 1 | 0.027 | 45 | 0.8018 | 0.025 | 0.00056 | Human transducin alpha-subunit (GNAZ) mRNA |
| 167 | Hs.322903 | -1 | 0.7189 | 1 | 0.028 | 1144 | 0.5752 | 1 | 0.47 | Human mRNA for KLAA0184 gene |
| 168 | Hs.106880 | 1 | 0.7189 | 1 | 0.028 | 321 | 0.6745 | 1 | 0.036 | Homo sapiens bystin mRNA |
| 169 | Hs.244621 | 1 | 0.7189 | 1 | 0.028 | 2231 | 0.5064 | 1 | 0.96 | 5551-5557 |

FIG. 5f

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 170 | Hs.19368 | -1 | 0.7189 | 1 | 0.027 | 363 | 0.6676 | 1 | 0.046 | Human matrilin-2 precursor mRNA |
| 171 | Hs.77293 | -1 | 0.718 | 1 | 0.028 | 590 | 0.6289 | 1 | 0.15 | Human mRNA for KIAA0127 gene |
| 172 | Hs.170198 | 1 | 0.7171 | 1 | 0.03 | 131 | 0.7406 | 0.15 | 0.0011 | Human mRNA for KIAA0009 gene |
| 173 | Hs.79226 | -1 | 0.7171 | 1 | 0.029 | 41 | 0.8056 | 0.025 | 0.00061 | Human FEZ1 mRNA |
| 174 | Hs.82163 | -1 | 0.7162 | 1 | 0.031 | 153 | 0.7293 | 0.42 | 0.0028 | Human monoamine oxidase B (MAOB) mRNA |
| 175 | Hs.288215 | -1 | 0.7153 | 1 | 0.032 | 241 | 0.6976 | 1 | 0.014 | Human sialyltransferase SThM (sthm) mRNA |
| 176 | Hs.75692 | 1 | 0.7153 | 1 | 0.032 | 118 | 0.7476 | 0.075 | 0.00064 | Human asparagine synthetase mRNA |
| 177 | Hs.76901 | 1 | 0.7126 | 1 | 0.035 | 662 | 0.6203 | 1 | 0.19 | Human mRNA for protein disulfide isomerase-related protein (PDIR) |
| 178 | Hs.76064 | 1 | 0.7117 | 1 | 0.037 | 849 | 0.5999 | 1 | 0.31 | Human ribosomal protein L27a mRNA |
| 179 | Hs.80409 | -1 | 0.7108 | 1 | 0.038 | 902 | 0.5951 | 1 | 0.34 | Human growth arrest and DNA-damage-inducible protein (gadd4s) |
| 180 | Hs.155530 | -1 | 0.7108 | 1 | 0.038 | 812 | 0.6026 | 1 | 0.29 | Human interferon-gamma induced protein (IFI 16) gene |
| 181 | Hs.9614 | 1 | 0.7108 | 1 | 0.039 | 157 | 0.7288 | 0.45 | 0.0029 | Human nucleophosmin mRNA |
| 182 | Hs.76927 | 1 | 0.7108 | 1 | 0.038 | 389 | 0.6611 | 1 | 0.059 | Human putative outer mitochondrial membrane 34 kDa translocase hT |
| 183 | Hs.82961 | 1 | 0.7108 | 1 | 0.038 | 871 | 0.5977 | 1 | 0.32 | Human intestinal trefoil factor mRNA |
| 184 | Hs.75232 | -1 | 0.7099 | 1 | 0.039 | 1154 | 0.5747 | 1 | 0.48 | Human SEC14L mRNA |
| 185 | Hs.1524 | 1 | 0.709 | 1 | 0.041 | 2050 | 0.5172 | 1 | 0.9 | Human receptor 4-1BB ligand mRNA |
| 186 | Hs.106070 | -1 | 0.709 | 1 | 0.04 | 1255 | 0.5666 | 1 | 0.54 | Human Cdk-inhibitor ps57KIP2 (KIP2) mRNA |
| 187 | Hs.3260 | 1 | 0.709 | 1 | 0.04 | 1686 | 0.5376 | 1 | 0.76 | Human presenilin 1-374 (AD3-212) mRNA |
| 188 | Hs.334 | -1 | 0.7081 | 1 | 0.041 | 298 | 0.6788 | 1 | 0.031 | Human guanine nucleotide regulatory protein (tim1) mRNA |
| 189 | Hs.108885 | -1 | 0.7081 | 1 | 0.041 | 1823 | 0.5301 | 1 | 0.81 | Human mRNA for collagen VI alpha-1 C-terminal globular domain |
| 190 | Hs.22785 | -1 | 0.7072 | 1 | 0.042 | 357 | 0.6681 | 1 | 0.046 | Human GABA-A receptor epsilon subunit mRNA. |
| 191 | Hs.173912 | 1 | 0.7063 | 1 | 0.043 | 761 | 0.6069 | 1 | 0.27 | Human mRNA for eukaryotic initiation factor 4AII |
| 192 | Hs.29279 | -1 | 0.7063 | 1 | 0.043 | 1476 | 0.5505 | 1 | 0.67 | Human eyes absent homolog (Eab1) mRNA |
| 193 | Hs.151531 | -1 | 0.7054 | 1 | 0.044 | 210 | 0.71 | 1 | 0.0076 | Human calcineurin A2 mRNA |
| 194 | Hs.102267 | 1 | 0.7045 | 1 | 0.046 | 91 | 0.7637 | 0.025 | 0.00027 | Human lysyl oxidase (LOX) gene |
| 195 | Hs.74615 | -1 | 0.7045 | 1 | 0.046 | 592 | 0.6289 | 1 | 0.15 | Human platelet-derived growth factor receptor alpha (PDGFRA) mRNA |
| 196 | Hs.278503 | -1 | 0.7045 | 1 | 0.046 | 1643 | 0.5403 | 1 | 0.74 | Human RIG mRNA |
| 197 | Hs.1602 | -1 | 0.7045 | 1 | 0.046 | 524 | 0.638 | 1 | 0.12 | Human dihydropyrimidine dehydrogenase mRNA |

FIG. 5g

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 198 | Hs.181028 | 1 | 0.7036 | 1 | 0.047 | 168 | 0.7229 | 0.85 | 0.0051 | Homo sapiens nuclear-encoded mitochondrial cytochrome c oxidase |
| 199 | Hs.89457 | 1 | 0.7036 | 1 | 0.047 | 1471 | 0.551 | 1 | 0.66 | Human mRNA for a1(XIX) collagen chain |
| 200 | Hs.62192 | 1 | 0.7036 | 1 | 0.047 | 870 | 0.5977 | 1 | 0.32 | Human tissue factor gene |

2003 Study

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 1 | Hs.771 | -1 | 0.8953 | 0.025 | 0.025 | 15 | 0.8532 | 0.025 | 0.0017 | Human liver glycogen phosphorylase mRNA |
| 2 | Hs.195850 | -1 | 0.8813 | 0.025 | 0.012 | 7 | 0.8811 | 0.025 | 0.0036 | Human keratin type II (58 kD) mRNA |
| 3 | Hs.171731 | -1 | 0.8754 | 0.025 | 0.0083 | 1 | 0.9495 | 0.025 | 0.025 | Human RACH1 (RACH1) mRNA |
| 4 | Hs.198760 | -1 | 0.869 | 0.025 | 0.0062 | 19 | 0.8495 | 0.025 | 0.0013 | H.sapiens NF-H gene |
| 5 | Hs.65029 | -1 | 0.8647 | 0.025 | 0.005 | 8 | 0.8802 | 0.025 | 0.0031 | Human gas1 gene |
| 6 | Hs.1227 | -1 | 0.8555 | 0.025 | 0.0042 | 2132 | 0.5117 | 1 | 0.95 | Human delta-aminolevulinate dehydratase mRNA |
| 7 | Hs.79217 | 1 | 0.855 | 0.025 | 0.0036 | 16 | 0.8532 | 0.025 | 0.0016 | Human pyrroline 5-carboxylate reductase mRNA |
| 8 | Hs.75151 | 1 | 0.8545 | 0.025 | 0.0031 | 104 | 0.7486 | 0.88 | 0.0084 | Human GTPase activating protein (rap1GAP) mRNA |
| 9 | Hs.9615 | -1 | 0.8459 | 0.025 | 0.0028 | 224 | 0.6919 | 1 | 0.072 | Human 20-kDa myosin light chain (MLC-2) mRNA |
| 10 | Hs.174151 | -1 | 0.8448 | 0.025 | 0.0025 | 4 | 0.8892 | 0.025 | 0.0062 | Human aldehyde oxidase (hAOX) mRNA |
| 11 | Hs.82422 | -1 | 0.8426 | 0.025 | 0.0023 | 465 | 0.6387 | 1 | 0.25 | Homo sapiens macrophage capping protein mRNA |
| 12 | Hs.76307 | -1 | 0.841 | 0.025 | 0.0021 | 86 | 0.7658 | 0.38 | 0.0044 | Human mRNA for unknown product |
| 13 | Hs.74120 | -1 | 0.841 | 0.025 | 0.0019 | 424 | 0.6468 | 1 | 0.21 | Human apM2 mRNA for GS2374 (unknown product specific to adipose tissue) |
| 14 | Hs.44 | -1 | 0.841 | 0.025 | 0.0018 | 12 | 0.8685 | 0.025 | 0.0021 | Human nerve growth factor (HBNF-1) mRNA |
| 15 | Hs.3128 | 1 | 0.841 | 0.025 | 0.0017 | 2 | 0.9081 | 0.025 | 0.012 | Human RNA polymerase II subunit (hsRPB8) mRNA |
| 16 | Hs.21223 | -1 | 0.8378 | 0.025 | 0.0016 | 243 | 0.6847 | 1 | 0.088 | Human mRNA for calponin |
| 17 | Hs.10755 | -1 | 0.8373 | 0.025 | 0.0015 | 53 | 0.7955 | 0.1 | 0.0019 | Human mRNA for dihydropyrimidinase |
| 18 | Hs.239926 | -1 | 0.8373 | 0.025 | 0.0014 | 297 | 0.6712 | 1 | 0.13 | Human methyl sterol oxidase (ERG25) mRNA |
| 19 | Hs.2388 | 1 | 0.8362 | 0.025 | 0.0013 | 160 | 0.7225 | 1 | 0.023 | Human apolipoprotein F (APOF) mRNA |
| 20 | Hs.34853 | -1 | 0.8314 | 0.025 | 0.0012 | 5 | 0.8892 | 0.025 | 0.005 | Human Id-related helix-loop-helix protein Id4 mRNA |
| 21 | Hs.77256 | 1 | 0.8298 | 0.025 | 0.0012 | 407 | 0.6505 | 1 | 0.2 | Human enhancer of zeste homolog 2 (EZH2) mRNA |
| 22 | Hs.23838 | 1 | 0.8287 | 0.025 | 0.0011 | 50 | 0.7982 | 0.1 | 0.002 | Human neuronal DHP-sensitive |

FIG. 5h

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 23 | Hs.2006 | -1 | 0.8255 | 0.025 | 0.0011 | 40 | 0.8099 | 0.075 | 0.0019 | Human glutathione transferase M3 (GSTM3) mRNA |
| 24 | Hs.113 | -1 | 0.8217 | 0.025 | 0.001 | 13 | 0.8658 | 0.025 | 0.0019 | Human cytosolic epoxide hydrolase mRNA |
| 25 | Hs.1813 | -1 | 0.8201 | 0.025 | 0.001 | 31 | 0.827 | 0.05 | 0.0016 | Homo sapiens synaptic vesicle amine transporter (SVAT) mRNA |
| 26 | Hs.687 | -1 | 0.8195 | 0.025 | 0.00096 | 102 | 0.7495 | 0.88 | 0.0086 | Human lung cytochrome P450 (IV subfamily) BI protein |
| 27 | Hs.81892 | 1 | 0.819 | 0.025 | 0.00093 | 123 | 0.7387 | 1 | 0.013 | Human mRNA for KIAA0101 gene |
| 28 | Hs.169401 | 1 | 0.819 | 0.025 | 0.00089 | 595 | 0.6198 | 1 | 0.36 | Human apolipoprotein E mRNA |
| 29 | Hs.1861 | -1 | 0.819 | 0.025 | 0.00086 | 748 | 0.6009 | 1 | 0.49 | Human palmitoylated erythrocyte membrane protein (MPP1) mRNA |
| 30 | Hs.173063 | -1 | 0.819 | 0.025 | 0.00083 | 367 | 0.6577 | 1 | 0.17 | Human transducin-like enhancer protein (TLE2) mRNA |
| 31 | Hs.89497 | 1 | 0.8174 | 0.025 | 0.00081 | 703 | 0.6063 | 1 | 0.45 | Human lamin B mRNA |
| 32 | Hs.323032 | 1 | 0.8163 | 0.025 | 0.00078 | 117 | 0.7423 | 1 | 0.012 | Human SIL mRNA |
| 33 | Hs.300772 | -1 | 0.8163 | 0.025 | 0.00076 | 414 | 0.6495 | 1 | 0.2 | Human fibroblast muscle-type tropomyosin mRNA |
| 34 | Hs.77899 | -1 | 0.8147 | 0.025 | 0.00074 | 402 | 0.6514 | 1 | 0.19 | Human tropomyosin mRNA |
| 35 | Hs.63510 | 1 | 0.8104 | 0.025 | 0.00071 | 1646 | 0.5387 | 1 | 0.84 | Human mRNA for KIAA0141 gene |
| 36 | Hs.56045 | -1 | 0.8099 | 0.025 | 0.00069 | 156 | 0.7261 | 1 | 0.02 | Human mRNA for stac |
| 37 | Hs.184339 | 1 | 0.8093 | 0.025 | 0.00068 | 250 | 0.682 | 1 | 0.097 | Human mRNA for KIAA0175 gene |
| 38 | Hs.84113 | 1 | 0.8083 | 0.025 | 0.00066 | 288 | 0.6721 | 1 | 0.13 | Homo sapiens protein tyrosine phosphatase (CIP2)mRNA |
| 39 | Hs.76224 | -1 | 0.8083 | 0.025 | 0.00064 | 28 | 0.836 | 0.025 | 0.00089 | Human extracellular protein (S1-5) mRNA |
| 40 | Hs.75335 | -1 | 0.8061 | 0.025 | 0.00062 | 798 | 0.5973 | 1 | 0.51 | H.sapiens mRNA for L-arginine:glycine amidinotransferase |
| 41 | Hs.79226 | -1 | 0.8056 | 0.025 | 0.00061 | 173 | 0.7171 | 1 | 0.029 | Human FEZ1 mRNA |
| 42 | Hs.27311 | 1 | 0.8056 | 0.025 | 0.0006 | 11 | 0.8694 | 0.025 | 0.0023 | Human transcription factor SIM2 long form mRNA |
| 43 | Hs.119301 | -1 | 0.8029 | 0.025 | 0.00058 | 246 | 0.6838 | 1 | 0.09 | Homo sapiens cellular ligand of annexin II (p11) mRNA |
| 44 | Hs.180107 | 1 | 0.8024 | 0.025 | 0.00057 | 96 | 0.7541 | 0.57 | 0.006 | Human mRNA for DNA polymerase beta |
| 45 | Hs.92002 | -1 | 0.8018 | 0.025 | 0.00056 | 166 | 0.7198 | 1 | 0.027 | Human transducin alpha-subunit (GNAZ) mRNA |
| 46 | Hs.77546 | -1 | 0.8008 | 0.025 | 0.00054 | 14 | 0.8649 | 0.025 | 0.0018 | Human mRNA for KIAA0172 gene |
| 47 | Hs.311 | 1 | 0.7965 | 0.025 | 0.00053 | 249 | 0.6829 | 1 | 0.094 | Homo sapiens glutamine PRPP amidotransferase (GPAT) mRNA complete 48 Hs.326 1 0.7943 |
| 49 | Hs.6540 | 1 | 0.7938 | 0.025 | 0.00051 | 1198 | 0.5676 | 1 | 0.67 | Human fibroblast growth factor homologous factor 2 (FHF-2) mRNA |
| 50 | Hs.75741 | -1 | 0.7932 | 0.025 | 0.0005 | 136 | 0.7333 | 1 | 0.017 | Human clone HP-DAO1 diamine oxidase |

FIG. 5i

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 51 | Hs.2785 | -1 | 0.7911 | 0.025 | 0.00049 | 24 | 0.8414 | 0.025 | 0.001 | H.sapiens gene for cytokeratin 17 |
| 52 | Hs.57783 | 1 | 0.79 | 0.025 | 0.00048 | 232 | 0.6901 | 1 | 0.075 | Human eukaryotic translation initiation factor (eIF3) mRNA |
| 53 | Hs.156346 | 1 | 0.7895 | 0.025 | 0.00047 | 322 | 0.6667 | 1 | 0.14 | Human DNA topoisomerase II (top2) mRNA |
| 54 | Hs.159525 | 1 | 0.7895 | 0.025 | 0.00046 | 151 | 0.7279 | 1 | 0.019 | Human cell growth regulator CGR11 mRNA |
| 55 | Hs.172471 | -1 | 0.7889 | 0.025 | 0.00045 | 133 | 0.7342 | 1 | 0.016 | Homo sapiens (clone hKvBeta3) K+ channel beta subunit mRNA |
| 56 | Hs.82916 | 1 | 0.7884 | 0.025 | 0.00045 | 413 | 0.6495 | 1 | 0.2 | Human chaperonin protein (Tcp20) gene complete cds |
| 57 | Hs.181046 | -1 | 0.7879 | 0.025 | 0.00044 | 1881 | 0.5252 | 1 | 0.9 | Human dual specificity phosphatase tyrosine/serine mRNA |
| 58 | Hs.21639 | -1 | 0.7873 | 0.025 | 0.00043 | 1566 | 0.5441 | 1 | 0.81 | Human APEG-1 mRNA |
| 59 | Hs.14968 | -1 | 0.7868 | 0.025 | 0.00042 | 990 | 0.582 | 1 | 0.59 | Human zinc finger protein PLAG1 mRNA |
| 60 | Hs.296259 | -1 | 0.7857 | 0.025 | 0.00042 | 1632 | 0.5396 | 1 | 0.83 | Homo sapiens paraoxonase 3 (PON3) mRNA |
| 61 | Hs.237356 | -1 | 0.7846 | 0.025 | 0.00041 | 81 | 0.7712 | 0.3 | 0.0037 | Human intercrine-alpha (hIRH) mRNA |
| 62 | Hs.153954 | 1 | 0.7841 | 0.025 | 0.0004 | 2017 | 0.5171 | 1 | 0.94 | Human mRNA for KIAA0057 gene |
| 63 | Hs.170414 | 1 | 0.7836 | 0.025 | 0.0004 | 458 | 0.6396 | 1 | 0.25 | Human subtilisin-like protein (PACE4) mRNA |
| 64 | Hs.1584 | 1 | 0.783 | 0.025 | 0.00039 | 616 | 0.6162 | 1 | 0.39 | Human germline oligomeric matrix protein (COMP) mRNA |
| 65 | Hs.234642 | -1 | 0.7814 | 0.025 | 0.00038 | 2239 | 0.5054 | 1 | 0.98 | Human AQP3 gene for aquaporine 3 (water channel) |
| 66 | Hs.93841 | -1 | 0.7814 | 0.025 | 0.00038 | 231 | 0.6901 | 1 | 0.074 | Human MaxiK potassium channel beta subunit mRNA |
| 67 | Hs.83450 | -1 | 0.7803 | 0.025 | 0.00037 | 101 | 0.7495 | 0.88 | 0.0087 | Homo sapiens laminin-related protein (LamA3) mRNA |
| 68 | Hs.172153 | -1 | 0.7798 | 0.025 | 0.00037 | 274 | 0.6748 | 1 | 0.12 | Human plasma (extracellular) mRNA for glutathione peroxidase |
| 69 | Hs.190787 | -1 | 0.7782 | 0.025 | 0.00036 | 94 | 0.7568 | 0.47 | 0.0051 | Human tissue inhibitor of metalloproteinase 4 mRNA |
| 70 | Hs.86978 | 1 | 0.7777 | 0.025 | 0.00036 | 75 | 0.7748 | 0.25 | 0.0033 | H.sapiens mRNA for prolyl oligopeptidase |
| 71 | Hs.831 | -1 | 0.7755 | 0.025 | 0.00035 | 656 | 0.6099 | 1 | 0.44 | Human hydroxymethylglutaryl-CoA lyase mRNA |
| 72 | Hs.265829 | -1 | 0.7755 | 0.025 | 0.00035 | 724 | 0.6036 | 1 | 0.47 | Human integrin alpha-3 chain mRNA |
| 73 | Hs.2025 | -1 | 0.7744 | 0.025 | 0.00034 | 3 | 0.9027 | 0.025 | 0.0083 | Human transforming growth factor-beta 3 (TGF-beta3) mRNA |
| 74 | Hs.30054 | 1 | 0.7734 | 0.025 | 0.00034 | 45 | 0.8054 | 0.1 | 0.0022 | Human coagulation factor V mRNA |
| 75 | Hs.90744 | -1 | 0.7723 | 0.025 | 0.00033 | 1616 | 0.5405 | 1 | 0.83 | Human mRNA for proteasome subunit p44.5 |
| 76 | Hs.155591 | -1 | 0.7723 | 0.025 | 0.00033 | 52 | 0.7973 | 0.1 | 0.0019 | Human forkhead protein FREAC-1 mRNA |

FIG. 5j

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 77 | Hs.77899 | -1 | 0.7723 | 0.025 | 0.00032 | 1741 | 0.5342 | 1 | 0.85 | H.sapiens tropomyosin isoform mRNA |
| 78 | Hs.155597 | -1 | 0.7712 | 0.025 | 0.00032 | 85 | 0.7676 | 0.38 | 0.0044 | Human adipsin/complement factor D mRNA |
| 79 | Hs.418 | 1 | 0.7712 | 0.025 | 0.00032 | 376 | 0.6559 | 1 | 0.18 | Human fibroblast activation protein mRNA |
| 80 | Hs.211933 | -1 | 0.7707 | 0.025 | 0.00031 | 70 | 0.7784 | 0.18 | 0.0025 | Human (clones HT-[125 |
| 81 | Hs.75746 | 1 | 0.7691 | 0.025 | 0.00031 | 78 | 0.7721 | 0.27 | 0.0035 | Human aldehyde dehydrogenase 6 mRNA |
| 82 | Hs.23311 | -1 | 0.7685 | 0.025 | 0.0003 | 304 | 0.6694 | 1 | 0.13 | Human mRNA for KIAA0367 gene |
| 83 | Hs.80296 | -1 | 0.768 | 0.025 | 0.0003 | 671 | 0.609 | 1 | 0.44 | Human PEP19 (PCP4) mRNA |
| 84 | Hs.81343 | 1 | 0.768 | 0.025 | 0.0003 | 302 | 0.6703 | 1 | 0.13 | Human mRNA for pro-alpha 1 (II) collagen 3' end C-term. triple helical |
| 86 | Hs.75137 | -1 | 0.7664 | 0.025 | 0.00029 | 37 | 0.8108 | 0.075 | 0.002 | Human mRNA for KIAA0193 gene |
| 87 | Hs.79059 | -1 | 0.7653 | 0.025 | 0.00029 | 44 | 0.8063 | 0.075 | 0.0017 | Human transforming growth factor-beta type III receptor (TGF-beta) mRNA |
| 88 | Hs.198241 | -1 | 0.7653 | 0.025 | 0.00028 | 247 | 0.6838 | 1 | 0.09 | Human placenta copper monamine oxidase mRNA |
| 89 | Hs.57698 | -1 | 0.7653 | 0.025 | 0.00028 | 824 | 0.5946 | 1 | 0.53 | Human H105e3 mRNA |
| 90 | Hs.114346 | -1 | 0.7648 | 0.025 | 0.00028 | 313 | 0.6676 | 1 | 0.14 | Human cytochrome c oxidase subunit VIIa (COX7A) muscle isoform mRNA |
| 91 | Hs.102267 | 1 | 0.7637 | 0.025 | 0.00027 | 194 | 0.7045 | 1 | 0.046 | Human lysyl oxidase (LOX) gene |
| 92 | Hs.1440 | 1 | 0.7632 | 0.025 | 0.00027 | 36 | 0.8108 | 0.075 | 0.0021 | Human gamma amino butyric acid (GABAA) receptor beta-3 subunit mRNA |
| 93 | Hs.66052 | -1 | 0.7626 | 0.025 | 0.00027 | 60 | 0.7883 | 0.15 | 0.0025 | 1299-1305 |
| 94 | Hs.155585 | -1 | 0.7626 | 0.025 | 0.00027 | 6 | 0.8838 | 0.025 | 0.0042 | Human transmembrane receptor (ror2) mRNA |
| 95 | Hs.100293 | 1 | 0.761 | 0.025 | 0.00026 | 229 | 0.691 | 1 | 0.072 | Human O-linked GlcNAc transferase mRNA |
| 96 | Hs.34789 | 1 | 0.7599 | 0.025 | 0.00026 | 338 | 0.6631 | 1 | 0.15 | Human mRNA for KIAA0115 gene |
| 97 | Hs.226213 | -1 | 0.7599 | 0.025 | 0.00026 | 202 | 0.7036 | 1 | 0.047 | Human lanosterol 14-demethylase cytochrome P450 (CYP51) mRNA |
| 98 | Hs.153322 | -1 | 0.7589 | 0.025 | 0.00026 | 35 | 0.8126 | 0.075 | 0.0021 | Human mRNA for phospholipase C |
| 99 | Hs.77448 | -1 | 0.7583 | 0.025 | 0.00025 | 87 | 0.7658 | 0.38 | 0.0043 | Human pyrroline-5-carboxylate dehydrogenase (P5CDh) mRNA |
| 100 | Hs.76289 | -1 | 0.7567 | 0.075 | 0.00075 | 998 | 0.5811 | 1 | 0.6 | Human mRNA for NADPH-flavin reductase |
| 101 | Hs.172851 | -1 | 0.7567 | 0.075 | 0.00074 | 48 | 0.8 | 0.1 | 0.0021 | Human arginase type II mRNA |
| 102 | Hs.170177 | -1 | 0.7567 | 0.075 | 0.00074 | 447 | 0.6414 | 1 | 0.24 | Human leukemogenic homolog protein (MEIS1) mRNA |

FIG. 5k

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 103 | Hs.85146 | -1 | 0.7562 | 0.075 | 0.00073 | 20 | 0.8459 | 0.025 | 0.0012 | Human erythroblastosis virus oncogene homolog 2 (ets-2) mRNA |
| 104 | Hs.301613 | 1 | 0.7562 | 0.075 | 0.00072 | 130 | 0.7351 | 1 | 0.015 | Human JTV-1 (JTV-1) mRNA |
| 105 | Hs.10526 | -1 | 0.7556 | 0.075 | 0.00071 | 17 | 0.8532 | 0.025 | 0.0015 | Human smooth muscle LIM protein (h-SmLIM) mRNA |
| 106 | Hs.81412 | -1 | 0.7551 | 0.075 | 0.00071 | 61 | 0.7865 | 0.18 | 0.0029 | Human mRNA for KIAA0188 gene |
| 107 | Hs.1989 | -1 | 0.7551 | 0.075 | 0.0007 | 141 | 0.7315 | 1 | 0.018 | Human steroid 5-alpha-reductase 2 (SRD5A2) mRNA |
| 108 | Hs.173724 | -1 | 0.7546 | 0.075 | 0.00069 | 315 | 0.6676 | 1 | 0.14 | Human creatine kinase-B mRNA |
| 109 | Hs.75893 | 1 | 0.7535 | 0.075 | 0.00069 | 210 | 0.6991 | 1 | 0.053 | Human ankyrin G (ANK-3) mRNA |
| 110 | Hs.283749 | -1 | 0.7524 | 0.075 | 0.00068 | 106 | 0.7468 | 1 | 0.01 | Human mRNA for RNase 4 |
| 111 | Hs.78748 | -1 | 0.7524 | 0.075 | 0.00068 | 1378 | 0.555 | 1 | 0.75 | Human mRNA for KIAA0237 gene |
| 112 | Hs.111903 | -1 | 0.7524 | 0.075 | 0.00067 | 1174 | 0.5694 | 1 | 0.66 | Human IgG Fc receptor hFcRn mRNA |
| 113 | Hs.245188 | -1 | 0.7519 | 0.075 | 0.00066 | 56 | 0.7937 | 0.1 | 0.0018 | Human tissue inhibitor of metalloproteinases-3 mRNA |
| 114 | Hs.56145 | 1 | 0.7508 | 0.075 | 0.00066 | 55 | 0.7946 | 0.1 | 0.0018 | Human mRNA for NB thymosin beta |
| 115 | Hs.620 | -1 | 0.7497 | 0.075 | 0.00065 | 18 | 0.8523 | 0.025 | 0.0014 | Human bullous pemphigoid antigen (BPAG1) mRNA |
| 116 | Hs.75652 | -1 | 0.7476 | 0.075 | 0.00065 | 705 | 0.6054 | 1 | 0.46 | Human glutathione S-transferase (GSTM5) mRNA |
| 117 | Hs.194765 | 1 | 0.7476 | 0.075 | 0.00064 | 253 | 0.682 | 1 | 0.096 | H.sapiens GENX-5624 mRNA |
| 118 | Hs.75692 | 1 | 0.7476 | 0.075 | 0.00064 | 176 | 0.7153 | 1 | 0.032 | Human asparagine synthetase mRNA |
| 119 | Hs.118825 | 1 | 0.747 | 0.075 | 0.00063 | 1384 | 0.555 | 1 | 0.75 | Human MAP kinase kinase 6 (MKK6) mRNA |
| 120 | Hs.287921 | -1 | 0.746 | 0.1 | 0.00083 | 2075 | 0.5144 | 1 | 0.95 | Homo sapiens Luman mRNA |
| 121 | Hs.181013 | -1 | 0.746 | 0.1 | 0.00083 | 732 | 0.6027 | 1 | 0.48 | Homo sapiens phosphoglycerate mutase (PGAM-B) mRNA |
| 122 | Hs.79265 | -1 | 0.7454 | 0.1 | 0.00082 | 394 | 0.6523 | 1 | 0.19 | Human p126 (ST5) mRNA |
| 123 | Hs.77854 | -1 | 0.7444 | 0.1 | 0.00081 | 473 | 0.6378 | 1 | 0.26 | Human mRNA for SMP-30 (senescence marker protein-30) |
| 124 | Hs.2471 | 1 | 0.7438 | 0.1 | 0.00081 | 263 | 0.6793 | 1 | 0.1 | Human mRNA for KIAA0020 gene |
| 125 | Hs.74566 | -1 | 0.7433 | 0.1 | 0.0008 | 26 | 0.8369 | 0.025 | 0.00096 | Human mRNA for dihydropyrimidinase related protein-3 |
| 126 | Hs.1298 | -1 | 0.7433 | 0.1 | 0.00079 | 38 | 0.8108 | 0.075 | 0.002 | Human common acute lymphoblastic leukemia antigen (CALLA) mRNA |
| 127 | Hs.48450 | -1 | 0.7427 | 0.1 | 0.00079 | 412 | 0.6495 | 1 | 0.2 | Human mRNA for KIAA0222 gene |
| 128 | Hs.80620 | 1 | 0.7427 | 0.1 | 0.00078 | 1125 | 0.5721 | 1 | 0.65 | Human mRNA for KIAA0277 gene |
| 129 | Hs.211579 | -1 | 0.7427 | 0.1 | 0.00078 | 134 | 0.7342 | 1 | 0.016 | Human MUC18 glycoprotein mRNA |
| 130 | Hs.37682 | -1 | 0.7411 | 0.15 | 0.0012 | 388 | 0.6541 | 1 | 0.18 | Human tazarotene-induced gene 2 (TIG2) mRNA |

FIG. 5I

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 131 | Hs.170198 | 1 | 0.7406 | 0.15 | 0.0011 | 172 | 0.7171 | 1 | 0.03 | Human mRNA for KIAA0009 gene |
| 132 | Hs.155606 | -1 | 0.7406 | 0.15 | 0.0011 | 112 | 0.745 | 1 | 0.01 | Human homeobox protein (PHOX1) mRNA |
| 133 | Hs.250692 | -1 | 0.739 | 0.23 | 0.0017 | 41 | 0.8099 | 0.075 | 0.0018 | Human hepatic leukemia factor (HLF) mRNA |
| 134 | Hs.286 | 1 | 0.7374 | 0.27 | 0.0021 | 82 | 0.7694 | 0.33 | 0.004 | Human mRNA for ribosomal protein |
| 135 | Hs.0 | 1 | 0.7368 | 0.27 | 0.002 | 323 | 0.6667 | 1 | 0.14 | Human estrogen receptor-related protein (hERRa1) mRNA |
| 136 | Hs.227751 | -1 | 0.7363 | 0.27 | 0.002 | 593 | 0.6198 | 1 | 0.36 | Human 14 kd lectin mRNA |
| 137 | Hs.80552 | -1 | 0.7363 | 0.27 | 0.002 | 541 | 0.627 | 1 | 0.32 | |
| 138 | Hs.94581 | -1 | 0.7363 | 0.27 | 0.002 | 152 | 0.7279 | 1 | 0.019 | Homo sapiens hydroxysteroid sulfotransferase SULT2B1a (HSST2) mRNA |
| 139 | Hs.75260 | -1 | 0.7358 | 0.27 | 0.002 | 74 | 0.7757 | 0.25 | 0.0034 | H.sapiens mitogen inducible gene mig-2 |
| 140 | Hs.8136 | -1 | 0.7352 | 0.33 | 0.0023 | 1729 | 0.5351 | 1 | 0.85 | Human endothelial PAS domain protein 1 (EPAS1) mRNA |
| 141 | Hs.923 | 1 | 0.7347 | 0.33 | 0.0023 | 219 | 0.6937 | 1 | 0.067 | Human mitochondrial specific single stranded DNA binding protein mRNA |
| 142 | Hs.1594 | 1 | 0.7347 | 0.33 | 0.0023 | 239 | 0.6856 | 1 | 0.086 | Human centromere protein-A (CENP-A) mRNA |
| 143 | Hs.84728 | -1 | 0.7347 | 0.33 | 0.0023 | 379 | 0.655 | 1 | 0.18 | Human mRNA for GC-Box binding protein BTEB2 |
| 144 | Hs.505 | -1 | 0.7336 | 0.33 | 0.0023 | 139 | 0.7324 | 1 | 0.017 | Human ISL-1 (Islet-1) mRNA |
| 145 | Hs.93199 | -1 | 0.7325 | 0.33 | 0.0022 | 2271 | 0.5036 | 1 | 0.99 | Human 2 |
| 146 | Hs.76780 | -1 | 0.732 | 0.38 | 0.0026 | 111 | 0.7459 | 1 | 0.01 | Human protein phosphatase-1 inhibitor mRNA |
| 147 | Hs.77695 | 1 | 0.7315 | 0.38 | 0.0026 | 509 | 0.6306 | 1 | 0.3 | Human mRNA for KIAA0008 gene |
| 148 | Hs.0 | -1 | 0.7315 | 0.38 | 0.0025 | 33 | 0.8171 | 0.075 | 0.0023 | Human CX3C chemokine precursor |
| 149 | Hs.71622 | -1 | 0.7309 | 0.38 | 0.0025 | 108 | 0.7468 | 1 | 0.01 | Human SWI/SNF complex 60 KDa subunit (BAF60c) mRNA |
| 150 | Hs.93002 | 1 | 0.7309 | 0.38 | 0.0025 | 361 | 0.6595 | 1 | 0.16 | Human cyclin-selective ubiquitin carrier protein mRNA |
| 151 | Hs.33084 | -1 | 0.7304 | 0.38 | 0.0025 | 22 | 0.8432 | 0.025 | 0.0011 | Human glucose transport-like 5 (GLUT5) mRNA |
| 152 | Hs.288642 | -1 | 0.7299 | 0.4 | 0.0026 | 919 | 0.5874 | 1 | 0.56 | Human GTP-binding protein superfamily |
| 153 | Hs.82163 | -1 | 0.7293 | 0.42 | 0.0028 | 174 | 0.7162 | 1 | 0.031 | Human monoamine oxidase B (MAOB) mRNA |
| 154 | Hs.2133 | -1 | 0.7293 | 0.42 | 0.0028 | 1371 | 0.5559 | 1 | 0.75 | Human retinal pigment epithelium-specific 61 kDa protein (RPE65) mRNA |
| 155 | Hs.50130 | -1 | 0.7293 | 0.42 | 0.0027 | 93 | 0.7568 | 0.47 | 0.0051 | Human NECDIN related protein mRNA |
| 156 | Hs.159608 | -1 | 0.7293 | 0.42 | 0.0027 | 266 | 0.6784 | 1 | 0.11 | Human microsomal aldehyde dehydrogenase (ALD10) mRNA |

FIG. 5m

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 157 | Hs.9614 | 1 | 0.7288 | 0.45 | 0.0029 | 181 | 0.7108 | 1 | 0.039 | Human nucleophosmin mRNA |
| 158 | Hs.1827 | -1 | 0.7277 | 0.55 | 0.0035 | 293 | 0.6712 | 1 | 0.13 | Human nerve growth factor receptor mRNA |
| 159 | Hs.69360 | 1 | 0.7277 | 0.55 | 0.0035 | 72 | 0.7766 | 0.23 | 0.0031 | Human mitotic centromere-associated kinesin mRNA |
| 160 | Hs.145279 | 1 | 0.7277 | 0.55 | 0.0034 | 666 | 0.6099 | 1 | 0.43 | Human set gene |
| 161 | Hs.51299 | 1 | 0.7272 | 0.6 | 0.0037 | 92 | 0.7568 | 0.47 | 0.0052 | Human nuclear-encoded mitochondrial NADH-ubiquinone reductase 24Kd 162 Hs.78888 -1 0.7261 0.67 0.0042 |
| 163 | Hs.62041 | -1 | 0.7261 | 0.67 | 0.0041 | 445 | 0.6414 | 1 | 0.24 | Human nidogen mRNA |
| 164 | Hs.89463 | -1 | 0.7261 | 0.67 | 0.0041 | 729 | 0.6036 | 1 | 0.47 | Human calcium activated potassium channel (hslo) mRNA |
| 165 | Hs.89463 | -1 | 0.7261 | 0.67 | 0.0041 | 2231 | 0.5063 | 1 | 0.97 | Human large-conductance calcium-activated potassium channel (hSl |
| 166 | Hs.1560 | 1 | 0.724 | 0.83 | 0.005 | 974 | 0.5829 | 1 | 0.59 | Human mRNA for KIAA0086 gene |
| 167 | Hs.108332 | 1 | 0.7234 | 0.85 | 0.0051 | 1725 | 0.5351 | 1 | 0.85 | Human E2 ubiquitin conjugating enzyme UbcH5B (UBCH5B) mRNA |
| 168 | Hs.181028 | 1 | 0.7229 | 0.85 | 0.0051 | 198 | 0.7036 | 1 | 0.047 | Homo sapiens nuclear-encoded mitochondrial cytochrome c oxidase Va subunit 169 Hs.290 -1 |
| 170 | Hs.283952 | 1 | 0.7223 | 0.85 | 0.005 | 1654 | 0.5387 | 1 | 0.84 | Homo sapiens Xq28 genomic DNA in the region of the ALD locus |
| 173 | Hs.75981 | -1 | 0.7213 | 0.9 | 0.0052 | 1252 | 0.5631 | 1 | 0.71 | Human tRNA-guanine transglycosylase mRNA |
| 174 | Hs.75794 | -1 | 0.7197 | 0.95 | 0.0055 | 528 | 0.6288 | 1 | 0.31 | Human lysophosphatidic acid receptor homolog mRNA |
| 175 | Hs.220689 | 1 | 0.7191 | 1 | 0.0057 | 1333 | 0.5586 | 1 | 0.73 | Human GAP SH3 binding protein mRNA |
| 176 | Hs.83656 | 1 | 0.7191 | 1 | 0.0057 | 109 | 0.7459 | 1 | 0.01 | Human GDP-dissociation inhibitor protein (Ly-GDI) mRNA |
| 177 | Hs.3235 | -1 | 0.7186 | 1 | 0.0058 | 2128 | 0.5117 | 1 | 0.95 | Human mRNA for cytokeratin 4 C-terminal region |
| 178 | Hs.183109 | 1 | 0.718 | 1 | 0.006 | 212 | 0.6982 | 1 | 0.055 | Human monoamine oxidase A (MAOA) mRNA |
| 179 | Hs.118625 | -1 | 0.718 | 1 | 0.006 | 290 | 0.6721 | 1 | 0.13 | Human hexokinase 1 (HK1) mRNA |
| 180 | Hs.2022 | 1 | 0.7175 | 1 | 0.0064 | 1222 | 0.5649 | 1 | 0.7 | Homo sapiens transglutaminase E3 (TGASE3) mRNA |
| 181 | Hs.1239 | -1 | 0.7175 | 1 | 0.0064 | 135 | 0.7333 | 1 | 0.017 | Human aminopeptidase N/CD13 mRNA encoding aminopeptidase N |
| 182 | Hs.3446 | 1 | 0.7175 | 1 | 0.0063 | 2103 | 0.5135 | 1 | 0.94 | Homo sapiens MAP kinase kinase mRNA |
| 183 | Hs.259802 | -1 | 0.717 | 1 | 0.0067 | 215 | 0.6973 | 1 | 0.057 | Human trophinin mRNA |
| 184 | Hs.41691 | -1 | 0.717 | 1 | 0.0067 | 1947 | 0.5216 | 1 | 0.92 | Human bZip protein B-ATF mRNA |

FIG. 5n

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 185 | Hs.97496 | 1 | 0.7164 | 1 | 0.0068 | 2245 | 0.5054 | 1 | 0.98 | Homo sapiens GLI-Krupple related protein (YY1) mRNA |
| 186 | Hs.82109 | -1 | 0.7164 | 1 | 0.0067 | 131 | 0.7351 | 1 | 0.015 | H.sapiens syndecan-1 gene (exons 2-5) |
| 187 | Hs.110903 | -1 | 0.7159 | 1 | 0.0068 | 946 | 0.5847 | 1 | 0.58 | Homo sapiens transmembrane protein mRNA |
| 188 | Hs.4437 | 1 | 0.7159 | 1 | 0.0068 | 66 | 0.7811 | 0.18 | 0.0027 | Human ribosomal protein L28 mRNA |
| 189 | Hs.86724 | 1 | 0.7159 | 1 | 0.0067 | 399 | 0.6514 | 1 | 0.19 | Human GTP cyclohydrolase I mRNA |
| 190 | Hs.277704 | 1 | 0.7159 | 1 | 0.0067 | 233 | 0.6892 | 1 | 0.076 | Human 150 kDa oxygen-regulated protein ORP150 mRNA |
| 191 | Hs.79295 | 1 | 0.7154 | 1 | 0.0071 | 1185 | 0.5685 | 1 | 0.67 | Human G-rich sequence factor-1 (GRSF-1) mRNA |
| 192 | Hs.283006 | 1 | 0.7148 | 1 | 0.0074 | 222 | 0.6928 | 1 | 0.068 | Homo sapiens phospholipase C beta 4 (PLCB4) mRNA |
| 193 | Hs.8265 | 1 | 0.7148 | 1 | 0.0074 | 1432 | 0.5514 | 1 | 0.78 | Human transglutaminase (TGase) mRNA |
| 194 | Hs.36508 | -1 | 0.7148 | 1 | 0.0073 | 351 | 0.6613 | 1 | 0.16 | Human beige protein homolog (chs) mRNA |
| 195 | Hs.0 | 1 | 0.7143 | 1 | 0.0073 | 59 | 0.7892 | 0.15 | 0.0025 | M17390 Human erg protein (ets-related gene) mRNA |
| 196 | Hs.211579 | -1 | 0.7137 | 1 | 0.0074 | 1966 | 0.5207 | 1 | 0.92 | Human isolate JuSo MUC18 glycoprotein mRNA (3' variant) |
| 197 | Hs.211579 | -1 | 0.7137 | 1 | 0.0074 | 419 | 0.6486 | 1 | 0.2 | Human isolate JuSo MUC18 glycoprotein mRNA (3' variant) |
| 198 | Hs.158282 | -1 | 0.7132 | 1 | 0.0074 | 435 | 0.6432 | 1 | 0.23 | Human mRNA for KIAA0040 gene |
| 199 | Hs.78894 | 1 | 0.7127 | 1 | 0.0074 | 76 | 0.773 | 0.27 | 0.0036 | Human mRNA for KIAA0161 gene |
| 200 | Hs.80617 | 1 | 0.7127 | 1 | 0.0074 | 347 | 0.6622 | 1 | 0.15 | Human ribosomal protein S16 mRNA |

FIG. 5o

| Rk | Unigene ID | Over Expr | Scor | Rk0 | Score0 | Rk1 | Score1 | Description |
|---|---|---|---|---|---|---|---|---|
| 1 | Hs.195850 | -1 | 0.8811 | 7 | 0.8811 | 2 | 0.8813 | Human keratin type II (58 kD) mRNA |
| 2 | Hs.171731 | -1 | 0.8754 | 1 | 0.9495 | 3 | 0.8754 | Human RACH1 (RACH1) mRNA |
| 3 | Hs.65029 | -1 | 0.8647 | 8 | 0.8802 | 5 | 0.8647 | Human gas1 gene |
| 4 | Hs.771 | -1 | 0.8532 | 15 | 0.8532 | 1 | 0.8953 | Human liver glycogen phosphorylase mRNA |
| 5 | Hs.79217 | 1 | 0.8532 | 16 | 0.8532 | 7 | 0.855 | Human pyrroline 5-carboxylate reductase mRNA |
| 6 | Hs.198760 | -1 | 0.8495 | 19 | 0.8495 | 4 | 0.869 | H.sapiens NF-H gene |
| 7 | Hs.174151 | -1 | 0.8448 | 4 | 0.8892 | 10 | 0.8448 | Human aldehyde oxidase (hAOX) mRNA |
| 8 | Hs.44 | -1 | 0.841 | 12 | 0.8685 | 14 | 0.841 | Human nerve growth factor (HBNF-1) mRNA |
| 9 | Hs.3128 | 1 | 0.841 | 2 | 0.9081 | 15 | 0.841 | Human RNA polymerase II subunit (hsRPB8) mRNA |
| 10 | Hs.34853 | -1 | 0.8314 | 5 | 0.8892 | 20 | 0.8314 | Human Id-related helix-loop-helix protein Id4 mRNA |
| 11 | Hs.113 | -1 | 0.8217 | 13 | 0.8658 | 24 | 0.8217 | Human cytosolic epoxide hydrolase mRNA |
| 12 | Hs.1813 | -1 | 0.8201 | 31 | 0.827 | 25 | 0.8201 | Homo sapiens synaptic vesicle amine transporter (SVAT) mRNA |
| 13 | Hs.2006 | -1 | 0.8099 | 40 | 0.8099 | 23 | 0.8255 | Human glutathione transferase M3 (GSTM3) mRNA |
| 14 | Hs.76224 | -1 | 0.8083 | 28 | 0.836 | 39 | 0.8083 | Human extracellular protein (S1-5) mRNA |
| 15 | Hs.27311 | 1 | 0.8056 | 11 | 0.8694 | 42 | 0.8056 | Human transcription factor SIM2 long form mRNA |
| 16 | Hs.77546 | -1 | 0.8008 | 14 | 0.8649 | 46 | 0.8008 | Human mRNA for KIAA0172 gene |
| 17 | Hs.23838 | 1 | 0.7982 | 50 | 0.7982 | 22 | 0.8287 | Human neuronal DHP-sensitive |
| 18 | Hs.10755 | -1 | 0.7955 | 53 | 0.7955 | 17 | 0.8373 | Human mRNA for dihydropyrimidinase |
| 19 | Hs.2785 | -1 | 0.7911 | 24 | 0.8414 | 51 | 0.7911 | H.sapiens gene for cytokeratin 17 |
| 20 | Hs.86978 | 1 | 0.7748 | 75 | 0.7748 | 70 | 0.7777 | H.sapiens mRNA for prolyl oligopeptidase |
| 21 | Hs.2025 | -1 | 0.7744 | 3 | 0.9027 | 73 | 0.7744 | Human transforming growth factor-beta 3 (TGF-beta3) mRNA |
| 22 | Hs.30054 | 1 | 0.7734 | 45 | 0.8054 | 74 | 0.7734 | Human coagulation factor V mRNA |
| 23 | Hs.155591 | -1 | 0.7723 | 52 | 0.7973 | 76 | 0.7723 | Human forkhead protein FREAC-1 mRNA |
| 24 | Hs.237356 | -1 | 0.7712 | 81 | 0.7712 | 61 | 0.7846 | Human intercrine-alpha (hIRH) mRNA |
| 25 | Hs.211933 | -1 | 0.7707 | 70 | 0.7784 | 80 | 0.7707 | Human (clones HT-[125 |
| 26 | Hs.75746 | 1 | 0.7691 | 78 | 0.7721 | 81 | 0.7691 | Human aldehyde dehydrogenase 6 mRNA |
| 27 | Hs.155597 | -1 | 0.7676 | 85 | 0.7676 | 78 | 0.7712 | Human adipsin/complement factor D mRNA |
| 28 | Hs.75111 | -1 | 0.7669 | 21 | 0.8432 | 85 | 0.7669 | Human cancellous bone osteoblast mRNA for serin protease with IGF-binding motif |

FIG. 6a

| Rk | Unigene ID | Over Expr | Scor | Rk0 | Score0 | Rk1 | Score1 | Description |
|---|---|---|---|---|---|---|---|---|
| 29 | Hs.75137 | -1 | 0.7664 | 37 | 0.8108 | 86 | 0.7664 | Human mRNA for KIAA0193 gene |
| 30 | Hs.76307 | -1 | 0.7658 | 86 | 0.7658 | 12 | 0.841 | Human mRNA for unknown product |
| 31 | Hs.79059 | -1 | 0.7653 | 44 | 0.8063 | 87 | 0.7653 | Human transforming growth factor-beta type III receptor (TGF-beta) mRNA |
| 32 | Hs.1440 | 1 | 0.7632 | 36 | 0.8108 | 92 | 0.7632 | Human gamma amino butyric acid (GABAA) receptor beta-3 subunit mRNA |
| 33 | Hs.66052 | -1 | 0.7626 | 60 | 0.7883 | 93 | 0.7626 | 1299-1305 |
| 34 | Hs.155585 | -1 | 0.7626 | 6 | 0.8838 | 94 | 0.7626 | Human transmembrane receptor (ror2) mRNA |
| 35 | Hs.153322 | -1 | 0.7589 | 35 | 0.8126 | 98 | 0.7589 | Human mRNA for phospholipase C |
| 36 | Hs.77448 | -1 | 0.7583 | 87 | 0.7658 | 99 | 0.7583 | Human pyrroline-5-carboxylate dehydrogenase (P5CDh) mRNA |
| 37 | Hs.190787 | -1 | 0.7568 | 94 | 0.7568 | 69 | 0.7782 | Human tissue inhibitor of metalloproteinase 4 mRNA |
| 38 | Hs.172851 | -1 | 0.7567 | 48 | 0.8 | 101 | 0.7567 | Human arginase type II mRNA |
| 39 | Hs.85146 | -1 | 0.7562 | 20 | 0.8459 | 103 | 0.7562 | Human erythroblastosis virus oncogene homolog 2 (ets-2) mRNA |
| 40 | Hs.10526 | -1 | 0.7556 | 17 | 0.8532 | 105 | 0.7556 | Human smooth muscle LIM protein (h-SmLIM) mRNA |
| 41 | Hs.81412 | -1 | 0.7551 | 61 | 0.7865 | 106 | 0.7551 | Human mRNA for KIAA0188 gene |
| 42 | Hs.180107 | 1 | 0.7541 | 96 | 0.7541 | 44 | 0.8024 | Human mRNA for DNA polymerase beta |
| 43 | Hs.245188 | -1 | 0.7519 | 56 | 0.7937 | 113 | 0.7519 | Human tissue inhibitor of metalloproteinases-3 mRNA |
| 44 | Hs.56145 | 1 | 0.7508 | 55 | 0.7946 | 114 | 0.7508 | Human mRNA for NB thymosin beta |
| 45 | Hs.620 | -1 | 0.7497 | 18 | 0.8523 | 115 | 0.7497 | Human bullous pemphigoid antigen (BPAG1) mRNA |
| 46 | Hs.83450 | -1 | 0.7495 | 101 | 0.7495 | 67 | 0.7803 | Homo sapiens laminin-related protein (LamA3) mRNA |
| 47 | Hs.687 | -1 | 0.7495 | 102 | 0.7495 | 26 | 0.8195 | Human lung cytochrome P450 (IV subfamily) BI protein |
| 48 | Hs.75151 | 1 | 0.7486 | 104 | 0.7486 | 8 | 0.8545 | Human GTPase activating protein (rap1GAP) mRNA |
| 49 | Hs.283749 | -1 | 0.7468 | 106 | 0.7468 | 110 | 0.7524 | Human mRNA for RNase 4 |
| 50 | Hs.74566 | -1 | 0.7433 | 26 | 0.8369 | 125 | 0.7433 | Human mRNA for dihydropyrimidinase related protein-3 |
| 51 | Hs.1298 | -1 | 0.7433 | 38 | 0.8108 | 126 | 0.7433 | Human common acute lymphoblastic leukemia antigen (CALLA) mRNA |
| 52 | Hs.323032 | 1 | 0.7423 | 117 | 0.7423 | 32 | 0.8163 | Human SIL mRNA |
| 53 | Hs.155606 | -1 | 0.7406 | 112 | 0.745 | 132 | 0.7406 | Human homeobox protein (PHOX1) mRNA |
| 54 | Hs.250692 | -1 | 0.739 | 41 | 0.8099 | 133 | 0.739 | Human hepatic leukemia factor (HLF) mRNA |
| 55 | Hs.81892 | 1 | 0.7387 | 123 | 0.7387 | 27 | 0.819 | Human mRNA for KIAA0101 gene |
| 56 | Hs.286 | 1 | 0.7374 | 82 | 0.7694 | 134 | 0.7374 | Human mRNA for ribosomal protein |

FIG. 6b

| Rk | Unigene ID | Over Expr | Scor | Rk0 | Score0 | Rk1 | Score1 | Description |
|---|---|---|---|---|---|---|---|---|
| 57 | Hs.75260 | -1 | 0.7358 | 74 | 0.7757 | 139 | 0.7358 | H.sapiens mitogen inducible gene mig-2 |
| 58 | Hs.301613 | 1 | 0.7351 | 130 | 0.7351 | 104 | 0.7562 | Human JTV-1 (JTV-1) mRNA |
| 59 | Hs.172471 | -1 | 0.7342 | 133 | 0.7342 | 55 | 0.7889 | Homo sapiens (clone hKvBeta3) K+ channel beta subunit mRNA |
| 60 | Hs.211579 | -1 | 0.7342 | 134 | 0.7342 | 129 | 0.7427 | Human MUC18 glycoprotein mRNA |
| 61 | Hs.75741 | -1 | 0.7333 | 136 | 0.7333 | 50 | 0.7932 | Human clone HP-DAO1 diamine oxidase |
| 62 | Hs.505 | -1 | 0.7324 | 139 | 0.7324 | 144 | 0.7336 | Human ISL-1 (Islet-1) mRNA |
| 63 | Hs.76780 | -1 | 0.732 | 111 | 0.7459 | 146 | 0.732 | Human protein phosphatase-1 inhibitor mRNA |
| 64 | Hs.1989 | -1 | 0.7315 | 141 | 0.7315 | 107 | 0.7551 | Human steroid 5-alpha-reductase 2 (SRD5A2) mRNA |
| 65 | Hs.0 | -1 | 0.7315 | 33 | 0.8171 | 148 | 0.7315 | Human CX3C chemokine precursor |
| 66 | Hs.71622 | -1 | 0.7309 | 108 | 0.7468 | 149 | 0.7309 | Human SWI/SNF complex 60 KDa subunit (BAF60c) mRNA |
| 67 | Hs.33084 | -1 | 0.7304 | 22 | 0.8432 | 151 | 0.7304 | Human glucose transport-like 5 (GLUT5) mRNA |
| 68 | Hs.50130 | -1 | 0.7293 | 93 | 0.7568 | 155 | 0.7293 | Human NECDIN related protein mRNA |
| 69 | Hs.159525 | 1 | 0.7279 | 151 | 0.7279 | 54 | 0.7895 | Human cell growth regulator CGR11 mRNA |
| 70 | Hs.94581 | -1 | 0.7279 | 152 | 0.7279 | 138 | 0.7363 | Homo sapiens hydroxysteroid sulfotransferase SULT2B1a (HSST2) mRNA |
| 71 | Hs.69360 | 1 | 0.7277 | 72 | 0.7766 | 159 | 0.7277 | Human mitotic centromere-associated kinesin mRNA |
| 72 | Hs.51299 | 1 | 0.7272 | 92 | 0.7568 | 161 | 0.7272 | Human nuclear-encoded mitochondrial NADH-ubiquinone reductase 24Kd subunit mRNA |
| 73 | Hs.56045 | -1 | 0.7261 | 156 | 0.7261 | 36 | 0.8099 | Human mRNA for stac |
| 74 | Hs.2388 | 1 | 0.7225 | 160 | 0.7225 | 19 | 0.8362 | Human apolipoprotein F (APOF) mRNA |
| 75 | Hs.92002 | -1 | 0.7198 | 166 | 0.7198 | 45 | 0.8018 | Human transducin alpha-subunit (GNAZ) mRNA |
| 76 | Hs.83656 | 1 | 0.7191 | 109 | 0.7459 | 176 | 0.7191 | Human GDP-dissociation inhibitor protein (Ly-GDI) mRNA |
| 77 | Hs.1239 | -1 | 0.7175 | 135 | 0.7333 | 181 | 0.7175 | Human aminopeptidase N/CD13 mRNA encoding aminopeptidase N |
| 78 | Hs.170198 | 1 | 0.7171 | 172 | 0.7171 | 131 | 0.7406 | Human mRNA for KIAA0009 gene |
| 79 | Hs.79226 | -1 | 0.7171 | 173 | 0.7171 | 41 | 0.8056 | Human FEZ1 mRNA |
| 80 | Hs.82109 | -1 | 0.7164 | 131 | 0.7351 | 186 | 0.7164 | H.sapiens syndecan-1 gene (exons 2-5) |
| 81 | Hs.82163 | -1 | 0.7162 | 174 | 0.7162 | 153 | 0.7293 | Human monoamine oxidase B (MAOB) mRNA |
| 82 | Hs.4437 | 1 | 0.7159 | 66 | 0.7811 | 188 | 0.7159 | Human ribosomal protein L28 mRNA |
| 83 | Hs.75692 | 1 | 0.7153 | 176 | 0.7153 | 118 | 0.7476 | Human asparagine synthetase mRNA |
| 84 | Hs.0 | 1 | 0.7143 | 59 | 0.7892 | 195 | 0.7143 | M17390 Human erg protein (ets-related gene) mRNA |
| 85 | Hs.78894 | 1 | 0.7127 | 76 | 0.773 | 199 | 0.7127 | Human mRNA for KIAA0161 gene |
| 86 | Hs.9614 | 1 | 0.7108 | 181 | 0.7108 | 157 | 0.7288 | Human nucleophosmin mRNA |

FIG. 6c

| Rk | Unigene ID | Over Expr | Scor | Rk0 | Score0 | Rk1 | Score1 | Description |
|---|---|---|---|---|---|---|---|---|
| 87 | Hs.75244 | -1 | 0.71 | 89 | 0.7586 | 209 | 0.71 | Human mRNA for KIAA0271 gene |
| 88 | Hs.151531 | -1 | 0.7054 | 193 | 0.7054 | 210 | 0.71 | Human calcineurin A2 mRNA |
| 89 | Hs.89591 | -1 | 0.7052 | 42 | 0.809 | 219 | 0.7052 | Homo sapiens Kallmann syndrome (KAL) mRNA |
| 90 | Hs.102267 | 1 | 0.7045 | 194 | 0.7045 | 91 | 0.7637 | Human lysyl oxidase (LOX) gene |
| 91 | Hs.181028 | 1 | 0.7036 | 198 | 0.7036 | 168 | 0.7229 | Homo sapiens nuclear-encoded mitochondrial cytochrome c oxidase Va subunit mRNA |
| 92 | Hs.226213 | -1 | 0.7036 | 202 | 0.7036 | 97 | 0.7599 | Human lanosterol 14-demethylase cytochrome P450 (CYP51) mRNA |
| 93 | Hs.254105 | 1 | 0.7035 | 132 | 0.7351 | 224 | 0.7035 | Human alpha enolase mRNA |
| 94 | Hs.75655 | 1 | 0.703 | 157 | 0.7243 | 225 | 0.703 | Human thyroid hormone binding protein (p55) mRNA |
| 95 | Hs.170328 | -1 | 0.703 | 91 | 0.7577 | 227 | 0.703 | Human moesin mRNA |
| 96 | Hs.78909 | -1 | 0.7009 | 23 | 0.8423 | 234 | 0.7009 | Human Tis11d gene |
| 97 | Hs.83383 | 1 | 0.7009 | 54 | 0.7955 | 235 | 0.7009 | Human antioxidant enzyme AOE37-2 mRNA |
| 98 | Hs.76244 | 1 | 0.7009 | 49 | 0.8 | 236 | 0.7009 | Human spermidine synthase mRNA |
| 99 | Hs.75618 | 1 | 0.6998 | 153 | 0.727 | 237 | 0.6998 | Homo sapiens rab11a GTPase mRNA |
| 100 | Hs.75893 | 1 | 0.6991 | 210 | 0.6991 | 109 | 0.7535 | Human ankyrin G (ANK-3) mRNA |
| 101 | Hs.155560 | 1 | 0.6987 | 83 | 0.7676 | 238 | 0.6987 | Homo sapiens integral membrane protein |
| 102 | Hs.56937 | 1 | 0.6987 | 69 | 0.7793 | 239 | 0.6987 | Human SNC19 mRNA sequence |
| 103 | Hs.183109 | 1 | 0.6982 | 212 | 0.6982 | 178 | 0.718 | Human monoamine oxidase A (MAOA) mRNA |
| 104 | Hs.288215 | -1 | 0.6976 | 175 | 0.7153 | 241 | 0.6976 | Human sialyltransferase SThM (sthm) mRNA |
| 105 | Hs.259802 | -1 | 0.6973 | 215 | 0.6973 | 183 | 0.717 | Human trophinin mRNA |
| 106 | Hs.923 | 1 | 0.6937 | 219 | 0.6937 | 141 | 0.7347 | Human mitochondrial specific single stranded DNA binding protein mRNA |
| 107 | Hs.78913 | -1 | 0.6933 | 129 | 0.7351 | 252 | 0.6933 | Human G protein-coupled receptor V28 mRNA |
| 108 | Hs.283006 | 1 | 0.6928 | 222 | 0.6928 | 192 | 0.7148 | Homo sapiens phospholipase C beta 4 (PLCB4) mRNA |
| 109 | Hs.9615 | -1 | 0.6919 | 224 | 0.6919 | 9 | 0.8459 | Human 20-kDa myosin light chain (MLC-2) mRNA |
| 110 | Hs.100293 | 1 | 0.691 | 229 | 0.691 | 95 | 0.761 | Human O-linked GlcNAc transferase mRNA |
| 111 | Hs.93841 | -1 | 0.6901 | 231 | 0.6901 | 66 | 0.7814 | Human MaxiK potassium channel beta subunit mRNA |
| 112 | Hs.57783 | 1 | 0.6901 | 232 | 0.6901 | 52 | 0.79 | Human eukaryotic translation initiation factor (eIF3) mRNA |
| 113 | Hs.80712 | -1 | 0.6896 | 158 | 0.7243 | 260 | 0.6896 | Human mRNA for KIAA0202 gene |
| 114 | Hs.277704 | 1 | 0.6892 | 233 | 0.6892 | 190 | 0.7159 | Human 150 kDa oxygen-regulated protein ORP150 mRNA |
| 115 | Hs.85302 | -1 | 0.689 | 10 | 0.873 | 268 | 0.689 | Human dsRNA adenosine deaminase DRADA2b (DRADA2b) mRNA |

FIG. 6d

| | | | | | | | | |
|---|---|---|---|---|---|---|---|---|
| 116 | Hs.1594 | 1 | 0.6856 | 239 | 0.6856 | 142 | 0.7347 | Human centromere protein-A (CENP-A) mRNA |
| 117 | Hs.6196 | -1 | 0.6847 | 241 | 0.6847 | 242 | 0.6976 | Human integrin-linked kinase (ILK) mRNA |
| 118 | Hs.21223 | -1 | 0.6847 | 243 | 0.6847 | 16 | 0.8378 | Human mRNA for calponin |
| 119 | Hs.119301 | -1 | 0.6838 | 246 | 0.6838 | 43 | 0.8029 | Homo sapiens cellular ligand of annexin II (p11) mRNA |
| 120 | Hs.198241 | -1 | 0.6838 | 247 | 0.6838 | 88 | 0.7653 | Human placenta copper monamine oxidase mRNA |
| 121 | Hs.171862 | -1 | 0.6831 | 95 | 0.755 | 280 | 0.6831 | Human guanylate binding protein isoform II (GBP-2) mRNA |
| 122 | Hs.311 | 1 | 0.6829 | 249 | 0.6829 | 47 | 0.7965 | Homo sapiens glutamine PRPP amidotransferase (GPAT) mRNA complete cds |
| 123 | Hs.1869 | -1 | 0.6821 | 27 | 0.836 | 284 | 0.6821 | Human phosphoglucomutase 1 (PGM1) mRNA |
| 124 | Hs.184339 | 1 | 0.682 | 250 | 0.682 | 37 | 0.8093 | Human mRNA for KIAA0175 gene |
| 125 | Hs.194765 | 1 | 0.682 | 253 | 0.682 | 117 | 0.7476 | H.sapiens GENX-5624 mRNA |
| 126 | Hs.79404 | -1 | 0.682 | 256 | 0.682 | 212 | 0.7089 | Homo sapiens neuron-specific protein gene |
| 127 | Hs.23111 | 1 | 0.6799 | 159 | 0.7234 | 293 | 0.6799 | Human putative tRNA synthetase-like protein mRNA |
| 128 | Hs.149923 | 1 | 0.6794 | 127 | 0.736 | 294 | 0.6794 | Human X box binding protein-1 (XBP-1) mRNA |
| 129 | Hs.188 | -1 | 0.6794 | 88 | 0.764 | 295 | 0.6794 | Human phosphodiesterase mRNA |
| 130 | Hs.85050 | -1 | 0.6794 | 150 | 0.7279 | 296 | 0.6794 | Human phospholamban mRNA |
| 131 | Hs.2471 | 1 | 0.6793 | 263 | 0.6793 | 124 | 0.7438 | Human mRNA for KIAA0020 gene |
| 132 | Hs.334 | -1 | 0.6788 | 188 | 0.7081 | 298 | 0.6788 | Human guanine nucleotide regulatory protein (tim1) mRNA |
| 133 | Hs.159608 | -1 | 0.6784 | 266 | 0.6784 | 156 | 0.7293 | Human microsomal aldehyde dehydrogenase (ALD10) mRNA |
| 134 | Hs.183752 | -1 | 0.6767 | 270 | 0.6775 | 310 | 0.6767 | Human prostatic secretory protein 57 mRNA |
| 135 | Hs.62661 | -1 | 0.6751 | 105 | 0.7477 | 319 | 0.6751 | Human guanylate binding protein isoform I (GBP-2) mRNA |
| 136 | Hs.172153 | -1 | 0.6748 | 274 | 0.6748 | 68 | 0.7798 | Human plasma (extracellular) mRNA for glutathione peroxidase |
| 137 | Hs.184298 | 1 | 0.6748 | 277 | 0.6748 | 248 | 0.6939 | |
| 138 | Hs.106880 | 1 | 0.6745 | 168 | 0.7189 | 321 | 0.6745 | Homo sapiens bystin mRNA |
| 139 | Hs.76688 | -1 | 0.6735 | 29 | 0.8342 | 325 | 0.6735 | Human carboxylesterase mRNA |
| 140 | Hs.155545 | -1 | 0.6735 | 225 | 0.6919 | 326 | 0.6735 | Human p37NB mRNA |
| 141 | Hs.155418 | -1 | 0.6729 | 34 | 0.8153 | 329 | 0.6729 | Human cancellous bone osteoblast mRNA for GS3955 |
| 142 | Hs.0 | -1 | 0.6724 | 271 | 0.6766 | 333 | 0.6724 | Homo sapiens ubiquitin-activating enzyme E1 related protein mRNA |
| 143 | Hs.84113 | 1 | 0.6721 | 288 | 0.6721 | 38 | 0.8083 | Homo sapiens protein tyrosine phosphatase (CIP2)mRNA |
| 144 | Hs.118625 | -1 | 0.6721 | 290 | 0.6721 | 179 | 0.718 | Human hexokinase 1 (HK1) mRNA |

FIG. 6e

| | | | | | | | | |
|---|---|---|---|---|---|---|---|---|
| 145 | Hs.81875 | -1 | 0.6713 | 84 | 0.7676 | 341 | 0.6713 | Human mRNA for KIAA0207 gene |
| 146 | Hs.1827 | -1 | 0.6712 | 293 | 0.6712 | 158 | 0.7277 | Human nerve growth factor receptor mRNA |
| 147 | Hs.239926 | -1 | 0.6712 | 297 | 0.6712 | 18 | 0.8373 | Human methyl sterol oxidase (ERG25) mRNA |
| 148 | Hs.366 | 1 | 0.6703 | 298 | 0.6703 | 256 | 0.6917 | Human mRNA for 6-pyruvoyl-tetrahydropterin synthase |
| 149 | Hs.81343 | 1 | 0.6703 | 302 | 0.6703 | 84 | 0.768 | Human mRNA for pro-alpha 1 (II) collagen 3' end C-term. triple helical |
| 150 | Hs.80986 | 1 | 0.6702 | 73 | 0.7757 | 343 | 0.6702 | |
| 151 | Hs.23311 | -1 | 0.6694 | 304 | 0.6694 | 82 | 0.7685 | Human mRNA for KIAA0367 gene |
| 152 | Hs.78864 | 1 | 0.6692 | 80 | 0.7721 | 351 | 0.6692 | Human IgG low affinity Fc fragment receptor (FcRIIa) mRNA |
| 153 | Hs.22785 | -1 | 0.6681 | 190 | 0.7072 | 357 | 0.6681 | Human GABA-A receptor epsilon subunit mRNA |
| 154 | Hs.249495 | 1 | 0.6681 | 114 | 0.7432 | 358 | 0.6681 | H.sapiens mRNA for hnRNPcore protein A1. |
| 155 | Hs.114346 | -1 | 0.6676 | 313 | 0.6676 | 90 | 0.7648 | Human cytochrome c oxidase subunit VIIa (COX7A) muscle isoform mRNA |
| 156 | Hs.78991 | -1 | 0.6676 | 314 | 0.6676 | 205 | 0.7105 | Human GS1 (protein of unknown function) mRNA |
| 157 | Hs.173724 | -1 | 0.6676 | 315 | 0.6676 | 108 | 0.7546 | Human creatine kinase-B mRNA |
| 158 | Hs.19368 | -1 | 0.6676 | 170 | 0.7189 | 363 | 0.6676 | Human matrilin-2 precursor mRNA |
| 159 | Hs.156346 | 1 | 0.6667 | 322 | 0.6667 | 53 | 0.7895 | Human DNA topoisomerase II (top2) mRNA |
| 160 | Hs.0 | 1 | 0.6667 | 323 | 0.6667 | 135 | 0.7368 | Human estrogen receptor-related protein (hERRa1) mRNA |
| 161 | Hs.89643 | 1 | 0.6667 | 325 | 0.6667 | 337 | 0.6724 | Homo sapiens transketolase (tk) mRNA |
| 162 | Hs.183487 | 1 | 0.6649 | 331 | 0.6649 | 269 | 0.689 | Human HEM45 mRNA |
| 163 | Hs.182825 | 1 | 0.6638 | 126 | 0.7387 | 379 | 0.6638 | Human ribosomal protein L35 mRNA |
| 164 | Hs.34789 | 1 | 0.6631 | 338 | 0.6631 | 96 | 0.7599 | Human mRNA for KIAA0115 gene |
| 165 | Hs.79276 | -1 | 0.6631 | 339 | 0.6631 | 359 | 0.6676 | Human mRNA for KIAA0232 gene |
| 166 | Hs.171921 | -1 | 0.6627 | 337 | 0.6631 | 380 | 0.6627 | Human mRNA for semaphorin E |
| 167 | Hs.77311 | -1 | 0.6622 | 107 | 0.7468 | 384 | 0.6622 | Human mRNA for tob family |
| 168 | Hs.80617 | 1 | 0.6622 | 347 | 0.6622 | 200 | 0.7127 | Human ribosomal protein S16 mRNA |
| 169 | Hs.101850 | -1 | 0.6617 | 307 | 0.6694 | 386 | 0.6617 | Human cellular retinol-binding protein mRNA |
| 170 | Hs.153863 | -1 | 0.6617 | 242 | 0.6847 | 387 | 0.6617 | Human chromosome 15 Mad homolog Smad6 mRNA |
| 171 | Hs.74598 | 1 | 0.6613 | 349 | 0.6613 | 291 | 0.6805 | Human DNA polymerase delta small subunit mRNA |
| 172 | Hs.184270 | 1 | 0.6613 | 350 | 0.6613 | 338 | 0.6719 | Human capping protein alpha subunit isoform 1 mRNA |
| 173 | Hs.36508 | -1 | 0.6613 | 351 | 0.6613 | 194 | 0.7148 | Human beige protein homolog (chs) mRNA |
| 174 | Hs.76927 | 1 | 0.6611 | 182 | 0.7108 | 389 | 0.6611 | Human putative outer mitochondrial membrane 34 kDa translocase hTOM34 mRNA |

FIG. 6f

| | | | | | | | | |
|---|---|---|---|---|---|---|---|---|
| 175 | Hs.76194 | 1 | 0.6606 | 32 | 0.8216 | 391 | 0.6606 | Human ribosomal protein S5 mRNA |
| 176 | Hs.142827 | -1 | 0.6604 | 355 | 0.6604 | 316 | 0.6756 | Human P311 HUM -3.1 mRNA |
| 177 | Hs.88778 | -1 | 0.6595 | 245 | 0.6838 | 396 | 0.6595 | Human carbonyl reductase mRNA |
| 178 | Hs.182979 | 1 | 0.6595 | 276 | 0.6748 | 397 | 0.6595 | Human ribosomal protein L12 mRNA |
| 179 | Hs.93002 | 1 | 0.6595 | 361 | 0.6595 | 150 | 0.7309 | Human cyclin-selective ubiquitin carrier protein mRNA |
| 180 | Hs.182018 | 1 | 0.659 | 252 | 0.682 | 402 | 0.659 | Homo sapiens interleukin-1 receptor-associated kinase (IRAK) mRNA |
| 181 | Hs.83734 | -1 | 0.6586 | 364 | 0.6586 | 315 | 0.6756 | Human syntaxin mRNA |
| 182 | Hs.1119 | 1 | 0.6579 | 275 | 0.6748 | 408 | 0.6579 | Human mRNA for TR3beta |
| 183 | Hs.724 | -1 | 0.6579 | 346 | 0.6622 | 410 | 0.6579 | Human triiodothyronine (ear7) mRNA |
| 184 | Hs.173063 | -1 | 0.6577 | 367 | 0.6577 | 30 | 0.819 | Human transducin-like enhancer protein (TLE2) mRNA |
| 185 | Hs.127376 | -1 | 0.6574 | 318 | 0.6667 | 412 | 0.6574 | Human mRNA for KIAA0266 gene |
| 186 | Hs.274313 | -1 | 0.6574 | 208 | 0.6991 | 415 | 0.6574 | Human insulin-like growth factor binding protein 6 (IGFBP6) mRNA |
| 187 | Hs.50964 | -1 | 0.6563 | 165 | 0.7198 | 421 | 0.6563 | Human mRNA for transmembrane carcinoembryonic antigen BGPa (formerly TM1-CEA) |
| 188 | Hs.418 | 1 | 0.6559 | 376 | 0.6559 | 79 | 0.7712 | Human fibroblast activation protein mRNA |
| 189 | Hs.84728 | -1 | 0.655 | 379 | 0.655 | 143 | 0.7347 | Human mRNA for GC-Box binding protein BTEB2 |
| 190 | Hs.21365 | -1 | 0.6547 | 344 | 0.6622 | 425 | 0.6547 | Human mRNA for nucleosome assembly protein |
| 191 | Hs.307164 | -1 | 0.6547 | 161 | 0.7225 | 428 | 0.6547 | Human 3' |
| 192 | Hs.37682 | -1 | 0.6541 | 388 | 0.6541 | 130 | 0.7411 | Human tazarotene-induced gene 2 (TIG2) mRNA |
| 193 | Hs.290 | -1 | 0.6523 | 393 | 0.6523 | 169 | 0.7223 | Human Ca2+-dependent phospholipase A2 mRNA |
| 194 | Hs.79265 | -1 | 0.6523 | 394 | 0.6523 | 122 | 0.7454 | Human p126 (ST5) mRNA |
| 195 | Hs.278338 | -1 | 0.6515 | 387 | 0.6541 | 441 | 0.6515 | Human LGN protein mRNA |
| 196 | Hs.86724 | 1 | 0.6514 | 399 | 0.6514 | 189 | 0.7159 | Human GTP cyclohydrolase I mRNA |
| 197 | Hs.77899 | -1 | 0.6514 | 402 | 0.6514 | 34 | 0.8147 | Human tropomyosin mRNA |
| 198 | Hs.95140 | -1 | 0.6505 | 404 | 0.6505 | 286 | 0.6815 | Human mRNA for KIAA0189 gene |
| 199 | Hs.171501 | -1 | 0.6505 | 406 | 0.6505 | 373 | 0.6649 | Human putative ubiquitin C-terminal hydrolase (UHX1) mRNA |
| 200 | Hs.77256 | 1 | 0.6505 | 407 | 0.6505 | 21 | 0.8298 | Human enhancer of zeste homolog 2 (EZH2) mRNA |

FIG. 6g

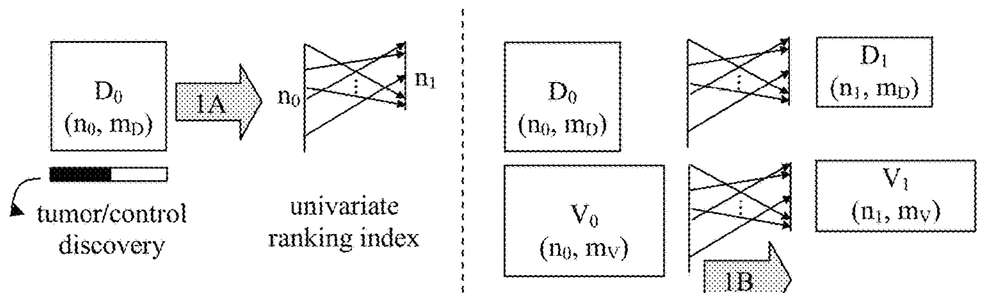
Step 1: Univariate filtering
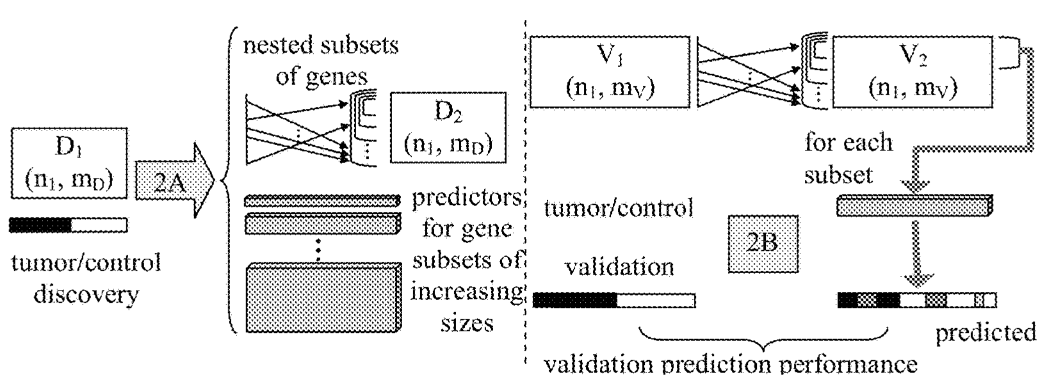
Step 2: Multivariate analysis
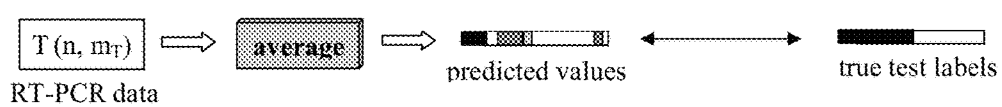
Step 3: RT-PCR assay
FIG. 14

METHODS FOR SCREENING, PREDICTING AND MONITORING PROSTATE CANCER

RELATED APPLICATIONS

This is a continuation of application Ser. No. 12/349,437, filed Jan. 6, 2009, now abandoned which is a continuation-in-part of application Ser. No. 12/327,823, filed Dec. 4, 2008, now abandoned, which is a continuation-in-part of application Ser. No. 12/025,724, filed Feb. 4, 2008, now abandoned, which claims the priority of Provisional Application No. 60/888,070, filed Feb. 2, 2007, and is a continuation-in-part of application Ser. No. 11/274,931, filed Nov. 14, 2005, now abandoned, which claims the priority of each of Provisional Applications No. 60/627,626, filed Nov. 12, 2004, and No. 60/651,340, filed Feb. 9, 2005.

This application is also related to, but does not claim the priority of application Ser. No. 10/057,849, now issued as U.S. Pat. No. 7,117,188, which claims priority to each of Provisional Applications No. 60/263,696, filed Jan. 24, 2001, No. 60/298,757, filed Jun. 15, 2001, and No. 60/275,760, filed Mar. 14, 2001, and application Ser. No. 09/633,410, filed Aug. 7, 2000, now issued as U.S. Pat. No. 6,882,990, which claims priority to each of Provisional Applications No. 60/161,806, filed Oct. 27, 1999, No. 60/168,703, filed Dec. 2, 1999, No. 60/184,596, filed Feb. 24, 2000, No. 60/191,219, filed Mar. 22, 2000, and No. 60/207,026, filed May 25, 2000. Each of the above identified related applications and patents is incorporated herein by reference.

INCORPORATION OF SEQUENCE LISTING

The sequence listing that is contained in the file named "0701C3_GeneSequenceAmend_ST25_corrected.txt", which is 130 KB (as measured in Microsoft Windows®) and was created on Aug. 13, 2015, is incorporated by reference herein.

FIELD OF THE INVENTION

The present invention relates to the use of learning machines to identify relevant patterns in datasets containing large quantities of gene expression data, and more particularly to biomarkers so identified for use in screening, predicting, and monitoring prostate cancer.

BACKGROUND OF THE INVENTION

Knowledge discovery is the most desirable end product of data collection. Recent advancements in database technology have lead to an explosive growth in systems and methods for generating, collecting and storing vast amounts of data. While database technology enables efficient collection and storage of large data sets, the challenge of facilitating human comprehension of the information in this data is growing ever more difficult. With many existing techniques the problem has become unapproachable. In particular, methods are needed for identifying patterns in biological systems as reflected in gene expression data.

A significant percentage of men (20%) in the U.S. are diagnosed with prostate cancer during their lifetime, with nearly 300,000 men diagnosed annually, a rate second only to skin cancer. However, only 3% of those die of the disease. About 70% of all diagnosed prostate cancers occur in men aged 65 years and older. Many prostate cancer patients have undergone aggressive treatments that can have life-altering side effects such as incontinence and sexual dysfunction. It is believed that a substantial portion of the cancers are over-treated. Currently, most early prostate cancer identification is done using prostate-specific antigen (PSA) screening, but few indicators currently distinguish between progressive prostate tumors that may metastasize and escape local treatment and indolent cancers of benign prostate hyperplasia (BPH). Further, some studies have shown that PSA is a poor predictor of cancer, instead tending to predict BPH, which requires no or little treatment.

There is an urgent need for new biomarkers for distinguishing between normal, benign and malignant prostate tissue and for predicting the size and malignancy of prostate cancer. Blood serum biomarkers, or biomarkers found in semen or urine, would be particularly desirable for screening prior to biopsy, however, evaluation of gene expression microarrays from biopsied prostate tissue is also useful.

SUMMARY OF THE INVENTION

Gene expression data are analyzed using learning machines such as support vector machines (SVM) and ridge regression classifiers to rank genes according to their ability to separate prostate cancer from other prostate conditions including BPH and normal. Genes are identified that individually provide sensitivities and selectivities of better than 80% and, when combined in small groups, 90%, for separating prostate cancer from other prostate conditions.

An exemplary embodiment comprises methods and systems for detecting genes involved with prostate cancer and determination of methods and compositions for treatment of prostate cancer. In one embodiment, to improve the statistical significance of the results, supervised learning techniques can analyze data obtained from a number of different sources using different microarrays, such as the Affymetrix U95 and U133A GeneChip® chip sets.

BRIEF DESCRIPTION OF THE DRAWINGS

FIGS. 4*a*-4*d* combined are a table showing the ranking of the top 200 genes for separating prostate tumor from other tissues.

FIGS. 5*a*-5*o* combined are two tables showing the top 200 genes for separating prostate cancer from all other tissues that were identified in each of the 2001 study and the 2003 study.

FIG. 6*a*-6*g* combined are a table showing the top 200 genes for separating G3 and G4 tumor versus others using feature ranking by consensus between the 2001 study and the 2003 study.

FIG. 14 is a flow diagram showing an exemplary data analysis procedure.

DETAILED DESCRIPTION OF THE PREFERRED EMBODIMENTS

Figure 1:
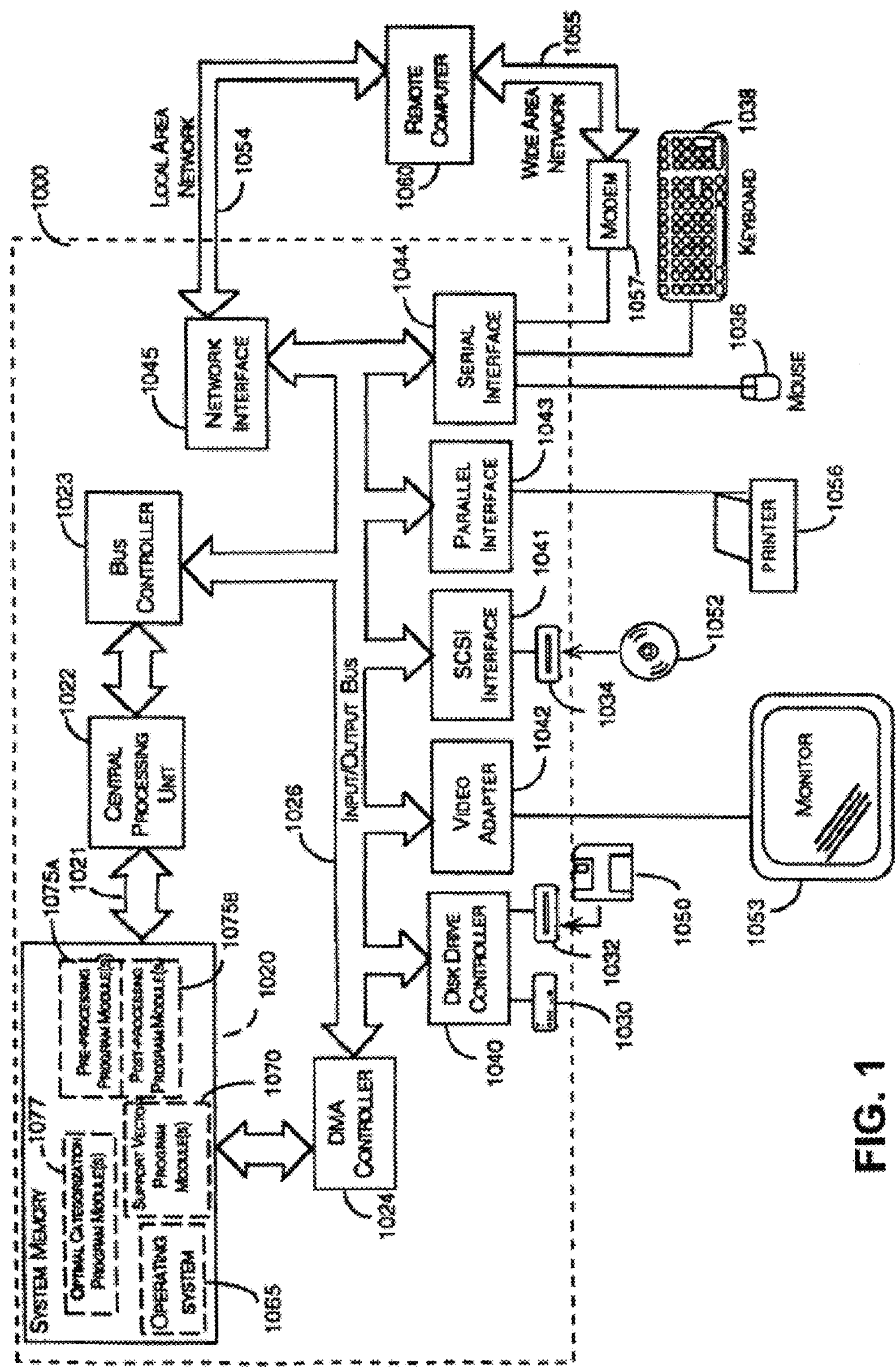
FIG. 1 is a functional block diagram illustrating an exemplary operating environment for an embodiment of the present invention.

The present invention utilizes learning machine techniques, including support vector machines and ridge regression, to discover knowledge from gene expression data obtained by measuring hybridization intensity of gene and gene fragment probes on microarrays. The knowledge so discovered can be used for diagnosing and prognosing changes in biological systems, such as diseases. Preferred embodiments comprise identification of genes that will distinguish between different types of prostate disorders, such as benign prostate hyperplasy and cancer, and normal, and use of such information for decisions on treatment of patients with prostate disorders.

For purposes of the present invention, "gene" refers to the gene expression products corresponding to genes, gene fragments, ESTs and olionucleotides that are included on the Affymetrix microarrays used in the tests described in the examples. Identification of a gene by a GeneBank accession number (GAN), Unigene No. and/or gene name constitutes an express incorporation by reference of the record corresponding to that identifier in the National Center for Biotechnology Information (NCBI) databases, which is publicly accessible and well known to those of skill in the art.

As used herein, "primer" refers to an oligonucleotide that is capable of annealing to a target sequence, thereby creating a double stranded region which can serve as an initiation point for DNA synthesis under suitable conditions. A primer may occur naturally, as in a purified restriction digest, or produced synthetically. The primer is preferably single stranded for maximum efficiency in amplification, but may alternatively be double stranded. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide, whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest.

The problem of selection of a small amount of data from a large data source, such as a gene subset from a microarray, is particularly solved using the methods described herein. Preferred methods described herein use support vector machine (SVM) methods based and recursive feature elimination (RFE), which is described in detail in U.S. Pat. No. 7,117,188, which is incorporated by reference. (It should be noted that "RFE-SVM" and "SVM-RFE" may be used interchangeably throughout the detailed description, however, both refer to the same technique.) In examining gene expression data to find determinative genes, these methods eliminate gene redundancy automatically and yield better and more compact gene subsets.

The data is input into computer system programmed for executing an algorithm using a learning machine for performing a feature selection and/or ranking, preferably a SVM-RFE. The SVM-RFE is run one or more times to generate the best feature selections, which can be displayed in an observation graph or listed in a table or other display format. (Examples of listings of selected features (in this case, genes) are included in many of the tables below.) The SVM may use any algorithm and the data may be preprocessed and postprocessed if needed. Preferably, a server contains a first observation graph that organizes the results of the SVM activity and selection of features.

The information generated by the SVM may be examined by outside experts, computer databases, or other complementary information sources. For example, if the resulting feature selection information is about selected genes, biologists or experts or computer databases may provide complementary information about the selected genes, for example, from medical and scientific literature. Using all the data available, the genes are given objective or subjective grades. Gene interactions may also be recorded.

FIG. 1 and the following discussion are intended to provide a brief and general description of a suitable computing environment for implementing biological data analysis according to the present invention. Although the system shown in FIG. 1 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm. Furthermore, optimal categorization program modules 1077 may comprise computer-executable instructions for optimally categorizing a data set.

The computer 1000 may operate in a networked environment using logical connections to one or more remote computers, such as remote computer 1060. The remote computer 1060 may be a server, a router, a peer to peer device or other common network node, and typically includes many or all of the elements described in connection with the computer 1000. In a networked environment, program modules and data may be stored on the remote computer 1060. Appropriate logical connections include a local area network ("LAN") and a wide area network ("WAN"). In a LAN environment, a network interface, such as an Ethernet adapter card, can be used to connect the computer to the remote computer. In a WAN environment, the computer may use a telecommunications device, such as a modem, to establish a connection. It will be appreciated that the network connections shown are illustrative and other devices of establishing a communications link between the computers may be used.

A preferred selection browser is preferably a graphical user interface that would assist final users in using the generated information. For example, in the examples herein, the selection browser is a gene selection browser that assists the final user is selection of potential drug targets from the genes identified by the SVM RFE. The inputs are the observation graph, which is an output of a statistical analysis package and any complementary knowledge base information, preferably in a graph or ranked form. For example, such complementary information for gene selection may include knowledge about the genes, functions, derived proteins, measurement assays, isolation techniques, etc. The user interface preferably allows for visual exploration of the graphs and the product of the two graphs to identify promising targets. The browser does not generally require intensive computations and if needed, can be run on other computer means. The graph generated by the server can be precomputed, prior to access by the browser, or is generated in situ and functions by expanding the graph at points of interest.

In a preferred embodiment, the server is a statistical analysis package, and in the gene feature selection, a gene selection server. For example, inputs are patterns of gene expression, from sources such as DNA microarrays or other data sources. Outputs are an observation graph that organizes the results of one or more runs of SVM RFE. It is optimum to have the selection server run the computationally expensive operations.

A preferred method of the server is to expand the information acquired by the SVM. The server can use any SVM results, and is not limited to SVM RFE selection methods. As an example, the method is directed to gene selection, though any data can be treated by the server. Using SVM RFE for gene selection, gene redundancy is eliminated, but it is informative to know about discriminant genes that are correlated with the genes selected. For a given number N of genes, only one combination is retained by SVM-RFE. In actuality, there are many combinations of N different genes that provide similar results.

A combinatorial search is a method allowing selection of many alternative combinations of N genes, but this method is prone to overfitting the data. SVM-RFE does not overfit the data. SVM-RFE is combined with supervised clustering to provide lists of alternative genes that are correlated with the optimum selected genes. Mere substitution of one gene by another correlated gene yields substantial classification performance degradation.

The examples included herein show preferred methods for determining the genes that are most correlated to the presence of cancer or can be used to predict cancer occurrence in an individual. There is no limitation to the source of the data and the data can be combinations of measurable criteria, such as genes, proteins or clinical tests, that are capable of being used to differentiate between normal conditions and changes in conditions in biological systems.

In the following examples, preferred numbers of genes were determined that result from separation of the data that discriminate. These numbers are not limiting to the methods of the present invention. Preferably, the preferred optimum number of genes is a range of approximately from 1 to 500, more preferably, the range is from 10 to 250, from 1 to 50, even more preferably the range is from 1 to 32, still more preferably the range is from 1 to 21 and most preferably, from 1 to 10. The preferred optimum number of genes can be affected by the quality and quantity of the original data and thus can be determined for each application by those skilled in the art.

Once the determinative genes are found by the learning machines of the present invention, methods and compositions for treatments of the biological changes in the organisms can be employed. For example, for the treatment of cancer, therapeutic agents can be administered to antagonize or agonize, enhance or inhibit activities, presence, or synthesis of the gene products. Therapeutic agents and methods include, but are not limited to, gene therapies such as sense or antisense polynucleotides, DNA or RNA analogs, pharmaceutical agents, plasmaphoresis, antiangiogenics, and derivatives, analogs and metabolic products of such agents.

Such agents may be administered via parenteral or noninvasive routes. Many active agents are administered through parenteral routes of administration, intravenous, intramuscular, subcutaneous, intraperitoneal, intraspinal, intrathecal, intracerebroventricular, intraarterial and other routes of injection. Noninvasive routes for drug delivery include oral, nasal, pulmonary, rectal, buccal, vaginal, transdermal and ocular routes.

The following examples illustrate the results of using SVMs and other learning machines to identify genes associated with disorders of the prostate. Such genes may be used for diagnosis, treatment, in terms of identifying appropriate therapeutic agents, and for monitoring the progress of treatment.

Example 1: Isolation of Genes Involved with Prostate Cancer

Using the methods disclosed herein, genes associated with prostate cancer were isolated. Various methods of treating and analyzing the cells, including SVM, were utilized to determine the most reliable method for analysis.

Tissues were obtained from patients that had cancer and had undergone prostatectomy. The tissues were processed according to a standard protocol of Affymetrix and gene expression values from 7129 probes on the Affymetrix HuGeneFL GeneChip® were recorded for 67 tissues from 26 patients.

Specialists of prostate histology recognize at least three different zones in the prostate: the peripheral zone (PZ), the central zone (CZ), and the transition zone (TZ). In this study, tissues from all three zones are analyzed because previous findings have demonstrated that the zonal origin of the tissue is an important factor influencing the genetic profiling. Most prostate cancers originate in the PZ. Cancers originating in the PZ have worse prognosis than those originating in the TZ. Contemporary biopsy strategies concentrate on the PZ and largely ignore cancer in the TZ. Benign prostate hyperplasia (BPH) is found only in the TZ. BPH is a suitable control that may be used to compare cancer tissues in genetic profiling experiments. BPH is also convenient to use as control because it is abundant and easily dissected. However, controls coming from normal tissues microdissected with lasers in the CZ and PZ can also provide important complementary controls. The gene expression profile differences have been found to be larger between PZ-G4-G5 cancer and CZ-normal used as control, compared to PZ-normal used as control. A possible explanation comes from the fact that is presence of cancer, even normal adjacent tissues have undergone DNA changes (Malins et al, 2003-2004). Table 1 gives zone properties.

TABLE 1

| Zone | Properties |
|---|---|
| PZ | From apex posterior to base, surrounds transition and central zones.<br>Largest zone (70% in young men).<br>Largest number cancers (60-80%).<br>Dysplasia and atrophy common in older men. |
| CZ | Surrounds transition zone to angle of urethra to bladder base.<br>Second largest zone (25% in young men to 30% at 40 year old).<br>50% of PSA secreting epithelium.<br>5-20% of cancers. |
| TZ | Two pear shaped lobes surrounding the proximal urethra.<br>Smallest zone in young men (less than 5%).<br>Gives rise to BPH in older men. May expand to the bulk of the gland.<br>10-18% of cancers.<br>Better cancer prognosis than PZ cancer. |

Classification of cancer determines appropriate treatment and helps determine a prognosis. Cancer develops progressively from an alteration in a cell's genetic structure due to mutations, to cells with uncontrolled growth patterns. Classification is made according to the site of origin, histology (or cell analysis; called grading), and the extent of the disease (called staging).

Prostate cancer specialists classify cancer tissues according to grades, called Gleason grades, which are correlated with the malignancy of the diseases. The larger the grade, the worse the prognosis (chance of survival). In this study, tissues of grade 3 and above are used. Grades 1 and 2 are more difficult to characterize with biopsies and not very malignant. Grades 4 and 5 are not very differentiated and correspond to the most malignant cancers: for every 10% increase in the percent of grade 4/5 tissue found, there is a concomitant increase in post radical prostatectomy failure rate. Each grade is defined in Table 2.

TABLE 2

| Grade | Description |
|---|---|
| 1 | Single, separate, uniform, round glands closely packed with a definite rounded edge limiting the area of the tumor. Separation of glands at the periphery from the main collection by more than one gland diameter indicates a component of at least grade 2. Uncommon pattern except in the TZ. Almost never seen in needle biopsies. |
| 2 | Like grade 1 but more variability in gland shape and more stroma separating glands. Occasional glands show angulated or distorted contours. More common in TZ than PZ. Pathologists don't diagnose Gleason grades 1 or 2 on prostate needle biopsies since they are uncommon in the PZ, there is inter-pathologist variability and poor correlation with radical prostatectomy. |
| 3 | G3 is the most commonly seen pattern. Variation in size, shape (may be angulated or compressed), and spacing of glands (may be separated by >1 gland diameter). Many small glands have occluded or abortive lumens (hollow areas). There is no evidence of glandular fusion. The malignant glands infiltrate between benign glands. |
| 4 | The glands are fused and there is no intervening stroma. |
| 5 | Tumor cells are arranged in solid sheets with no attempts at gland formation. The presence of Gleason grade 5 and high percent carcinoma at prostatectomy predicts early death. |

Staging is the classification of the extent of the disease. There are several types of staging methods. The tumor, node, metastases (TNM) system classifies cancer by tumor size (T), the degree of regional spread or lymph node involvement (N), and distant metastasis (M). The stage is determined by the size and location of the cancer, whether it has invaded the prostatic capsule or seminal vesicle, and whether it has metastasized. For staging, MRI is preferred to CT because it permits more accurate T staging. Both techniques can be used in N staging, and they have equivalent accuracy. Bone scintigraphy is used in M staging.

The grade and the stage correlate well with each other and with the prognosis. Adenocarcinomas of the prostate are given two grade based on the most common and second most common architectural patterns. These two grades are added to get a final score of 2 to 10. Cancers with a Gleason score of <6 are generally low grade and not aggressive.

The samples collected included tissues from the Peripheral Zone (PZ); Central Zone (CZ) and Transition Zone (TZ). Each sample potentially consisted of four different cell types: Stomal cells (from the supporting tissue of the prostate, not participating in its function); Normal organ cells; Benign prostatic hyperplasia cells (BPH); Dysplasia cells (cancer precursor stage) and Cancer cells (of various grades indicating the stage of the cancer). The distribution of the samples in Table 3 reflects the difficulty of obtaining certain types of tissues:

TABLE 3

| | Stroma | Normal | BPH | Dysplasia | Cancer G3 | Cancer G4 | G3 + G4 |
|---|---|---|---|---|---|---|---|
| PZ | 1 | 5 | | 3 | 10 | 24 | 3 |
| CZ | | 3 | | | | | |
| TZ | | | 18 | | | | |

Benign Prostate Hyperplasia (BPH), also called nodular prostatic hyperplasia, occurs frequently in aging men. By the eighth decade, over 90% of males will have prostatic hyperplasia. However, in only a minority of cases (about 10%) will this hyperplasia be symptomatic and severe enough to require surgical or medical therapy. BPH is not a precursor to carcinoma.

It has been argued in the medical literature that TZ BPH could serve as a good reference for PZ cancer. The highest grade cancer (G4) is the most malignant. Part of these experiments are therefore directed towards the separation of BPH vs. G4.

Some of the cells were prepared using laser confocal microscopy (LCM which was used to eliminate as much of the supporting stromal cells as possible and provides purer samples.

Gene expression was assessed from the presence of mRNA in the cells. The mRNA is converted into cDNA and amplified, to obtain a sufficient quantity. Depending on the amount of mRNA that can be extracted from the sample, one or two amplifications may be necessary. The amplification process may distort the gene expression pattern. In the data set under study, either 1 or 2 amplifications were used. LCM data always required 2 amplifications. The treatment of the samples is detailed in Table 4.

TABLE 4

| | 1 amplification | 2 amplifications |
|---|---|---|
| No LCM | 33 | 14 |
| LCM | | 20 |

The end result of data extraction is a vector of 7129 gene expression coefficients.

Gene expression measurements require calibration. A probe cell (a square on the array) contains many replicates of the same oligonucleotide (probe) that is a 25 bases long sequence of DNA. Each "perfect match" (PM) probe is designed to complement a reference sequence (piece of gene). It is associated with a "mismatch" (MM) probe that is identical except for a single base difference in the central position. The chip may contain replicates of the same PM probe at different positions and several MM probes for the same PM probe corresponding to the substitution of one of the four bases. This ensemble of probes is referred to as a probe set. The gene expression coefficient is calculated as:

$$\text{Average Difference}=1/\text{pair num}\ \Sigma_{probe\ set}(PM-MM)$$

If the magnitude of the probe pair values is not sufficiently contrasted, the probe pair is considered dubious. Thresholds are set to accept or reject probe pairs. Affymetrix considers samples with 40% or over acceptable probe pairs of good quality. Lower quality samples can also be effectively used with the SVM techniques.

A simple "whitening" was performed as pre-processing, so that after pre-processing, the data matrix resembles "white noise". In the original data matrix, a line of the matrix represented the expression values of 7129 genes for a given sample (corresponding to a particular combination of patient/tissue/preparation method). A column of the matrix represented the expression values of a given gene across the 67 samples. Without normalization, neither the lines nor the columns can be compared. There are obvious offset and scaling problems. The samples were pre-processed to: normalize matrix columns; normalize matrix lines; and normalize columns again. Normalization consists of subtracting the mean and dividing by the standard deviation. A further normalization step was taken when the samples are split into a training set and a test set.

The mean and variance column-wise was computed for the training samples only. All samples (training and test samples) were then normalized by subtracting that mean and dividing by the standard deviation.

Samples were evaluated to determine whether LCM data preparation yields more informative data than unfiltered tissue samples and whether arrays of lower quality contain useful information when processed using the SVM technique.

Two data sets were prepared, one for a given data preparation method (subset 1) and one for a reference method (subset 2). For example, method 1=LCM and method 2=unfiltered samples. Golub's linear classifiers were then trained to distinguish between cancer and normal cases using subset 1 and another classifier using subset 2. The classifiers were then tested on the subset on which they had not been trained (classifier 1 with subset 2 and classifier 2 with subset 1).

If classifier 1 performs better on subset 2 than classifier 2 on subset 1, it means that subset 1 contains more information to do the separation cancer vs. normal than subset 2.

The input to the classifier is a vector of n "features" that are gene expression coefficients coming from one microarray experiment. The two classes are identified with the symbols (+) and (−) with "normal" or reference samples belong to class (+) and cancer tissues to class (−). A training set of a number of patterns $\{x_1, x_2, \ldots x_k, \ldots x_l\}$ with known class labels $\{y_1, y_2, \ldots y_k, \ldots y_l\}$, $y_k \in \{-1,+1\}$, is given. The training samples are used to build a decision function (or discriminant function) D(x), that is a scalar function of an input pattern x. New samples are classified according to the sign of the decision function:

$$D(x)>0 \Rightarrow x \in \text{class}(+)$$

$$D(x)<0 \Rightarrow x \in \text{class}(-)$$

$$D(x)=0, \text{decision boundary.}$$

Decision functions that are simple weighted sums of the training patterns plus a bias are called linear discriminant functions.

$$D(x)=w\cdot x+b,$$

where w is the weight vector and b is a bias value.

In the case of Golub's classifier, each weight is computed as:

$$W_i=(\mu_i+)-\mu_i(-))/(\sigma_i(+)+\sigma_i(-)),$$

where ($\mu_i$ and $\sigma_i$ are the mean and standard deviation of the gene expression values of gene i for all the patients of class (+) or class (−), i=1, n. Large positive $w_i$ values indicate strong correlation with class (+) whereas large negative $w_i$ values indicate strong correlation with class (−). Thus the weights can also be used to rank the features (genes) according to relevance. The bias is computed as $b=-w\cdot\mu$, where $\mu=(\mu(+)+\mu(-))/2$.

Golub's classifier is a standard reference that is robust against outliers. Once a first classifier is trained, the magnitude of $w_i$ is used to rank the genes. The classifiers are then retrained with subsets of genes of different sizes, including the best ranking genes.

To assess the statistical significance of the results, ten random splits of the data including samples were prepared from either preparation method and submitted to the same method. This allowed the computation of an average and standard deviation for comparison purposes.

Tissue from the same patient was processed either directly (unfiltered) or after the LCM procedure, yielding a pair of microarray experiments. This yielded 13 pairs, including: four G4; one G3+4; two G3; four BPH; one CZ (normal) and one PZ (normal).

For each data preparation method (LCM or unfiltered tissues), the tissues were grouped into two subsets:

Cancer=*G*4+*G*3(7 cases)

Normal=BPH+CZ+PZ(6 cases).

Figure 2:
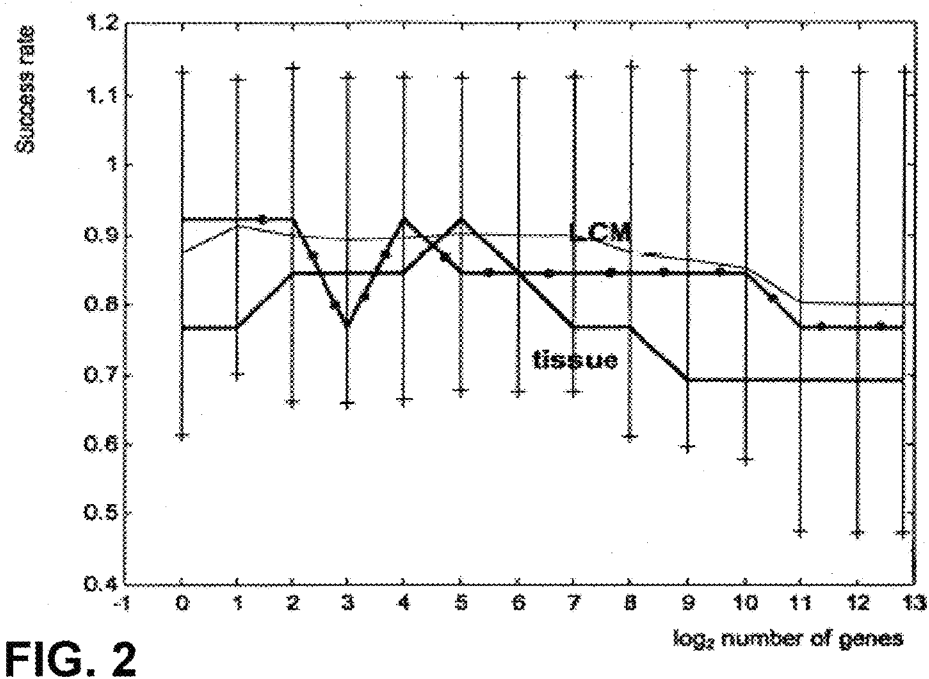
FIG. 2 is a plot showing the results based on LCM data preparation for prostate cancer analysis.

The results are shown in FIG. 2. The large error bars are due to the small size. However, there is an indication that LCM samples are better than unfiltered tissue samples. It is also interesting to note that the average curve corresponding to random splits of the data is above both curves. This is not surprising since the data in subset 1 and subset 2 are differently distributed. When making a random split rather than segregating samples, both LCM and unfiltered tissues are represented in the training and the test set and performance on the test set are better on average.

The same methods were applied to determine whether microarrays with gene expression data rejected by the Affymetrix quality criterion contained useful information by focusing on the problem of separating BPH tissue vs. G4 tissue with a total of 42 arrays (18 BPH and 24 G4).

The Affymetrix criterion identified 17 good quality arrays, 8 BPH and 9 G4. Two subsets were formed:

Subset 1="good" samples,8 BPH+9 *G*4

Subset 2="mediocre" samples,10 BPH+15 *G*4

For comparison, all of the samples were lumped together and 10 random subset 1 containing 8 BPH+9 G4 of any quality were selected. The remaining samples were used as subset 2 allowing an average curve to be obtained. Additionally the subsets were inverted with training on the "mediocre" examples and testing on the "good" examples.

When the mediocre samples are trained, perfect accuracy on the good samples is obtained, whereas training on the good examples and testing on the mediocre yield substantially worse results.

All the BPH and G4 samples were divided into LCM and unfiltered tissue subsets to repeat similar experiments as in the previous Section:

Subset1=LCM samples(5 BPH+6 LCM)

Subset2=unfiltered tissue samples(13 BPH+18 LCM)

There, in spite of the difference in sample size, training on LCM data yields better results. In spite of the large error bars, this is an indication that the LCM data preparation method might be of help in improving sample quality.

BPH vs. G4

The Affymetrix data quality criterion were irrelevant for the purpose of determining the predictive value of particular genes and while the LCM samples seemed marginally better than the unfiltered samples, it was not possible to determine a statistical significance. Therefore, all samples were grouped together and the separation BPH vs. G4 with all 42 samples (18 BPH and 24 G4) was preformed.

To evaluate performance and compare Golub's method with SVMs, the leave-one-out method was used. The fraction of successfully classified left-out examples gives an estimate of the success rate of the various classifiers.

Figure 3:
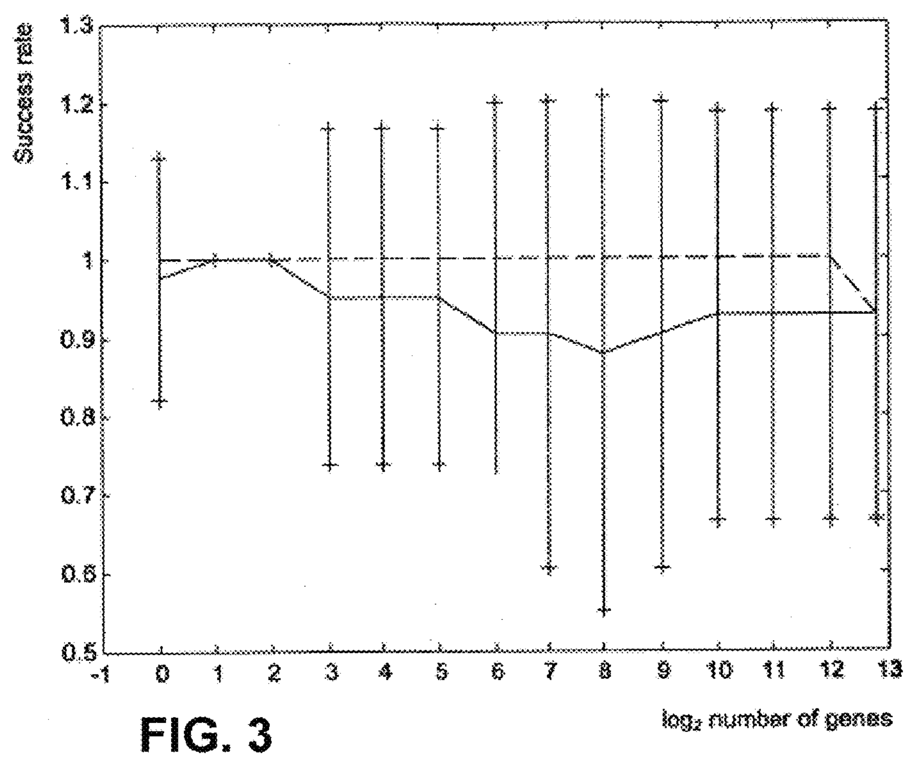
FIG. 3 is a plot graphically comparing SVM-RFE of the present invention with leave-one-out classifier for prostate cancer.

In this procedure, the gene selection process was run 41 times to obtain subsets of genes of various sizes for all 41 gene rankings One classifier was then trained on the corresponding 40 genes for every subset of genes. This leave-one-out method differs from the "naive" leave-one-out that consists of running the gene selection only once on all 41 examples and then training 41 classifiers on every subset of genes. The naive method gives overly optimistic results because all the examples are used in the gene selection process, which is like "training on the test set". The increased accuracy of the first method is illustrated in FIG. 3. The method used in the figure is RFE-SVM and the classifier used is an SVM. All SVMs are linear with soft margin parameters C=100 and $t=10^{14}$. The dashed line represents the "naive" leave-one-out (LOO), which consists in running the gene selection once and performing loo for classifiers using subsets of genes thus derived, with different sizes. The solid line represents the more computationally expensive "true" LOO, which consists in running the gene selection 41 times, for every left out example. The left out example is classified with a classifier trained on the corresponding 40 examples for every selection of genes. If f is the success rate obtained (a point on the curve), the standard deviation is computed as sqrt(f(1−f).

Example 2: Analyzing Small Data Sets with Multiple Features

Small data sets with large numbers of features present several problems. In order to address ways of avoiding data overfitting and to assess the significance in performance of multivariate and univariate methods, the samples from Example 1 that were classified by Affymetrix as high quality samples were further analyzed. The samples included 8 BPH and 9 G4 tissues. Each microarray recorded 7129 gene expression values. About ⅔ of the samples in the BPH/G4 subset were considered of inadequate quality for use with standard non-SVM methods.

Simulations resulting from multiple splits of the data set of 17 examples (8 BPH and 9 G4) into a training set and a test set were run. The size of the training set is varied. For each training set drawn, the remaining data are used for testing.

For number of training examples greater than 4 and less than 16, 20 training sets were selected at random. For 16 training examples, the leave-one-out method was used, in that all the possible training sets obtained by removing 1 example at a time (17 possible choices) were created. The test set is then of size 1. Note that the test set is never used as part of the feature selection process, even in the case of the leave-one-out method.

For 4 examples, all possible training sets containing 2 examples of each class (2 BPH and 2 G4), were created and 20 of them were selected at random.

For SVM methods, the initial training set size is 2 examples, one of each class (1 BPH and 1 G4). The examples of each class are drawn at random. The performance of the LDA methods cannot be computed with only 2 examples, because at least 4 examples (2 of each class) are required to compute intraclass standard deviations. The number of training examples is incremented by steps of 2.

The top ranked genes are presented in Tables 5-8. Having determined that the SVM method provided the most compact set of features to achieve 0 leave-one-out error and that the SF-SVM method is the best and most robust method for small numbers of training examples, the top genes found by these methods were researched in the literature. Most of the genes have a connection to cancer or more specifically to prostate cancer.

Table 5 shows the top ranked genes for SF LDA using 17 best BPH/G4.

TABLE 5

| Rank | GAN | EXP | Description |
|---|---|---|---|
| 10 | X83416 | −1 | *H. sapiens* PrP gene |
| 9 | U50360 | −1 | Human calcium calmodulin-dependent protein kinase II gamma mRNA |
| 8 | U35735 | −1 | Human RACH1 (RACH1) mRNA |
| 7 | M57399 | −1 | Human nerve growth factor (HBNF-1) mRNA |
| 6 | M55531 | −1 | Human glucose transport-like 5 (GLUT5) mRNA |
| 5 | U48959 | −1 | Human myosin light chain kinase (MLCK) mRNA |
| 4 | Y00097 | −1 | Human mRNA for protein p68 |
| 3 | D10667 | −1 | Human mRNA for smooth muscle myosin heavy chain |
| 2 | L09604 | −1 | *Homo sapiens* differentiation-dependent A4 protein MRNA |
| 1 | HG1612-HT1612 | 1 | McMarcks |

where GAN=Gene Acession Number; EXP=Expression (−1=underexpressed in cancer (G4) tissues; +1=overexpressed in cancer tissues).

Table 6 lists the top ranked genes obtained for LDA using 17 best BPH/G4.

TABLE 6

| Rank | GAN | EXP | Description |
|---|---|---|---|
| 10 | J03592 | 1 | Human ADP/ATP translocase mRNA |
| 9 | U40380 | 1 | Human presenilin I-374 (AD3-212) mRNA |
| 8 | D31716 | −1 | Human mRNA for GC box bindig protein |
| 7 | L24203 | −1 | *Homo sapiens* ataxia-telangiectasia group D |
| 6 | J00124 | −1 | *Homo sapiens* 50 kDa type I epidermal keratin gene |
| 5 | D10667 | −1 | Human mRNA for smooth muscle myosin heavy chain |

TABLE 6-continued

| Rank | GAN | EXP | Description |
|---|---|---|---|
| 4 | J03241 | −1 | Human transforming growth factor-beta 3 (TGF-beta3) MRNA |
| 3 | 017760 | −1 | Human laminin S B3 chain (LAMB3) gene |
| 2 | X76717 | −1 | *H. sapiens* MT-11 mRNA |
| 1 | X83416 | −1 1 | *H. sapiens* PrP gene |

Table 7 lists the top ranked genes obtained for SF SVM using 17 best BPH/G4.

TABLE 7

| Rank | GAN | EXP | Description |
|---|---|---|---|
| 10 | X07732 | 1 | Human hepatoma mRNA for serine protease hepsin |
| 9 | J03241 | −1 | Human transforming growth factor-beta 3 (TGF-beta3) MRNA |
| 8 | X83416 | −1 | *H. sapiens* PrP gene |
| 7 | X14885 | −1 | *H. sapiens* gene for transforming growth factor-beta 3 (TGF-beta 3) exon 1 (and joined CDS) |
| 6 | U32114 | −1 | Human caveolin-2 mRNA |
| 5 | M16938 | 1 | Human homeo-box c8 protein |
| 4 | L09604 | −1 | *H. sapiens* differentiation-dependent A4 protein MRNA |
| 3 | Y00097 | −1 | Human mRNA for protein p68 |
| 2 | D88422 | −1 | Human DNA for cystatin A |
| 1 | U35735 | −1 | Human RACH1 (RACH1) mRNA |

Table 8 provides the top ranked genes for SVM using 17 best BPH/G4.

TABLE 8

| Rank | GAN | EXP | Description |
|---|---|---|---|
| 10 | X76717 | −1 | *H. sapiens* MT-11 mRNA |
| 9 | U32114 | −1 | Human caveolin-2 mRNA |
| 8 | X85137 | 1 | *H. sapiens* mRNA for kinesin-related protein |
| 7 | D83018 | −1 | Human mRNA for nel-related protein 2 |
| 6 | D10667 | −1 | Human mRNA for smooth muscle myosin heavy chain |
| 5 | M16938 | 1 | Human homeo box c8 protein |
| 4 | L09604 | −1 | *Homo sapiens* differentiation-dependent A4 protein mRNA |
| 3 | HG1612 | 1 | McMarcks |
| 2 | M10943 | −1 | Human metallothionein-If gene (hMT-If) |
| 1 | X83416 | −1 | *H. sapiens* PrP gene |

Using the "true" leave-one-out method (including gene selection and classification), the experiments indicate that 2 genes should suffice to achieve 100% prediction accuracy. The two top genes were therefore more particularly researched in the literature. The results are summarized in Table 10. It is interesting to note that the two genes selected appear frequently in the top 10 lists of Tables 5-8 obtained by training only on the 17 best genes.

Table 9 is a listing of the ten top ranked genes for SVM using all 42 BPH/G4.

TABLE 9

| Rank | GAN | EXP | Description |
|---|---|---|---|
| 10 | X87613 | −1 | *H. sapiens* mRNA for skeletal muscle abundant |
| 9 | X58072 | −1 | Human hGATA3 mRNA for trans-acting T-cell specific |
| 8 | M33653 | −1 | Human alpha-2 type IV collagen (COL4A2) |
| 7 | S76473 | 1 | trkB [human brain mRNA] |
| 6 | X14885 | −1 | *H. sapiens* gene for transforming growth factor-beta 3 |

TABLE 9-continued

| Rank | GAN | EXP | Description |
|---|---|---|---|
| 5 | S83366 | −1 | region centromeric to t(12; 17) brakepoint |
| 4 | X15306 | −1 | *H. sapiens* NF-H gene |
| 3 | M30894 | 1 | Human T-cell receptor Ti rearranged gamma-chain |
| 2 | M16938 | 1 | Human homeo box c8 protein |
| 1 | U35735 | −1 | Human RACH1 (RACH1) mRNA |

Table 10 provides the findings for the top 2 genes found by SVM using all 42 BPH/G4. Taken together, the expression of these two genes is indicative of the severity of the disease.

TABLE 10

| GAN | Synonyms | Possible function/link to prostate cancer |
|---|---|---|
| M16938 | HOXC8 | Hox genes encode transcriptional regulatory proteins that are largely responsible for establishing the body plan of all metazoan organisms. There are hundreds of papers in PubMed reporting the role of HOX genes in various cancers. HOXC5 and HOXC8 expression are selectively turned on in human cervical cancer cells compared to normal keratinocytes. Another homeobox gene (GBX2) may participate in metastatic progression in prostatic cancer. Another HOX protein (hoxb-13) was identified as an androgen-independent gene expressed in adult mouse prostate epithelial cells. The authors indicate that this provides a new potential target for developing therapeutics to treat advanced prostate cancer |
| U35735 | Jk<br>Kidd<br>RACH1<br>RACH2<br>SLC14A1<br>UT1<br>UTE | Overexpression of RACH2 in human tissue culture cells induces apoptosis. RACH1 is downregulated in breast cancer cell line MCF-7. RACH2 complements the RAD1 protein. RAM is implicated in several cancers. Significant positive lod scores of 3.19 for linkage of the Jk (Kidd blood group) with cancer family syndrome (CFS) were obtained. CFS gene(s) may possibly be located on chromosome 2, where Jk is located. |

Table 11 shows the severity of the disease as indicated by the top 2 ranking genes selected by SVMs using all 42 BPH and G4 tissues.

TABLE 11

| | HOXC8 Underexpressed | HOXC8 Overexpressed |
|---|---|---|
| RACH1 Overexpressed | Benign | N/A |
| RACH1 Underexpressed | Grade 3 | Grade 4 |

Example 3: Prostate Cancer Study on Affymetrix Gene Expression Data (09-2004)

A set of Affymetrix microarray GeneChip® experiments from prostate tissues were obtained from Dr. Thomas A. Stamey at Stanford University. The data from samples obtained for the prostate cancer study are summarized in Table 12 (which represents the same data as in Table 3 but organized differently.) Preliminary investigation of the data included determining the potential need for normalizations. Classification experiments were run with a linear SVM on the separation of Grade 4 tissues vs. BPH tissues. In a 32×3-fold experiment, an 8% error rate could be achieved with a selection of 100 genes using the multiplicative updates technique (similar to RFE-SVM). Performances without feature selection are slightly worse but comparable. The gene most often selected by forward selection was independently chosen in the top list of an independent published study, which provided an encouraging validation of the quality of the data.

TABLE 12

| Prostate zone | Histological classification | No. of samples |
|---|---|---|
| Central (CZ) | Normal (NL) | 9 |
| | Dysplasia (Dys) | 4 |
| | Grade 4 cancer (G4) | 1 |
| Peripheral (PZ) | Normal (NL) | 13 |
| | Dysplasia (Dys) | 13 |
| | Grade 3 cancer (G3) | 11 |
| | Grade 4 cancer (G4) | 18 |
| Transition (TZ) | Benign Prostate Hyperplasia (BPH) | 10 |
| | Grade 4 cancer (G4) | 8 |
| Total | | 87 |

As controls, normal tissues and two types of abnormal tissues are used in the study: BPH and Dysplasia.

To verify the data integrity, the genes were sorted according to intensity. For each gene, the minimum intensity across all experiments was taken. The top 50 most intense values were taken. Heat maps of the data matrix were made by sorting the lines (experiments) according to zone, grade, and time processed. No correlation was found with zone or grade, however, there was a significant correlation with the time the sample was processed. Hence, the arrays are poorly normalized.

In other ranges of intensity, this artifact is not seen. Various normalization techniques were tried, but no significant improvements were obtained. It has been observed by several authors that microarray data are log-normal distributed. A qqplot of all the log of the values in the data matrix confirms that the data are approximately log-normal distributed. Nevertheless, in preliminary classification experiments, there was not a significant advantage of taking the log.

Tests were run to classify BPH vs. G4 samples. There were 10 BPH samples and 27 G4 samples. 32×3 fold experiments were performed in which the data was split into 3 subsets 32 times. Two of the subsets were used for training while the third was used for testing. The results were averaged. A feature selection was performed for each of the 32×3 data splits; the features were not selected on the entire dataset.

A linear SVM was used for classification, with ridge parameter 0.1, adjusted for each class to balance the number of samples per class. Three feature selection methods were used: (1) multiplicative updates down to 100 genes (MU100); (2) forward selection with approximate gene orthogonalisation up to 2 genes (FS2); and (3) no gene selection (NO).

The data was either raw or after taking the log (LOG). The genes were always standardized (STD: the mean over all samples is subtracted and the result is divided by the standard deviation; mean and stdev are computed on training data only, the same coefficients are applied to test data).

The results for the performances for the BPH vs. G4 separation are shown in Table 13 below, with the standard errors are shown in parentheses. "Error rate" is the average number of misclassification errors; "Balanced errate" is the average of the error rate of the positive class and the error rate of the negative class; "AUC" is the area under the ROC (receiver operating characteristic) curves that plots the sensitivity (error rate of the positive class, G4) as a function of the specificity (error rate of the negative class, BPH).

It was noted that the SVM performs quite well without feature selection, and MU 100 performs similarly, but slightly better. The number of features was not adjusted—100 was chosen arbitrarily.

TABLE 13

| Preprocessing | Feat. Select. | Error rate | Balanced errate | AUC |
|---|---|---|---|---|
| Log + STD | MU 100 | 8.09 (0.66) | 11.68 (1.09) | 98.93 (0.2) |
| Log + STD | FS 2 | 13.1 (1.1) | 15.9 (1.3) | 92.02 (1.15) |
| Log + STD | No selection | 8.49 (0.71) | 12.37 (1.13) | 97.92 (0.33) |
| STD | No selection | 8.57 (0.72) | 12.36 (1.14) | 97.74 (0.35) |

In Table 13, the good AUC and the difference between the error rate and the balanced error rate show that the bias of the classifier must be optimized to obtained a desired tradeoff between sensitivity and specificity.

Two features are not enough to match the best performances, but do quite well already.

It was determined which features were selected most often with the FS 2 method. The first gene (3480) was selected 56 times, while the second best one (5783) was selected only 7 times. The first one is believed to be relevant to cancer, while the second one has probably been selected for normalization purposes. It is interesting that the first gene (Hs.79389) is among the top three genes selected in another independent study (Febbo-Sellers, 2003).

The details of the two genes are as follows:

Gene 3480: gb:NM_006159.1 /DEF=*Homo sapiens* nel (chicken)-like 2 (NELL2), mRNA. /FEA=mRNA /GEN=NELL2/PROD=nel (chicken)-like2 /DB_XREF=gi:5453765 /UG=Hs.79389 nel (chicken)-like 2 /FL=gb:D83018.1 gb:NM_006159.1

Gene 5783: gb:NM_018843.1 /DEF=*Homo sapiens* mitochondrial carrier family protein(L0055972), mRNA. /FEA=mRNA /GEN=L0055972 /PROD=mitochondrial carrier family protein /DB_XREF=gi:10047121 /UG=Hs.172294 mitochondrial carrier family protein /FL=gb:NM_018843.1 gb:AF125531.1.

Example 4: Prostate Cancer Study from Affymetrix Gene Expression Data (10-2004)

This example is a continuation of the analysis of Example 3 above on the Stamey prostate cancer microarray data. PSA has long been used as a biomarker of prostate cancer in serum, but is no longer useful. Other markers have been studied in immunohistochemical staining of tissues, including p27, Bcl-2, E-catherin and P53. However, to date, no marker has gained acceptance for use in routine clinical practice.

The gene rankings obtained correlate with those of the Febbo paper, confirming that the top ranking genes found from the Stamey data have a significant intersection with the genes found in the Febbo study. In the top 1000 genes, about 10% are Febbo genes. In comparison, a random ordering would be expected to have less than 1% are Febbo genes.

BPH is not by itself an adequate control. When selecting genes according to how well they separate grade 4 cancer tissues (G4) from BPH, one can find genes that group all non-BPH tissues with the G4 tissues (including normal, dysplasia and grade 3 tissues). However, when BPH is excluded from the training set, genes can be found that correlate well with disease severity. According to those genes, BPH groups with the low severity diseases, leading to a conclusion that BPH has its own molecular characteristics and that normal adjacent tissues should be used as controls.

TZG4 is less malignant than PZG4. It is known that TZ cancer has a better prognosis than PZ cancer. The present analysis provides molecular confirmation that TZG4 is less malignant than PZG4. Further, TZG4 samples group with the less malignant samples (grade 3, dysplasia, normal, or BPH) than with PZG4. This differentiated grouping is emphasized in genes correlating with disease progression (normal<dysplasia<g3<g4) and selected to provide good separation of TZG4 from PZG4 (without using an ordering for TZG4 and PZG4 in the gene selection criterion).

Ranking criteria implementing prior knowledge about disease malignancy are more reliable. Ranking criteria validity was assessed both with p values and with classification performance. The criterion that works best implements a tissue ordering normal<dysplasia<G3<G4 and seeks a good separation TZG4 from PZG4. The second best criterion implements the ordering normal<dysplasia<G3<TZG4<PZG4.

Comparing with other studies may help reducing the risk of overfitting. A subset of 7 genes was selected that ranked high in the present study and that of Febbo et al. 2004. Such genes yield good separating power for G4 vs. other tissues. The training set excludes BPH samples and is used both to select genes and train a ridge regression classifier. The test set includes 10 BPH and 10 G4 samples (½ from the TZ and ½ from the PZ). Success was evaluated with the area under the ROC curve ("AUC")(sensitivity vs. specificity) on test examples. AUCs between 0.96 and 1 are obtained, depending on the number of genes. Two genes are of special interest (GSTP1 and PTGDS) because they are found in semen and could be potential biomarkers that do not require the use of biopsied tissue.

The choice of the control may influence the findings (normal tissue or BPH). as may the zones from which the tissues originate. The first test sought to separate Grade 4 from BPH. Two interesting genes were identified by forward selection as gene 3480 (NELL2) and gene 5783(L0055972). As explained in Example 3, gene 3480 is the informative gene, and it is believed that gene 5783 helps correct local on-chip variations. Gene 3480, which has Unigene cluster id. Hs.79389, is a Nel-related protein, which has been found at high levels in normal tissue by Febbo et al.

All G4 tissues seem intermixed regardless of zone. The other tissues are not used for gene selection and they all fall on the side of G4. Therefore, the genes found characterize BPH, not G4 cancer, such that it is not sufficient to use tissues of G4 and BPH to find useful genes to characterize G4 cancer.

For comparison, two filter methods were used: the Fisher criterion and the shrunken centroid criterion (Tibshirani et al, 2002). Both methods found gene 3480 to be highly informative (first or second ranking) The second best gene is 5309, which has Unigene cluster ID Hs. 100431 and is described as small inducible cytokine B subfamily (Cys-X-Cys motif). This gene is highly correlated to the first one.

The Fisher criterion is implemented by the following routine:

A vector x containing the values of a given feature for all patt_num samples cl_num classes, k=1, 2, . . . cl_num, grouping the values of x mu_val(k) is the mean of the x values for class k var_val(k) is the variance of the x values for class k patt_per class(k) is the number of elements of class k Unbiased_within_var is the unbiased pooled within class variance, i.e., we make a weighted average of var_val (k) with coefficients patt_per_class(k)/(patt_num--cl_num)

Unbiased_between_var=var(mu_val); % Divides by cl_num-1 then Fisher_crit=Unbiased_between_var /Unbiased_within_var Although the shrunken centroid criterion is somewhat more complicated than the Fisher criterion, it is quite similar. In both cases, the pooled within class variance is used to normalize the criterion. The main difference is that instead of ranking according to the between class variance (that is, the average deviation of the class centroids to the overall centroid), the shrunken centroid criterion uses the maximum deviation of any class centroid to the global centroid. In doing so, the criterion seeks features that well separate at least one class, instead of features that well separate all classes (on average).

The other small other differences are:

A fudge factor is added to Unbiased_within_std=sqrt (Unbiased_within_var) to prevent divisions by very small values. The fudge factor is computed as: fudge=mean(Unbiased_within_std); the mean being taken over all the features. Each class is weighted according to its number of elements cl_elem(k). The deviation for each class is weighted by 1/sqrt(1/cl_elem (k)+1/patt_num). Similar corrections could be applied to the Fisher criterion.

The two criteria are compared using pvalues. The Fisher criterion produces fewer false positive in the top ranked features. It is more robust, however, it also produces more redundant features. It does not find discriminant features for the classes that are least abundant or hardest to separate.

Also for comparison, the criterion of Golub et al., also known as signal to noise ratio, was used. This criterion is used in the Febbo paper to separate tumor vs. normal tissues. On this data that the Golub criterion was verified to yield a similar ranking as the Pearson correlation coefficient. For simplicity, only the Golub criterion results are reported. To mimic the situation, three binary separations were run: (G3+4 vs. all other tissues), (G4 vs. all other tissues), and (G4 vs. BPH). As expected, the first gene selected for the G4 vs. BPH is 3480, but it does not rank high in the G3+4 vs. all other and G4 vs. all other.

Compared to a random ranking, the genes selected using the various criteria applied are enriched in Febbo genes, which cross-validates the two study. For the multiclass criteria, the shrunken centroid method provides genes that are more different from the Febbo genes than the Fisher criterion. For the two-class separations, the tumor vs normal (G3+4 vs others) and the G4 vs. BPH provide similar Febbo enrichment while the G4 vs. all others gives gene sets that depart more from the Febbo genes. Finally, it is worth noting that the initial enrichment up to 1000 genes is of about 10% of Febbo genes in the gene set. After that, the enrichment decreases. This may be due to the fact that the genes are identified by their Unigene Ids and more than one probe is attributed to the same Id. In any case, the enrichment is very significant compared to the random ranking.

A number of probes do not have Unigene numbers. Of 22,283 lines in the Affymetrix data, 615 do not have Unigene numbers and there are only 14,640 unique Unigene numbers. In 10,130 cases, a unique matrix entry corresponds to a particular Unigene ID. However, 2,868 Unigene IDs are represented by 2 lines, 1,080 by 3 lines, and 563 by more than 3 lines. One Unigene ID covers 13 lines of data. For example, Unigene ID Hs.20019, identifies variants of *Homo sapiens* hemochromatosis (HFE) corresponding to GenBank accession numbers: AF115265.1, NM 000410.1, AF144240.1, AF150664.1, AF149804.1, AF144244.1, AF115264.1, AF144242.1, AF144243.1, AF144241.1, AF079408.1, AF079409.1, and (consensus) BG402460.

The Unigene IDs of the paper of Febbo et al. (2003) were compared using the U95AV2 Affymetrix array and the IDs found in the U133A array under study. The Febbo paper reported 47 unique Unigene IDs for tumor high genes, 45 of which are IDs also found in the U133A array. Of the 49 unique Unigene IDs for normal high genes, 42 are also found in the U133A array. Overall, it is possible to see cross-correlations between the findings. There is a total of 96 Febbo genes that correspond to 173 lines (some genes being repeated) in the current matrix.

Based on the current results, one can either conclude that the "normal" tissues that are not BPH and drawn near the cancer tissues are on their way to cancer, or that BPH has a unique molecular signature that, although it may be considered "normal", makes it unfit as a control. A test set was created using 10 BPH samples and 10 grade 4 samples. Naturally, all BPH are in the TZ. The grade 4 are ½ in the TZ and ½ in the PZ.

Gene selection experiments were performed using the following filter methods:

(1)—Pearson's correlation coefficient to correlate with disease severity, where disease severity is coded as normal=1, dysplasia=2, grade3=3, grade4=4.

(2)—Fisher's criterion to separate the 4 classes (normal, dysplasia, grade3, grade4) with no consideration of disease severity.

(3)—Fisher's criterion to separate the 3 classes (PZ, CZ, TZ)

(4)—Relative Fisher criterion by computing the ratio of the between class variances of the disease severity and the zones, in an attempt to de-emphasize the zone factor.

(5)—Fisher's criterion to separate 8 classes corresponding to all the combinations of zones and disease severity found in the training data.

(6)—Using the combination of 2 rankings: the ranking of (1) and a ranking by zone for the grade 4 samples only. The idea is to identify genes that separate TZ from PZ cancers that have a different prognosis.

For each experiment, scatter plots were analyzed for the two best selected genes, the heat map of the 50 top ranked genes was reviewed, and p values were compared. The conclusions are as follows:

The Pearson correlation coefficient tracking disease severity (Experiment (1)) gives a similar ranking to the Fisher criterion, which discriminates between disease classes without ranking according to severity. However, the Pearson criterion has slightly better p values and, therefore, may give fewer false positives. The two best genes found by the Pearson criterion are gene 6519, ranked $6^{th}$ by the Fisher criterion, and gene 9457, ranked $1^{st}$ by the Fisher criterion. The test set examples are nicely separated, except for one outlier.

The zonal separation experiments were not conclusive because there are only 3 TZ examples in the training set and no example of CZ in the test set. Experiment (3) revealed a good separation of PZ and CZ on training data. TZ was not very well separated. Experiments (4) and (5) did not show very significant groupings. Experiment (6) found two genes that show both disease progression and that TZ G4 is grouped with "less severe diseases" than PZ G4, although that constraint was not enforced. To confirm the latter finding, the distance for the centroids of PZG4 and TZG4 were compared to control samples. Using the test set only (controls are BPH), 63% of all the genes show that TZG4 is closer to the control than PZG4. That number increases to 70% if the top 100 genes of experiment (6) are considered. To further confirm, experiment (6) was repeated with the entire dataset (without splitting between training and test). TZG4 is closer to normal than PZG4 for most top ranked genes. In the first 15 selected genes, 100% have TZG4 closer to normal than PZG4. This finding is significant because TZG4 has better prognosis than PZG4.

Classification experiments were performed to assess whether the appropriate features had been selected using the following setting:

The data were split into a training set and a test set. The test set consists of 20 samples: 10 BPH, 5 TZG4 and 5 PZG4. The training set contains the rest of the samples from the data set, a total of 67 samples (9 CZNL, 4 CZDYS, 1 CZG4, 13 PZNL, 13 PZDYS, 11 PZG3, 13 PZG4, 3 TZG4). The training set does not contain any BPH.

Feature selection was performed on training data only. Classification was performed using linear ridge regression. The ridge value was adjusted with the leave-one-out error estimated using training data only. The performance criterion was the area under the ROC curve (AUC), where the ROC curve is a plot of the sensitivity as a function of the specificity. The AUC measures how well methods monitor the tradeoff sensitivity/specificity without imposing a particular threshold.

P values are obtained using a randomization method proposed by Tibshirani et al. Random "probes" that have a distribution similar to real features (gene) are obtained by randomizing the columns of the data matrix, with samples in lines and genes in columns. The probes are ranked in a similar manner as the real features using the same ranking criterion. For each feature having a given score s, where a larger score is better, a p value is obtained by counting the fraction of probes having a score larger than s. The larger the number of probes, the more accurate the p value.

For most ranking methods, and for forward selection criteria using probes to compute p values does not affect the ranking. For example, one can rank the probes and the features separately for the Fisher and Pearson criteria.

P values measure the probability that a randomly generated probe imitating a real gene, but carrying no information, gets a score larger or equal to s. Considering a single gene, if it has a score of s, the p value test can be used to test whether to reject the hypothesis that it is a random meaningless gene by setting a threshold on the p value, e.g., 0.0. The problem is that there are many genes of interest (in the present study, N=22,283.) Therefore, it becomes probable that at least one of the genes having a score larger than s will be meaningless. Considering many genes simultaneously is like doing multiple testing in statistics. If all tests are independent, a simple correction known as the Bonferroni correction can be performed by multiplying the p values by N. This correction is conservative when the test are not independent.

From p values, one can compute a "false discovery rate" as FDR(s)=pvalue(s)*N/r, where r is the rank of the gene with score s, pvalue(s) is the associated p value, N is the total number of genes, and pvalue(s)*N is the estimated number of meaningless genes having a score larger than s. FDR estimates the ratio of the number of falsely significant genes over the number of genes call significant.

Of the classification experiments described above, the method that performed best was the one that used the combined criteria of the different classification experiments. In general, imposing meaningful constraints derived from prior knowledge seems to improve the criteria. In particular, simply applying the Fisher criterion to the G4 vs. all-the-rest separation (G4vsAll) yields good separation of the training examples, but poorer generalization than the more constrained criteria. Using a number of random probes equal to the number of genes, the G4vsAll identifies 170 genes before the first random probe, multiclass Fisher obtains 105 and the Pearson criterion measuring disease progression gets 377. The combined criteria identifies only 8 genes, which may be attributed to the different way in which values are computed. With respect to the number of Febbo genes found in the top ranking genes, G4 vs All has 20, multiclass Fisher 19, Pearson 19, and the combined criteria 8. The combined criteria provide a characterization of zone differentiation. On the other hand, the top 100 ranking genes found both by Febbo and by criteria G4 vs All, Fisher or Pearson have a high chance of having some relevance to prostate cancer. These genes are listed in Table 14.

TABLE 14

| Order Num | Unigene ID | Fisher | Pearson | G4 vs ALL | AUC | Description |
|---|---|---|---|---|---|---|
| 12337 | Hs.7780 | 11 | 6 | 54 | 0.96 | cDNA DKFZp56A072 |
| 893 | Hs.226795 | 17 | 7 | 74 | 0.99 | Glutathione S-transferase pi (GSTP1) |
| 5001 | Hs.823 | 41 | 52 | 72 | 0.96 | Hepsin (transmembrance protease, serine 1) (HPN) |
| 1908 | Hs.692 | 62 | 34 | 111 | 0.96 | Tumor-associated calcium signal transducer 1 (TACSTD1) |
| 5676 | Hs.2463 | 85 | 317 | 151 | 1 | Angiopoietin 1 (ANGPT1) |
| 12113 | Hs.8272 | 181 | 93 | 391 | 1 | Prostaglandin D2 synthase (21 kD, brain) (PTGDS) |
| 12572 | Hs.9651 | 96 | 131 | 1346 | 0.99 | RAS related viral oncogene homolog (RRAS) |

Table 14 shows genes found in the top 100 as determined by the three criteria, Fisher, Pearson and G4vsALL, that were also reported in the Febbo paper. In the table, Order num is the order in the data matrix. The numbers in the criteria columns indicate the rank. The genes are ranked according to the sum of the ranks of the 3 criteria. Classifiers were trained with increasing subset sizes showing that a test AUC of 1 is reached with 5 genes.

The published literature was checked for the genes listed in Table 14. Third ranked Hepsin has been reported in several papers on prostate cancer: Chen et al. (2003) and Febbo et al. (2003) and is picked up by all criteria. Polymorphisms of second ranked GSTP1 (also picked by all criteria) are connected to prostate cancer risk (Beer et al, 2002). The fact that GSTP1 is found in semen (Lee (1978)) makes it a potentially interesting marker for non-invasive screening and monitoring. The clone DKFZp564A072, ranked first, is cited is several gene expression studies.

Fourth ranked Gene TACSTD1 was also previously described as more-highly expressed in prostate adenocarcinoma (see Lapointe et al, 2004 and references therein). Angiopoietin (ranked fifth) is involved in angiogenesis and known to help the blood irrigation of tumors in cancers and, in particular, prostate cancer (see e.g. Cane, 2003). Prostaglandin D2 synthase (ranked sixth) has been reported to be linked to prostate cancer in some gene expression analysis papers, but more interestingly, prostaglandin D synthase is found in semen (Tokugawa, 1998), making it another biomarker candidate for non-invasive screening and monitoring. Seventh ranked RRAS is an oncogene, so it makes sense to find it in cancer, however, its role in prostate cancer has not been documented.

A combined criterion was constructed for selecting genes according to disease severity NL<DYS<G3<G4 and simultaneously tries to differentiate TZG4 from PZG4 without ordering them. This following procedure was used:

Build an ordering using the Pearson criterion with encoded target vector having values NL=1, DYS=2, G3=3, G4=4 (best genes come last.)

Build an ordering using the Fisher criterion to separate TZG4 from PZG$ (best genes come last.)

Obtain a combined criterion by adding for each gene its ranks obtained with the first and second criterion.

Sort according to the combined criterion (in descending order, best first).

P values can be obtained for the combined criterion as follows:

Unsorted score vectors for real features (genes) and probes are concatenated for both criteria (Pearson and Fisher).

Genes and probes are sorted together for both criteria, in ascending order (best last).

The combined criterion is obtained by summing the ranks, as described above.

For each feature having a given combined criterion value s (larger values being better), a p value is obtained by counting the fraction of probes a having a combined criterion larger than s.

Note that this method for obtaining p values disturbs the ranking, so the ranking that was obtained without the probes listed in Table 15 was used.

A listing of genes obtained with the combined criterion are shown in Table 15. The ranking is performed on training data only. "Order num" designates the gene order number in the data matrix; p values are adjusted by the Bonferroni correction; "FDR" indicates the false discovery rate; "Test AUC" is the area under the ROC curve computed on the test set; and "Cancer cor" indicates over-expression in cancer tissues.

TABLE 15

| Rank | Order num | Unigene ID | P value | FDR | Test AUC | Cancer cor | Gene description |
|---|---|---|---|---|---|---|---|
| 1 | 3059 | Hs.771 | <0.1 | <0.01 | 0.96 | −1 | gb:NM_002863.1/DEF = *Homo sapiens* phosphorylase, /UG = Hs.771 phosphorylase, glycogen; liver |
| 2 | 13862 | Hs.66744 | <0.1 | <0.01 | 0.96 | 1 | Consensus includes gb:X99268.1/DEF = H./FL = gb:NM_000474.1 |
| 3 | 13045 | Hs.173094 | <0.1 | <0.01 | 1 | −1 | Consensus includes gb:AI096375/FEA = EST |
| 4 | 5759 | Hs.66052 | <0.1 | <0.01 | 0.97 | −1 | gb:NM_001775.1/DEF = *Homo sapiens* CD38 |
| 5 | 18621 | Hs.42824 | <0.1 | <0.01 | 0.95 | −1 | gb:NM_018192.1/DEF = *Homo sapiens* hypothetical |
| 6 | 3391 | Hs.139851 | <0.1 | <0.01 | 0.94 | −1 | gb:NM_001233.1/DEF = *Homo sapiens* caveolin |
| 7 | 18304 | Hs.34045 | <0.1 | <0.01 | 0.95 | 1 | gb:NM_017955.1/DEF = *Homo sapiens* hypothetical |
| 8 | 14532 | Hs.37035 | <0.1 | <0.01 | 1 | 1 | Consensus includes gb:AI738662/FEA = EST |
| 9 | 3577 | Hs.285754 | 0.1 | 0.01 | 1 | −1 | Consensus includes gb:BG170541/FEA = EST |
| 10 | 9010 | Hs.180446 | 0.1 | 0.01 | 1 | 1 | gb:L38951.1/DEF = *Homo sapiens* importin |
| 11 | 13497 | Hs.71465 | 0.1 | 0.01 | 1 | −1 | Consensus includes gb:AA639705/FEA = EST |
| 12 | 19488 | Hs.17752 | 0.1 | 0.01 | 1 | 1 | gb:NM_0159000.1/DEF = *Homo sapiens* phosph phospholipase A1alpha/FL = gb:AF035268.1 |
| 13 | 8838 | Hs.237825 | 0.1 | 0.01 | 1 | 1 | gb:AF069765.1/DEF = *Homo sapiens* signal gb:NM_006947.1 |
| 14 | 14347 | Hs.170250 | 0.1 | 0.01 | 1 | 1 | Consensus includes gb:K02403.1/DEF = Human |
| 15 | 2300 | Hs.69469 | 0.2 | 0.01 | 1 | 1 | gb:NM_0063600.1/DEF = *Homo sapiens* dendritic |
| 16 | 10973 | Hs.77899 | 0.2 | 0.01 | 1 | −1 | gb:Z24727.1/DEF = *H. sapiens* tropomyosin |
| 17 | 11073 | Hs.0 | 0.2 | 0.01 | 1 | 1 | gb:Z25434.1/DEF = *H. sapiens* protein-serinethreonine |
| 18 | 22193 | Hs.165337 | 0.2 | 0.01 | 1 | −1 | Consensus includes gb:AW971415/FE |
| 19 | 12742 | Hs.237506 | 0.2 | 0.01 | 1 | −1 | Consensus includes gb:AK023253.1/DEF= |
| 20 | 21823 | Hs.9614 | 0.3 | 0.01 | 1 | 1 | Consensus includes gb:AA191576/FEA = EST |
| 21 | 13376 | Hs.246885 | 0.3 | 0.01 | 1 | −1 | Consensus includes gb:W87466/FEA = EST |
| 22 | 6182 | Hs.77899 | 0.3 | 0.01 | 1 | −1 | gb:NM_000366.1/DEF = *Homo sapiens* tropomyosin |
| 23 | 3999 | Hs.1162 | 0.4 | 0.02 | 1 | 1 | gb:NM_002118.1/DEF = *Homo sapiens* major II, DM beta/FL = gb:NM_002118.1 gb:U15085.1 |
| 24 | 1776 | Hs.168670 | 0.7 | 0.03 | 1 | −1 | gb:NM_002857.1/DEF = *Homo sapiens* peroxisomal gb:AB018541.1 |
| 25 | 4046 | Hs.82568 | 0.7 | 0.03 | 1 | −1 | gb:NM_000784.1/DEF = *Homo sapiens* cytochrome cerebrotendinous xanthomatosis), polypeptide |
| 26 | 6924 | Hs.820 | 0.8 | 0.03 | 1 | 1 | gb:NM_004503.1/DEF = *Homo sapiens* homeo |
| 27 | 2957 | Hs.1239 | 0.9 | 0.03 | 1 | −1 | gb:NM_0011500.1 /DEF = *Homo sapiens* alanyl/DB_XREF = gi:4502094/UG = Hs.1239 alanyl |
| 28 | 5699 | Hs.78406 | 1.3 | 0.05 | 1 | −1 | gb:NM_003558.1/DEF = *Homo sapiens* phosphatidylinositol phosphate 5-kinase, type I, beta/FL = gb:NM |
| 29 | 19167 | Hs.9238 | 1.4 | 0.05 | 1 | −1 | gb:NM_024539.1/DEF = *Homo sapiens* hypothetical |
| 30 | 4012 | Hs.172851 | 1.4 | 0.05 | 1 | −1 | gb:NM_001172.2/DEF = *Homo sapiens* arginase, gb:D86724.1 gb:U75667.1 gb:U82256.1 |

TABLE 15-continued

| Rank | Order num | Unigene ID | P value | FDR | Test AUC | Cancer cor | Gene description |
|---|---|---|---|---|---|---|---|
| 31 | 9032 | Hs.80658 | 1.4 | 0.05 | 1 | −1 | gb:U94592.1/DEF = Human uncoupling protein gb:U82819.1 gb:U94592.1 |
| 32 | 15425 | Hs.20141 | 1.5 | 0.05 | 1 | 1 | Consensus includes gb:AK0009700.1/DEF= |
| 33 | 14359 | Hs.155956 | 1.6 | 0.05 | 1 | −1 | Consensus includes gb:NM_000662.1/DEF = acetyltransferase)/FL = gb: NM_000662.1 |
| 34 | 6571 | Hs.89691 | 1.6 | 0.05 | 1 | 1 | gb:NM_021139.1/DEF = *Homo sapiens* UDP polypeptide B4/FL = gb:NM_021139.1 gb:AF0642000.1 |
| 35 | 13201 | Hs.301552 | 1.8 | 0.05 | 1 | 1 | Consensus includes gb:AK000478.1/DEF= |
| 36 | 21754 | Hs.292911 | 1.8 | 0.05 | 1 | −1 | Consensus includes gb:AI378979/FEA = EST |
| 37 | 5227 | Hs.31034 | 2 | 0.05 | 1 | −1 | Consensus includes gb:AL360141.1/DEF= |
| 38 | 18969 | Hs.20814 | 2.1 | 0.06 | 1 | 1 | gb:NM_015955.1/DEF = *Homo sapiens* CGI |
| 39 | 17907 | Hs.24395 | 2.2 | 0.06 | 1 | 1 | gb:NM_004887.1/DEF = *Homo sapiens* small small inducible cytokine subfamily B (Cys |
| 40 | 3831 | Hs.77695 | 2.3 | 0.06 | 1 | 1 | gb:NM_014750.1/DEF = *Homo sapiens* KIAA0008 |
| 41 | 10519 | Hs.4975 | 2.4 | 0.06 | 0.98 | 1 | gb:D82346.1/DEF = *Homo sapiens* mRNA |
| 42 | 2090 | Hs.150580 | 2.4 | 0.06 | 0.97 | −1 | gb:AF083441.1/DEF = *Homo sapiens* SUI1 |
| 43 | 9345 | Hs.75244 | 2.6 | 0.06 | 0.97 | −1 | gb:D87461.1/DEF = Human mRNA for KIAA0271 |
| 44 | 3822 | Hs.36708 | 2.7 | 0.06 | 0.97 | 1 | gb:NM_001211.2/DEF = *Homo sapiens* budding uninhibited by benzimidazoles 1 (yeast homolog) |
| 45 | 17999 | Hs.179666 | 2.9 | 0.06 | 0.97 | −1 | gb:NM_018478.1/DEF = *Homo sapiens* uncharacterized HSMNP1/FL = gb:BC001105.1 gb:AF220191.1 |
| 46 | 5070 | Hs.118140 | 2.9 | 0.06 | 0.96 | 1 | gb:NM_014705.1/DEF = *Homo sapiens* KIAA0716 |
| 47 | 20627 | Hs.288462 | 3 | 0.06 | 0.98 | −1 | gb:NM_025087.1/DEF = *Homo sapiens* hypothetical |
| 48 | 14690 | Hs.110826 | 3 | 0.06 | 0.99 | 1 | Consensus includes gb:AK027006.1/DEF= |
| 49 | 18137 | Hs.9641 | 3 | 0.06 | 0.98 | 1 | gb:NM_015991.1/DEF = *Homo sapiens* complement component 1, q subcomponent, alpha polypeptide-1 |
| 50 | 9594 | Hs.182278 | 3 | 0.06 | 0.98 | −1 | gb:BC000454.1/DEF = *Homo sapiens*, cal/FL = gb:BC000454.1 |

From Table 15, the combined criteria give an AUC of 1 between 8 and 40 genes. This indicates that subsets of up to 40 genes taken in the order of the criteria have a high predictive power. However, genes individually can also be judged for their predictive power by estimating p values. P values provide the probability that a gene is a random meaningless gene. A threshold can be set on that p value, e.g. 0.05.

Using the Bonferroni correction ensures that p values are not underestimated when a large number of genes are tested. This correction penalizes p values in proportion to the number of genes tested. Using 10*N probes (N=number of genes) the number of genes that score higher than all probes are significant at the threshold 0.1. Eight such genes were found with the combined criterion, while 26 genes were found with a p value<1.

It may be useful to filter out as many genes as possible before ranking them in order to avoid an excessive penalty. When the genes were filtered with the criterion that the the standard deviation should exceed twice the mean (a criterion not involving any knowledge of how useful this gene is to predict cancer). This reduced the gene set to N'=571, but there were also only 8 genes at the significance level of 0.1 and 22 genes had p value<1.

The 8 first genes found by this method are given in Table 16. Genes over-expressed in cancer are under Rank 2, 7, and 8 (underlined). The remaining genes are under-expressed.

TABLE 16

| Rank | Unigene ID | Description and findings |
|---|---|---|
| 1 | Hs.771 | Phosphorylase, glycogen; liver (Hers disease, glycogen storage disease type VI) (PYGL). |
| 2 | Hs.66744 | B-HLH DNA binding protein. H-twist. |
| 3 | Hs.173094 | KIAA1750 |
| 4 | Hs.66052 | CD38 antigen (p45) |
| 5 | Hs.42824 | FLJ10718 hypothetical protein |
| 6 | Hs.139851 | Caveolin 2 (CAV2) |
| 7 | Hs.34045 | FLJ20764 hypothetical protein |
| 8 | Hs.37035 | Homeo box HB9 |

Genes were ranked using the Pearson correlation criterion, see Table 17, with disease progression coded as Normal=1, Dysplasia=2, Grade3=3, Grade4=4. The p values are smaller than in the genes of Table 15, but the AUCs are worse. Three Febbo genes were found, corresponding to genes ranked $6^{th}$, $7^{th}$ and $34^{th}$.

TABLE 17

| Rank | Order num | Unigene ID | Pvalue | FDR | Test AUC | Cancer cor | Febbo | Gene description |
|---|---|---|---|---|---|---|---|---|
| 1 | 6519 | Hs.243960 | <0.1 | <0.0003 | 0.85 | −1 | 0 | gb:NM_016250.1/DEF = *Homo s* |
| 2 | 9457 | Hs.128749 | <0.1 | <0.0003 | 0.93 | 1 | 0 | Consensus includes gb:AI796120 |
| 3 | 9976 | Hs.103665 | <0.1 | <0.0003 | 0.89 | −1 | 0 | gb:BC004300.1/DEF = *Homo sapiens*, |
| 4 | 9459 | Hs.128749 | | <0.0003 | 0.87 | 1 | 0 | gb:AF047020.1/DEF = *Homo sapiens* gb:NM_014324.1 |

TABLE 17-continued

| Rank | Order num | Unigene ID | Pvalue | FDR | Test AUC | Cancer cor | Febbo | Gene description |
|---|---|---|---|---|---|---|---|---|
| 5 | 9458 | Hs.128749 | <0.1 | <0.0003 | 0.89 | 1 | 0 | Consensus includes gb:AA888 |
| 6 | 12337 | Hs.7780 | <0.1 | <0.0003 | 0.96 | 1 | 1 | Consensus includes gb:AV715767 |
| 7 | 893 | Hs.226795 | <0.1 | <0.0003 | 0.97 | −1 | 1 | gb:NM_000852.2/DEF = *Homo sapiens* |
| 8 | 19589 | Hs.45140 | <0.1 | <0.0003 | 0.98 | −1 | 0 | gb:NM_021637.1/DEF = *Homo sapiens* |
| 9 | 11911 | Hs.279009 | <0.1 | <0.0003 | 0.98 | −1 | 0 | Consensus includes gb:AI653730 |
| 10 | 17944 | Hs.279905 | <0.1 | <0.0003 | 0.96 | 1 | 0 | gb:NM_016359.1/DEF = *Homo sapiens* gb:AF290612.1 gb:AF090915.1 |
| 11 | 9180 | Hs.239926 | <0.1 | <0.0003 | 0.96 | −1 | 0 | Consensus includes gb:AV704962 |
| 12 | 18122 | Hs.106747 | <0.1 | <0.0003 | 0.96 | −1 | 0 | gb:NM_021626.1/DEF = *Homo sapiens* protein/FL = gb:AF282618.1 gb:NM_ |
| 13 | 12023 | Hs.74034 | <0.1 | <0.0003 | 0.96 | −1 | 0 | Consensus includes gb:AU14739 |
| 14 | 374 | Hs.234642 | <0.1 | <0.0003 | 0.96 | −1 | 0 | Cluster Incl. 74607:za55a01.s1 |
| 15 | 12435 | Hs.82432 | <0.1 | <0.0003 | 0.96 | −1 | 0 | Consensus includes b:AA135522 |
| 16 | 18598 | Hs.9728 | <0.1 | <0.0003 | 0.96 | −1 | 0 | gb:NM_016608.1/DEF = *Homo sapiens* |
| 17 | 3638 | Hs.74120 | <0.1 | <0.0003 | 0.97 | −1 | 0 | gb:NM_006829.1/DEF = *Homo sapiens* |
| 18 | 5150 | Hs.174151 | <0.1 | <0.0003 | 0.97 | −1 | 0 | gb:NM_001159.2/DEF = *Homo sapiens* |
| 19 | 1889 | Hs.195850 | <0.1 | <0.0003 | 0.97 | −1 | 0 | gb:NM_000424.1/DEF = *Homo sapiens*/DB_XREF = gi:4557889/UG = Hs. |
| 20 | 3425 | Hs.77256 | <0.1 | <0.0003 | 0.97 | 1 | 0 | gb:NM_004456.1/DEF = *Homo sapiens*/FL = gb:U61145.1 gb:NM_004456.1 |
| 21 | 5149 | Hs.174151 | <0.1 | <0.0003 | 0.96 | −1 | 0 | gb:AB046692.1/DEF = *Homo sapiens* |
| 22 | 4351 | Hs.303090 | <0.1 | <0.0003 | 0.97 | −1 | 0 | Consensus includes gb:N26005 |
| 23 | 4467 | Hs.24587 | <0.1 | <0.0003 | 0.97 | −1 | 0 | gb:NM_005864.1/DEF = *Homo sapiens*/FL = gb:AB001466.1 gb:NM_005864.1 |
| 24 | 12434 | Hs.250723 | <0.1 | <0.0003 | 0.96 | −1 | 0 | Consensus includes gb:BF968134 |
| 25 | 12809 | Hs.169401 | <0.1 | <0.0003 | 0.95 | 1 | 0 | Consensus includes gb:AI358867 |
| 26 | 7082 | Hs.95197 | <0.1 | <0.0003 | 0.95 | −1 | 0 | gb:AB015228.1/DEF = *Homo sapiens* gb:AB015228.1 |
| 27 | 18659 | Hs.73625 | <0.1 | <0.0003 | 0.95 | 1 | 0 | gb:NM_005733.1/DEF = *Homo sapiens* (rabkinesin6)/FL = gb:AF070672.1 |
| 28 | 13862 | Hs.66744 | <0.1 | <0.0003 | 0.98 | 1 | 0 | Consensus includes gb:X99268.1 syndrome)/FL = gb:NM_000474 |
| 29 | 3059 | Hs.771 | <0.1 | <0.0003 | 0.98 | −1 | 0 | gb:NM_002863.1/DEF = *Homo sapiens*/DB_XREF = gi:4506352/UG = Hs. |
| 30 | 15294 | Hs.288649 | <0.1 | <0.0003 | 0.98 | 1 | 0 | Consensus includes gb:AK0 |
| 31 | 9325 | Hs.34853 | <0.1 | <0.0003 | 0.99 | −1 | 0 | Consensus includes gb:AW157094 |
| 32 | 18969 | Hs.20814 | <0.1 | <0.0003 | 0.98 | 1 | 0 | gb:NM_015955.1/DEF = *Homo sapiens* |
| 33 | 4524 | Hs.65029 | <0.1 | <0.0003 | 0.96 | −1 | 0 | gb:NM_002048.1/DEF = *Homo sapiens* |
| 34 | 1908 | Hs.692 | <0.1 | <0.0003 | 0.97 | 1 | 1 | gb:NM_002354.1/DEF = *Homo sapiens* signal transducer 1/FL = gb:M32306.1 |
| 35 | 11407 | Hs.326776 | <0.1 | <0.0003 | 0.96 | −1 | 0 | gb:AF180519.1/DEF = *Homo sapiens* cds/FL = gb:AF180519.1 |
| 36 | 19501 | Hs.272813 | <0.1 | <0.0003 | 0.96 | −1 | 0 | gb:NM_017434.1/DEF = *Homo sapiens* |
| 37 | 11248 | Hs.17481 | <0.1 | <0.0003 | 0.96 | −1 | 0 | gb:AF063606.1/DEF = *Homo sapiens* |
| 38 | 5894 | Hs.80247 | <0.1 | <0.0003 | 0.95 | −1 | 0 | gb:NM_000729.2/DEF = *Homo sapiens* |
| 39 | 19455 | Hs.26892 | <0.1 | <0.0003 | 0.96 | −1 | 0 | gb:NM_018456.1/DEF = *Homo sapie* BM040/FL = gb:AF217516.1 gb: |
| 40 | 3448 | Hs.169401 | <0.1 | <0.0003 | 0.96 | 1 | 0 | Consensus includes gb:N33009 |
| 41 | 6666 | Hs.90911 | <0.1 | <0.0003 | 0.96 | −1 | 0 | gb:NM_004695.1/DEF = *Homo sapiens*/UG = Hs.90911 solute carrier family |
| 42 | 6924 | Hs.820 | <0.1 | <0.0003 | 0.98 | 1 | 0 | gb:NM_004503.1/DEF = *Homo sapiens* |
| 43 | 2169 | Hs.250811 | <0.1 | <0.0003 | 0.98 | −1 | 0 | Consensus includes gb:BG169673 |
| 44 | 12168 | Hs.75318 | <0.1 | <0.0003 | 0.98 | −1 | 0 | Consensus includes gb:AL565074 |
| 45 | 18237 | Hs.283719 | <0.1 | <0.0003 | 0.98 | −1 | 0 | gb:NM_018476.1/DEF = *Homo sapiens* HBEX2/FL = gb:AF220189.1 gb: |
| 46 | 5383 | Hs.182575 | <0.1 | <0.0003 | 0.98 | −1 | 0 | Consensus includes gb:BF223679 |
| 47 | 19449 | Hs.17296 | <0.1 | <0.0003 | 0.99 | −1 | 0 | gb:NM_023930.1/DEF = *Homo sapiens* gb:BC001929.1 gb:NM_023930.1 |
| 48 | 4860 | Hs.113082 | <0.1 | <0.0003 | 0.99 | −1 | 0 | gb:NM_014710.1/DEF = *Homo sapiens* |
| 49 | 17714 | Hs.5216 | <0.1 | <0.0003 | 0.99 | 1 | 0 | gb:NM_014038.1/DEF = *Homo sapiens* |
| 50 | 12020 | Hs.137476 | <0.1 | <0.0003 | 0.97 | −1 | 0 | Consensus includes gb:AL582836 |

The dataset is rich in potential biomarkers. To find the most promising markers, criteria were designed to implement prior knowledge of disease severity and zonal information. This allowed better separation of relevant genes from genes that coincidentally well separate the data, thus alleviating the problem of overfitting. To further reduce the risk of overfitting, genes were selected that were also found in an independent study Table 15. Those genes include well-known proteins involved in prostate cancer and some potentially interesting targets.

Example 5: Prostate Cancer Gene Expression Microarray Data (11-2004)

Separations of class pairs were performed for "tumor (G3+4) vs. all other tissues". These separations are relatively easy and can be performed with fewer than 10 genes, however, hundreds of significant genes were identified.

Separations of "G4 vs. all others", "Dysplasia vs. all others", and "Normal vs. all others" are less easy (best AUCs between 0.75 and 0.85) and separation of "G3 vs. all others" is almost impossible in this data (AUC around 0.5). With over 100 genes, G4 can be separated from all other tissues with about 10% BER. Hundreds of genes separate G4 from all other tissues significantly, yet one cannot find a good separation with just a few genes.

Separations of "TZG4 vs. PZG4", "Normal vs. Dysplasia" and "G3 vs. G4" are also hard. 10×10-fold CV yielded very poor results. Using leave-one out CV and under 20 genes, we separated some pairs of classes: $ERR_{TZG4/PZG4}\approx 6\%$, $ERR_{NL/Dys}$ and $ERRG_{3/G4}\approx 9\%$. However, due to the small sample sizes, the significance of the genes found for those separations is not good, shedding doubt on the results.

Pre-operative PSA was found to correlate poorly with clinical variables ($R^2$=0.316 with cancer volume, 0.025 with prostate weight, and 0.323 with CAvol/Weight). Genes were found with activity that correlated with pre-operative PSA either in BPH samples or G34 samples or both. Possible connections of those genes were found to cancer and/or prostate in the literature, but their relationship to PSA is not documented. Genes associated to PSA by their description do not have expression values correlated with pre-operative PSA. This illustrates that gene expression coefficients do not necessarily reflect the corresponding protein abundance.

Genes were identified that correlate with cancer volume in G3+4 tissues and with cure/fail prognosis. Neither are statistically significant, however, the gene most correlated with cancer volume has been reported in the literature as connected to prostate cancer. Prognosis information can be used in conjunction with grade levels to determine the significance of genes. Several genes were identified for separating G4 from non-G4 and G3 from G3 in the group the samples of patients with the poor prognosis in regions of lowest expression values.

The following experiments were performed using data consisting of a matrix of 87 lines (samples) and 22283 columns (genes) obtained from an Affymetrix U133A GeneChip®. The distributions of the samples of the microarray prostate cancer study are the same as those listed in Table 12.

Genes were selected on the basis of their individual separating power, as measured by the AUC (area under the ROC curve that plots sensitivity vs. specificity).

Similarly "random genes" that are genes obtained by permuting randomly the values of columns of the matrix are ranked. Where N is the total number of genes (here, N=22283, 40 times more random genes than real genes are used to estimate p values accurately ($N_r$=40*22283). For a given AUC value A, $n_r(A)$ is the number of random genes that have an AUC larger than A. The p value is estimated by the fraction of random genes that have an AUC larger than A, i.e.:

$$Pvalue=(1+n_r(A))/N_r$$

Adding 1 to the numerator avoids having zero p values for the best ranking genes and accounts for the limited precision due to the limited number of random genes. Because the pvalues of a large number of genes are measured simultaneously, correction must be applied to account for this multiple testing. As in the previous example, the simple Bonferroni correction is used:

$$Bonferroni\_pvalue=N*(1+n_r(A))/N_r$$

Hence, with a number of probes that is 40 times the number of genes, the p values are estimated with an accuracy of 0.025.

For a given gene of AUC value A, one can also compute the false discovery rate (FDR), which is an estimate of the ratio of the number of falsely significant genes over the number of genes called significant. Where n(A) is the number of genes found above A, the FDR is computed as the ratio of the p value (before Bonferroni correction) and the fraction of real genes found above A:

$$FDR=pvalue*N/n(A)=((1+n_r(A))*N)/(n(A)*N_r).$$

Linear ridge regression classifiers (similar to SVMs) were trained with 10×10-fold cross validation, i.e., the data were split 100 times into a training set and a test set and the average performance and standard deviation were computed. In these experiments, the feature selection is performed within the cross-validation loop. That is, a separate featuring ranking is performed for each data split. The number of features are varied and a separate training/testing is performed for each number of features. Performances for each number of features are averaged to plot performance vs. number of features. The ridge value is optimized separately for each training subset and number of features, using the leave-one-out error, which can be computed analytically from the training error. In some experiments, the 10×10-fold cross-validation was done by leave-one-out cross-validation. Everything else remains the same.

Using the rankings obtained for the 100 data splits of the machine learning experiments (also called "bootstraps"), average gene ranks are computed. Average gene rank carries more information in proportion to the fraction of time a gene was always found in the top N ranking genes. This last criterion is sometimes used in the literature, but the number of genes always found in the top N ranking genes appears to grows linearly with N.

The following statistics were computed for cross-validation (10 times 10-fold or leave-one-out) of the machine learning experiments:

AUC mean: The average area under the ROC curve over all data splits.

AUC stdev: The corresponding standard deviation. Note that the standard error obtained by dividing stdev by the square root of the number of data splits is inaccurate because sampling is done with replacements and the experiments are not independent of one another.

BER mean: The average BER over all data splits. The BER is the balanced error rate, which is the average of the error rate of examples of the first class and examples of the second class. This provides a measure that is not biased toward the most abundant class.

BER stdev: The corresponding standard deviation.

Pooled AUC: The AUC obtained using the predicted classification values of all the test examples in all data splits altogether.

Pooled BER: The BER obtained using the predicted classification values of all the test examples in all data splits altogether.

Note that for leave-one-out CV, it does not make sense to compute BER-mean because there is only one example in each test set. Instead, the leave-one-out error rate or the pooled BER is computed.

High classification accuracy (as measured by the AUC) can be achieved a small number of genes (3 or more) to provide an AUC above 0.90. If the experimental repeats were independent, the standard error of the mean obtained by dividing the standard deviation by 10 could be used as an error bar. A more reasonable estimate of the error bar may be obtained by dividing it by three to account for the dependencies between repeats.

The genes listed in the following tables are ranked according to their individual AUC computed with all the data. The first column is the rank, followed by the Gene ID (order number in the data matrix), and the Unigene ID. The column "Under Expr" is +1 if the gene is underexpressed and −1 otherwise. AUC is the ranking criterion. Pval is the pvalue computed with random genes as explained above. FDR is the false discovery rate. "Ave. rank" is the average rank of the feature when subsamples of the data are taken in a 10×10-fold cross-validation experiment in Tables 18, 21, 23, 25 & 27 and with leave-one-out in Tables 29, 31 & 33.

In the test to separate tumors (cancer G3 and G4) from other tissues, the results show that it is relatively easy to separate tumor from other tissues. The list of the top 50 tumor genes, both overexpressed and underexpressed in cancer, is shown in Table 18. A complete listing of the top 200 tumor genes is provided in FIGS. 4*a*-4*d*. The three best genes, Gene IDs no. 9457, 9458 and 9459 all have same Unigene ID. Additional description about the top three genes is provided in Table 19 below.

TABLE 18

| Rank | Gene ID | Unigene ID | Under Expr. In tumor | AUC | Pval | FDR | Ave. rank |
|---|---|---|---|---|---|---|---|
| 1 | 9459 | Hs.128749 | −1 | 0.9458 | 0.02 | 0.025 | 1.16 |
| 2 | 9458 | Hs.128749 | −1 | 0.9425 | 0.02 | 0.012 | 2.48 |
| 3 | 9457 | Hs.128749 | −1 | 0.9423 | 0.02 | 0.0083 | 2.51 |
| 4 | 11911 | Hs.279009 | 1 | 0.9253 | 0.02 | 0.0062 | 4.31 |
| 5 | 12337 | Hs.7780 | −1 | 0.9125 | 0.02 | 0.005 | 7.23 |
| 6 | 983 | Hs.226795 | 1 | 0.9076 | 0.02 | 0.0042 | 8.42 |
| 7 | 18792 | Hs.6823 | −1 | 0.9047 | 0.02 | 0.0036 | 10.04 |
| 8 | 1908 | Hs.692 | −1 | 0.9044 | 0.02 | 0.0031 | 10.03 |
| 9 | 19589 | Hs.45140 | 1 | 0.9033 | 0.02 | 0.0028 | 10.47 |
| 10 | 6519 | Hs.243960 | 1 | 0.8996 | 0.02 | 0.0025 | 12.67 |
| 11 | 17714 | Hs.5216 | −1 | 0.8985 | 0.02 | 0.0023 | 13.93 |
| 12 | 18122 | Hs.106747 | 1 | 0.8985 | 0.02 | 0.0021 | 13.86 |
| 13 | 18237 | Hs.283719 | 1 | 0.8961 | 0.02 | 0.0019 | 16.61 |
| 14 | 3059 | Hs.771 | 1 | 0.8942 | 0.02 | 0.0018 | 17.86 |
| 15 | 16533 | Hs.110826 | −1 | 0.8921 | 0.02 | 0.0017 | 19.44 |
| 16 | 18598 | Hs.9728 | 1 | 0.8904 | 0.02 | 0.0016 | 19.43 |
| 17 | 12434 | Hs.250723 | 1 | 0.8899 | 0.02 | 0.0015 | 20.19 |
| 18 | 4922 | Hs.55279 | 1 | 0.884 | 0.02 | 0.0014 | 27.23 |
| 19 | 13862 | Hs.66744 | −1 | 0.8832 | 0.02 | 0.0013 | 30.59 |
| 20 | 9976 | Hs.103665 | 1 | 0.8824 | 0.02 | 0.0012 | 30.49 |
| 21 | 18835 | Hs.44278 | −1 | 0.8824 | 0.02 | 0.0012 | 30.94 |
| 22 | 3331 | Hs.54697 | 1 | 0.8802 | 0.02 | 0.0011 | 32.35 |
| 23 | 18969 | Hs.20814 | −1 | 0.8797 | 0.02 | 0.0011 | 35.89 |
| 24 | 9373 | Hs.21293 | −1 | 0.8786 | 0.02 | 0.001 | 35.52 |
| 25 | 15294 | Hs.288649 | −1 | 0.8786 | 0.02 | 0.001 | 35.69 |
| 26 | 4497 | Hs.33084 | 1 | 0.8776 | 0.02 | 0.00096 | 37.77 |
| 27 | 5001 | Hs.823 | −1 | 0.8765 | 0.02 | 0.00093 | 40.25 |
| 28 | 9765 | Hs.22599 | 1 | 0.8765 | 0.02 | 0.00089 | 39.32 |
| 29 | 4479 | Hs.198760 | 1 | 0.8759 | 0.02 | 0.00086 | 40.82 |
| 30 | 239 | Hs.198760 | 1 | 0.8749 | 0.02 | 0.00083 | 43.04 |
| 31 | 6666 | Hs.90911 | 1 | 0.8749 | 0.02 | 0.00081 | 42.53 |
| 32 | 12655 | Hs.10587 | 1 | 0.8749 | 0.02 | 0.00078 | 41.56 |
| 33 | 19264 | Hs.31608 | −1 | 0.8743 | 0.02 | 0.00076 | 44.66 |
| 34 | 5923 | Hs.171731 | 1 | 0.8738 | 0.02 | 0.00074 | 44.3 |
| 35 | 1889 | Hs.195850 | 1 | 0.8727 | 0.02 | 0.00071 | 46.1 |
| 36 | 21568 | Hs.111676 | 1 | 0.8716 | 0.02 | 0.00069 | 48.3 |
| 37 | 3264 | Hs.139336 | −1 | 0.8714 | 0.02 | 0.00068 | 51.17 |
| 38 | 14738 | Hs.8198 | 1 | 0.8706 | 0.02 | 0.00066 | 52.7 |
| 39 | 1867 | Hs.234680 | 1 | 0.8695 | 0.02 | 0.00064 | 52.99 |
| 40 | 4467 | Hs.24587 | 1 | 0.8695 | 0.02 | 0.00062 | 52.25 |
| 41 | 9614 | Hs.8583 | 1 | 0.8695 | 0.02 | 0.00061 | 53.62 |
| 42 | 18659 | Hs.73625 | −1 | 0.8692 | 0.02 | 0.0006 | 56.86 |
| 43 | 20137 | Hs.249727 | 1 | 0.8692 | 0.02 | 0.00058 | 55.2 |
| 44 | 12023 | Hs.74034 | 1 | 0.869 | 0.02 | 0.00057 | 55.69 |
| 45 | 12435 | Hs.82432 | 1 | 0.869 | 0.02 | 0.00056 | 56.63 |
| 46 | 14626 | Hs.23960 | −1 | 0.8687 | 0.02 | 0.00054 | 58.95 |
| 47 | 7082 | Hs.95197 | 1 | 0.8684 | 0.02 | 0.00053 | 56.27 |
| 48 | 15022 | Hs.110826 | −1 | 0.8679 | 0.02 | 0.00052 | 59.51 |
| 49 | 20922 | Hs.0 | −1 | 0.8679 | 0.02 | 0.00051 | 59.93 |
| 50 | 4361 | Hs.102 | 1 | 0.8673 | 0.02 | 0.0005 | 60.94 |

TABLE 19

| Gene ID | Description |
|---|---|
| 9457 | gb: AI796120 /FEA = EST /DB_XREF = gi: 5361583 /DB_XREF = est: wh42f03.x1 /CLONE = IMAGE: 2383421 /UG = Hs.128749 alphamethylacyl-CoA racemase /FL = gb: AF047020.1 gb: AF158378.1 gb: NM_014324.1 |
| 9458 | gb: AA888589 /FEA = EST /DB_XREF = gi: 3004264 /DB_XREF = est: oe68e10.s1 /CLONE = IMAGE: 1416810 /UG = Hs.128749 alphamethylacyl-CoA racemase /FL = gb: AF047020.1 gb: AF158378.1 gb: NM_014324.1 |
| 9459 | gb: AF047020.1 /DEF = *Homo sapiens* alpha-methylacyl-CoA racemase mRNA, complete cds. /FEA = mRNA /PROD = alpha-methylacyl-CoA racemase /DB_XREF = gi: 4204096 /UG = Hs.128749 alpha-methylacyl-CoA racemase /FL = gb: AF047020.1 gb: AF158378.1 gb: NM_014324.1 |

This gene has been reported in numerous papers including Luo, et al., *Molecular Carcinogenesis,* 33(1): 25-35 (January 2002); Luo J, et al., *Abstract Cancer Res.,* 62(8): 2220-6 (2002 Apr. 15).

Table 20 shows the separation with varying number of features for tumor (G3+4) vs. all other tissues.

TABLE 20

| | feat. num. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 16 | 32 | 64 | 128 |
| 100 * AUC | 92.28 | 93.33 | 93.83 | 94 | 94.33 | 94.43 | 94.1 | 93.8 | 93.43 | 93.53 | 93.45 | 93.37 | 93.18 | 93.03 |
| 100 * AUCstd | 11.73 | 10.45 | 10 | 9.65 | 9.63 | 9.61 | 10.3 | 10.54 | 10.71 | 10.61 | 10.75 | 10.44 | 11.49 | 11.93 |
| BER (%) | 14.05 | 13.1 | 12.6 | 10.25 | 9.62 | 9.72 | 9.75 | 9.5 | 9.05 | 9.05 | 9.7 | 9.6 | 10.12 | 9.65 |
| BERstd (%) | 13.51 | 12.39 | 12.17 | 11.77 | 9.95 | 10.06 | 10.15 | 10.04 | 9.85 | 10.01 | 10.2 | 10.3 | 10.59 | 10.26 |

Using the same experimental setup, separations were attempted for G4 from non G4, G3 from non G3, Dysplasia from non-dys and Normal from non-Normal. These separations were less successful than the above-described tests, indicating that G3, dysplasia and normal do not have molecular characteristics that distinguish them easily from all other samples. Lists of genes are provided in Tables 21-37.

Table 21 lists the top 10 genes separating Grade 4 prostate cancer (G4) from all others.

TABLE 21

| Rank | Gene ID | Unigene ID | Under Expr. In G4 | AUC | Pval | FDR | Ave. rank |
|---|---|---|---|---|---|---|---|
| 1 | 5923 | Hs.171731 | 1 | 0.9204 | 0.02 | 0.025 | 3.25 |
| 2 | 18122 | Hs.106747 | 1 | 0.9136 | 0.02 | 0.012 | 6.17 |
| 3 | 19573 | Hs.232165 | 1 | 0.9117 | 0.02 | 0.0083 | 7.92 |
| 4 | 893 | Hs.226795 | 1 | 0.9099 | 0.02 | 0.0062 | 7.22 |
| 5 | 9889 | Hs.137569 | 1 | 0.9093 | 0.02 | 0.005 | 8.8 |
| 6 | 19455 | Hs.26892 | 1 | 0.908 | 0.02 | 0.0042 | 10.54 |
| 7 | 19589 | Hs.45140 | 1 | 0.9074 | 0.02 | 0.0036 | 10.54 |
| 8 | 18598 | Hs.9728 | 1 | 0.9062 | 0.02 | 0.0031 | 10.83 |
| 9 | 6519 | Hs.243960 | 1 | 0.9037 | 0.02 | 0.0028 | 12.79 |
| 10 | 11175 | Hs.137569 | 1 | 0.9031 | 0.02 | 0.0025 | 13.46 |

Table 22 below provides the details for the top two genes of this group.

TABLE 22

| Gene ID | Description |
|---|---|
| 5923 | gb: NM_015865.1 /DEF = *Homo sapiens* solute carrier family 14 (urea transporter), member 1 (Kidd blood group) (SLC14A1), mRNA. /FEA = mRNA /GEN = SLC14A1 /PROD = RACH1 /DB_XREF = gi: 7706676 /UG = Hs.171731 solute carrier family 14 (urea transporter), member 1 (Kidd blood group) /FL = gb:U35735.1 gb: NM_015865.1 |
| 18122 | gb: NM_021626.1 /DEF = *Homo sapiens* serine carboxypeptidase 1 precursor protein (HSCP1), mRNA. /FEA = mRNA /GEN = HSCP1 /PROD = serine carboxypeptidase 1 precursor protein /DB_XREF = gi: 11055991 /UG = Hs.106747 serine carboxypeptidase 1 precursor protein /FL = gb: AF282618.1 gb: NM_021626.1 gb: AF113214.1 gb: AF265441.1 |

The following provide the gene descriptions for the top two genes identified in each separation:

Table 23 lists the top 10 genes separating Normal prostate versus all others.

TABLE 23

| Rank | Gene ID | Unigene ID | Under Expr. in Normal | AUC | Pval | FDR | Ave. Rank |
|---|---|---|---|---|---|---|---|
| 1 | 6519 | Hs.243960 | −1 | 0.886 | 0.02 | 0.025 | 1.3 |
| 2 | 3448 | Hs.169401 | 1 | 0.8629 | 0.02 | 0.012 | 4.93 |
| 3 | 17900 | Hs.8185 | −1 | 0.8601 | 0.02 | 0.0083 | 6.17 |
| 4 | 6666 | Hs.90911 | −1 | 0.8552 | 0.02 | 0.0062 | 6.59 |
| 5 | 893 | Hs.226795 | −1 | 0.8545 | 0.02 | 0.005 | 7.22 |
| 6 | 6837 | Hs.159330 | −1 | 0.8545 | 0.02 | 0.0042 | 8.05 |
| 7 | 374 | Hs.234642 | −1 | 0.8483 | 0.02 | 0.0036 | 9.69 |
| 8 | 9976 | Hs.103665 | −1 | 0.8458 | 0.02 | 0.0031 | 11.62 |
| 9 | 3520 | Hs.2794 | −1 | 0.8399 | 0.02 | 0.0028 | 15.29 |
| 10 | 3638 | Hs.74120 | −1 | 0.8357 | 0.02 | 0.0025 | 18.17 |

The top two genes from Table 23 are described in detail in Table 24.

TABLE 24

| Gene ID | Description |
|---|---|
| 6519 | gb: NM_016250.1 /DEF = *Homo sapiens* N-myc downstream-regulated gene 2 (NDRG2), mRNA. /FEA = mRNA /GEN = NDRG2 /PROD = KIAA1248 protein /DB_XREF = gi: 10280619 /UG = Hs.243960 N-myc downstream-regulated gene 2 /FL = gb: NM_016250.1 gb: AF159092. |
| 3448 | gb: N33009 /FEA = EST /DB_XREF = gi: 1153408 /DB_XREF = est: yy31f09.s1 /CLONE = IMAGE: 272873 /UG = Hs.169401 apolipoprotein E /FL = gb: BC003557.1 gb: M12529.1 gb: K00396.1 gb: NM_000041.1 |

Table 25 lists the top 10 genes separating G3 prostate cancer from all others.

TABLE 25

| Rank | Gene ID | Unigene ID | Under Expr. in G3 | AUC | Pval | FDR | Ave. rank |
|---|---|---|---|---|---|---|---|
| 1 | 18446 | Hs.283683 | −1 | 0.8481 | 1 | 1.5 | 2.14 |
| 2 | 2778 | Hs.230 | −1 | 0.8313 | 1 | 1.8 | 8.14 |
| 3 | 16102 | Hs.326526 | 1 | 0.8212 | 1 | 2.2 | 10.71 |
| 4 | 12046 | Hs.166982 | 1 | 0.817 | 1 | 2.1 | 15.14 |
| 5 | 9156 | Hs.3416 | −1 | 0.8158 | 1 | 1.8 | 14.71 |
| 6 | 9459 | Hs.128749 | −1 | 0.8158 | 1 | 1.5 | 20.43 |
| 7 | 21442 | Hs.71819 | −1 | 0.8158 | 1 | 1.3 | 13.86 |
| 8 | 6994 | Hs.180248 | −1 | 0.814 | 1 | 1.3 | 11.71 |
| 9 | 17019 | Hs.128749 | −1 | 0.8116 | 1 | 1.3 | 23.14 |
| 10 | 9457 | Hs.128749 | −1 | 0.8074 | 1 | 1.3 | 34.71 |

The top two genes listed in Table 25 are described in detail in Table 26.

TABLE 26

| Gene ID | Description |
|---|---|
| 18446 | gb: NM_020130.1 /DEF = *Homo sapiens* chromosome 8 open reading frame 4 (C8ORF4), mRNA. /FEA = mRNA /GEN = C8ORF4 /PROD = chromosome 8 open reading frame 4 /DB_XREF = gi: 9910147 /UG = Hs.283683 chromosome 8 open reading frame 4 /FL = gb: AF268037.1 gb: NM_020130.1 |
| 2778 | gb: NM_002023.2 /DEF = *Homo sapiens* fibromodulin (FMOD), mRNA. /FEA = mRNA /GEN = FMOD /PROD = fibromodulin precursor /DB_XREF = gi: 5016093 /UG = Hs.230 fibromodulin /FL = gb: NM_002023.2 |

Table 27 shows the top 10 genes separating Dysplasia from everything else.

TABLE 27

| Rank | Gene ID | Unigene ID | Under Expr. in dysplasia | AUC | Pval | FDR | Ave. rank |
|---|---|---|---|---|---|---|---|
| 1 | 5509 | Hs.178121 | −1 | 0.8336 | 0.15 | 0.15 | 4.53 |
| 2 | 4102 | Hs.75426 | −1 | 0.8328 | 0.15 | 0.075 | 4.31 |
| 3 | 10777 | Hs.101047 | 1 | 0.8319 | 0.17 | 0.058 | 5.6 |
| 4 | 18814 | Hs.319088 | 1 | 0.8189 | 0.45 | 0.11 | 10.95 |
| 5 | 4450 | Hs.154879 | 1 | 0.8168 | 0.5 | 0.1 | 11.57 |
| 6 | 14885 | Hs.2554 | 1 | 0.8164 | 0.53 | 0.088 | 18.04 |
| 7 | 10355 | Hs.169832 | 1 | 0.8126 | 0.63 | 0.089 | 14.3 |
| 8 | 5072 | Hs.122647 | −1 | 0.8063 | 0.72 | 0.091 | 26.77 |
| 9 | 3134 | Hs.323469 | −1 | 0.805 | 0.8 | 0.089 | 22.76 |
| 10 | 15345 | Hs.95011 | 1 | 0.8017 | 1 | 0.11 | 29.3 |

Table 28 provides the details for the top two genes listed in Table 27.

TABLE 28

| Gene ID | Description |
|---|---|
| 5509 | gb: NM_021647.1 /DEF = *Homo sapiens* KIAA0626 gene product (KIAA0626), mRNA. /FEA = mRNA /GEN = KIAA0626 /PROD = KIAA0626 gene product /DB_XREF = gi: 11067364 /UG = Hs.178121 KIAA0626 gene product /FL = gb: NM_021647.1 gb: AB014526.1 |
| 4102 | gb: NM_003469.2 /DEF = *Homo sapiens* secretogranin II (chromogranin C) (SCG2), mRNA. /FEA = mRNA /GEN = SCG2 /PROD = secretogranin II precursor /DB_XREF = gi: 10800415 /UG = Hs.75426 secretogranin II (chromogranin C) /FL = gb: NM_003469.2 gb: M25756.1 |

Due to the small sample sizes, poor performance was obtained with 10×10-fold cross-validation. To avoid this problem, leave-one-out cross-validation was used instead. In doing so, the average AUC for all repeats cannot be reported because there is only one test example in each repeat. Instead, the leave-one-out error rate and the pooled AUC are evaluated. However, all such pairwise separations are difficult to achieve with high accuracy and a few features.

Table 29 lists the top 10 genes separating G3 from G4. Table 30 provides the details for the top two genes listed.

TABLE 29

| Rank | Gene ID | Unigene ID | (+) Expr. in G4; (−) Expr. in G3 | AUC | Pval | FDR | Ave. rank |
|---|---|---|---|---|---|---|---|
| 1 | 19455 | Hs.26892 | −1 | 0.9057 | 0.45 | 0.45 | 1.09 |
| 2 | 11175 | Hs.137569 | −1 | 0.8687 | 1 | 1.8 | 2.95 |
| 3 | 9156 | Hs.3416 | −1 | 0.8653 | 1 | 1.4 | 4 |
| 4 | 18904 | Hs.315167 | 1 | 0.8653 | 1 | 1.1 | 4.71 |
| 5 | 9671 | Hs.98658 | 1 | 0.8636 | 1 | 0.99 | 5.45 |
| 6 | 2338 | Hs.62661 | −1 | 0.8586 | 1 | 0.96 | 6.64 |
| 7 | 2939 | Hs.82906 | 1 | 0.8586 | 1 | 0.82 | 7.46 |
| 8 | 450 | Hs.27262 | 1 | 0.8552 | 1 | 0.8 | 8.44 |
| 9 | 18567 | Hs.193602 | 1 | 0.8535 | 1 | 0.85 | 9.49 |
| 10 | 5304 | Hs.252136 | −1 | 0.8519 | 1 | 0.77 | 10.67 |

TABLE 30

| Gene ID | Description |
|---|---|
| 19455 | gb: NM_018456.1 /DEF = *Homo sapiens* uncharacterized bone marrow protein BM040 (BM040), mRNA. /FEA = mRNA /GEN = BM040/PROD = uncharacterized bone marrow protein BM040 /DB_XREF = gi: 8922098 /UG = Hs.26892 uncharacterized bone marrow protein BM040 /FL = gb: AF217516.1 gb: NM_018456.1 |
| 11175 | gb: AB010153.1 /DEF = *Homo sapiens* mRNA for p73H, complete cds. /FEA = mRNA /GEN = p73H /PROD = p73H /DB_XREF = gi: 3445483 /UG = Hs.137569 tumor protein 63 kDa with strong homology to p53 /FL = gb: AB010153.1 |

Table 31 lists the top 10 genes for separating Normal prostate from Dysplasia. Details of the top two genes for performing this separation are provided in Table 32.

TABLE 31

| Rank | Gene ID | Unigene ID | (−) Expr. in NL; (+) Expr. in Dys | AUC | Pval | FDR | Ave. rank |
|---|---|---|---|---|---|---|---|
| 1 | 4450 | Hs.154879 | −1 | 0.9037 | 0.05 | 0.05 | 1.09 |
| 2 | 10611 | Hs.41682 | 1 | 0.8957 | 0.075 | 0.037 | 2.02 |
| 3 | 9048 | Hs.177556 | −1 | 0.8743 | 0.45 | 0.15 | 3.17 |
| 4 | 18069 | Hs.103147 | −1 | 0.8717 | 0.57 | 0.14 | 4.06 |
| 5 | 7978 | Hs.20815 | −1 | 0.8583 | 1 | 0.23 | 5.56 |
| 6 | 6837 | Hs.159330 | −1 | 0.8556 | 1 | 0.21 | 6.37 |
| 7 | 7229 | Hs.71816 | −1 | 0.8463 | 1 | 0.34 | 8.03 |
| 8 | 21059 | Hs.283753 | 1 | 0.8449 | 1 | 0.3 | 9.51 |
| 9 | 15345 | Hs.95011 | −1 | 0.8436 | 1 | 0.29 | 9.94 |
| 10 | 2463 | Hs.91251 | −1 | 0.8369 | 1 | 0.38 | 11.78 |

TABLE 32

| Gene ID | Description |
|---|---|
| 4450 | gb: NM_022719.1 /DEF = *Homo sapiens* DiGeorge syndrome critical region gene DGSI (DGSI), mRNA. /FEA = mRNA /GEN = DGSI /PROD = DiGeorge syndrome critical region gene DGSIprotein /DB_XREF = gi: 13027629 /UG = Hs.154879 DiGeorge syndrome critical region gene DGSI /FL =gb: NM_022719.1 |
| 10611 | gb: U30610.1 /DEF = Human CD94 protein mRNA, complete cds. /FEA = mRNA /PROD = CD94 protein /DB_XREF = gi: 1098616 /UG = Hs.41682 killer cell lectin-like receptor subfamily D, member 1 /FL = gb: U30610.1 gb: NM_002262.2 |

Table 33 lists the top 10 genes for separating peripheral zone G4 prostate cancer from transition zone G4 cancer. Table 34 provides the details for the top two genes in this separation.

TABLE 33

| Rank | Gene ID | Unigene ID | (−) Expr. in TZ; (+) Expr. In PZ | AUC | Pval | FDR | Ave. rank |
|---|---|---|---|---|---|---|---|
| 1 | 4654 | Hs.194686 | 1 | 0.9444 | 1 | 1.2 | 1.1 |
| 2 | 14953 | Hs.306423 | 1 | 0.9306 | 1 | 1.1 | 2.45 |
| 3 | 929 | Hs.279949 | −1 | 0.9167 | 1 | 1.7 | 4 |
| 4 | 6420 | Hs.274981 | 1 | 0.9167 | 1 | 1.3 | 4.84 |
| 5 | 7226 | Hs.673 | 1 | 0.9167 | 1 | 1 | 5.69 |
| 6 | 18530 | Hs.103291 | 1 | 0.9167 | 1 | 0.86 | 6.68 |
| 7 | 6618 | Hs.2563 | 1 | 0.9097 | 1 | 1.1 | 7.82 |
| 8 | 16852 | Hs.75626 | 1 | 0.9097 | 1 | 0.93 | 8.91 |
| 9 | 19242 | Hs.12692 | 1 | 0.9097 | 1 | 0.82 | 9.78 |
| 10 | 6106 | Hs.56294 | 1 | 0.9063 | 1 | 1 | 10.75 |

TABLE 34

| Gene ID | Description |
|---|---|
| 4654 | gb: NM_003951.2 /DEF = *Homo sapiens* solute carrier family 25 (mitochondrial carrier, brain), member 14 (SLC25A14), transcript variant long, nuclear gene encoding mitochondrial protein, mRNA. /FEA = mRNA /GEN = SLC25A14 /PROD = solute carrier family 25, member 14, isoformUCP5L /DB_XREF = gi: 6006039 /UG = Hs.194686 solute carrier family 25 (mitochondrial carrier, brain), member 14 /FL = gb: AF155809.1 gb: AF155811.1 gb: NM_022810.1 gb: AF078544.1 gb: NM_003951.2 |
| 14953 | gb: AK002179.1 /DEF = *Homo sapiens* cDNA FLJ11317 fis, clone PLACE1010261, moderately similar to SEGREGATION DISTORTER PROTEIN. /FEA = mRNA /DB_XREF = gi: 7023899 /UG = Hs.306423 *Homo sapiens* cDNA FLJ11317 fis, clone PLACE1010261, moderately similar to SEGREGATION DISTORTER PROTEIN |

As stated in an earlier discussion, PSA is not predictive of tissue malignancy. There is very little correlation of PSA and cancer volume (R2=0.316). The R2 was also computed for PSA vs. prostate weight (0.025) and PSA vs. CA/Weight (0.323). PSA does not separate well the samples in malignancy categories. In this data, there did not appear to be any correlation between PSA and prostate weight.

A test was conducted to identify the genes most correlated with PSA, in BPH samples or in G3/4 samples, which were found to be genes 11541 for BPH and 14523 for G3/4. The details for these genes are listed below in Table 35.

TABLE 35

| Gene ID | Description |
|---|---|
| 11541 | gb: AB050468.1 /DEF = *Homo sapiens* mRNA for membrane glycoprotein LIG-1, complete cds. /FEA = mRNA /GEN = lig-1 /PROD = membrane glycoprotein LIG-1 /DB_XREF = gi: 13537354 /FL = gb: AB050468.1 |
| 14523 | gb: AL046992 /FEA = EST /DB_XREF = gi: 5435048 /DB_XREF = est: DKFZp586L0417_r1 /CLONE = DKFZp586L0417 /UG = Hs.184907 G protein-coupled receptor 1 /FL = gb: NM_005279.1 |
| 5626 | gb: NM_006200.1 /DEF = *Homo sapiens* proprotein convertase subtilisinkexin type 5 (PCSK5), mRNA. /FEA = mRNA /GEN = PCSK5 /PROD = proprotein convertase subtilisinkexin type 5 /DB_XREF = gi: 11321618 /UG = Hs.94376 proprotein convertase subtilisinkexin type 5 /FL = gb: NM_006200.1 gb: U56387.2 |

Gene 11541 shows no correlation with PSA in G3/4 samples, whereas gene 14523 shows correlation in BPH samples. Thus, 11541 is possibly the result of some overfitting due to the fact that pre-operative PSAs are available for only 7 BPH samples. Gene 14523 appears to be the most correlated gene with PSA in all samples. Gene 5626, also listed in Table 35, has good correlation coefficients ($R_{BPH}^2$=0.44, $R_{G34}^2$=0.58).

Reports are found in the published literature indicating that G Protein-coupled receptors such as gene 14523 are important in characterizing prostate cancer. See, e.g. L. L. Xu, et al. *Cancer Research* 60, 6568-6572, Dec. 1, 2000.

For comparison, genes that have "prostate specific antigen" in their description (none had PSA) were considered:

Gene 4649: gb:NM_001648.1 /DEF=*Homo sapiens* kallikrein 3, (prostate specific antigen) (KLK3), mRNA. /FEA=mRNA /GEN=KLK3 /PROD=kallikrein 3, (prostate specific antigen) /DB_XREF=gi:4502172 /UG=Hs.171995 kallikrein 3, (prostate specific antigen) /FL=gb:BC005307.1 gb:NM_001648.1 gb:U17040.1 gb:M26663.1; and Gene 4650: gb:U17040.1 /DEF=Human prostate specific antigen precursor mRNA, complete cds. /FEA=mRNA /PROD=prostate specific antigen precursor /DB_XREF=gi:595945 /UG=Hs.171995 kallikrein 3, (prostate specific antigen) /FL=gb:BC005307.1 gb:NM_001648.1 gb:U17040.1 gb:M26663.1. Neither of these genes had activity that correlates with preoperative PSA.

Another test looked at finding genes whose expression correlate with cancer volume in grade 3 and 4 cancer tissues. However, even the most correlated gene is not found significant with respect to the Bonferroni-corrected pvalue (pval=0.42). Table 36 lists the top nine genes most correlated with cancer volume in G3+4 samples. The details of the top gene are provided in Table 37.

TABLE 36

| Rank | Gene ID | Unigene ID | Sign corr. | Pearson | Pval | FDR |
|---|---|---|---|---|---|---|
| 1 | 8851 | Hs.217493 | −1 | 0.6582 | 0.43 | 0.43 |
| 2 | 6892 | Hs.2868 | −1 | 0.6282 | 1 | 0.51 |
| 3 | 21353 | Hs.283803 | 1 | 0.6266 | 1 | 0.36 |
| 4 | 7731 | Hs.182507 | −1 | 0.6073 | 1 | 0.53 |
| 5 | 4853 | Hs.86958 | −1 | 0.6039 | 1 | 0.46 |
| 6 | 622 | Hs.14449 | −1 | 0.5958 | 1 | 0.48 |
| 7 | 8665 | Hs.74497 | 1 | 0.5955 | 1 | 0.41 |
| 8 | 13750 | Hs.2014 | −1 | 0.579 | 1 | 0.6 |
| 9 | 15413 | Hs.177961 | −1 | 0.5775 | 1 | 0.56 |

TABLE 37

| Gene ID | Description |
|---|---|
| 8851 | gb: M62898.1 /DEF = Human lipocortin (LIP) 2 pseudogene mRNA, complete cdslike region. /FEA = mRNA /DB_XREF = gi: 187147 /UG = Hs.217493 annexin A2 /FL = gb: M62898.1 |

A lipocortin has been described in U.S. Pat. No. 6,395,715 entitled "Uteroglobin gene therapy for epithelial cell cancer". Using RT-PCR, under-expression of lipocortin in cancer compared to BPH has been reported by Kang J S et al., *Clin Cancer Res.* 2002 January; 8(1):117-23.

Example 6: Prostate Cancer Comparative Study of Stamey Data (12-2004)

In this example sets of genes obtained with two different data sets are compared. Both data sets were generated by Dr. Thomas A. Stamey of Stanford University, the first in 2001 using Affymetrix HuGeneFL probe arrays ("Stamey 2001"), the second in 2003 using Affymetrix U133A chip ("Stamey 2003"). After matching the genes in both arrays, a set of about 2000 common genes was used in the study. Gene selection was performed on the data of both studies independently, then the resulting gene sets were compared. A remarkable agreement was found. In addition, classifiers were trained on one dataset and tested on the other. In the separation tumor (G3/4) vs. all other tissues, classification accuracies comparable to those obtained in previous reports were obtained by cross-validation on the second study: 10% error can be achieved with 10 genes (on the independent test set of the first study); by cross-validation, there was 8% error. In the separation BPH vs. all other tissues, there was also 10% error with 10 genes. The cross-validation results for BPH were overly optimistic (only one error), however this was not unexpected since there were only 10 BPH samples in the second study. Tables of genes were selected by consensus of both studies.

The Stamey 2001 (first) data set consisted of 67 samples from 26 patients. The Affymetrix HuGeneFL probe arrays used have 7129 probes, representing 6500 genes. The composition of the 2001 dataset (number of samples in parenthesis) is summarized in Table 38. Several grades and zones are represented, however, all TZ samples are BPH (no cancer), all CZ samples are normal (no cancer). Only the PZ contains a variety of samples. Also, many samples came from the same tissues.

TABLE 38

| Zone | Histological classification |
|---|---|
| CZ (3) | NL (3) |
| PZ (46) | NL (5) |
| | Stroma (1) |
| | Dysplasia (3) |
| | G3 (10) |
| | G4 (27) |
| TZ (18) | BPH (18) |
| Total 67 | |

The Stamey 2003 (second) dataset consisted of a matrix of 87 lines (samples) and 22283 columns (genes) obtained from an Affymetrix U133A chip. The distribution of the samples of the microarray prostate cancer study is given as been provided previously in Table 12.

Genes that had the same Gene Accession Number (GAN) in the two arrays HuGeneFL and U133A were selected. The selection was further limited to descriptions that matched reasonably well. For that purpose, a list of common words was created. A good match corresponds to a pair of description having at least one common word, excluding these common words, short words (fewer that 3 letters) and numbers. The resulting set included 2346 genes.

Because the data from both studies had previously been normalized using different methods, it was re-normalized using the routine provided below. Essentially, the data is translated and scaled, the log is taken, the lines and columns are normalized; the outlier values are squashed. This preprocessing was selected based on a visual examination of the data.

For the 2001 study, a bias of −0.08 was used. For the 2003 study, the bias was 0. Visual examination revealed that these values stabilize the variance of both classes reasonably well.

The set of 2346 genes was ranked using the data of both studies independently, with the area under the ROC curve (AUC) being used as the ranking criterion. P values were computed with the Bonferroni correction and False discovery rate (FDR) was calculated.

Both rankings were compared by examining the correlation of the AUC scores. Cross-comparisons were done by selecting the top 50 genes in one study and examining how "enriched" in those genes were the lists of top ranking genes from the other study, varying the number of genes. This can be compared to a random ranking. For a consensus ranking, the genes were ranked according to their smallest score in the two studies.

Reciprocal tests were run in which the data from one study was used for training of the classifier which was then tested on the data from the other study. Three different classifiers were used: Linear SVM, linear ridge regression, and Golub's classifier (analogous to Naïve Bayes). For every test, the features selected with the training set were used. For comparison, the consensus features were also used.

Separation of all tumor samples (G3 and G4) from all others was performed, with the G3 and G4 samples being grouped into the positive class and all samples grouped into the negative class. The top 200 genes in each study of Tumor G3/4 vs. others are listed in the tables in FIGS. 5*a*-5*o* for the 2001 study and the 2003 study. The genes were ranked in two ways, using the data of the first study (2001) and using the data of the second study (2003)

Most genes ranking high in one study also rank high in the other, with some notable exceptions. These exceptions may correspond to probes that do not match in both arrays even though their gene identification and descriptions match. They may also correspond to probes that "failed" to work in one array.

Table 39 lists the top 50 genes resulting from the feature ranking by consensus between the 2001 study and the 2003 study Tumor G3/4 vs. others. A listing of the top 200 genes, including the 50 genes in Table 39, is provided in FIG. 6*a*-6*g*. Ranking was performed according to a score that is the minimum of score0 and scorel.

TABLE 39

| Rk | Unigene ID | Over Expr | Scor | Rk0 | Score0 | Rk1 | Score1 | Description |
|---|---|---|---|---|---|---|---|---|
| 1 | Hs.195850 | −1 | 0.8811 | 7 | 0.8811 | 2 | 0.8813 | Human keratin type II (58 kD) mRNA |
| 2 | Hs.171731 | −1 | 0.8754 | 1 | 0.9495 | 3 | 0.8754 | Human RACH1 (RACH1) mRNA |
| 3 | Hs.65029 | −1 | 0.8647 | 8 | 0.8802 | 5 | 0.8647 | Human gas1 gene |
| 4 | Hs.771 | −1 | 0.8532 | 15 | 0.8532 | 1 | 0.8953 | Human liver glycogen phosphorylase mRNA |
| 5 | Hs.79217 | 1 | 0.8532 | 16 | 0.8532 | 7 | 0.855 | Human pyrroline 5-carboxylate reductase mRNA |
| 6 | Hs.198760 | −1 | 0.8495 | 19 | 0.8495 | 4 | 0.869 | *H. sapiens* NF-H gene |
| 7 | Hs.174151 | −1 | 0.8448 | 4 | 0.8892 | 10 | 0.8448 | Human aldehyde oxidase (hAOX) mRNA |
| 8 | Hs.44 | −1 | 0.841 | 12 | 0.8685 | 14 | 0.841 | Human nerve growth factor (HBNF-1) mRNA |
| 9 | Hs.3128 | 1 | 0.841 | 2 | 0.9081 | 15 | 0.841 | Human RNA polymerase II subunit (hsRPB8) mRNA |
| 10 | Hs.34853 | −1 | 0.8314 | 5 | 0.8892 | 20 | 0.8314 | Human Id-related helix-loop-helix protein Id4 mRNA |
| 11 | Hs.113 | −1 | 0.8217 | 13 | 0.8658 | 24 | 0.8217 | Human cytosolic epoxide hydrolase mRNA |
| 12 | Hs.1813 | −1 | 0.8201 | 31 | 0.827 | 25 | 0.8201 | *Homo sapiens* synaptic vesicle amine transporter (SVAT) mRNA |
| 13 | Hs.2006 | −1 | 0.8099 | 40 | 0.8099 | 23 | 0.8255 | Human glutathione transferase M3 (GSTM3) mRNA |
| 14 | Hs.76224 | −1 | 0.8083 | 28 | 0.836 | 39 | 0.8083 | Human extracellular protein (S1-5) mRNA |
| 15 | Hs.27311 | 1 | 0.8056 | 11 | 0.8694 | 42 | 0.8056 | Human transcription factor SIM2 long form mRNA |
| 16 | Hs.77546 | −1 | 0.8008 | 14 | 0.8649 | 46 | 0.8008 | Human mRNA for KIAA0172 gene |
| 17 | Hs.23838 | 1 | 0.7982 | 50 | 0.7982 | 22 | 0.8287 | Human neuronal DHP-sensitive |
| 18 | Hs.10755 | −1 | 0.7955 | 53 | 0.7955 | 17 | 0.8373 | Human mRNA for dihydropyrimidinase |
| 19 | Hs.2785 | −1 | 0.7911 | 24 | 0.8414 | 51 | 0.7911 | *H. sapiens* gene for cytokeratin 17 |
| 20 | Hs.86978 | 1 | 0.7748 | 75 | 0.7748 | 70 | 0.7777 | *H. sapiens* mRNA for prolyl oligopeptidase |
| 21 | Hs.2025 | −1 | 0.7744 | 3 | 0.9027 | 73 | 0.7744 | Human transforming growth factor-beta 3 (TGF-beta3) mRNA |
| 22 | Hs.30054 | 1 | 0.7734 | 45 | 0.8054 | 74 | 0.7734 | Human coagulation factor V mRNA |
| 23 | Hs.155591 | −1 | 0.7723 | 52 | 0.7973 | 76 | 0.7723 | Human forkhead protein FREAC-1 mRNA |
| 24 | Hs.237356 | −1 | 0.7712 | 81 | 0.7712 | 61 | 0.7846 | Human intercrine-alpha (hIRH) mRNA |
| 25 | Hs.211933 | −1 | 0.7707 | 70 | 0.7784 | 80 | 0.7707 | Human (clones HT-[125 |
| 26 | Hs.75746 | 1 | 0.7691 | 78 | 0.7721 | 81 | 0.7691 | Human aldehyde dehydrogenase 6 mRNA |
| 27 | Hs.155597 | −1 | 0.7676 | 85 | 0.7676 | 78 | 0.7712 | Human adipsin/complement factor D mRNA |
| 28 | Hs.75111 | −1 | 0.7669 | 21 | 0.8432 | 85 | 0.7669 | Human cancellous bone osteoblast mRNA for serin protease with IGF-binding motif |
| 29 | Hs.75137 | −1 | 0.7664 | 37 | 0.8108 | 86 | 0.7664 | Human mRNA for KIAA0193 gene |
| 30 | Hs.76307 | −1 | 0.7658 | 86 | 0.7658 | 12 | 0.841 | Human mRNA for unknown product |
| 31 | Hs.79059 | −1 | 0.7653 | 44 | 0.8063 | 87 | 0.7653 | Human transforming growth factor-beta type III receptor (TGF-beta) mRNA |
| 32 | Hs.1440 | 1 | 0.7632 | 36 | 0.8108 | 92 | 0.7632 | Human gamma amino butyric acid (GABAA) receptor beta-3 subunit mRNA |
| 33 | Hs.66052 | −1 | 0.7626 | 60 | 0.7883 | 93 | 0.7626 | 1299-1305 |
| 34 | Hs.155585 | −1 | 0.7626 | 6 | 0.8838 | 94 | 0.7626 | Human transmembrane receptor (ror2) mRNA |
| 35 | Hs.153322 | −1 | 0.7589 | 35 | 0.8126 | 98 | 0.7589 | Human mRNA for phospholipase C |
| 36 | Hs.77448 | −1 | 0.7583 | 87 | 0.7658 | 99 | 0.7583 | Human pyrroline-5-carboxylate dehydrogenase (P5CDh) mRNA |
| 37 | Hs.190787 | −1 | 0.7568 | 94 | 0.7568 | 69 | 0.7782 | Human tissue inhibitor of metalloproteinase 4 mRNA |
| 38 | Hs.172851 | −1 | 0.7567 | 48 | 0.8 | 101 | 0.7567 | Human arginase type II mRNA |
| 39 | Hs.85146 | −1 | 0.7562 | 20 | 0.8459 | 103 | 0.7562 | Human erythroblastosis virus oncogene homolog 2 (ets-2) mRNA |

TABLE 39-continued

| Rk | Unigene ID | Over Expr | Scor | Rk0 | Score0 | Rk1 | Score1 | Description |
|---|---|---|---|---|---|---|---|---|
| 40 | Hs.10526 | −1 | 0.7556 | 17 | 0.8532 | 105 | 0.7556 | Human smooth muscle LIM protein (h-SmLIM) mRNA |
| 41 | Hs.81412 | −1 | 0.7551 | 61 | 0.7865 | 106 | 0.7551 | Human mRNA for KIAA0188 gene |
| 42 | Hs.180107 | 1 | 0.7541 | 96 | 0.7541 | 44 | 0.8024 | Human mRNA for DNA polymerase beta |
| 43 | Hs.245188 | −1 | 0.7519 | 56 | 0.7937 | 113 | 0.7519 | Human tissue inhibitor of metalloproteinases-3 mRNA |
| 44 | Hs.56145 | 1 | 0.7508 | 55 | 0.7946 | 114 | 0.7508 | Human mRNA for NB thymosin beta |
| 45 | Hs.620 | −1 | 0.7497 | 18 | 0.8523 | 115 | 0.7497 | Human bullous pemphigoid antigen (BPAG1) mRNA |
| 46 | Hs.83450 | −1 | 0.7495 | 101 | 0.7495 | 67 | 0.7803 | *Homo sapiens* laminin-related protein (LamA3) mRNA |
| 47 | Hs.687 | −1 | 0.7495 | 102 | 0.7495 | 26 | 0.8195 | Human lung cytochrome P450 (IV subfamily) BI protein |
| 48 | Hs.75151 | 1 | 0.7486 | 104 | 0.7486 | 8 | 0.8545 | Human GTPase activating protein (rap1GAP) mRNA |
| 49 | Hs.283749 | −1 | 0.7468 | 106 | 0.7468 | 110 | 0.7524 | Human mRNA for RNase 4 |
| 50 | Hs.74566 | −1 | 0.7433 | 26 | 0.8369 | 125 | 0.7433 | Human mRNA for dihydro-pyrimidinase related protein-3 |

Training of the classifier was done with the data from one study while testing used the data from the other study. The results are similar for the three classifiers that were tried: SVM, linear ridge regression and Golub classifier. Approximately 90% accuracy can be achieved in both cases with about 10 features. Better "cheating" results are obtained with the consensus features. This serves to validate the consensus features, but the performances cannot be used to predict the accuracy of a classifier on new data. An SVM was trained using the two best features of the 2001 study and the sample of the 2001 study as the training data. The samples from the 2003 study were used as test data to achieve an error rate of 16% is achieved. The tumor and non-tumor samples are well separated, but that, in spite of normalization, the distributions of the samples is different between the two studies.

The definitions of the statistics used in the various rankings are provided in Table 40.

TABLE 40

| Statistic | Description |
|---|---|
| AUC | Area under the ROC curve of individual genes, using training tissues. The ROC curve (receiver operating characteristic) is a plot of the sensitivity (error rate of the "positive" class) vs. the specificity (error rate of the "negative" class). Insignificant genes have an AUC close to 0.5. Genes with an AUC closer to one are overexpressed in cancer. Genes with an AUC closer to zero are underexpressed. |
| pval | Pvalue of the AUC, used as a test statistic to test the equality of the median of the two population (cancer and non-cancer.) The AUC is the Mann-Withney statistic. The test is equivalent to the Wilcoxon rank sum test. Small pvalues shed doubt on the null hypothesis of equality of the medians. Hence smaller values are better. To account to the multiple testing the pvalue may be Bonferroni corrected by multiplying it by the number of genes 7129. |
| FDR | False discovery rate of the AUC ranking. An estimate of the fraction of insignificant genes in the genes ranking higher than a given gene. It is equal the pvalue multiplied by the number of genes and divided by the rank, i.e., pvalue · n/r |
| Fisher | Fisher statistic characterizing the multiclass discriminative power for the histological classes (normal, BPH, dysplasia, grade 3, and grade 4.) The Fisher statistic is the ratio of the between-class variance to the within-class variance. Higher values indicate better discriminative power. The Fisher statistic can be interpreted as a signal to noise ratio. It is computed with training data only. |
| Pearson | Pearson correlation coefficient characterizing "disease progression", with histological classes coded as 0 = normal, 1 = BPH, 2 = dysplasia, 3 = grade 3, and 4 = grade 4.) A value close to 1 indicates a good correlation with disease progression. |
| FC | Fold change computed as the ratio of the average cancer expression values to the avarage of the other expression values. It is computed with training data only. A value near one indicates an insignificant gene. A large value indicates a gene overexpressed in cancer; a small value an underexpressed gene. |
| Mag | Gene magnitude. The average of the largest class expression value (cancer or other) relative to that of the ACTB housekeeping gene. It is computed with training data only. |
| tAUC | AUC of the genes matched by probe and or description in the test set. It is computed with test data only, hence not all genes have a tAUC. |

Example 7: Genes Overexpressed in Prostate Cancer

Because they may be more readily detected using common analytical techniques, e.g., microarrays and RT-PCR assays, and therefore, make better biomarker candidates for separating tumor from normal in research and clinical applications, genes that are overexpressed in prostate cancer were the focus of this analysis. RFE-SVM was performed, with training using the Stamey 2003 data (Table 12) and testing using a dataset created by merging five publicly available datasets containing prostate cancer samples processed with an Affymetrix chip (chip U95A). The merged public datasets produced a set of 164 samples (102 tumor and 62 normal), which will be referred to as the "public data" or "public dataset", or, alternatively, the "test dataset". The probes in the U95A (~12,000 probes) chip were matched with those of the U133A chip used in the 87 sample, 2003 Stamey study (28 tumor, 49 normal, ~22000 probes) to obtain approximately 7,000 common probes.

To form the public dataset, several datasets were downloaded from the Internet (Table 41 and Table 42). The Oncomine website, on the Worldwide Web at oncomine.org, is a valuable resource to identify datasets, but the original data was downloaded from the author's websites. Table 41 lists prostate cancer datasets and Table 42 is multi-study or normal samples.

TABLE 41

| Name | Chip | Samples | Genes | Ref. | Comment |
|---|---|---|---|---|---|
| Febbo | U95A v2 | 52 tumor 50 normal | ~12600 | [2] | Have data. |
| Dhana | cDNA | Misc ~40 | 10000 | [21] | Difficult to understand and read data. |
| LaTulippe | U95A | 3 normal, 23 localized tumor and 9 metastatic | ~12600 | [3] | Have data. |
| LuoJH | Hu35k | 15 tumor, 15 normal | ~9000 | [4] | Have data. Some work to understand it. |
| Magee | Hu6800 Ge | 8 primary, 3 metastasic and 4 nonmalignant | 6800 | [5] | Not worth it. |
| Welsh | U95A | 9 normal, 24 localized and 1 metastatic, and 21 cell lines | ~12000 | [6] | Looks OK. |
| LuoJ | cDNA | 16 tumor 9 BPH | ~6500 | [7] | Probably not worth it. |

TABLE 42

| Name | Chip | Samples | Genes | Ref. | Comment |
|---|---|---|---|---|---|
| Rama | Hu6800 Hu35kSubA | 343 primary and 12 metastatic; include a few prostate | ~16000 | [8] | Looks interesting. Complex data. |
| Hsiao | HuGenFL | 59 normal | ~10000 | [9] | Looks good. Same chips as Stamey 2001. |
| Su | U95a | 175 tumors, of which 24 prostate | ~12600 | [10] | Looks good. |

The datasets of Febbo, LaTulippe, Welsh, and Su are formatted as described below because they correspond to a large gene set from the same Affymetrix chip U95A.

Febbo Dataset

File used:

Prostate_TN_final0701_allmeanScale.res

A data matrix of 102 lines (52 tumors, 50 normal) and 12600 columns was generated.

All samples are tumor or normal. No clinical data is available.

LaTulippe dataset—

The data was merged from individual text files (e.g. MET1_U95Av2.txt), yielding to a data matrix of 35 lines (3 normal, 23 localized, 9 metastatic) and 12626 columns. Good clinical data is available.

Welsh Dataset

The data was read from file:

GNF_prostate data CR61_5974.xls

A matrix of 55 lines (9 normal, 27 tumor, 19 cell lines) and 12626 lines was generated. Limited clinical data is available. Some inconsistencies in tissue labeling between files.

Su Dataset

The data was read from: classification data.txt

A matrix of 174 lines (174 tumors of which 24 prostate) and 12533 lines was obtained. No clinical data available.

The initial analysis revealed that the Su and Welsh data were identical, so the Su dataset was removed.

TABLE 43

| | Febbo | LaTulippe | Welsh | Su | Stamey 2003 |
|---|---|---|---|---|---|
| Febbo | 12600 | 12600 | 12600 | 12533 | 312 |
| LaTulippe | 12600 | 12626 | 12626 | 12533 | 312 |
| Welsh | 12600 | 12626 | 12626 | 12533 | 312 |
| Su | 12533 | 12533 | 12533 | 12533 | 271 |
| Stamey | 312 | 312 | 312 | 271 | 22283 |

From Table 43 it is apparent that the four selected datasets used the same microarray (Affymetrix U95A GeneChip®). The Stamey 2003 data, however, used a different microarray (Affymetrix U133A GeneChip®), so only those probes common to both chip sets were selected. Affymetrix has published a reference on its web site (Affymetrix.com) that provides the correspondence between probes of different chip sets based upon their sequences.

Unigene IDs were used to identify 7350 corresponding probes on the two different chips. Using the best match from Affymetrix, 9512 probes were found to correspond, however, a number of these probes did not have Unigene IDs, or had mismatched Unigene IDs. Of the matched probes using both comparisons, 6839 have the same Unigene IDs. This latter set of 6839 probes was used.

The final characteristics of publicly available data are summarized in Table 44. Each dataset from the public data was preprocessed individually using the script my_normalize, provided below. A bias of zero was used for all normalizations.

```
function X=my_normalize(X, bias)
  if nargin<2, bias=0; end
  mini=min(min(X));
  maxi=max(max(X));
  X=(X−mini)/(maxi−mini)+bias;
  idx=find(X<=0);
  X(idx)=Inf;
  epsi=min(min(X));
  X(idx)=epsi;
  X=log(X);
  X=med_normalize(X);
  X=med_normalize(X');
  X=med_normalize(X);
  X=med_normalize(X');
  X=tan h(0.1*X);
function X=med_normalize(X)
  mu=mean(X,2);
  One=ones(size(X,2),1);
  XM=X−mu(:,One);
  S=median(abs(XM),2);
  X=XM./S (:,One);
```

The public data was then merged and the feature set was reduced to n. The Stamey data was normalized with my_normalize script (above) after this reduction of feature set. The public data was re-normalized with my_normalize script after this reduction of feature set.

TABLE 44

| Data source | Histological classification | Number of samples |
|---|---|---|
| Febbo | Normal | 50 |
| | Tumor | 52 |
| LaTulippe | Normal | 3 |
| | Tumor | 23 |
| Welsh | Normal | 9 |
| | Tumor | 27 |
| Total | | 164 |

Figure 7:
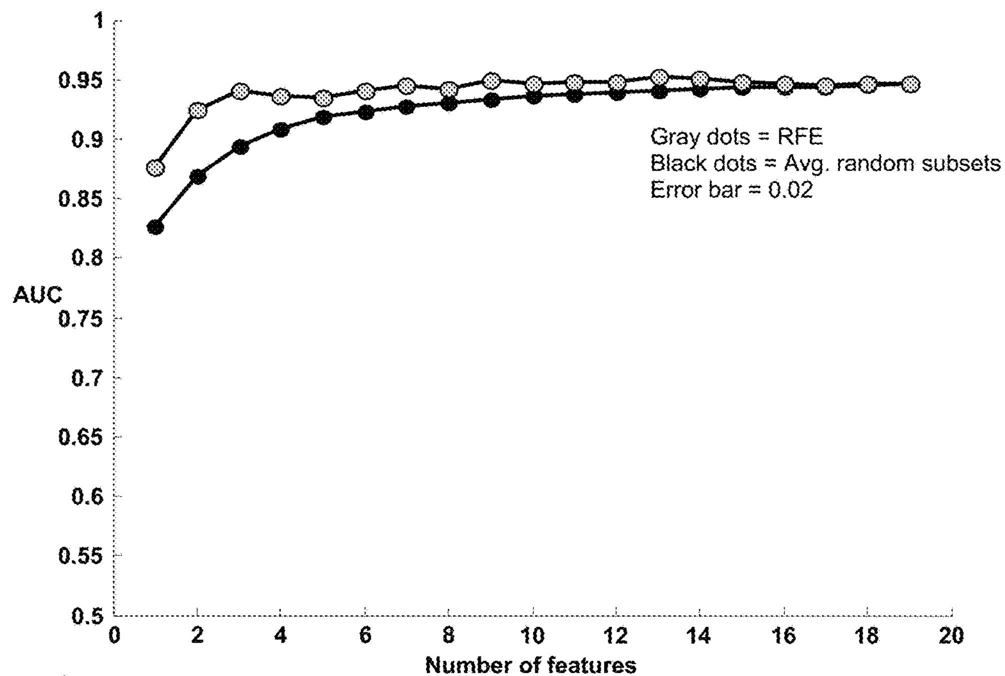
FIG. 7 is a plot of performance as a function of number of genes selected.
Figure 8:
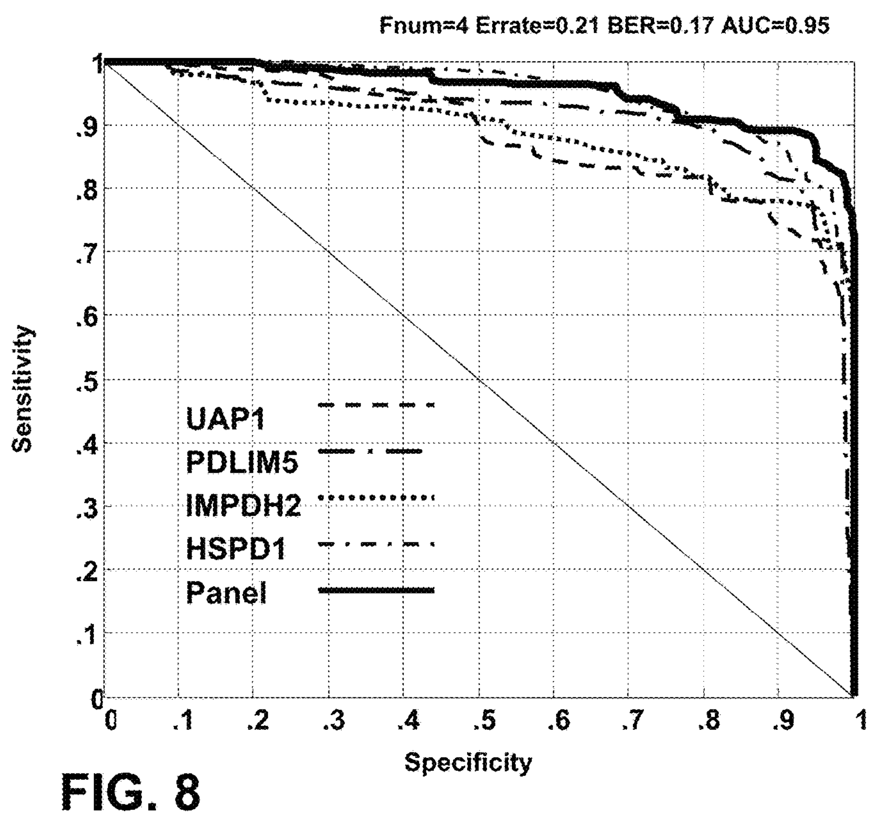
FIG. 8 is a plot of the ROC curves for the 3 top RFE selected genes and the ROC of the combination, on test data.

The 19 top ranking genes that were identified by RFE-SVM are listed in Tables 45a and 45b. Table 45a provides the analysis results corresponding to the original UniGene number, Affymetrix probe ID, gene symbol and description. Table 45b associates the SEQ ID NO. with the original (archival) UniGene number, the current UniGene number, and the more detailed "target description" obtained from the Affymetric GeneChip® annotation spreadsheet under the column under the same title. (The Affymetrix annotation spreadsheets for the U95 and U133 are publicly available on the World Wide Web at Affymetrix.com, and are incorporated herein by reference.) FIG. 7 is a plot of the performances of all 19 predictors obtained by the RFE method, as a function of the number of genes in the gene subset (gray dots). The analysis revealed that on average any combination of 4 or more from the 19 top ranked genes yielded an area under the curve (AUC) of 0.9 on test data. According to these results, an AUC of 0.94±0.02 can be obtained with as few as 2 to 4 genes. The top ranking combination of three genes as determined by RFE-SVM yielded AUC=0.94. This combination consisted of genes are AgX-1/UAP1 (Hs.21293), DKFZp564 (Hs.7780), and IMPDH2 (Hs.75432). While each of these genes performs well individually, their combination (identified as "Panel") outperforms any individual gene (FIG. 8).

TABLE 45a

| UniGene | AUC | pval | FDR | Fisher | Pearson | FC | Mag | tAUC | Affy probe | Symbol/Description |
|---|---|---|---|---|---|---|---|---|---|---|
| Hs.7780 | 0.9135 | 4.50E−11 | 2.00E−07 | 29.91 | 0.69 | 2.16 | 0.077 | 0.9037 | 212412_at | DKFZp564 (PDLIM5)/ *Homo sapiens* mRNA; cDNA DKFZp564A072 (from clone DKFZp564A072) |
| Hs.21293 | 0.8888 | 6.00E−10 | 7.40E−07 | 19.3 | 0.69 | 2.31 | 0.0012 | 0.877 | 209340_at | UAP1/AGX-1/*Homo sapiens* AgX-1 antigen mRNA |
| Hs.79037 | 0.8829 | 1.10E−09 | 1.00E−06 | 14.9 | 0.64 | 1.65 | 0.00059 | 0.944 | 200807_s_at | HSPD1/*Homo sapiens* heat shock 60 kD protein 1 (chaperonin) |
| Hs.30054 | 0.8657 | 5.80E−09 | 2.20E−06 | 9.82 | 0.59 | 4.11 | 0.0029 | 0.6932 | 204714_s_at | F5/*Homo sapiens* coagulation factor V (proaccelerin) |
| Hs.75432 | 0.8641 | 6.70E−09 | 2.30E−06 | 9.79 | 0.54 | 2.19 | 0.00045 | 0.8803 | 201892_s_at | IMPDH2/*Homo sapiens* IMP (inosine monophosphate) dehydrogenase 2 |
| Hs.699 | 0.8593 | 1.10E−08 | 3.10E−06 | 8.5 | 0.59 | 1.62 | 0.37 | 0.8131 | 200967_at | PPIB/*Homo sapiens* peptidylprolyl isomerase B (cyclophilin B) |
| Hs.1708 | 0.855 | 1.60E−08 | 3.80E−06 | 11.07 | 0.56 | 1.72 | 0.14 | 0.8053 | 200910_at | CCT3/*Homo sapiens* chaperonin containing TCP1 |
| Hs.69469 | 0.8485 | 2.90E−08 | 6.00E−06 | 8.47 | 0.59 | 1.61 | 0.12 | 0.7948 | 202231_at | GA17/*Homo sapiens* dendritic cell protein |

TABLE 45a-continued

| UniGene | AUC | pval | FDR | Fisher | Pearson | FC | Mag | tAUC | Affy probe | Symbol/Description |
|---|---|---|---|---|---|---|---|---|---|---|
| Hs.82280 | 0.848 | 3.00E−08 | 6.00E−06 | 9.05 | 0.58 | 2.1 | 0.089 | 0.8596 | 204319_s_at | RGS10/*Homo sapiens* regulator of G-protein signaling 10 |
| Hs.79217 | 0.8421 | 5.10E−08 | 8.70E−06 | 8.88 | 0.53 | 1.85 | 1.3 | 0.873 | 202148_s_at | PYCR1/*Homo sapiens* pyrroline-5-carboxylate reductase 1 |
| Hs.117950 | 0.8367 | 8.30E−08 | 1.20E−05 | 12.72 | 0.58 | 1.98 | 0.92 | 0.8066 | 201013_s_at | SAICAR/multifunctional polypeptide similar to SAICAR synthetase and AIR carboxylase |
| Hs.8858 | 0.833 | 1.10E−07 | 1.50E−05 | 8.54 | 0.56 | 1.66 | 0.11 | 0.8151 | 217986_s_at | BAZIA/*Homo sapiens* bromodomain adjacent to zinc finger domain. |
| Hs.75939 | 0.8287 | 1.70E−07 | 2.00E−05 | 9.15 | 0.48 | 1.88 | 0.019 | 0.8333 | 209825_s_at | UMPK/*Homo sapiens* |
| Hs.75061 | 0.8233 | 2.60E−07 | 2.70E−05 | 7.98 | 0.46 | 1.98 | 0.054 | 0.8835 | 200644_at | MACMARCKS/*Homo sapiens* macrophage myristoylated alanine-rich C kinase substrate |
| Hs.162209 | 0.8217 | 3.00E−07 | 3.10E−05 | 16.32 | 0.56 | 2.89 | 0.014 | 0.7902 | 214598_at | CLDN8/DKFZp564/ Claudin 8 *Homo sapiens* mRNA |
| Hs.154672 | 0.8147 | 5.40E−07 | 4.70E−05 | 8.96 | 0.53 | 1.74 | 0.046 | 0.8314 | 201761_at | MTHFD1/*Homo sapiens* methylene tetrahydrofolate dehydrogenase (NAD+ dependent) |
| Hs.18910 | 0.8115 | 7.10E−07 | 5.70E−05 | 6.91 | 0.52 | 1.89 | 0.037 | 0.7111 | 204394_at | POV1(SLC43A1)/*Homo sapiens* prostate cancer overexpressed gene 1 |
| Hs.109059 | 0.8104 | 7.70E−07 | 6.10E−05 | 7.4 | 0.52 | 1.84 | 0.027 | 0.8091 | 203931_s_at | MRPL12/*Homo sapiens* mitochondrial ribosomal protein L12 |
| Hs.98732 | 0.8104 | 7.70E−07 | 6.00E−05 | 5.45 | 0.42 | 6.42 | 0.01 | 0.8083 | 215432_at | EIF3S8/*Homo sapiens* Chromosome 16 BAC clone CIT987SK-A-923A4 |

TABLE 45b

| SEQ ID NO | UniGene (archival) | Unigene (current) | Target Description |
|---|---|---|---|
| 1 | Hs.7780 | Hs.480311 | Consensus includes gb: AV715767 /FEA = EST /DB_XREF = gi: 10797284 /DB_XREF = est: AV715767 /CLONE = DCBATH02 /UG = Hs.7780 *Homo sapiens* mRNA; cDNA DKFZp564A072 (from clone DKFZp564A072) |
| 2 | Hs.21293 | Hs.492859 | gb: S73498.1 /DEF = *Homo sapiens* AgX-1 antigen mRNA; complete cds. /FEA = mRNA /PROD = AgX-1 antigen /DB_XREF = gi: 688010 /UG = Hs.21293 UDP-N-acteylglucosamine pyrophosphorylase 1 /FL = gb: AB011004.1 gb: NM_003115.1 gb: S73498.1 |
| 3 | Hs.79037 | Hs.632539 | gb: NM_002156.1 /DEF = *Homo sapiens* heat shock 60 kD protein 1 (chaperonin) (HSPD1); mRNA. /FEA = mRNA /GEN = HSPD1 /PROD = heat shock 60 kD protein 1 (chaperonin) /DB_XREF = gi: 4504520 /UG = Hs.79037 heat shock 60 kD protein 1 (chaperonin) /FL = gb: BC002676.1 gb: BC003030.1 gb: M34664.1 gb: M22382.1 gb: NM_002156.1 |
| 4 | Hs.30054 | Hs.30054 | gb: NM_000130.2 /DEF = *Homo sapiens* coagulation factor V (proaccelerin; labile factor) (F5); mRNA. /FEA = mRNA /GEN = F5 /PROD = coagulation factor V precursor /DB_XREF = gi: 10518500 /UG = Hs.30054 coagulation factor V (proaccelerin; labile factor) /FL = gb: NM_000130.2 gb: M16967.1 gb: M14335.1 |
| 5 | Hs.75432 | Hs.654400 | gb: NM_000884.1 /DEF = *Homo sapiens* IMP (inosine monophosphate) dehydrogenase 2 (IMPDH2); mRNA. /FEA = mRNA /GEN = IMPDH2 /PROD = IMP (inosine monophosphate) dehydrogenase 2 /DB_XREF = gi: 4504688 /UG = Hs.75432 IMP (inosine monophosphate) dehydrogenase 2 /FL = gb: J04208.1 gb: NM_000884.1 |
| 6 | Hs.699 | Hs.434937 | gb: NM_000942.1 /DEF = *Homo sapiens* peptidylprolyl isomerase B (cyclophilin B) (PPIB); mRNA. /FEA = mRNA /GEN = PPIB /PROD = peptidylprolyl isomerase B (cyclophilin B) /DB_XREF = gi: 4758949 /UG = Hs.699 peptidylprolyl isomerase B (cyclophilin B) /FL = gb: BC001125.1 gb: M60857.1 gb: M63573.1 gb: NM_000942.1 |

TABLE 45b-continued

| SEQ ID NO | UniGene (archival) | Unigene (current) | Target Description |
|---|---|---|---|
| 7 | Hs.1708 | Hs.491494 | gb: NM__005998.1 /DEF = *Homo sapiens* chaperonin containing TCP1; subunit 3 (gamma) (CCT3); mRNA. /FEA = mRNA /GEN = CCT3 /PROD = chaperonin containing TCP1; subunit 3 (gamma) /DB__XREF = gi: 5174726 /UG = Hs.1708 chaperonin containing TCP1; subunit 3 (gamma) /FL = gb: NM__005998.1 |
| 8 | Hs.69469 | Hs.502244 | gb: NM__006360.1 /DEF = *Homo sapiens* dendritic cell protein (GA17); mRNA. /FEA = mRNA /GEN = GA17 /PROD = dendritic cell protein /DB__XREF = gi: 5453653 /UG = Hs.69469 dendritic cell protein /FL = gb: AF277183.1 gb: AF064603.1 gb: NM__006360.1 |
| 9 | Hs.82280 | Hs.501200 | gb: NM__002925.2 /DEF = *Homo sapiens* regulator of G-protein signaling 10 (RGS10); mRNA. /FEA = mRNA /GEN = RGS10 /PROD = regulator of G-protein signaling 10 /DB__XREF = gi: 11184225 /UG = Hs.82280 regulator of G-protein signaling 10 /FL = gb: NM__002925.2 gb: AF045229.1 |
| 10 | Hs.79217 | Hs.458332 | gb: NM__006907.1 /DEF = *Homo sapiens* pyrroline-5-carboxylate reductase 1 (PYCR1); nuclear gene encoding mitochondrial protein; mRNA. /FEA = mRNA /GEN = PYCR1 /PROD = pyrroline-5-carboxylate reductase 1 /DB__XREF = gi: 5902035 /UG = Hs.79217 pyrroline-5-carboxylate reductase 1 /FL = gb: M77836.1 gb: NM__006907.1 |
| 11 | Hs.117950 | Hs.518774 | Consensus includes gb: AA902652 /FEA = EST /DB__XREF = gi: 3037775 /DB__XREF = est:ok71a12.s1 /CLONE = IMAGE: 1519390 /UG = Hs.117950 multifunctional polypeptide similar to SAICAR synthetase and AIR carboxylase /FL = gb: NM__006452.1 |
| 12 | Hs.8858 | Hs.509140 | gb: NM__013448.1 /DEF = *Homo sapiens* bromodomain adjacent to zinc finger domain; 1A (BAZ1A); mRNA. /FEA = mRNA /GEN = BAZ1A /PROD = bromodomain adjacent to zinc finger domain; 1A /DB__XREF = gi: 7304918 /UG = Hs.8858 bromodomain adjacent to zinc finger domain; 1A /FL = gb: AB032252.1 gb: NM__013448.1 Bromodomain adjacent to zinc finger domain protein 1A (ATP-utilizing chromatin assembly and remodeling factor 1) (hACF1) (ATP-dependent chromatin remodelling protein) (Williams syndrome transcription factor-related chromatin remodeling factor 180) (WCRF180) (hWALp1) (CHRAC subunit ACF1) (HSPC317). From SPD |
| 13 | Hs.75939 | Hs.458360 | gb: BC002906.1 /DEF = *Homo sapiens*; Similar to uridine monophosphate kinase; clone MGC: 10318; mRNA; complete cds. /FEA = mRNA /PROD = Similar to uridine monophosphate kinase /DB__XREF = gi: 12804106 /UG = Hs.75939 uridine monophosphate kinase /FL = gb: BC002906.1 gb: AF236637.1 |
| 14 | Hs.75061 | Hs.75061 | gb: NM__023009.1 /DEF = *Homo sapiens* macrophage myristoylated alanine-rich C kinase substrate (MACMARCKS); mRNA. /FEA = mRNA /GEN = MACMARCKS /PROD = macrophage myristoylated alanine-rich C kinasesubstrate /DB__XREF = gi: 13491173 /UG = Hs.75061 macrophage myristoylated alanine-rich C kinase substrate /FL = gb: NM__023009.1 |
| 15 | Hs.162209 | Hs.162209 | Consensus includes gb: AL049977.1 /DEF = *Homo sapiens* mRNA; cDNA DKFZp564C122 (from clone DKFZp564C122). /FEA = mRNA /DB__XREF = gi: 4884227 /UG = Hs.162209 claudin 8 /FL = gb: NM__012132.1 |
| 16 | Hs.154672 | Hs.469030 | gb: NM__006636.2 /DEF = *Homo sapiens* methylene tetrahydrofolate dehydrogenase (NAD+ dependent); methenyltetrahydrofolate cyclohydrolase (MTHFD2); nuclear gene encoding mitochondrial protein; mRNA. /FEA = mRNA /GEN = MTHFD2 /PROD = methylene tetrahydrofolate dehydrogenase (NAD+dependent); methenyltetrahydrofolate cyclohydrolase; precursor /DB__XREF = gi: 13699869 /UG = Hs.154672 methylene tetrahydrofolate dehydrogenase (NAD+ dependent); methenyltetrahydrofolate cyclohydrolase /FL = gb: NM__006636.2 |
| 17 | Hs.18910 | Hs.591952 | gb: NM__003627.1 /DEF = *Homo sapiens* prostate cancer overexpressed gene 1 (POV1); mRNA. /FEA = mRNA /GEN = POV1 /PROD = prostate cancer overexpressed gene 1 /DB__XREF = gi: 4505970 /UG = Hs.18910 prostate cancer overexpressed gene 1 /FL = gb: BC001639.1 gb: AF045584.1 gb: NM__003627.1 |
| 18 | Hs.109059 | Hs.109059 | gb: NM__002949.1 /DEF = *Homo sapiens* mitochondrial ribosomal protein L12 (MRPL12); mRNA. /FEA = mRNA /GEN = MRPL12 /PROD = mitochondrial ribosomal protein L12 /DB__XREF = gi: 4506672 /UG = Hs.109059 mitochondrial ribosomal protein L12 /FL = gb: BC002344.1 gb: U25041.1 gb: AF105278.1 gb: NM__002949.1 |
| 19 | Hs.98732 | Hs.306812 | Consensus includes gb: AC003034 /DEF = *Homo sapiens* Chromosome 16 BAC clone CIT987SK-A-923A4 /FEA = mRNA__2 /DB__XREF = gi: 3219338 /UG = Hs.98732 *Homo sapiens* Chromosome 16 BAC clone CIT987SK-A-923A4 /FEA = mRNA__2 /DB__XREF = gi: 3219338 /UG = Hs.98732 *Homo sapiens* Chromosome 16 BAC clone CIT987SK-A-923A4 |

The following information provides further description of the top 10 ranking genes selected by RFE-SVM based upon public databases and references. Corresponding SEQ ID NOs are also provided.

DKFZp564 (Hs.7780 Old Cluster; Hs.480311 New Cluster) (SEQ ID NO. 1)

*Homo sapiens* mRNA; cDNA DKFZp564A072 (from clone DKFZp564A072)

Chromosome location: Chr.4, 527.0 cR

Summary: LIM domains are cysteine-rich double zinc fingers composed of 50 to 60 amino acids that are involved in protein-protein interactions. LIM domain-containing proteins are scaffolds for the formation of multiprotein complexes. The proteins are involved in cytoskeleton organization, cell lineage specification, organ development, and oncogenesis. Enigma family proteins (see ENIGMA; MIM 605900) possess a 100-amino acid PDZ domain in the N terminus and 1 to 3 LIM domains in the C terminus. [supplied by OMIM].

Genbank entry (with sequence): AL049969.1

Protein Product: PDZ and LIM-domain 5 (PDLIM5)(SEQ ID NO. 19)

cDNA SOURCES: Liver and Spleen, bone, brain, breast-normal, colon, heart, kidney, lung, mixed, ovary, pancreas, placenta, pooled, prostate, skin, stomach, testis, uterus, vascular, whole blood.

AgX-1/UAP1 (Hs.21293 Old Cluster; Hs.492859 New Cluster) (SEQ ID NO. 2)

UDP-N-acteylglucosamine pyrophosphorylase 1

Chromosome location: 1q23.3

Sequence from GenBank for 573498

Enzyme EC number: 2.7.7.23

Figure 9:
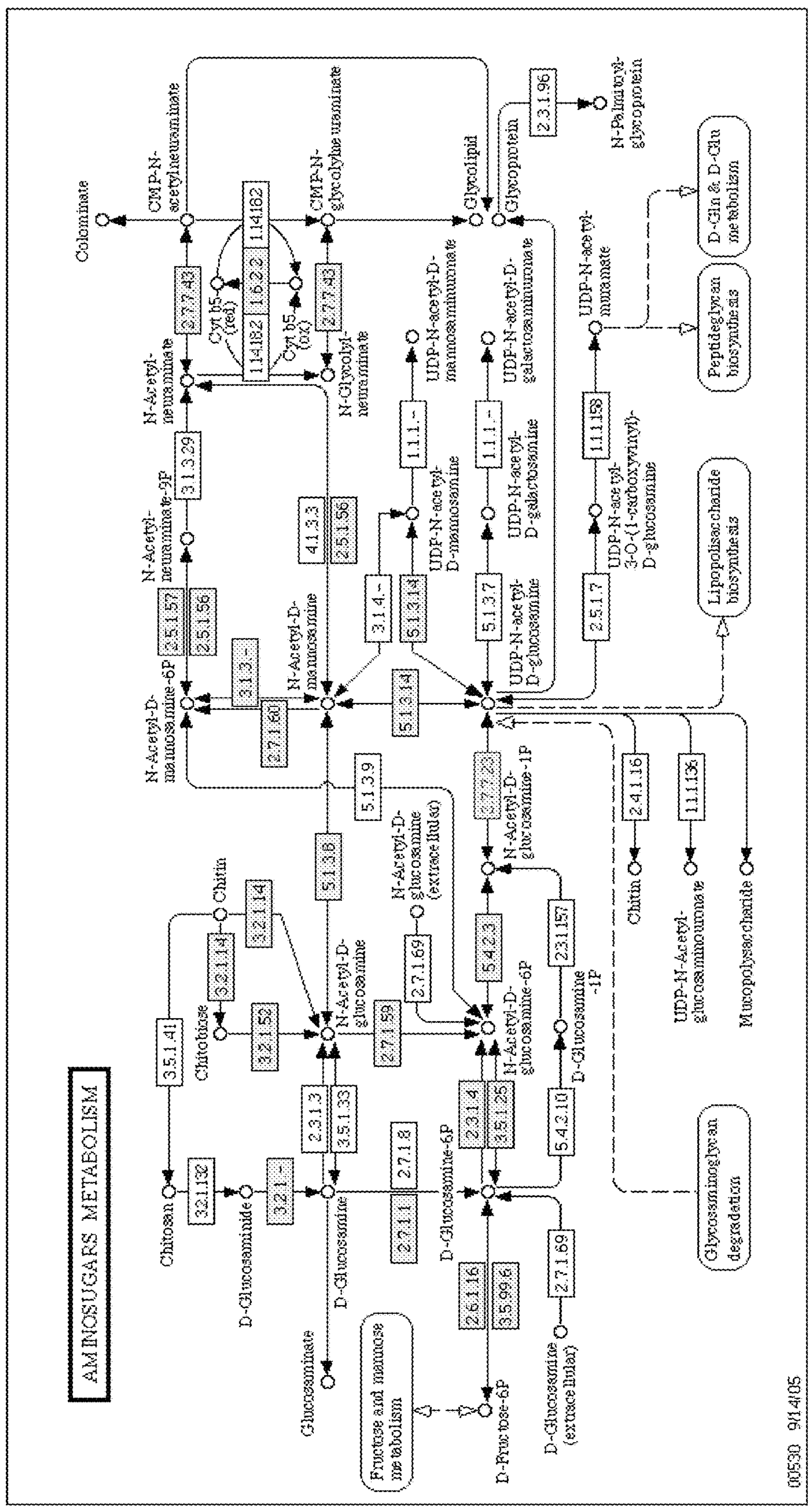
FIG. 9 is a prior art diagram showing the KEGG pathway around gene AgX-1/UAP1/SPAG2.

Enzyme involved in aminosugars metabolism (see Kegg pathway around AgX-1/UAP1/SPAG2, FIG. 9).

Reported to be an androgen responsive gene in:

"Transcriptional programs activated by exposure of human prostate cancer cells to androgen", S. E. DePrimo, et al., *Genome Biology* 2002, 3:research0032.1-032.12

Reported to be possibly implicated in cancer:

Other interesting alias: SPAG 2: sperm associated antigen 2. Has been connected to male infertility:

"Expression of the human antigen SPAG2 in the testis and localization to the outer dense fibers in spermatozoa", Diekman, A. B., et al., *Mol. Reprod. Dev.* 1998 July; 50(3):284-93.

Tissue specificity: Widely expressed. Isoform AGX1 is more abundant in testis than isoform AGX2, while isoform AGX2 is more abundant than isoform AGX1 in somatic tissue. Expressed at low level in placenta, muscle and liver.

Protein product: AgX-1 antigen, accession 573498.1 (SEQ ID NO. 20)

Secreted: May be present in blood and tissue.

UAP1 is correlated with genes involved in mitochondrial activity, including AMACR, and HSDP1.

HSPD1 (Hs.79037 Old Cluster; Hs.632539 New Cluster) (SEQ ID NO. 3)

Chaperonin

Chromosome Location: 2q33.1

Function: This gene encodes a member of the chaperonin family. The encoded mitochondrial protein may function as a signaling molecule in the innate immune system. This protein is essential for the folding and assembly of newly imported proteins in the mitochondria. This gene is adjacent to a related family member and the region between the 2 genes functions as a bidirectional promoter.

Protein product: chaperonin heat shock 60 kD protein 1 (chaperonin); heat shock protein 65; mitochondrial matrix protein P1; P60 lymphocyte protein; short heat shock protein 60 Hsp60s1; Accession NP_002147 (SEQ ID NO. 21)

HSPD1 is correlated with genes involved in mitochondrial activity.

F5 (Hs.30054) (SEQ ID NO. 4)

F5 coagulation factor V precursor

Chromosome Location: 1q23

Function: This gene encodes coagulation factor V which is an essential factor of the blood coagulation cascade. This factor circulates in plasma, and is converted to the active form by the release of the activation peptide by thrombin during coagulation. This generates a heavy chain and a light chain which are held together by calcium ions. The active factor V is a cofactor that participates with activated coagulation factor X to activate prothrombin to thrombin.

Protein Product: coagulation factor V precursor [*Homo sapiens*], Accession NP_000121 (SEQ ID NO. 22)

IMPDH2 (Hs.75432 Old Cluster; Hs.476231 New Cluster) (SEQ ID NO. 5)

IMP (inosine monophosphate) dehydrogenase 2

Chromosome location: Location: 3p21.2

Unigene cluster: Hs.476231

Enzyme: EC 1.1.1.205

Function: This gene encodes the rate-limiting enzyme in the de novo guanine nucleotide biosynthesis. It is thus involved in maintaining cellular guanine deoxy- and ribonucleotide pools needed for DNA and RNA synthesis. The encoded protein catalyzes the NAD-dependent oxidation of inosine-5'-monophosphate into xanthine-5'-monophosphate, which is then converted into guanosine-5'-monophosphate. This gene is up-regulated in some neoplasms, suggesting it may play a role in malignant transformation.

Protein product: inosine monophosphate dehydrogenase 2 [*Homo sapiens*]; Accession NP_000875 (SEQ ID NO. 23)

Sequences: Source sequence J04208:

Related to apoptosis.

PPIB (Hs.699 Old Cluster; Hs.434937 New Cluster) (SEQ ID NO. 6)

Peptidylprolyl isomerase B precursor (cyclophilin B)

Chromosome location: 15q21-q22

Function: The protein encoded by this gene is a cyclosporine-binding protein and is mainly located within the endoplasmic reticulum. It is associated with the secretory pathway and released in biological fluids. This protein can bind to cells derived from T- and B-lymphocytes, and may regulate cyclosporine A-mediated immunosuppression.

Protein Product: peptidylprolyl isomerase B precursor; Accession NP_000933 (SEQ ID NO. 24)

EC_number: 5.2.1.8

Cyclophilin B; peptidyl-prolyl cis-trans isomerase B; PPIase; cyclophilin-like protein; S-cyclophilin; rotamase Related to apoptosis.

CTT3 (Hs.1708 Old Cluster; Hs.491494 New Cluster) (SEQ ID NO. 7)

Chaperonin containing TCP1, subunit 3 (gamma)

Chromosome Location: 1q23

Function: This gene encodes a molecular chaperone that is member of the chaperonin containing TCP1 complex (CCT), also known as the TCP1 ring complex (TRiC). This complex consists of two identical stacked rings, each containing eight different proteins. Unfolded polypeptides enter the central cavity of the complex and are folded in an ATP-dependent manner. The complex folds various proteins, including actin and tubulin.

Protein product: chaperonin containing TCP1, subunit 3 isoform a; Accession NP_005989 (SEQ ID NO. 25)

TCP1 (t-complex-1) ring complex, polypeptide 5; T-complex protein 1, gamma subunit.

GA17 (Hs.69469 old cluster; Hs.502244 new cluster) (SEQ ID NO. 8)

Dendritic cell protein (GA17)

Chromosome location: 11p13

Function: HFLB5 encodes a broadly expressed protein containing putative membrane fusion domains that act as a receptor or coreceptor for entry of herpes simplex virus (HSV).

Protein product: Eukaryotic translation initiation factor 3, subunit M ACCESSION NP_006351. (SEQ ID NO. 26)

RGS10 (Hs.82280 old cluster; Hs.501200 new cluster) (SEQ ID NO. 9) regulator of G-protein signaling 10 isoform b Chromosome Location: 10q25

Function: Regulator of G protein signaling (RGS) family members are regulatory molecules that act as GTPase activating proteins (GAPs) for G alpha subunits of heterotrimeric G proteins. RGS proteins are able to deactivate G protein subunits of the Gi alpha, Go alpha and Gq alpha subtypes. They drive G proteins into their inactive GDP-bound forms. Regulator of G protein signaling 10 belongs to this family. All RGS proteins share a conserved 120-amino acid sequence termed the RGS domain. This protein associates specifically with the activated forms of the two related G-protein subunits, G-alphai3 and G-alphaz but fails to interact with the structurally and functionally distinct G-alpha subunits. Regulator of G protein signaling 10 protein is localized in the nucleus.

Protein product: regulator of G-protein signaling 10 isoform b; Accession NP_002916 (SEQ ID NO. 27)

Related to apoptosis.

PYCR1 (Hs.79217 Old Cluster; Hs.458332 New Cluster) (SEQ ID NO. 10)

Pyrroline-5-carboxylate reductase 1 isoform 1

Chromosome location: 17q25.3

Function: This gene encodes an enzyme that catalyzes the NAD(P)H-dependent conversion of pyrroline-5-carboxylate to proline. This enzyme may also play a physiologic role in the generation of NADP(+) in some cell types. The protein forms a homopolymer and localizes to the mitochondrion.

Protein product: pyrroline-5-carboxylate reductase 1 isoform 1; Accession NP_008838 (SEQ ID NO. 28)

Related to mitochrondrial function.

Additional information about the remaining top 19 genes and their protein products are found in accompanying sequence listings and on the NCBI database.

Using a subset of 100 genes that were significantly overexpressed in cancer in both the Stamey 2003 data and public data, a number of relevant pathways were identified using a pathway database compiled by MIT. (See, e.g., Subramanian, A., et al., “Gene set enrichment analysis: A knowledge-based approach for interpreting genome-wide expression profiles” (2005) *Proc. Natl. Acad. Sci. USA* 102, 15545-15550.) This pathway database contains lists of genes from various sources and is highly redundant. The pathways were grouped using a clustering method according to their overlap in number of genes found overexpressed in cancer, then manually verified that the groups were meaningful, to produce a simplified and more robust pathway analysis. Additional information was obtained from the Secreted Protein Database (SPD). (Chen, Y. et al., “SPD—a web-based secreted protein database”, (2005) *Nucleic Acids Res.* 33 Database Issue: D169-173.)

Figure 10:
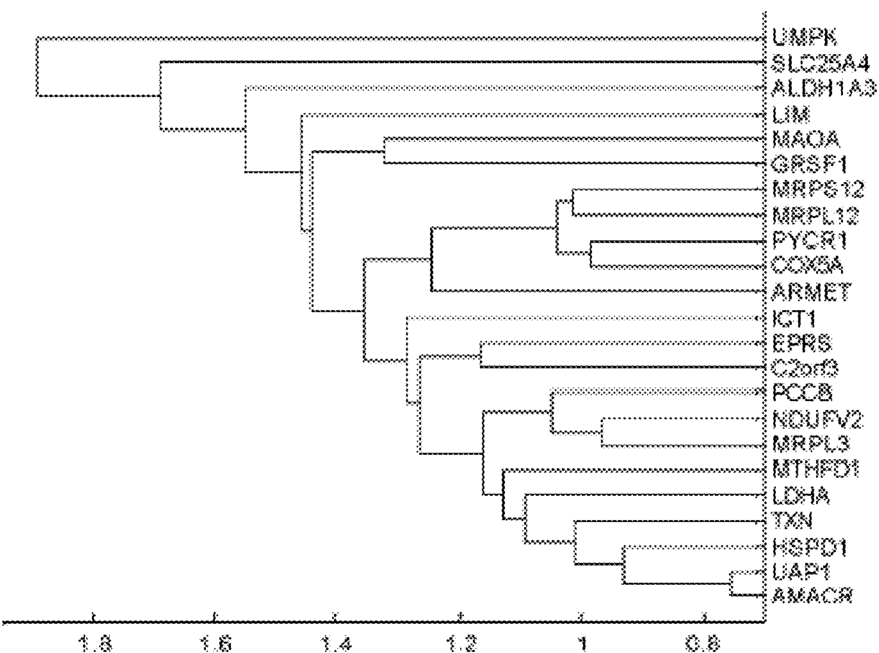
FIG. 10 is a dendogram showing gene expression clustering of mitochondrial genes.
Figure 11:
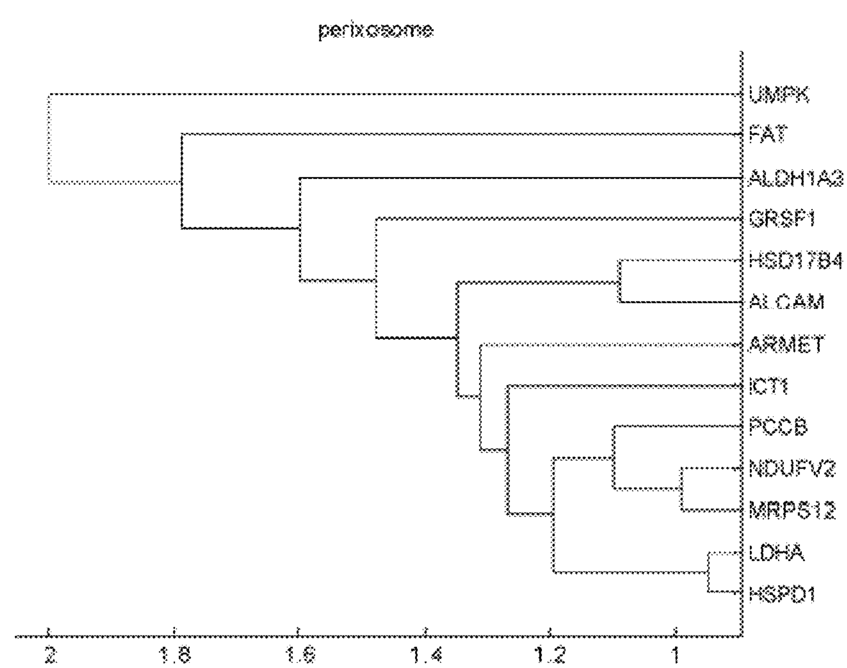
FIG. 11 is a dendogram showing gene expression clustering of perixosome and cell adhesion genes.
Figure 12:
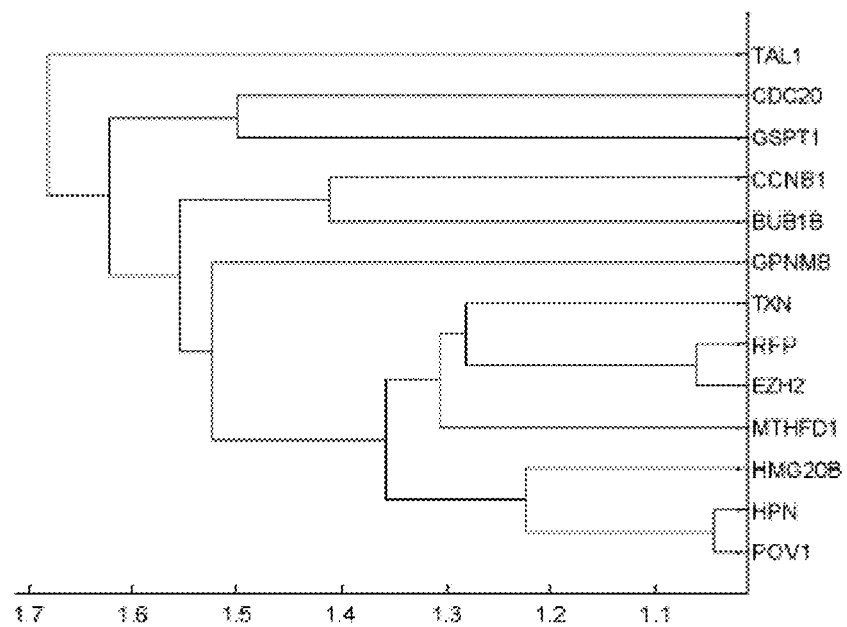
FIG. 12 is a dendogram showing gene expression clustering of genes linked to cell proliferation and growth.
Figure 13:
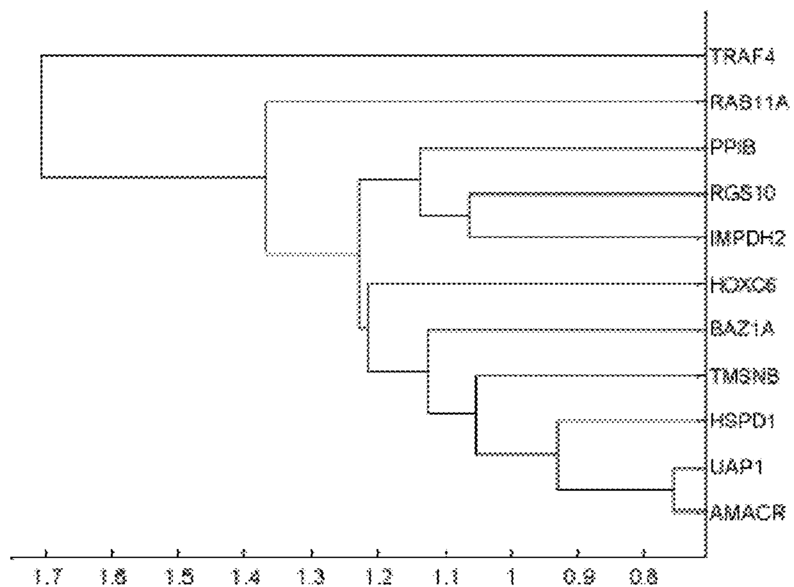
FIG. 13 is a dendogram showing gene expression clustering of genes linked to apoptosis or p53 pathway.

Four main clusters were identified: (1) mitochrondrial genes (UMPK, SLC25A4, ALDH1A3, LIM, MAOA, GRSF1, MRPS12, MRPL12, PYCR1, COX5A, ARMET, ICT1, EPRS, C2orf3, PCCB, NDUFV2, MRPL3, MTHFD1, LDHA, TXN, HSPD1, UAP1, AMACR) (clustering of these genes is shown in FIG. 10); (2) genes related to perixosome and cell adhesion (UMPK, FAT, ALDH1A3, GRSF1, HSD17B4, ALCAM, ARMET, ICT1, PCCB, NDUFV2, MRPS12, LDHA, HSPD1)(clustering of these genes is shown in FIG. 11); (3) cell proliferation and growth (TAL1, CDC20, GSPT1, CCNB1, BUB1B, GPNMB, TXN, RFP, EXH2, MTHFD1, HMG20B, HPN, POV1)(clustering of these genes is shown in FIG. 12); and (4) genes related to apoptosis, or the p53/p73 signaling pathways (TRAF4, RAB11A, PPIB, RGS10, IMPDH2, HOXC6, BAZ1A, TMSNB, HSPD1, UAP1, AMACR) (clustering of these genes is shown in FIG. 13). Additional pathways that were less represented, but which may be linked to cancer include coagulation and angiogenesis; cell structure/cyotskeleton/actin; DNA damage/repair; HOX-related genes; and kinases.

Because many of the genes identified in the study involved mitochondrial activity and/or apoptosis, it is hypothesized that mitochrondrial apoptosis plays a role in prostate cancer.

P53 has both transcriptional activity that mediates cell cycle arrest and induces mitochondrial apoptosis, possibly via interactions with the Bcl-2 protein family and rendering the membrane of the mitochondrion permeable. Because of the known role of p53 mutations in many cancers, the expression levels of p53 and related genes like p73 were investigated and found to be strongly underexpressed in the cancer tissue in the datasets that were used in the study. Connections are apparent between mitochondrial activity and apoptosis.

The preceding detailed description of the preferred embodiments disclosed methods for identification of biomarkers for prostate cancer using gene expression data from microarrays. RFE-SVM was used to identify a small number of biomarkers that should lead to the creation of inexpensive, accurate tests that may be used in conjunction with or in place of current diagnostic, prognostic and monitoring tests for prostate cancer by using gene expression or protein expression data. Preferred applications of the present invention will target proteins expressed by the identified genes that are detectable in serum, semen, or urine, thus providing non-invasive or minimally invasive screening for prostate cancer and monitoring of treatment.

Example 8: Validation of Biomarkers by RT-PCR

Quantitative RT-PCR (such as TAQMAN® from Applied Biosystems, Inc., Foster City, Calif.) may be used for detecting or comparing the RNA transcript level of the gene(s) of interest. Quantitative RT-PCR involves reverse transcription (RT) of RNA to cDNA followed by relative quantitative PCR(RT-PCR). To validate the results obtained using the datasets generated from microarray gene expression measurements, a RT-PCR assay was performed according to the procedures described below.

The gene expression of UAP1, PDLIM5, IMPDH2, HSPD1 in was measured in 71 additional prostate tissue samples using an RT-PCR assay. Table 46 lists the number of source of the validation samples. The samples were processed at different times and corresponding to the receipt of tissues that were collected at two locations (The M.D. Anderson Cancer Center, Houston, Tex. (“MDA”), for paraffin embedded tissues, and the Hue Central Hospital, Vietnam (:"HCH"), for fresh frozen prostate tissues.

TABLE 46

| Source | Histology | Number |
|---|---|---|
| MDA | Normal | 5 |
| | BPH | 5 |
| | Tumor | 11 |
| HCH | Normal | 5 |
| | BPH | 4 |
| | Tumor | 12 |
| MDA | Normal | 8 |
| | BPH | 10 |
| | Tumor | 9 |
| Total | | 71 |

The fresh tissue was homogenized in lysis buffer following collection. The lysate was further processed using the Qiagen QIAAMP® RNA Blood Mini extraction protocol (Qiagen, Valencia, Calif.). RNA Extraction protocols are generally known to those in the art. Briefly, the extraction protocol used in the present example for purification of RNA from tissue follows the steps of disrupting and homogenizing the starting material. Tissues can be disrupted using a rotor-stator homogenizer, such as the Qiagen TISSUERUPTOR™, which can simultaneously disrupt and homogenize a tissue sample in the presence of a lysis buffer. Bead-milling or a mortar and pestle may also be used for disruption, however homogenization must be performed separately. The leukocytes are then lysed using highly denaturing conditions the immediately inactivate RNases, allowing the isolation of intact RNA. After homogenation of the lysate by a brief centrifugation through a Qiagen QIASHREDDER™ spin column, ethanol is added to adjust binding conditions and the sample is applied to the QIAAMP® spin column. RNA is bound to the silica membrane during a brief centrifugation step. Contaminants are washed away and total RNA is eluted in RNase-free water for direct use in any downstream application.

The RNA samples were DNase treated following the RNA isolation. The RNA quality was assessed using the Agilent Bioanalyzer 2100 (Agilent Technologies, Santa Clara, Calif.).

The paraffin-embedded fixed tissues were sectioned at 4-7 μM on slides. The tissue sections were assessed for areas of interest by a pathologist using a Hematoxylin and Eosin (H&E)-stained slide. The targeted areas were selectively removed from an unstained slide using a manual micro-dissection technique. The collected tissue was digested for five hours using Proteinase K and a digestion buffer optimized for RNA isolations. The lysate was further processed using the column-based Qiagen RNA extraction protocol as described above. The samples were DNase treated following the isolation. The RNA yield was determined using a NANODROP™ 1000 spectrophotometer (Thermo Scientific NanoDrop Technologies, LLC, Wilmington Del.), and all samples were brought to a uniform final concentration.

Primer and probe sets for IMPDH2 and PDLIM5 were obtained from Applied Biosystems TAQMAN® Gene Expression Assays (Applied Biosystems, Inc.). The primer and probe sets for HSPD1 and UAP1 were designed using PRIMER EXPRESS® v. 2.0 software (Applied Biosystems). All primer and probe sets that were used crossed an exon boundary and generated amplification products of similar sizes. The reaction efficiencies were evaluated for each set and were all determined to have comparable efficiencies. Various combinations of primers and probes were evaluated in multiplex reactions to determine the best arrangement. Additionally, expression analysis was evaluated for each gene using prostate tissue to determine which genes had similar expression levels relative to each other. The most efficient and robust arrangement was found to be IMPDH2 and HSPD1 in one reaction and PDLIM5 and UAP1 in a second reaction.

During the initial development of the assay, a number of different reference genes were evaluated for use in the quantitative RT-PCR. Table 47 below provides the information for the probes and primers used in the assay, including those for the reference genes ABL1 (c-abl oncogene 1 (Unigene ID Hs.431048; RefSeq NM_005157.3, NM_007313.2)), ACTB (actin,beta (Unigene ID Hs.520640; RefSeq NM_001101.3)), B2M (beta-2-microglobulin (Unigene ID Hs.534255; RefSeq NM_004048.2)), GAPDH (glyceraldehyde-3-phosphate dehydrogenase (Unigene ID Hs.479728, Hs.544577, Hs.592355, Hs.648900; RefSeq NM_002046.3)) and GUSB (glucuronidase, beta (Unigene ID Hs.255230, RefSeq NM_000181.2)), all of which are standard TAQMAN® gene expression assay reagents available from Applied Biosystems inventory, identified in the table by their Applied Biosystems Assay ID.

TABLE 47

| Primer/Probe Mix | Sequence Information | PCR Product Size |
|---|---|---|
| HSPD1 Forward (SEQ ID NO. 34) | 5'AAC CTG TGA CCA CCC CTG AA 3' | 64 bp |
| HSPD1 Reverse (SEQ ID NO. 35) | 5'TCT TTG TCT CCG TTT GCA GAA A 3' | |
| HSPD1 Probe (SEQ ID NO. 36) | 5' VIC ATT GCA CAG GTT GCT AC NFQ 3' | |
| IMPDH2 | ABI 20X (TAQMAN ® Gene Expression Assay Reagent ID # Hs01021353_ml)FAM | 71 bp |
| PDLIM5 | ABI 20X (TAQMAN ® Gene Expression Assay Reagent ID # Hs00935062_ml)FAM | 70 bp |
| UAP1 Forward (SEQ ID NO. 37) | 5' TTG CAT TCA GAA AGG AGC AGA CT 3' | 68 bp |

TABLE 47-continued

| Primer/Probe Mix | Sequence Information | PCR Product Size |
|---|---|---|
| UAP1 Reverse (SEQ ID NO. 38) | 5' CAA CTG GTT CTG TAG GGT TCG TTT 3' | |
| UAP-1 Probe (SEQ ID NO. 39) | 5' VIC TGG AGC AAA GGT GGT AGA NFQ 3' | |
| ABL1 | ABI 20X (TAQMAN ® Gene Expression Assay Reagent ID # Hs99999002_mH) | 105 bp |
| ACTB | ABI 20X (TAQMAN ® Gene Expression Assay Reagent ID # Hs03023943_gl) | 96 bp |
| B2M | ABI 20X (TAQMAN ® Gene Expression Assay Reagent ID # Hs00187842_ml) | 64 bp |
| GAPDH | ABI 20X (TAQMAN ® Gene Expression Assay Reagent ID # Hs00266705_gl) | 74 bp |
| GUSB | ABI 20X (TAQMAN ® Gene Expression Assay Reagent ID # Hs99999908_ml) | 81 bp |

The prostate samples that were used were evaluated by a pathologist and determined to be either normal, benign prostatic hyperplasia (BPH) or cancer to evaluate the stability of the various reference genes. Five genes were found to be acceptable for use as reference genes for quantitative gene expression analysis of the prostate samples. All five reference genes were run for each sample processed during development. Quantification of the target gene expression was assessed for each gene individually and relative to the geometric mean expression of the reference genes. Following evaluation of all five reference genes, Beta-2-microglobulin ("B2M") was found to have the most stable expression overall and performed better than any individual gene and comparable to the average.

Standard curves were prepared using STRATAGENE® Universal Human Reference RNA (Stratagene, La Jolla, Calif.). The dilution series ranged from 100 ng to 10 pg of total RNA. Standard curves and calibration controls were run for each gene to generate relative quantitative values and assess amplification efficiency as well as run to run variation.

All RNA samples were assayed using the TAQMAN® RNA-to-$C_T$™ 1-Step Kit (Applied Biosystems). A uniform quantity of input RNA was evaluated for each gene in duplicate reactions. Various concentrations of primers and probes were tested for each reaction to find the optimal reaction conditions. The most efficient and robust amplification was generated using 0.9 μM for each primer and 0.25 μM for each probe. The reactions were all found to have balanced amplification using the same primer and probe concentrations for each gene. All samples were determined to be free of contaminating DNA by running minus RT reactions for each sample.

All samples were run on an Applied Biosystems 7900HT Real Time PCR System using Applied Biosystems Sequence Detection Software SDS version 2.3 to obtain quantitative gene expression values. The relative expression data was determined for each target and reference gene using consistent settings for each run.

The following discussion provides a brief review of the process involved in identifying the four genes using microarray data, then proceeds to the results of validation of the microarray results using RT-PCR testing. Similar or slight variations in the microarray data analysis process have been described above in earlier examples.

The gene expression coefficients, obtained as previously described in Example 1, (Average Difference=1/pair num $\Sigma_{probe\ set}$ (PM−MM)), were processed by a suite of data analysis algorithms that were implemented in MATLAB® (The Mathworks). The problem was framed as a two-class classification problem: in Table 12, "Grade 3" and "Grade 4" samples were labeled as "cancer" and all other as "non-cancer", and in Tables 48 and 46, "Tumor" samples were labeled as "cancer" and all other as "non-cancer".

TABLE 48*

| Source | Histology | Number |
|---|---|---|
| Febbo [Ref. 2] | Normal | 50 |
| | Tumor | 52 |
| LaTulippe [Ref. 3] | Normal | 3 |
| | Tumor | 23 |
| Welsh [Ref. 6] | Normal | 9 |
| | Tumor | 27 |
| Total | | 164 |

(Table 48* may also be referred to as the "Oncomine repository", or validation/test dataset, and is a subset of Table 41 described in Example 7.)

The gene signature was discovered using the discovery/training data (Table 12) and then validated using the microarray validation/test data that of Table 48 followed by validation using RT-PCR test data (Table 46) using a three-step procedure outlined in FIG. 14. As preprocessing to Steps 1 and 2, the discovery/training data and the validation/test data separately underwent the following steps: take the log to equalize the variances; standardize the columns and then the lines twice; take the tan h to squash the resulting values.

Referring to FIG. 14, in Step 1 the number of genes is reduced by univariate filtering. Using discovery data $D_0$ (Table 12), the gene expression coefficients were ranked on the basis of the area under the ROC curve (AUC) of individual genes to identify genes most characteristic of cancer, i.e., those that best separate cancer samples from non-cancer samples, to be used as controls (Step 1A). A single gene may be used for classification by setting a threshold on its expression value. Varying the threshold allows monitoring of the tradeoff between sensitivity and specificity and to obtain the ROC curve, which plots sensitivity versus specificity. ("Sensitivity" is defined as the rate of successful disease tissue classification; "specificity" is the rate of successful control tissue classification). The area under that curve (AUC) is a number between 0 and 1, providing a score that is independent of the choice of the threshold. Larger values indicate better classification power. Thus, ranking on the basis of the AUC provides a measure of the classification power of individual genes. The statistical significance of the genes selected with this criterion was assessed with the Wilcoxon-Mann-Withney test, from which a pvalue was obtained. The fraction of insignificant genes in the r top ranked genes or "false discovery rate" (FDR) was estimated using $FDR \approx pvalue \cdot n_0/r$, where $n_0$ is the total number of genes under consideration. Only those $n_1$ genes that were over-expressed in cancer with $FDR10^{-5}$ were retained for further analysis. In addition, genes that were subject to known intellectual property ownership claims were eliminated from further consideration. These genes included HPN (U.S. Pat. No. 6,518,028), LIM (U.S. Pat. Pub. 2006/0134688), HOXC6 (U.S. Pat. No. 6,949,342), EZH2 (U.S. Pat. No. 7,229,774) and AMACR (U.S. Pat. No. 7,332,290). In Step 1B, both the discovery table ($D_0$) and the validation table ($V_0$) are restricted to the $n_1$ selected genes identified in Step 1A.

In Step 2, using the $n_1$ genes retained in Step 1, a smaller subset of complementary genes was selected by multivariate analysis. Recursive feature elimination (RFE-SVM) was carried out on discovery/training data, using the magnitude of the weights of a regularized linear classifier as the selection criterion. (In this approach, "features" or "variables" are gene expression coefficients). This procedure results in nested subsets of genes, each of which is associated to a multivariate classifier performing a linear combination of gene expression coefficients to obtain a "discriminant value" for cancer vs. control using discovery table $D_1$ and their associated labels. A threshold is set on that value to determine whether a sample should be classified as "cancer" or "non-cancer". The predictive power of the gene subsets was then evaluated using the AUC criterion, similar to Step 1, but computed for the multivariate discriminant value rather than for single gene expression coefficients. The evaluation was done using the independent microarray validation/test data (Table 48) by reorganizing table $V_1$ into nested subsets in table $V_2$ and computing the prediction performance of the classifiers for each nested subset of genes (Step 2A). This results in selection of a subset of $n \leq n_1$ genes with high predictive power (referred to as the "gene signature") corresponding to the top genes identified in the previous examples: UAP1, PDLIM5, IMPDH2 and HSPD1.

In Step 3, the RT-PCR data (Table 46) were used to evaluate the gene signature (top genes) in the context of a realistic cost-effective assay that could be used in large scale research and clinical laboratory applications. The procedure can be characterized as "blind testing" because the tissues were classified using a simple average of the log expression values of the n selected genes normalized by B2M, without knowledge of the tissue categories. Confidence intervals ("CI") for the sensitivity (at 90% specificity) and specificity (at 90% sensitivity) were computed using the adjusted Wald method (see, e.g, Agresti and Coull [Ref. 20]). After the release of the class labels, ten times ten-fold (10×10-fold) cross-validation experiments were carried out to evaluate whether there might be a benefit in re-training a classifier with the RT-PCR data, rather than using as the prediction score a simple average of expression values. Finally, the prediction score was mapped to a probability using logistic regression using the implementation of the MATLAB® Statistics Toolbox.

Following the data analysis procedure outlined in FIG. 14, focus was placed on the $n_0=6830$ genes whose probes could be accurately matched in both U133A and U95A arrays. In Step1, using the $m_D=87$ samples of the discovery/test data (Table 12), the univariate AUC gene ranking method selected 63 genes with an $AUC \geq 0.84$ and a false discovery rate (FDR) of less than $10^{-5}$. From that group, to ensure a novel grouping of genes, those genes that were known to have existing intellectual property ownership claims were eliminated, leaving $n_1=19$ genes that were over-expressed in cancer.

Multivariate analysis of Step 2 was then carried out using the $m_v=164$ samples from the validation/test data (Table 48). FIG. 7 is a plot of the performances of all 19 predictors obtained by the RFE method, as a function of the number of genes in the gene subset (gray dots). According to these results, an AUC of $0.94 \pm 0.02$ can be obtained with only 2 to 4 genes. Even though 2 genes would be sufficient to achieve the best results from this analysis, since unknown or uncontrollable sources of variability may degrade performance when moving from microarray to RT-PCR platform, the previously identified n=4 genes were retained to develop the RT-PCR assay. For comparison, the average performance of fifty classifiers trained on subsets of genes of the same size drawn at random among the $n_1=19$ pre-selected genes (black dots) were also plotted. The curve indicates that an AUC value of greater than 0.9 is achieved on average with subsets of 4 randomly selected genes from the set of 19 best genes. This increased the confidence that 4 genes would suffice to develop the assay. FIG. 8 shows the individual ROC curves of the four genes selected and the ROC curve for the classifier based on all four genes, estimated with the validation/test data.

A molecular assay was created based on the gene expression of the four selected genes (UAP1, PDLIM5, IMPDH2, HSPD1) measured by RT-PCR. Normalization was performed by the expression of the gene B2M, which was selected from among the five housekeeping genes that were used because of its high signal and low variance. For prediction, a simple average of the normalized expression values of the four selected genes was used. The tissues are classified in a binary manner, in this case, according to the sign of a prediction score S, which can also be referred to as the "gene panel value":

$$S=\ln(HSPD1/B2M)+\ln(IMPDH2/B2M)+\ln(PDLIM5/B2M)+\ln(UAP1/B2M)+b.$$

A positive value of S indicates a cancer sample while a negative value corresponds to a non-cancer sample. Alternatively, the prediction score can be calculated to produce, for example, a "1" for cancer or a "0" for non-cancer. Procedures for selection of appropriate reference genes are generally known to those of skill in the art. Based on sample types, variations in experimental conditions, protocols and instruments, and available housekeeping genes, it is anticipated that other reference genes ("ref.gene") will provide better, substantially equivalent, or at least acceptable performance in terms of signal and variance levels in RT-PCR or other assays. Accordingly, B2M is provided as an example only, and the prediction score is not intended to be limited to the use of only B2M.

During the course of the study, the data was received in consecutive phases and blind tests were performed by adjusting the bias value b of the prediction score on data received previously, making predictions on the new data, without knowing the identity of the tissues in advance. Using phase 1 to adjust b, followed by testing on phase 2 data, only 2 tissues were misclassified. Similarly, by adjusting the bias on the data of the first two phases and testing on the last one, only 2 tissues were misclassified.

After the identity of the tissues was revealed, ten times ten-fold cross-validation experiments were performed to compare various classification techniques including SVM. No statistically significant performance differences were found, so the simplest model was selected for use, i.e., the prediction score S performing a simple average of normalized log expression values.

Figure 15:
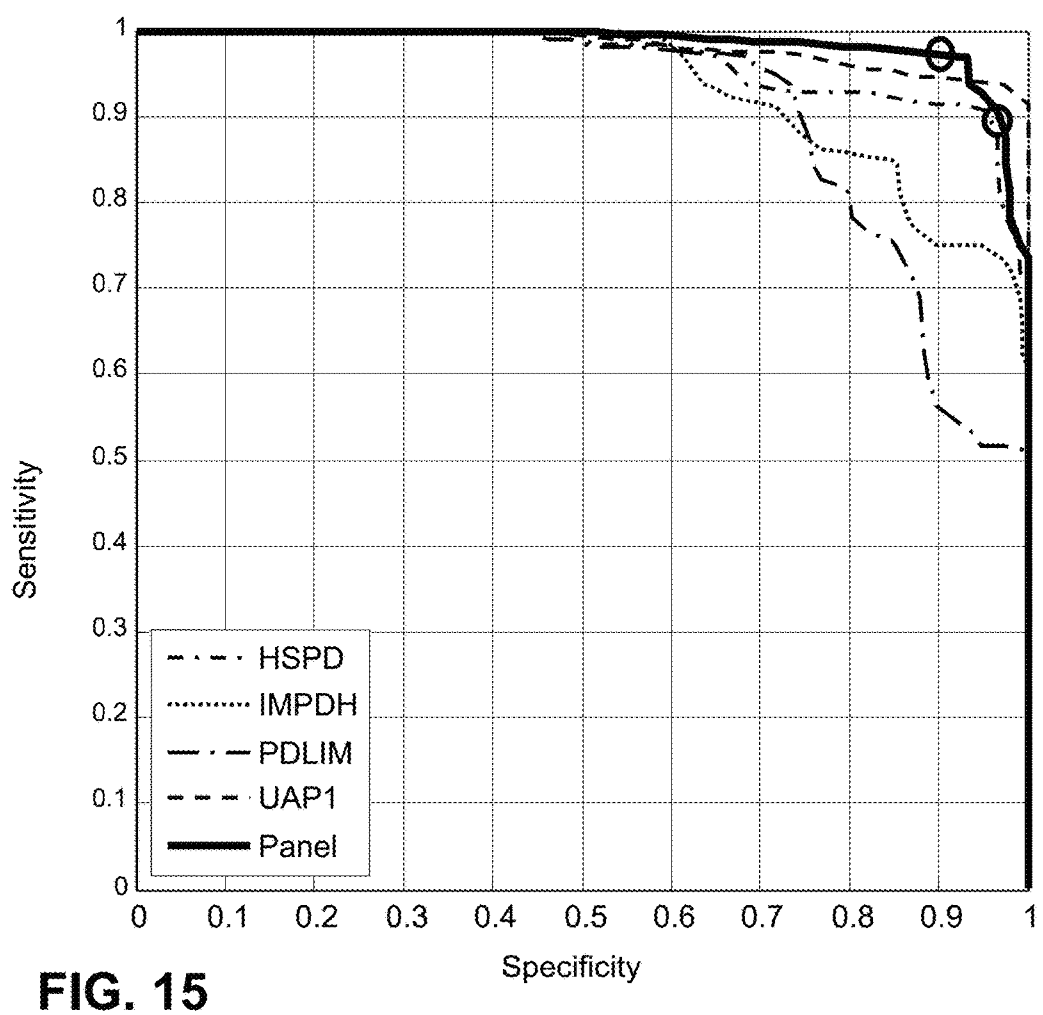
FIG. 15 is a plot of the ROC curves for the 4 gene panel and the ROC of the combination, for the RT-PCR test.

Varying the bias b on the prediction score S permits monitoring of the trade-off between the sensitivity (fraction of cancer tissue properly classified) and the specificity (fraction of control tissues properly classified). FIG. 15 provides a plot of sensitivity vs. specificity (ROC curve) for all 71 RT-PCR test samples. The diagnostic molecular signature achieves an area under the ROC curve (AUC) of 0.97. Two points of particular interest are indicated by circles on the curve corresponding to sensitivity at 90% specificity and specificity at 90% sensitivity. This yields, respectively, 97% specificity (86%-100% 95% CI) and 97% sensitivity (83%-100% 95% CI).

While the sign of the prediction score S provides means for classifying samples as "cancer" or "non-cancer", the magnitude of S further provides a measure of the confidence with which this classification is performed. For ease of interpretation of S as a confidence, it can be mapped to a score between 0 and 1 providing an estimate of the probability that the sample is cancerous:

$$P(\text{cancer})=1/(1+\exp(-aS)).$$

Using logistic regression, the following estimates were obtained for the scaling factor a and the bias b: a=2.53 and b=5.94. These values can be re-adjusted as more data becomes available.

Thus, in validation studies, the three or four gene panel previously identified via microarray testing as the best classifier for discriminating grade 3 and 4 cancer cells from normal and BPH cells retained its high predictive accuracy when assessed by RT-PCR assay.

Example 9: Detection of Biomarkers in Urine

Work by Hessels, et al. ("DD3$^{PCA3}$-based Molecular Urine analysis for the Diagnosis of Prostate Cancer", *European Urology* 44:8-16 (2003), incorporated herein by reference) and others has shown that at least some prostate cancer biomarkers can be detected in urine. In the reported testing, to stimulate release of prostate cells into the urine, the prostate should be massaged, or at least manipulated, in conjunction with a digital rectal exam (DRE) prior to collection of voided urine. The PCA3 testing confirmed that the marker could be detected in RT-PCR assay of such urine samples. Accordingly, it would be desirable to provide a urine-based test using the inventive gene signature under similar conditions, i.e., stimulated release of prostate cells prior to collection of the voided urine.

It is known that urine can inhibit or suppress expression in some cases. Therefore, to confirm the stability of the previously-identified prostate cancer biomarkers in urine specimens, the following test was conducted:

Five samples were prepared. Three of the samples contained varying amounts of prostate cancer cells from biopsied prostate tissue that were spiked into urine. Specifically, about 100 ml of urine was spiked with cells from a prostate cancer cell line at concentrations of 500, 100 and 50 cells per 10 ml of urine containing an RNA preservative (RNAlater®, Applied Biosystems). The remaining two samples were control preparations consisting of prostate cancer cells in buffer. After a short incubation time, the urine and buffered control cells were centrifuged. The urine sediment corresponding to each sample was placed in a smaller volume (~10 ml) of urine and subjected to RT-PCR assay using the procedures described in Example 8.

Table 49 provides the raw expression data determined by RT-PCR assay for each of the four prostate genes and the same five reference genes used in the previous example. The samples are identified as follows: Sample 1: 500 cancer cells/10 ml urine; Sample 2: 100 cancer cells/10 ml urine; Sample 3: 50 cancer cells/10 ml urine; Sample 4: 500 cancer cells in buffer (control); Sample 5: 100 cancer cells in buffer (control).

TABLE 49

| Sample | HSPD1 | IMPDH2 | PDLIM5 | UAP1 | ABL | ACTB | B2M | GAPDH | GUSB |
|---|---|---|---|---|---|---|---|---|---|
| 1 | 0.779 | 0.737 | 4.986 | 2.076 | 0.352 | 1.683 | 14.928 | 0.326 | 1.008 |
| 2 | 0.167 | 0.148 | 2.429 | 0.700 | 0.081 | 0.842 | 8.743 | 0.138 | 0.397 |
| 3 | 0.194 | 0.138 | 3.330 | 0.811 | 0.090 | 1.272 | 12.899 | 0.200 | 0.534 |
| 4 | 1.435 | 1.029 | 2.016 | 2.358 | 0.808 | 1.229 | 1.421 | 0.229 | 0.910 |
| 5 | 0.515 | 0.349 | 0.732 | 0.840 | 0.262 | 0.393 | 0.570 | 0.069 | 0.309 |

Tables 50-53 provide the relative expression for each of the four prostate cancer biomarkers HSPD1, IMPDH2, PDLIM5 and UAP1, respectively, compared to each of the five previously-identified reference genes and the average of the relative values.

TABLE 50

| Sample | HSPD1/ ABL | HSPD1/ ACTB | HSPD1/ B2M | HSPD1/ GAPDH | HSPD1/ GUSB | HSPD1/ AVE |
|---|---|---|---|---|---|---|
| 1 | 2.213 | 0.463 | 0.052 | 2.391 | 0.773 | 0.213 |
| 2 | 2.049 | 0.198 | 0.019 | 1.206 | 0.419 | 0.082 |
| 3 | 2.157 | 0.153 | 0.015 | 0.969 | 0.364 | 0.065 |
| 4 | 1.776 | 1.168 | 1.010 | 6.257 | 1.576 | 1.561 |
| 5 | 1.970 | 1.313 | 0.904 | 7.431 | 1.666 | 1.607 |

TABLE 51

| Sample | IMPDH2/ ABL | IMPDH2/ ACTB | IMPDH2/ B2M | IMPDH2/ GAPDH | IMPDH2/ GUSB | IMPDH2/AVE |
|---|---|---|---|---|---|---|
| 1 | 2.093 | 0.438 | 0.049 | 2.262 | 0.731 | 0.201 |
| 2 | 1.815 | 0.175 | 0.017 | 1.068 | 0.371 | 0.072 |
| 3 | 1.537 | 0.109 | 0.011 | 0.691 | 0.259 | 0.046 |
| 4 | 1.274 | 0.837 | 0.724 | 4.488 | 1.131 | 1.119 |
| 5 | 1.335 | 0.889 | 0.612 | 5.034 | 1.128 | 1.089 |

TABLE 52

| Sample | PDLIM5/ ABL | PDLIM5/ ACTB | PDLIM5/ B2M | PDLIM5/ GAPDH | PDLIM5/ GUSB | PDLIM5/AVE |
|---|---|---|---|---|---|---|
| 1 | 14.166 | 2.962 | 0.334 | 15.309 | 4.947 | 1.362 |
| 2 | 29.870 | 2.884 | 0.278 | 17.577 | 6.111 | 1.190 |
| 3 | 36.975 | 2.617 | 0.258 | 16.609 | 6.241 | 1.110 |
| 4 | 2.495 | 1.640 | 1.419 | 8.791 | 2.214 | 2.192 |
| 5 | 2.799 | 1.864 | 1.283 | 10.554 | 2.366 | 2.283 |

TABLE 53

| Sample | UAP1/ ABL | UAP1/ ACTB | UAP1/ B2M | UAP1/ GAPDH | UAP1/ GUSB | UAP1/ AVE |
|---|---|---|---|---|---|---|
| 1 | 5.900 | 1.234 | 0.139 | 6.376 | 2.060 | 0.567 |
| 2 | 8.602 | 0.830 | 0.080 | 5.062 | 1.760 | 0.343 |
| 3 | 9.001 | 0.637 | 0.063 | 4.043 | 1.519 | 0.270 |
| 4 | 2.918 | 1.919 | 1.660 | 10.282 | 2.590 | 2.564 |
| 5 | 3.213 | 2.140 | 1.473 | 12.116 | 2.716 | 2.620 |

Figure 16:
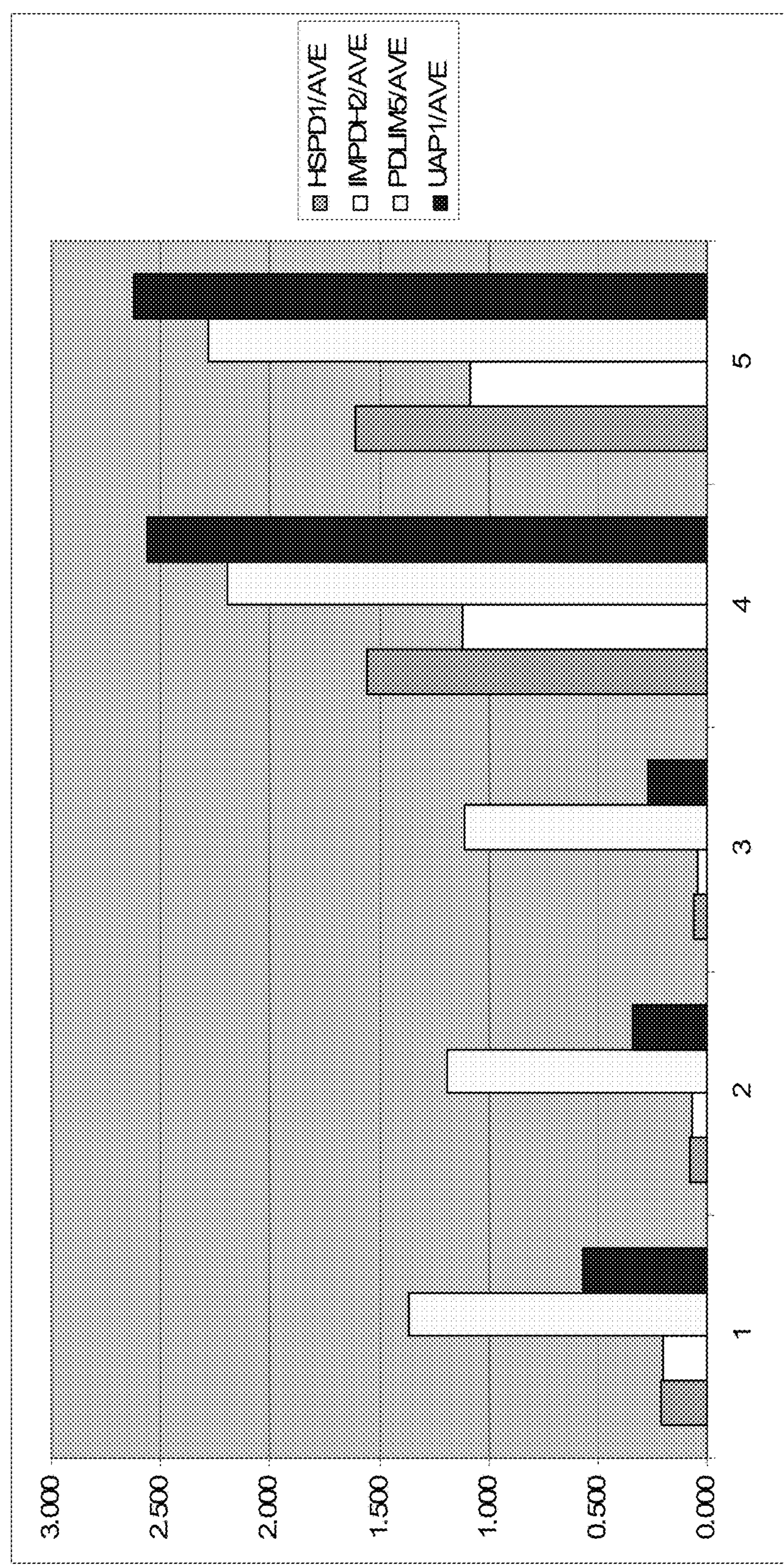
FIG. 16 is a histogram showing relative expression of prostate cancer biomarkers in urine.

FIG. 16 is a histogram showing the average relative expression values for each of the four marker genes in each sample. The controls (Samples 4 and 5) display the highest relative expression levels for all four genes. In the three urine samples, inhibition is apparent, particularly for HSPD1 and IMPDH2, but expression is nonetheless detectable. Compensation for the reduced expression level can be made by adjusting the bias b value in the prediction score S, which changes the threshold (zero point) between cancer (negative) and non-cancer (positive). While expression of PDLIM5 (Hs.7780) is reduced in the urine sample when compared to the controls, the relative expression is still fairly strong, possibly indicating that this marker may alone be a good diagnostic tool for a urine-based test. The area under the curve (AUC) for PDLIM5 is 0.9135 (from Table 45a) and the fold change is over 2 in prostate cancer, indicating good differentiation over non-cancer. UAP1 is detectable in urine at significantly higher relative levels than are HSPD1 and IMPDH2. The AUC for UAP1 is 0.8888 and the fold change is over 2 in prostate cancer. Thus, another potential diagnostic tool for a urine-based test would be a two gene (or protein) biomarker combination consisting of PDLIM5 and UAP1.

Optimization of the urine test may require selection of different reference genes to ensure that the reference genes are also stable in urine. One possible additional or alternative reference gene for urine-based testing could be KLK3 (kallikrein-related peptidase 3), also known as PSA (prostate-specific antigen). This gene, which is used as a reference gene in the commercially-available GEN-PROBE® PCA3 assay, is known to be stable in urine and therefore could be used to normalize for the amount of prostate-specific RNA in the samples. Applied Biosystems offers several appropriate KLK3 reagents in its inventory of TAQMAN® gene expression assays including Assay ID Nos. Hs03063374_m1 (64 bp) and Hs00426859_g1 (153 bp) (Unigene ID Hs.171995, RefSeq NM_001030047.1, NM_001030049.1, NM_001648.2), and Assay ID No. Hs01105076_m1 (65 bp, Unigene ID Hs.171995, RefSeq NM_001030048.1), among others.

The foregoing examples describe procedures for identifying and validating small groups of genes, i.e., "biomarkers" or "combination biomarkers", that can be used to create an easy-to-read, cost-effective test (kit) for research and clinical applications that call for the screening and predicting prostate cancer, and for monitoring the progress of prostate cancer and effectiveness of treatment. Such tests would measure gene expression products of the identified genes in either a microarray format, such as a simple microarray with a small number of probes plus reference probes (in contrast to standard microarrays with tens of thousands of probes), or a PCR-based assay such as those that are well known in the art. The testing can be performed on biopsied prostate tissue, or less invasively-obtained semen, blood or urine samples, and the identities of the specific genes may be varied from among the top 19 or 50 or 100 genes based upon the presence or not of such genes in the source of the biological sample. In the examples provided, combinations of two, three or four genes have been identified that can be detected within multiple sample types. It is anticipated that other small subsets of genes (or their expression products), e.g., 3-10 genes, selected from the top 19 or 50 or 100 genes could be combined to produce different prostate cancer biomarkers for different sample types and/or different protocols and/or different instrumentation by observing the relationship between selectivity and sensitivity as described herein.

Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

REFERENCES (INCORPORATED HEREIN BY REFERENCE)

[1] Singh D, et al., Gene expression correlates of clinical prostate cancer behavior *Cancer Cell,* 2:203-9, Mar. 1, 2002.

[2] Febbo P., et al., Use of expression analysis to predict outcome after radical prostatectomy, *The Journal of Urology, Vol.* 170, pp. S11-S20, December 2003.

[3] LaTulippe E, Satagopan J, Smith A, Scher H, Scardino P, Reuter V, Gerald W L., "Comprehensive gene expression analysis of prostate cancer reveals distinct transcriptional programs associated with metastatic disease", *Cancer Res.* 2002 Aug. 1; 62(15):4499-506.

[4] Luo J H, Yu Y P, Cieply K, Lin F, Deflavia P, Dhir R, Finkelstein S, Michalopoulos G, Becich M., "Gene expression analysis of prostate cancers", *Mol Carcinog.* 2002 January; 33(1):25-35

[5] Magee J A, Araki T, Patil S, Ehrig T, True L, Humphrey P A, Catalona W J, Watson M A, Milbrandt J., "Expression profiling reveals hepsin overexpression in prostate cancer", *Cancer Res.* 2001 Aug. 1; 61(15):5692-6.

[6] Welsh J B, Sapinoso L M, Su A I, Kern S G, Wang-Rodriguez J, Moskaluk C A, Frierson H F Jr, Hampton G M., "Analysis of gene expression identifies candidate markers and pharmacological targets in prostate cancer", *Cancer Res.* 2001 Aug. 15; 61(16):5974-8.

[7] Luo J, Duggan D J, Chen Y, Sauvageot J, Ewing C M, Bittner M L, Trent J M, Isaacs W B., "Human prostate cancer and benign prostatic hyperplasia: molecular dissection by gene expression profiling", *Cancer Res.* 2001 Jun. 15; 61(12):4683-8.

[8] Ramaswamy S, Ross K N, Lander E S, Golub T R., "A molecular signature of metastasis in primary solid tumors", *Nat Genet.* 2003 January; 33(1):49-54. Epub 2002 Dec. 9.

[9] Hsiao L L, Dangond F, Yoshida T, Hong R, Jensen R V, Misra J, Dillon W, Lee K F, Clark K E, Haverty P, Weng Z, Mutter G L, Frosch M P, Macdonald M E, Milford E L, Crum C P, Bueno R, Pratt R E, Mahadevappa M, Warrington J A, Stephanopoulos G, Stephanopoulos G, Gullans S R., "A compendium of gene expression in normal human tissues", *Physiol Genomics.* 2001 Dec. 21; 7(2):97-104.

[10] Su, A. I., Welsh, J. B., Sapinoso, L. M., Kern S. G., Dimitrov, P., Lapp, H., Schultz, P. G., Powell, S. M., Moskaluk, C. A., Frierson, H. F. Jr., Hampton, G. M., "Molecular classification of human carcinomas by use of gene expression signatures", *Cancer Res.* 2001 Oct. 5; 61(20):7388-93.

[11] DePrimo, S. E., Diehn, M., Nelson, J. B., Reiter, R. E., Matese, J., Fero, M., Tibshirani, R., Brown, P. O., Brooks, J. D., "Transcriptional Programs Activated by Exposure of Human Prostate Cancer Cells to Androgen", *Genome Biology,* 3(7) 2002.

[12] Lai, Y., Wu, B., Chen, L. and Zhao, H. "A statistical method for identifying differential gene-gene co-expression patterns", *Bioinformatics*, vol. 20 issue 17.

[13] Lodygin, D., Menssen, A., and Hermeking, H., "Induction of the Cdk inhibitor p21 by LY83583 inhibits tumor cell proliferation in a p53-independent manner", *J. Clin. Invest.* 110:1717-1727 (2002).

[14] Yap, Y., Zhang, X. W., Ling, M. T., Wang, X-Ho, Wong, Y. C., and Danchin, A., "Classification between normal and tumor tissues based on the pair-wise gene expression ratio"; BMC Cancer. 2004; 4: 72.

[15] Kishino H, Waddell P J., "Correspondence analysis of genes and tissue types and finding genetic links from microarray data", *Genome Inform Ser. Workshop Genome Inform* 2000; 11: 83-95.

[16] Verma, M., Kagan, J., Sidransky, D. & Srivastava, S., "Proteomic analysis of cancer-cell mitochondria", *Nature Reviews Cancer* 3, 789-795 (2003).

[17] Burns-Cox, N., Avery, N. C., Gingell, J. C., Bailey, A. J., "Changes in collagen metabolism in prostate cancer: a host response that may alter progression", *J Urol.* 2001, November; 166(5): 1698-701.

[18] Floryk, D., Tollaksen, S. L., Giometti, C. S. and Huberman, E., "Differentiation of Human Prostate Cancer PC-3 Cells Induced by Inhibitors of Inosine 5'-Monophosphate Dehydrogenase", *Cancer Research* 64, 9049-9056, Dec. 15, 2004.

[19] Mobasheri, A., Fox, R., Evans, I., Cullingham, F. Martin-Vasallo, P. & Foster, C. S., "Epithelial Na, K-ATPase expression is down-regulated in canine prostate cancer; a possible consequence of metabolic transformation in the process of prostate malignancy", *Cancer Cell International* 2003, 3:8

[20] Agresti A, Coull B (1998), "Approximate is better than 'exact' for interval estimation of binomial proportions", *The American Statistician* 52: 119-126.

[21] Dhanasekaran, S. M., Barrette, T. R., Ghosh, D., Shah, R., Varambally, S., Kurachi, K., Pienta, K. J., Rubin, M. A., Chinnaiyan, A. M., Delineation of prognostic biomarkers in prostate cancer. *Nature,* 2001 Aug. 23; 412 (6849):822-6.

The invention claimed is:

1. A computer-based method for screening a male human subject for the presence of and treating prostate cancer, comprising:

screening the subject by:

obtaining a biological sample from the subject;

detecting a plurality of relative expression values within the biological sample for each of a group of polynucleotides comprising nucleic acids 1 through 498 of SEQ ID NO. 1, SEQ ID NO. 2, SEQ ID NO. 3, SEQ ID NO. 5, relative to one or more reference genes;

performing a diagnostic procedure comprising:

downloading the plurality of expression values into a computer processor;

calculating within the computer processor a prediction score S according to the relationship S=ln(HSPD1/ref.gene)+ln(IMPDH2/ref.gene)+ln(PDLIM5/ref-.gene)+ln(UAP1/ref.gene)+b, where ref.gene is the one or more reference gene and b is a bias value, wherein b is adjusted to compensate for reduced expression level in the biological sample and b is further adjusted to obtain a selected sensitivity and a selected specificity;

administering an effective anti-cancer treatment to the subject.

2. The method of claim 1, further comprising generating an estimate of a probability P that the biological sample is cancerous according to the relationship $$P(\text{cancer})=1/(1+\exp(-aS)),$$ where $a$ is a scaling factor.

3. The method of claim 1, wherein the selected sensitivity and the selected specificity are each greater than 90%.

4. The method of claim 1, wherein the relative expression values are detected within the biological sample using RT-PCR.

5. The method of claim 1, wherein the biological sample comprises urine.

6. The method of claim 1, wherein the one or more reference genes comprises B2M.

7. The method of claim 1, wherein the one or more reference genes comprises KLK3.

8. A computer-based method for screening a male human subject for and treating prostate cancer, comprising:

obtaining a biological sample from the subject;

detecting values corresponding to relative expression products values within the biological sample for at least each polynucleotide of a group of polynucleotides comprising nucleic acids 1 through 498 of SEQ ID NO. 1, SEQ ID NO. 2, SEQ ID NO. 3, SEQ ID NO. 5, relative to one or more reference genes;

downloading the plurality of expression values into a computer processor;

calculating within the computer processor a prediction score S according to the relationship S=ln(HSPD1/ref.gene)+ln(IMPDH2/ref.gene)+ln(PDLIM5/ref-.gene)+ln(UAP1/ref.gene)+b, where ref.gene is the one or more reference gene and b is a bias value, wherein b is adjusted to compensate for reduced expression level in the biological sample and b is further adjusted to obtain a sensitivity and a specificity each greater than 90%;

and administering an effective anti-cancer treatment to the subject.

9. The method of claim 8, further comprising generating an estimate of a probability P that the biological sample is cancerous according to the relationship $$P(\text{cancer})=1/(1+\exp(-aS)),$$ where $a$ is a scaling factor.

10. The method of claim 8, wherein the relative expression values are detected within the biological sample using RT-PCR.

11. The method of claim 8, wherein the biological sample comprises urine.

12. The method of claim 8, wherein the one or more reference genes comprises B2M.

13. The method of claim 8, wherein the one or more reference genes comprises KLK3.

* * * * *

SEQUENCE LISTING

```
<160> NUMBER OF SEQ ID NOS: 39

<210> SEQ ID NO 1
<211> LENGTH: 734
<212> TYPE: DNA
<213> ORGANISM: Homo sapiens
<220> FEATURE:
<221> NAME/KEY: gene
<223> OTHER INFORMATION: Unigene:  Hs.7780; GenBank Accession: AV715767
      DCB Homo sapiens cDNA clone DCBATH02 5', cDNA DKFZp564A072, mRNA
      sequence
<220> FEATURE:
<221> NAME/KEY: misc_feature
<222> LOCATION: 513, 519
<223> OTHER INFORMATION: n = A, T, C or G

<400> SEQUENCE: 1

aacagctcaa atcttcaaaa tattactata gcattatgtt taaaataatc tacaacaaaa      60

atgtaccatt ttcaagcagt actacattag gagccctttt atagaaaata atttcttctt     120
```

```
taccccgtt ccagtgtgaa tctagtattc tgttaacatt tgtgtggcat ttggagtttg    180

tcatccccat tgaagggaga gccttctcag acatgaagca agggaaacat actgaatagt    240

tttacacaaa tttgatctgg cttccatttg tccccctcat ttcccaaatg tttaaatgta    300

ttggatttgg attctcaatg tataagttgc cttatctgtt aatgtctatc ttctgtctct    360

ttaattttgt atatctgctg ttttgctttt ggatacattt tctaattaga agtcacatga    420

taaatataat cagtatagta ataataccat aatgtgcaca tactcaataa ataaatgact    480

gcattgttgt aaatgaaaaa aaaaaaaaaa aanaaaaana aaacccttgt cggccgcctc    540

ggcccagtcg actctagact cgagcaagct tatgcatgcg gccgcaattc gagctcactg    600

ggccaattcg ccctataggg agtcgtatta cattccactg ccgccgtttt acaacgtcgt    660

gactgggaaa accctgccgt tacccaactt aatgcgcttg aagcacattc cctttcgcca    720

gctggcgtaa atgc                                                      734


<210> SEQ ID NO 2
<211> LENGTH: 2279
<212> TYPE: DNA
<213> ORGANISM: Homo sapiens
<220> FEATURE:
<221> NAME/KEY: gene
<223> OTHER INFORMATION: Unigene: Hs.21293; GenBank Accession: S73498.1;
      Homo sapiens AgX-1 antigen mRNA, complete cds.

<400> SEQUENCE: 2

gaattcgggg tggcgagagg ggcggggtgg ccggggctgt ctccacttgg ccccgctccc     60

ggcccgcccc gccgccgccc cccggatgag ggtatatatt cggagtgagc gcgggaccga    120

tgagtggccg cgccgaagga gctggagacg gtcgtagctg cggtcgccga gaaaggttta    180

caggtacata cattacaccc ctatttctac aaagcttggc tattagagca ttatgaacat    240

taatgacctc aaactcacgt tgtccaaagc tgggcaagag cacctactac gtttctggaa    300

tgagcttgaa gaagcccaac aggtagaact ttatgcagag ctccaggcca tgaactttga    360

ggagctgaac ttctttttcc aaaaggccat tgaaggtttt aaccagtctt ctcaccaaaa    420

gaatgtggat gcacgaatgg aacctgtgcc tcgagaggta ttaggcagtg ctacaaggga    480

tcaagatcag ctccaggcct gggaaagtga aggacttttc cagatttctc agaataaagt    540

agcagttctt cttctagctg gtgggcaggg gacaagactc ggcgttgcat atcctaaggg    600

gatgtatgat gttggtttgc catcccgtaa gacacttttt cagattcaag cagagcgtat    660

cctgaagcta cagcaggttg ctgaaaaata ttatggcaac aaatgcatta ttccatggta    720

tataatgacc agtggcagaa caatggaatc tacaaaggag ttcttcacca agcacaagta    780

ctttggttta aaaaaagaga atgtaatctt ttttcagcaa ggaatgctcc ccgccatgag    840

ttttgatggg aaaattattt tggaagagaa gaacaaagtt tctatggctc cagatgggaa    900

tggtggtctt tatcgggcac ttgcagccca gaatattgtg gaggatatgg agcaaagagg    960

catttggagc attcatgtct attgtgttga caacatatta gtaaaagtgg cagacccacg   1020

gttcattgga ttttgcattc agaaaggagc agactgtgga gcaaaggtgg tagagaaaac   1080

gaaccctaca gaaccagttg gagtggtttg ccgagtggat ggagtttacc aggtggtaga   1140

atatagtgag atttccctgg caacagctca aaaacgaagc tcagacggac gactgctgtt   1200

caatgcgggg aacattgcca accatttctt cactgtacca tttctgagag atgttgtcaa   1260

tgtttatgaa cctcagttgc agcaccatgt ggctcaaaag aagattcctt atgtggatac   1320

ccaaggacag ttaattaagc cagacaaacc caatggaata aagatggaaa aatttgtctt   1380
```

```
tgacatcttc cagtttgcaa agaagtttgt ggtatatgaa gtattgcgag aagatgagtt   1440

ttccccacta aagaatgctg atagtcagaa tgggaaagac aaccctacta ctgcaaggca   1500

tgctttgatg tcccttcatc attgctgggt cctcaatgca gggggccatt tcatagatga   1560

aaatagctct cgccttccag caattccccg cttgaaggat gccaatgatg taccaatcca   1620

atgtgaaatc tctcctctta tctcctatgc tggagaagga ttagaaagtt atgtggcaga   1680

taaagaattc catgcacctc taatcatcga tgagaatgga gttcatgagc tggtgaaaaa   1740

tggtatttga accagatacc aagttttgtt tgccacgata ggaatagctt ttatttttga   1800

tagaccaact gtgaacctac aagacgtctt ggacaactga agtttaaata tccacagggt   1860

tttattttgc ttgttgaact cttagagcta ttgcaaactt cccaagatcc agatgactga   1920

atttcagata gcatttttat gattcccaac tcattgaagg tcttatttat ataatttttt   1980

ccaagccaag gagaccattg gccatccagg aaatttcgta cagctgaaat ataggcagga   2040

tgttcaacat cagtttactt gcagctggaa gcatttgttt ttgaagttgt acatagtaat   2100

aatatgtcat tgtacatgtt gaaaggtttc tatggtacta aaagtttgtt ttattttatc   2160

aaacattaag ctttttaag aaaataattg ggcagtgaaa taaatgtatc ttcttgtctc   2220

tggaaaaaaa aaaaaaaaaa aaaaaaaaaa aaaaaaaaaa aaaaaaaaaa cccgaattc    2279
```

<210> SEQ ID NO 3
<211> LENGTH: 2202
<212> TYPE: DNA
<213> ORGANISM: Homo sapiens
<220> FEATURE:
<221> NAME/KEY: gene
<223> OTHER INFORMATION: Unigene: Hs.79037; GenBank Accession: NM_002156.1 Homo sapiens heat shock 60kDa protein 1 (chaperonin) (HSPD1), mRNA

<400> SEQUENCE: 3

```
cacgcttgcc gccgccccgc agaaatgctt cggttaccca cagtctttcg ccagatgaga     60

ccggtgtcca gggtactggc tcctcatctc actcgggctt atgccaaaga tgtaaaattt    120

ggtgcagatg cccgagcctt aatgcttcaa ggtgtagacc ttttagccga tgctgtggcc    180

gttacaatgg ggccaaaggg aagaacagtg attattgagc agggttgggg aagtcccaaa    240

gtaacaaaag atggtgtgac tgttgcaaag tcaattgact taaaagataa atacaagaac    300

attggagcta aacttgttca agatgttgcc aataacacaa atgaagaagc tggggatggc    360

actaccactg ctactgtact ggcacgctct atagccaagg aaggcttcga gaagattagc    420

aaaggtgcta atccagtgga aatcaggaga ggtgtgatgt tagctgttga tgctgtaatt    480

gctgaactta aaaagcagtc taaacctgtg accacccctg aagaaattgc acaggttgct    540

acgatttctg caaacggaga caaagaaatt ggcaatatca tctctgatgc aatgaaaaaa    600

gttggaagaa agggtgtcat cacagtaaag gatggaaaaa cactgaatga tgaattagaa    660

attattgaag gcatgaagtt tgatcgaggc tatatttctc catactttat taatacatca    720

aaaggtcaga aatgtgaatt ccaggatgcc tatgttctgt tgagtgaaaa gaaaatttct    780

agtatccagt ccattgtacc tgctcttgaa attgccaatg ctcaccgtaa gcctttggtc    840

ataatcgctg aagatgttga tggagaagct ctaagtacac tcgtcttgaa taggctaaag    900

gttggtcttc aggttgtggc agtcaaggct ccagggtttg gtgacaatag aaagaaccag    960

cttaaagata tggctattgc tactggtggt gcagtgtttg gagaagaggg attgaccctg   1020

aatcttgaag acgttcagcc tcatgactta ggaaaagttg gagaggtcat tgtgaccaaa   1080
```

```
gacgatgcca tgctcttaaa aggaaaaggt gacaaggctc aaattgaaaa acgtattcaa   1140

gaaatcattg agcagttaga tgtcacaact agtgaatatg aaaaggaaaa actgaatgaa   1200

cggcttgcaa aactttcaga tggagtggct gtgctgaagg ttggtgggac aagtgatgtt   1260

gaagtgaatg aaaagaaaga cagagttaca gatgccctta atgctacaag agctgctgtt   1320

gaagaaggca ttgttttggg agggggttgt gccctccttc gatgcattcc agccttggac   1380

tcattgactc cagctaatga agatcaaaaa attggtatag aaattattaa aagaacactc   1440

aaaattccag caatgaccat tgctaagaat gcaggtgttg aaggatcttt gatagttgag   1500

aaaattatgc aaagttcctc agaagttggt tatgatgcta tggctggaga ttttgtgaat   1560

atggtggaaa aaggaatcat tgacccaaca aaggttgtga gaactgcttt attggatgct   1620

gctggtgtgg cctctctgtt aactacagca gaagttgtag tcacagaaat tcctaaagaa   1680

gagaaggacc ctggaatggg tgcaatgggt ggaatgggag gtggtatggg aggtggcatg   1740

ttctaactcc tagactagtg ctttaccttt attaatgaac tgtgacagga agcccaaggc   1800

agtgttcctc accaataact tcagagaagt cagttggaga aaatgaagaa aaaggctggc   1860

tgaaaatcac tataaccatc agttactggt ttcagttgac aaaatatata atggtttact   1920

gctgtcattg tccatgccta cagataattt attttgtatt tttgaataaa aaacatttgt   1980

acattcctga tactgggtac aagagccatg taccagtgta ctgctttcaa cttaaatcac   2040

tgaggcattt ttactactat tctgttaaaa tcaggatttt agtgcttgcc accaccagat   2100

gagaagttaa gcagcctttc tgtggagagt gagaataatt gtgtacaaag tagagaagta   2160

tccaattatg tgacaacctt tgtgtaataa aaatttgttt aa                       2202
```

```
<210> SEQ ID NO 4
<211> LENGTH: 6914
<212> TYPE: DNA
<213> ORGANISM: Homo sapiens
<220> FEATURE:
<221> NAME/KEY: gene
<223> OTHER INFORMATION: Unigene:  Hs.30054; GenBank Accession:
      NM_000130.2; Homo sapiens coagulation factor V (proaccelerin,
      labile factor)(F5), mRNA.

<400> SEQUENCE: 4
```

```
tcattgcagc tgggacagcc cggagtgtgg ttagcagctc ggcaagcgct gcccaggtcc     60

tggggtggtg gcagccagcg ggagcaggaa aggaagcatg ttcccaggct gcccacgcct    120

ctgggtcctg gtggtcttgg gcaccagctg ggtaggctgg gggagccaag ggacagaagc    180

ggcacagcta aggcagttct acgtggctgc tcagggcatc agttggagct accgacctga    240

gcccacaaac tcaagtttga atctttctgt aacttccttt aagaaaattg tctacagaga    300

gtatgaacca tattttaaga aagaaaaacc acaatctacc atttcaggac ttcttgggcc    360

tactttatat gctgaagtcg gagacatcat aaaagttcac tttaaaaata aggcagataa    420

gcccttgagc atccatcctc aaggaattag gtacagtaaa ttatcagaag gtgcttctta    480

ccttgaccac acattccctg cagagaagat ggacgacgct gtggctccag gccgagaata    540

cacctatgaa tggagtatca gtgaggacag tggacccacc catgatgacc ctccatgcct    600

cacacacatc tattactccc atgaaaatct gatcgaggat ttcaactctg ggctgattgg    660

gcccctgctt atctgtaaaa aagggaccct aactgagggt gggacacaga agacgtttga    720

caagcaaatc gtgctactat ttgctgtgtt tgatgaaagc aagagctgga gccagtcatc    780

atccctaatg tacacagtca atggatatgt gaatgggaca atgccagata taacagtttg    840
```

```
tgcccatgac cacatcagct ggcatctgct gggaatgagc tcggggccag aattattctc    900
cattcatttc aacggccagg tcctggagca gaaccatcat aaggtctcag ccatcaccct    960
tgtcagtgct acatccacta ccgcaaatat gactgtgggc ccagagggaa agtggatcat   1020
atcttctctc accccaaaac atttgcaagc tgggatgcag gcttacattg acattaaaaa   1080
ctgcccaaag aaaaccagga atcttaagaa aataactcgt gagcagaggc ggcacatgaa   1140
gaggtgggaa tacttcattg ctgcagagga agtcatttgg gactatgcac ctgtaatacc   1200
agcgaatatg gacaaaaaat acaggtctca gcatttggat aatttctcaa accaaattgg   1260
aaaacattat aagaaagtta tgtacacaca gtacgaagat gagtccttca ccaaacatac   1320
agtgaatccc aatatgaaag aagatgggat tttgggtcct attatcagag cccaggtcag   1380
agacacactc aaaatcgtgt tcaaaaatat ggccagccgc ccctatagca tttaccctca   1440
tggagtgacc ttctcgcctt atgaagatga agtcaactct tctttcacct caggcaggaa   1500
caacaccatg atcagagcag ttcaaccagg ggaaacctat acttataagt ggaacatctt   1560
agagtttgat gaacccacag aaaatgatgc ccagtgctta acaagaccat actacagtga   1620
cgtggacatc atgagagaca tcgcctctgg gctaatagga ctacttctaa tctgtaagag   1680
cagatccctg gacaggcgag gaatacagag ggcagcagac atcgaacagc aggctgtgtt   1740
tgctgtgttt gatgagaaca aaagctggta ccttgaggac aacatcaaca agttttgtga   1800
aaatcctgat gaggtgaaac gtgatgaccc caagttttat gaatcaaaca tcatgagcac   1860
tatcaatggc tatgtgcctg agagcataac tactcttgga ttctgctttg atgacactgt   1920
ccagtggcac ttctgtagtg tggggaccca gaatgaaatt ttgaccatcc acttcactgg   1980
gcactcattc atctatggaa agaggcatga ggacaccttg accctcttcc ccatgcgtgg   2040
agaatctgtg acggtcacaa tggataatgt tggaacttgg atgttaactt ccatgaattc   2100
tagtccaaga agcaaaaagc tgaggctgaa attcagggat gttaaatgta tcccagatga   2160
tgatgaagac tcatatgaga tttttgaacc tccagaatct acagtcatgg ctacacggaa   2220
aatgcatgat cgtttagaac ctgaagatga agagagtgat gctgactatg attaccagaa   2280
cagactggct gcagcattag gaattaggtc attccgaaac tcatcattga accaggaaga   2340
agaagagttc aatcttactg ccctagctct ggagaatggc actgaattcg tttcttcgaa   2400
cacagatata attgttggtt caaattattc ttccccaagt aatattagta agttcactgt   2460
caataacctt gcagaacctc agaaagcccc ttctcaccaa caagccacca cagctggttc   2520
cccactgaga cacctcattg gcaagaactc agttctcaat tcttccacag cagagcattc   2580
cagcccatat tctgaagacc ctatagagga tcctctacag ccagatgtca cagggatacg   2640
tctactttca cttggtgctg gagaattcag aagtcaagaa catgctaagc gtaagggacc   2700
caaggtagaa agagatcaag cagcaaagca caggttctcc tggatgaaat tactagcaca   2760
taaagttggg agacacctaa gccaagacac tggttctcct tccggaatga ggccctggga   2820
ggaccttcct agccaagaca ctggttctcc ttccagaatg aggccctggg aggaccctcc   2880
tagtgatctg ttactcttaa aacaaagtaa ctcatctaag attttggttg ggagatggca   2940
tttggcttct gagaaaggta gctatgaaat aatccaagat actgatgaag acacagctgt   3000
taacaattgg ctgatcagcc cccagaatgc ctcacgtgct tggggagaaa gcacccctct   3060
tgccaacaag cctggaaagc agagtggcca cccaaagttt cctagagtta gacataaatc   3120
tctacaagta agacaggatg gaggaaagag tagactgaag aaaagccagt ttctcattaa   3180
```

```
gacacgaaaa aagaaaaaag agaagcacac acaccatgct cctttatctc cgaggacctt   3240
tcaccctcta agaagtgaag cctacaacac attttcagaa agaagactta agcattcgtt   3300
ggtgcttcat aaatccaatg aaacatctct tcccacagac ctcaatcaga cattgccctc   3360
tatggatttt ggctggatag cctcacttcc tgaccataat cagaattcct caaatgacac   3420
tggtcaggca agctgtcctc caggtcttta tcagacagtg cccccagagg aacactatca   3480
aacattcccc attcaagacc ctgatcaaat gcactctact tcagacccca gtcacagatc   3540
ctcttctcca gagctcagtg aaatgcttga gtatgaccga agtcacaagt ccttccccac   3600
agatataagt caaatgtccc cttcctcaga acatgaagtc tggcagacag tcatctctcc   3660
agacctcagc caggtgaccc tctctccaga actcagccag acaaacctct ctccagacct   3720
cagccacacg actctctctc cagaactcat tcagagaaac ctttccccag ccctcggtca   3780
gatgcccatt tctccagacc tcagccatac aaccctttct ccagacctca gccatacaac   3840
cctttcttta gacctcagcc agacaaacct ctctccagaa ctcagtcaga caaacctttc   3900
tccagccctc ggtcagatgc cccttttctcc agacctcagc catacaacca tttctctaga   3960
cttcagccag acaaacctct ctccagaact cagccatatg actctctctc cagaactcag   4020
tcagacaaac ctttccccag ccctcggtca gatgcccatt tctccagacc tcagccatac   4080
aaccctttct ctagacttca gccagacaaa cctctctcca gaactcagtc aaacaaacct   4140
ttccccagcc ctcggtcaga tgccccttttc tccagacccc agccatacaa ccctttctct   4200
agacctcagc cagacaaacc tctctccaga actcagtcag acaaaccttt ccccagacct   4260
cagtgagatg cccctctttg cagatctcag tcaaattccc cttaccccag acctcgacca   4320
gatgacactt tctccagacc ttggtgagac agatctttcc ccaaactttg gtcagatgtc   4380
cctttcccca gacctcagcc aggtgactct ctctccagac atcagtgaca ccacccttct   4440
cccggatctc agccagatat cacctcctcc agaccttgat cagatattct acccttctga   4500
atctagtcag tcattgcttc ttcaagaatt taatgagtct ttttccttatc cagaccttgg   4560
tcagatgcca tctccttcat ctcctactct caatgatact tttctatcaa aggaatttaa   4620
tccactggtt atagtgggcc tcagtaaaga tggtacagat tacattgaga tcattccaaa   4680
ggaagaggtc cagagcagtg aagatgacta tgctgaaatt gattatgtgc cctatgatga   4740
cccctacaaa actgatgtta ggacaaacat caactcctcc agagatcctg acaacattgc   4800
agcatggtac ctccgcagca acaatggaaa cagaagaaat tattacattg ctgctgaaga   4860
aatatcctgg gattattcag aatttgtaca aagggaaaca gatattgaag actctgatga   4920
tattccagaa gataccacat ataagaaagt agtttttcga aagtacctcg acagcacttt   4980
taccaaacgt gatcctcgag gggagtatga agagcatctc ggaattcttg gtcctattat   5040
cagagctgaa gtggatgatg ttatccaagt tcgttttaaa aatttagcat ccagaccgta   5100
ttctctacat gcccatggac tttcctatga aaaatcatca gagggaaaga cttatgaaga   5160
tgactctcct gaatggttta aggaagataa tgctgttcag ccaaatagca gttataccta   5220
cgtatggcat gccactgagc gatcagggcc agaaagtcct ggctctgcct gtcgggcttg   5280
ggcctactac tcagctgtga acccagaaaa agatattcac tcaggcttga taggtcccct   5340
cctaatctgc caaaaaggaa tactacataa ggacagcaac atgcctgtgg acatgagaga   5400
atttgtctta ctatttatga cctttgatga aaagaagagc tggtactatg aaaagaagtc   5460
ccgaagttct tggagactca catcctcaga aatgaaaaaa tcccatgagt ttcacgccat   5520
taatgggatg atctacagct tgcctggcct gaaaatgtat gagcaagagt gggtgaggtt   5580
```

```
acacctgctg aacataggcg gctcccaaga cattcacgtg gttcactttc acggccagac   5640
cttgctggaa aatggcaata aacagcacca gttaggggtc tggccccttc tgcctggttc   5700
atttaaaact cttgaaatga aggcatcaaa acctggctgg tggctcctaa acacagaggt   5760
tggagaaaac cagagagcag ggatgcaaac gccatttctt atcatggaca gagactgtag   5820
gatgccaatg ggactaagca ctggtatcat atctgattca cagatcaagg cttcagagtt   5880
tctgggttac tgggagccca gattagcaag attaaacaat ggtggatctt ataatgcttg   5940
gagtgtagaa aaacttgcag cagaatttgc ctctaaacct tggatccagg tggacatgca   6000
aaaggaagtc ataatcacag ggatccagac ccaaggtgcc aaacactacc tgaagtcctg   6060
ctataccaca gagttctatg tagcttacag ttccaaccag atcaactggc agatcttcaa   6120
agggaacagc acaaggaatg tgatgtattt taatggcaat tcagatgcct ctacaataaa   6180
agagaatcag tttgacccac ctattgtggc tagatatatt aggatctctc caactcgagc   6240
ctataacaga cctacccttc gattggaact gcaaggttgt gaggtaaatg gatgttccac   6300
acccctgggt atggaaaatg gaaagataga aaacaagcaa atcacagctt cttcgtttaa   6360
gaaatcttgg tggggagatt actgggaacc cttccgtgcc cgtctgaatg cccagggacg   6420
tgtgaatgcc tggcaagcca aggcaaacaa caataagcag tggctagaaa ttgatctact   6480
caagatcaag aagataacgg caattataac acagggctgc aagtctctgt cctctgaaat   6540
gtatgtaaag agctatacca tccactacag tgagcaggga gtggaatgga aaccatacag   6600
gctgaaatcc tccatggtgg acaagatttt tgaaggaaat actaatacca aaggacatgt   6660
gaagaacttt ttcaaccccc caatcatttc caggtttatc cgtgtcattc ctaaaacatg   6720
gaatcaaagt attgcacttc gcctggaact ctttggctgt gatatttact agaattgaac   6780
attcaaaaac ccctggaaga gactctttaa gacctcaaac catttagaat gggcaatgta   6840
ttttacgctg tgttaaatgt taacagtttt ccactatttc tctttctttt ctattagtga   6900
ataaaatttt atac                                                      6914
```

```
<210> SEQ ID NO 5
<211> LENGTH: 1654
<212> TYPE: DNA
<213> ORGANISM: Homo sapiens
<220> FEATURE:
<221> NAME/KEY: gene
<223> OTHER INFORMATION: Unigene: Hs.75432; GeneBank Accession:
      NM_000884.1; Homo sapiens IMP (inosine monophosphate)
      dehydrogenase 2 (IMPDH2), mRNA.

<400> SEQUENCE: 5
```

```
gaattcgggc ggtcctcgga gacacgcggc ggtgtcctgt gttggccatg gccgactacc     60
tgattagtgg gggcacgtcc tacgtgccag acgacggact cacagcacag cagctcttca    120
actgcggaga cggcctcacc tacaatgact ttctcattct ccctgggtac atcgacttca    180
ctgcagacca ggtggacctg acttctgctc tgaccaagaa aatcactctt aagaccccac    240
tggtttcctc tcccatggac acagtcacag aggctgggat ggccatagca atggcgctta    300
caggcggtat tggcttcatc caccacaact gtacacctga attccaggcc aatgaagttc    360
ggaaagtgaa gaaatatgaa cagggattca tcacagaccc tgtggtcctc agccccaagg    420
atcgcgtgcg ggatgttttt gaggccaagg cccggcatgg tttctgcggt atcccaatca    480
cagacacagg ccggatgggg agccgcttgg tgggcatcat ctcctccagg gacattgatt    540
ttctcaaaga ggaggaacat gactgtttct tggaagagat aatgacaaag agggaagact    600
```

```
tggtggtagc cccccgcagc atcacactga aggaggcaaa tgaaattctg cagcgcagca    660

agaagggaaa gttgcccatt gtaaatgaag atgatgagct tgtggccatc attgcccgga    720

cagacctgaa gaagaatcgg gactacccac tagcctccaa agatgccaag aaacagctgc    780

tgtgtggggc agccattggc actcatgagg atgacaagta taggctggac ttgctcgccc    840

aggctggtgt ggatgtagtg gttttggact cttcccaggg aaattccatc ttccagatca    900

atatgatcaa gtacatcaaa gacaaatacc ctaatctcca agtcattgga ggcaatgtgg    960

tcactgctgc ccaggccaag aacctcattg atgcaggtgt ggatgccctg cgggtgggca   1020

tgggaagtgg ctccatctgc attacgcagg aagtgctggc ctgtgggcgg ccccaagcaa   1080

cagcagtgta caaggtgtca gagtatgcac ggcgctttgg tgttccggtc attgctgatg   1140

gaggaatcca aaatgtgggt catattgcga aagccttggc ccttggggcc tccacagtca   1200

tgatgggctc tctcctggct gccaccactg aggcccctgg tgaatacttc ttttccgatg   1260

ggatccggct aaagaaatat cgcggtatgg gttctctcga tgccatggac aagcacctca   1320

gcagccagaa cagatatttc agtgaagctg acaaaatcaa agtggcccag ggagtgtctg   1380

gtgctgtgca ggacaaaggg tcaatccaca aatttgtccc ttacctgatt gctggcatcc   1440

aacactcatg ccaggacatt ggtgccaaga gcttgaccca agtccgagcc atgatgtact   1500

ctggggagct taagtttgag aagagaacgt cctcagccca ggtggaaggt ggcgtccata   1560

gcctccattc gtatgagaag cggcttttct gaaaagggat ccagcacacc tcctcggttt   1620

tttttcaat aaaagtttag aaagacccga attc                                1654
```

```
<210> SEQ ID NO 6
<211> LENGTH: 893
<212> TYPE: DNA
<213> ORGANISM: Homo sapiens
<220> FEATURE:
<221> NAME/KEY: gene
<223> OTHER INFORMATION: Unigene: Hs.699; GenBank Accession:
      NM_00942.1; Homo sapiens peptidylprolyl isomerase B
      (cyclophilin B) (PPIB),mRNA.

<400> SEQUENCE: 6

gggtttcgcc tccgcctgtg gatgctgcgc ctctccgaac gcaacatgaa ggtgctcctt     60

gccgccgccc tcatcgcggg gtccgtcttc ttcctgctgc tgccgggacc ttctgcggcc    120

gatgagaaga agaaggggcc caaagtcacc gtcaaggtgt attttgacct acgaattgga    180

gatgaagatg taggccgggt gatctttggt ctcttcggaa agactgttcc aaaaacagtg    240

gataattttg tggccttagc tacaggagag aaaggatttg gctacaaaaa cagcaaattc    300

catcgtgtaa tcaaggactt catgatccag ggcggagact tcaccagggg agatggcaca    360

ggaggaaaga gcatctacgg tgagcgcttc cccgatgaga acttcaaact gaagcactac    420

gggcctggct gggtgagcat ggccaacgca ggcaaagaca ccaacggctc ccagttcttc    480

atcacgacag tcaagacagc ctggctagat ggcaagcatg tggtgtttgg caaagttcta    540

gagggcatgg aggtggtgcg gaaggtggag agcaccaaga cagacagccg ggataaaccc    600

ctgaaggatg tgatcatcgc agactgcggc aagatcgagg tggagaagcc ctttgccatc    660

gccaaggagt agggcacagg gacatctttc tttgagtgac cgtctgtgca ggccctgtag    720

tccgccacag ggctctgagc tgcactggcc ccggtgctgg catctggtgg agcggaccca    780

ctcccctcac attccacagg cccatggact cacttttgta acaaactcct accaacactg    840

accaataaaa aaaaatgtgg gttttttttt tttttaatat aaaaaaaccc ccc           893
```

<210> SEQ ID NO 7
<211> LENGTH: 1901
<212> TYPE: DNA
<213> ORGANISM: Homo sapiens
<220> FEATURE:
<221> NAME/KEY: gene
<223> OTHER INFORMATION: Unigene: Hs.1708; GenBank Accession: NM_005998.1; Homo sapiens chaperonin containing TCP1, subunit 3 (gamma) (CCT3), mRNA

<400> SEQUENCE: 7

```
atggggcatc ggccggtgct cgtgctcagc cagaacacaa agcgtgaatc cggaagaaaa     60
gttcaatctg gaaacatcaa tgctgccaag actattgcag atatcatccg aacatgtttg    120
ggacccaagt ccatgatgaa gatgcttttg gacccaatgg gaggcattgt gatgaccaat    180
gatggcaatg ccattcttcg agagattcaa gtccagcatc cagcggccaa gtccatgatc    240
gaaattagcc ggacccagga tgaagaagtt ggagatggga ccacatcagt aattattctt    300
gcaggggaaa tgctgtctgt agctgagcac ttcctggagc agcagatgca cccaacagtg    360
gtgatcagtg cttaccgcaa ggcattggat gatatgatca gcaccctaaa gaaaataagt    420
atcccagtcg acatcagtga cagtgatatg atgctgaaca tcatcaacag ctctattact    480
accaaagcca tcagccggtg gtcatctttg gcttgcaaca ttgccctgga tgctgtcaag    540
atggtacagt ttgaggagaa tggtcggaaa gagattgaca taaaaaaata tgcaagagtg    600
gaaaagatac ctggaggcat cattgaagac tcctgtgtct tgcgtggagt catgattaac    660
aaggatgtga cccatccacg tatgcggcgc tatatcaaga accctcgcat tgtgctgctg    720
gattcttctc tggaatacaa gaaaggagga agccagactg acattgagat tacacgagag    780
gaggacttca cccgaattct ccagatggag gaagagtaca tccagcagct ctgtgaggac    840
attatccaac tgaagcccga tgtggtcatc actgaaaagg gcatctcaga tttagctcag    900
cactacctta tgcgggccaa tatcacagcc atccgcagag tccggaagac agacaataat    960
cgcattgcta gagcctgtgg ggcccggata gtcagccgac cagaggaact gagagaagat   1020
gatgttggaa caggagcagg cctgttggaa atcaagaaaa ttggagatga atactttact   1080
ttcatcactg actgcaaaga ccccaaggcc tgcaccattc tcctccgggg ggctagcaaa   1140
gagattctct cggaagtaga acgcaacctc caggatgcca tgcaagtgtg tcgcaatgtt   1200
ctcctggacc ctcagctggt gccagggggt ggggcctccg agatggctgt cgcccatgcc   1260
ttgacagaaa aatccaaggc catgactggt gtggaacaat ggccatacag ggctgttgcc   1320
caggccctag aggtcattcc tcgtaccctg atccagaact gtggggccag caccatccgt   1380
ctacttacct cccttcgggc caagcacacc caggagaact gtgagacctg gggtgtaaat   1440
ggtgagacgg gtactttggt ggacatgaag gaactgggca tatgggagcc attggctgtg   1500
aagctgcaga cttataagac agcagtggag acggcagttc tgctactgcg aattgatgac   1560
atcgtttcag gccacaaaaa gaaaggcgat gaccagagcc ggcaaggcgg ggctcctgat   1620
gctggccagg agtgagtgct aggcaaggct acttcaatgc acagaaccag cagagtctcc   1680
ccttttcctg agccagagtg ccaggaacac tgtggacgtc tttgttcaga agggatcagg   1740
ttgggggca gcccccagtc cctttctgtc ccagctcagt tttccaaaag acactgacat   1800
gtaattcttc tctattgtaa ggtttccatt tagtttgctt ccgatgatta aatctaagtc   1860
atttgaaaaa aaaaaaaaaa aaaaaaaaaa aaaaaaaaaa a                       1901
```

<210> SEQ ID NO 8
<211> LENGTH: 1249
<212> TYPE: DNA
<213> ORGANISM: Homo sapiens
<220> FEATURE:
<221> NAME/KEY: gene
<223> OTHER INFORMATION: Unigene: Hs.69469; GenBank Accession: NM_006360.1; Homo sapiens dendritic cell protein (GA17), mRNA.

<400> SEQUENCE: 8

```
gggtcggcgt ggtcttgcga gtggagtgtc cgctgtgccc gggcctgcac catgagcgtc     60
ccggccttca tcgacatcag tgaagaagat caggctgctg agcttcgtgc ttatctgaaa    120
tctaaaggag ctgagatttc agaagagaac tcggaaggtg gacttcatgt tgatttagct    180
caaattattg aagcctgtga tgtgtgtctg aaggaggatg ataaagatgt tgaaagtgtg    240
gtgaacagtg tggtatccct actcttgatc ctggaaccag acaagcaaga agctttgatt    300
gaaagcctat gtgaaaagct ggtcaaattt cgcgaaggtg aacgcccgtc tctgagactg    360
cagttgttaa gcaacctttt ccacgggatg gataagaata ctcctgtaag atacacagtg    420
tattgcagcc ttattgaagt ggtagcatct tgtggggcca tccagtacat cccaactgag    480
ctggatcaag ttagaaaatg gatttctgac tggaatctca ccactgaaaa aaagcacacc    540
cttttaagac tactttatga ggcacttgcg gattgtaaga agagtgatgc tgcttcaaaa    600
gtcatggtgg aattgctcgg aagttacaca gaggacaatg cttcccaggc tcgagttgat    660
gcccacaggt gtattgtcga accattgaaa gatccaaatg catttctttt tgaccacctt    720
cttactttaa aaccagtcaa gtttttggaa ggcgagctta ttcatgatct tttaaccatt    780
tttgtgagtg ctaaattggc atcatatgtc aagttttatc agaataataa agacttcatt    840
gattcacttg gcctgttaca tgaacagaat atggcaaaaa tgagactact tacttttatg    900
ggaatggcaa tagaaaataa ggaaatttct tttgacacaa tgcagcaaga acttcagatt    960
ggagctgatg atgttgaagc atttgttatt gacgccgtaa gaactaaaat ggtctactgc   1020
aaaattgatc agacccagag aaaagtagtt gtcagtcata gcacacatcg gacatttgga   1080
aaacagcggt ggcaacaact gtatgacaca cttaatgcct ggaaacaaaa tctgaacaaa   1140
gtgaaaaaca gccttttgag tctttccgat acctgagttt ttatgcttat aatttttgtt   1200
ctttgaaaaa aaagccctaa atcatagtaa gacattataa accaaaaaa              1249
```

<210> SEQ ID NO 9
<211> LENGTH: 664
<212> TYPE: DNA
<213> ORGANISM: Homo sapiens
<220> FEATURE:
<221> NAME/KEY: gene
<223> OTHER INFORMATION: Unigene: Hs.82280; GenBank Accession: NM_002925.2; Homo sapiens regulator of G-protein signalling 10 (RGS10), mRNA.

<400> SEQUENCE: 9

```
ggattgttgg tctgcgtgga acttctcagg tggacaccag agcatggaac acatccacga     60
cagcgatggc agttccagca gcagccacca gagcctcaag agcacagcca aatgggcggc    120
atccctggag aatctgctgg aagacccaga aggcgtgaaa agatttaggg aatttttaaa    180
aaaggaattc agtgaagaaa atgttttgtt ttggctagca tgtgaagatt ttaagaaaat    240
gcaagataag acgcagatgc aggaaaaggc aaaggagatc tacatgacct ttctgtccag    300
caaggcctca tcacaggtca acgtggaggg gcagtctcgg ctcaacgaga agatcctgga    360
agaaccgcac cctctgatgt tccagaaact ccaggaccag atctttaatc tcatgaagta    420
```

```
cgacagctac agccgctttc ttaagtctga cttgttttta aaacacaagc gaaccgagga    480

agaggaagaa gatttgcctg atgctcaaac tgcagctaaa agagcttcca gaatttataa    540

cacatgagcc cccaaaaagc cgggactggc agctttaaga agcaaaggaa tttcctctca    600

ggacgtgccg ggtttatcat tgctttgtta tttgtaagga ctgaaatgta caaaaccctt    660

caat                                                                 664
```

<210> SEQ ID NO 10
<211> LENGTH: 1792
<212> TYPE: DNA
<213> ORGANISM: Homo sapiens
<220> FEATURE:
<221> NAME/KEY: gene
<223> OTHER INFORMATION: Unigene: Hs.79217; GenBank Accession: NM_006907.1 Homo sapiens pyrroline-5-carboxylate reductase 1 (PYCR1), nuclear gene encoding mitochondrial protein, mRNA

<400> SEQUENCE: 10

```
ctccggacag catgagcgtg ggcttcatcg gcgctggcca gctggctttt gccctggcca     60

agggcttcac agcagcaggc gtcttggctg cccacaagat aatggctagc tccccagaca    120

tggacctggc cacagtttct gctctcagga agatgggggt gaagttgaca ccccacaaca    180

aggagacggt gcagcacagt gatgtgctct tcctggctgt gaagccacac atcatcccct    240

tcatcctgga tgaaataggc gccgacattg aggacagaca cattgtggtg tcctgcgcgg    300

ccggcgtcac catcagctcc attgagaaga agctgtcagc gtttcggcca gcccccaggg    360

tcatccgctg catgaccaac actccagtcg tggtgcggga gggggccacc gtgtatgcca    420

caggcacgca cgcccaggtg gaggacggga ggctcatgga gcagctgctg agcacggtgg    480

gcttctgcac ggaggtggaa gaggacctga ttgatgccgt cacggggctc agtggcagcg    540

gccccgccta cgcattcaca gccctggatg ccctggctga tgggggtgtg aagatgggac    600

ttccaaggcg cctggcagtc cgcctcgggg cccaggccct cctgggggct gccaagatgc    660

tgctgcactc agaacagcac ccaggccagc tcaaggacaa cgtcagctct cctggtgggg    720

ccaccatcca tgccttgcat gtgctggaga gtgggggctt ccgctccctg ctcatcaacg    780

ctgtggaggc ctcctgcatc cgcacacggg agctgcagtc catggctgac caggagcagg    840

tgtcaccagc cgccatcaag aagaccatcc tggacaaggt gaagctggac tcccctgcag    900

ggaccgctct gtcgccttct ggccacacca agctgctccc ccgcagcctg gccccagcgg    960

gcaaggattg acacgtcctg cctgaccacc atcctgccac caccttctct tctcttgtca   1020

ctagggggac tagggggtcc ccaaagtggc ccactttctg tggctctgat cagcgcaggg   1080

gccagccagg gacatagcca gggaggggcc acatcacttc ccactggaaa tctctgtggt   1140

ctgcaagtgc ttcccagccc agaacagggg tggattcccc aacctcaacc tcctttcttc   1200

tctgctccca aaccatgtca ggaccacctt cctctagagc tcgggagccc ggagggtctt   1260

cacccactcc tactccagta tcagctggca cgggctcctt cctgagagca aaggtcaagg   1320

acccccctctg tgaaggctca gcagaggtgg gatcccacgc cccctcccgg cccctccctg   1380

ccctccattc agggagaaac ctctccttcc cgtgtgagaa gggccagagg gtccaggcat   1440

cccaagtcca gcgtgaaggg ccacagcccc tcttggctgc caagcacgca gatcccatgg   1500

acatttgggg aaagggctcc ttgggctgct ggtgaacttc tgtggccacc acctcctgct   1560

cctgacctcc ctgggagggt gctatcagtt ctgtcctggc cctttcagtt ttataagttg   1620

gtttccagcc cccagtgtcc tgacttctgt ctgccacatg aggagggagg ccctgcctgt   1680
```

```
gtgggagggt ggttactgtg ggtggaatag tggaggcctt caactgatta gacaaggccc   1740

gcccacatct tggagggcat ctgccttact gattaaaatg tcaatgtaat ct           1792


<210> SEQ ID NO 11
<211> LENGTH: 529
<212> TYPE: DNA
<213> ORGANISM: Homo sapiens
<220> FEATURE:
<221> NAME/KEY: gene
<223> OTHER INFORMATION: Unigene: Hs.117950; GenBank Accession:
      AA902652 Homo sapiens cDNA clone IMAGE:1519390 3, mRNA sequence.

<400> SEQUENCE: 11

aatcttctaa gtccttttaa ttgttcttat aaactagcat aagatataaa cttaagtagt     60

acacatgagt tttataattt actaatctct gacagatagc taagcatagc acatcagagc    120

ataacacagt gtgagggaaa taaagtgtac aatgacatct tctattctgg acctaataat    180

tcaatagaga aagaactact tgtagtcact gtggttacag aaggtttcat ggacagcgaa    240

cataaagctc tactagctaa caaataggtc ttaatgataa aaacgtgggc cttcagagaa    300

ctaaaggtac caatgtgtgg cagtccaaaa ttacgaggaa aatgagttcc cttcatgggt    360

cacatcagca attttttttt tccccttttg agacagagtc ttgctctgct gcccaggttg    420

gagtgcagtg gcatgatcca ggctcactgc aacctccgcc tcccgggttc aagcaattct    480

catgcctcag cctcccgagt agctgggatt acaggtgcct gtcatcacg                529


<210> SEQ ID NO 12
<211> LENGTH: 6031
<212> TYPE: DNA
<213> ORGANISM: Homo sapiens
<220> FEATURE:
<221> NAME/KEY: gene
<223> OTHER INFORMATION: Unigene: Hs.8858; GenBank Accession: NM_013448
      Homo sapiens bromodomain adjacent to zinc finger domain, 1A
      (BAZ1A), transcript variant 1, mRNA

<400> SEQUENCE: 12

cttttcccat cgtgtagtca agagtctgtg ccagacttga aggctttact ttgttagcca     60

tgtgtttatg aacccccagc gctttcccta gatcttttgg ctgataatct caaacatgga    120

ggatgcttct gaatcttcac gaggggttgc tccattaatt aataatgtag ttctcccagg    180

ctctccgctg tctcttcctg tatcagtgac aggctgtaaa agtcatcgag tagccaataa    240

aaaggtagaa gcgaggagtg aaaagctcct cccaacagct cttcctcctt cagagccgaa    300

agtagatcag aaacttccca ggagctccga gaggcgggga agtggcggtg ggacgcaatt    360

ccccgcgcgg agtcgggcag tggcagcggg agaagcggca gccaggggcg cggcggggcc    420

ggagagaggc ggtcccctgg gaggacgggg tctcccctcg ttgcctttgt agtggagaag    480

gtggacaagt ggcagtcggc gtgatcgcag ggaagcgggg ccggcgcggg cggccgaggg    540

tccaggcgag cccgcgggcg gacgggagat gccgctgcta caccgaaagc cgtttgtgag    600

acagaagccg cccgcggacc tgcggcccga cgaggaagtt ttctactgta aagtcaccaa    660

cgagatcttc cgccactacg atgacttttt tgaacgaacc attctgtgca acagccttgt    720

gtggagttgt gctgtgacgg gtagacctgg actgacgtat caggaagcac ttgagtcaga    780

aaaaaaagca agacagaatc ttcagagttt tccagaacca ctaattattc cagttttata    840

cttgaccagc cttacccatc gttcgcgctt acatgaaatt tgtgatgata tctttgcata    900

tgtcaaggat cgatattttg tcgaagaaac tgtggaagtc attaggaaca atggtgcaag    960
```

```
gttgcagtgt aggattttgg aagtcctccc tccatcacat caaaatggtt ttgctaatgg   1020
acatgttaac agtgtggatg gagaaactat tatcatcagt gatagtgatg attcagaaac   1080
acaaagctgt tcttttcaaa atgggaagaa aaaagatgca attgatccct tactattcaa   1140
gtataaagtg caacccacta aaaaagaatt acatgagtct gctattgtta aagcaacaca   1200
aatcagccgg agaaaacacc tattttctcg tgataaacta aagctttttc tgaagcaaca   1260
ctgtgaacca caagatggag tcattaaaat aaaggcatca tctctttcaa cgtataaaat   1320
agcagaacaa gatttttctt atttcttccc tgatgatcca cccacattta tcttcagtcc   1380
tgctaacaga cgaagaggga gacctcccaa acgaatacat attagtcaag aggacaatgt   1440
tgctaataaa cagactcttg caagttatag gagcaaagct actaaagaaa gagataaact   1500
tttgaaacaa gaagaaatga agtcactggc ttttgaaaag gctaaattaa aaagagaaaa   1560
agcagatgcc ctagaagcga agaaaaaaga aaaagaagat aaagagaaaa agagggaaga   1620
attgaaaaaa attgttgaag aagagagact aaagaaaaaa gaagaaaaag agaggcttaa   1680
agtagaaaga gaaaaggaaa gagagaagtt acgtgaagaa aagcgaaagt atgtggaata   1740
cttaaaacag tggagtaaac ctagagaaga tatggaatgt gatgacctta aggaacttcc   1800
agaaccaaca ccagtgaaaa ctagactacc tcctgaaatc tttggtgatg ctctgatggt   1860
tttggagttc cttaatgcat ttggggaact tttgatctt caagatgagt ttcctgatgg   1920
agtaacccta gaagtattag aggaagctct tgtaggaaat gacagtgaag gcccactgtg   1980
tgaattgctt tttttcttcc tgactgcaat cttccaggca atagctgaag aagaagagga   2040
agtagccaaa gagcaactaa ctgatgctga caccaaagat ttaacagagg ctttggatga   2100
agatgcagac cccacaaaat ctgcactgtc tgcagttgca tctttggcag ctgcatggcc   2160
acagttacac cagggctgca gtttgaaaag tttggatctt gatagctgca ctctttcaga   2220
aatcctcaga ctgcacatct tagcttcagg tgctgatgta acatcagcaa atgcaaagta   2280
tagatatcaa aaacgaggag gatttgatgc tacagatgat gcttgtatgg agcttcgttt   2340
gagcaatccc agtctagtga agaaactgtc aagcacctca gtgtatgatt tgacaccagg   2400
agaaaaaatg aagatactcc atgctctctg tggaaagcta ctgaccctag tttcaactag   2460
ggattttatt gaagattatg ttgatatatt acgacaggca aagcaggagt tccgggaatt   2520
aaaagcagaa caacatcgaa aagagaggga agaagcagct gccagaattc gtaaaaggaa   2580
ggaagaaaaa cttaaggagc aagaacaaaa aatgaaagag aaacaagaaa aactgaaaga   2640
agatgagcaa agaaattcaa cggcagatat atctattggg gaggaagaaa gggaagattt   2700
tgatactagc attgagagca aagacacaga gcaaaaggaa ttagatcaag atatggtcac   2760
tgaagatgaa gatgacccag gatcacataa aagaggcaga agggggaaaa gaggacaaaa   2820
tggatttaaa gaatttacaa ggcaagaaca gatcaactgt gtaacaagag agcctcttac   2880
tgctgatgag gaagaagcat taaaacagga acaccaacga aaagagaaag agctcttaga   2940
aaaaatccaa agtgccatag cctgtaccaa tatctttccc ttgggtcgcg accgcatgta   3000
tagacgatac tggattttcc cttctattcc tggactcttt attgaagagg attattctgg   3060
tcttactgaa gacatgctgt tgcctagacc ttcatcattt cagaataatg tacagtctca   3120
agatcctcag gtatccacta aaactggaga gcctttgatg tctgaatcta cctccaacat   3180
tgaccaaggt ccacgtgacc attctgtgca gctgccaaaa ccagtgcata agccaaatcg   3240
gtggtgcttt tacagttctt gtgaacagct agaccagctt attgaagctc ttaattctag   3300
```

```
aggacataga gaaagtgcct taaaagaaac tttgttacaa gagaaaagca gaatatgtgc   3360
acagctagcc cgtttttctg aagagaaatt tcatttttca gacaaacctc agcctgatag   3420
caaaccaaca tatagtcggg gaagatcttc caatgcatat gatccatctc agatgtgtgc   3480
agaaaagcaa cttgaactaa ggctgagaga ttttctttta gatattgaag atagaatcta   3540
ccaaggaaca ttaggagcca tcaaggttac agatcgacat atctggagat cagcattaga   3600
aagtggacgg tatgagctgt taagtgagga aaacaaggaa aatgggataa ttaaaactgt   3660
gaatgaagac gtagaagaga tggaaattga tgaacaaaca aaggtcatag taaaagacag   3720
acttttgggg ataaaaacag aaactccaag tactgtatca acaaatgcaa gtacaccaca   3780
atcagtgagc agtgtggttc attatctggc aatggcactc tttcaaatag agcagggcat   3840
tgagcggcgt tttctgaaag ctccacttga tgccagtgac agtgggcgtt cttataaaac   3900
agttctggac cgttggagag agtctctcct ttcttctgct agtctatccc aagtttttct   3960
tcacctatcc accttggatc gtagcgtgat atggtctaaa tctatactga atgcgcgttg   4020
caagatatgt cgaaagaaag gcgatgctga aaacatggtt ctttgtgatg gctgtgatag   4080
gggtcatcat acctactgtg ttcgaccaaa gctcaagact gtgcctgaag gagactggtt   4140
ttgtccagaa tgtcgaccaa agcaacgttc tagaagactc tcctctagac agagaccatc   4200
cttggaaagt gatgaagatg tggaagacag tatgggaggt gaggatgatg aagttgatgg   4260
cgatgaagaa gaaggtcaaa gtgaggagga agagtatgag gtagaacaag atgaagatga   4320
ctctcaagaa gaggaagaag tcagcctacc caaacgagga agaccacaag ttagattgcc   4380
agttaaaaca agagggaaac ttagctcttc tttctcaagt cgtggccaac aacaagaacc   4440
tggaagatac ccttcaagga gtcagcagag cacacccaaa acaactgttt cttctaaaac   4500
tggtagaagc ctaagaaaga taaactctgc tcctcctaca gaaacaaaat ctttaagaat   4560
tgccagtcgt tctactcgcc acagtcatgg cccactgcaa gcagatgtat ttgtggaatt   4620
gcttagtcct cgtagaaaac gcagaggcag gaaaagtgct aataatacac cagaaaatag   4680
tcccaacttc cctaacttca gagtcattgc cacaaagtca agtgaacagt caagatctgt   4740
aaatattgct tcaaaacttt ctctccaaga gagtgaatcc aaaagaagat gcagaaaaag   4800
acaatctcca gagccatcgc ctgtgacact gggtcgaagg agttctggcc gacagggagg   4860
agttcatgaa ttgtctgctt ttgaacaact tgttgtagaa ttggtacgac atgatgacag   4920
ctggcctttt ttgaaacttg tttctaaaat ccaggtccca gactactatg acatcatcaa   4980
aaagcccatt gccttaaata taattcgtga aaaagtgaat aagtgtgaat ataaattagc   5040
atctgagttt attgatgaca ttgagttaat gttttcgaac tgctttgaat acaaccctcg   5100
taacacaagt gaagcaaaag ctggaactag gcttcaagca ttttttcata ttcaggctca   5160
aaagcttgga ctccacgtca cacccagtaa tgtggaccaa gttagcacac caccggctgc   5220
gaaaaagtca cgaatctgac tttgtccttc taaaggatat atttgaagaa aaacaaattg   5280
ttcatgaaaa tggaacatta aatcatgctg tataaagcaa taacaattga ttgaccacat   5340
gaaagtgtgg cctgcactat attctcaatt ttaatattaa gcactcagga gaatgtagga   5400
aagatatcct ttgctacagt tttgttcagt atctaataag tttgatagat gtattggata   5460
cagtactggt ttacagaggt ttttgtacat ttttgagatc attcatgtgt ccagagatct   5520
tggaaaatat tttttcaccc acgatttatt ttgttattga tgattttttt ttaaagtggt   5580
ggtattaagg gagagttatc tacatggatg agtcttccgc tatagcacag tttagaaaag   5640
gtgtttatgt cttaattaat tgtttgagta cattctttca acactacaca tgaatgaatc   5700
```

```
caatcttata accttgaagt gctgtaccag tgctggctgc aggtattaag tccaagttta   5760

ttaactagat atttatttag tattgagagt aatttgtgaa tttgttttgt atttataaaa   5820

tttatacctg aaaaatgttc cttaatgttt taaacctttt actgtgtttt tattcctcta   5880

acttccttaa tgatcaatca aaaaaagtaa caccctccct ttttcctgac agttctttca   5940

gctttacaga actgtattat aagtttctat gtataacttt ttaactgtac aaataaaata   6000

acatttttc aaataaaaaa aaaaaaaaaa a                                   6031


<210> SEQ ID NO 13
<211> LENGTH: 1200
<212> TYPE: DNA
<213> ORGANISM: Homo sapiens
<220> FEATURE:
<221> NAME/KEY: gene
<223> OTHER INFORMATION: Unigene: Hs.75939; GenBank Accession: BC002906
      Homo sapiens uridine-cytidine kinase 2, mRNA (cDNA clone MGC:10318
      IMAGE:3940564), complete cds.

<400> SEQUENCE: 13

ctccttcggg aaacccagcc ccgtcaccgg gctccgagcg gctcgcaggc gagcgacagc     60

ggcctcagcc ccggcagcgc ccagcggcgg ctgcggaaag cggagggagt ccgacgcggg    120

cgcgggcggg gagcgtgcgt ccgttcgcac aggcagcggg aggaggggcg gcgcgaacca    180

tggccgggga cagcgagcag accctgcaga accaccagca gcccaacggc ggcgagccct    240

tccttatagg cgtcagcggg ggaacagcta gcggcaagtc ttccgtgtgt gctaagatcg    300

tgcagctcct ggggcagaat gaggtggact atcgccagaa gcaggtggtc atcctgagcc    360

aggatagctt ctaccgtgtc cttacctcgg agcagaaggc caaagccctg aagggccagt    420

tcaactttga ccacccggat gcctttgaca atgaactcat tctcaaaaca ctcaaagaaa    480

tcactgaagg gaaaacagtc cagatccccg tgtatgactt tgtctcccat tcccggaagg    540

aggagacagt tactgtctat cccgcagacg tggtgctctt tgaagggatc ctggccttct    600

actcccagga ggtacgagac ctgttccaga tgaagctttt tgtggataca gatgcggaca    660

cccggctctc acgcagagta ttaagggaca tcagcgagag aggcagggat cttgagcaga    720

ttttatctca gtacattacg ttcgtcaagc ctgcctttga ggaattctgc ttgccaacaa    780

agaagtatgc tgatgtgatc atccctagag gtgcagataa tctggtggcc atcaacctca    840

tcgtgcagca catccaggac atcctgaatg gagggccctc caaacggcag accaatggct    900

gtctcaacgg ctacacccct tcacgcaaga ggcaggcatc ggagtccagc agcaggccgc    960

attgacccgt ctccatcgga ccccagcccc tatctccaag agacagagga ggggtcagga   1020

ggcactgctc atctgtacat actgtttcct atgacattac tgtatttaag aaaacaccat   1080

ggagatgaaa tgcctttgat tttttttttc tttttgtact ttggaacgac aaaatgaaac   1140

agaacttgac cctgagctta aataacaaaa ctgtgccaac taaaaaaaaa aaaaaaaaaa   1200


<210> SEQ ID NO 14
<211> LENGTH: 1562
<212> TYPE: DNA
<213> ORGANISM: Homo sapiens
<220> FEATURE:
<221> NAME/KEY: gene
<223> OTHER INFORMATION: Unigene: Hs.75061; MACMARCKS; GenBank
      Accession: NM_023009.4 MARCKS-like 1 [Homo sapiens]

<400> SEQUENCE: 14

gcgcggagcg gagcggcggc gggcgcagct agcgggtcgg ccgcggagcg gaggtgcagc     60
```

```
tcggcttccc ccggcacccc tccccctcgg gcgccagccc caccccctccg ccggccgggc    120

cgaccccgcc gtactatccc ctgcggcgcg agcccggggc ggctccaagc gccccccagc    180

agacccccat catgggcagc cagagctcca aggctccccg gggcgacgtg accgccgagg    240

aggcagcagg cgcttccccc gcgaaggcca acggccagga gaatggccac gtgaaaagca    300

atggagactt atcccccaag ggtgaagggg agtcgccccc tgtgaacgga acagatgagg    360

cagccggggc cactggcgat gccatcgagc cagcaccccc tagccagggt gctgaggcca    420

agggggaggt cccccccaag gagacccccca agaagaagaa gaaattctct ttcaagaagc    480

ctttcaaatt gagcggcctg tccttcaaga gaaatcggaa ggagggtggg ggtgattctt    540

ctgcctcctc acccacagag gaagagcagg agcaggggga gatcggtgcc tgcagcgacg    600

agggcactgc tcaggaaggg aaggccgcag ccacccctga gagccaggaa ccccaggcca    660

agggggcaga ggctagtgca gcctcagaag aagaggcagg gccccaggct acagagccat    720

ccactccctc ggggccggag agtggcccta caccagccag cgctgagcag aatgagtagc    780

taggtagggg caggtgggtg atctctaagc tgcaaaaact gtgctgtcct tgtgaggtca    840

ctgcctggac ctggtgccct ggctgccttc ctgtgcccag aaaggaaggg gctattgcct    900

cctcccagcc acgttccctt tcctcctctc cctcctgtgg attctcccat cagccatctg    960

gttctcctct taaggccagt tgaagatggt ccccttacagc ttcccaagtt aggttagtga   1020

tgtgaaatgc tcctgtccct ggccctacct ccttccctgt ccccacccct gcataaggca   1080

gttgttggtt ttcttcccca attcttttcc aagtaggttt tgtttaccct actccccaaa   1140

tccctgagcc agaagtgggg tgcttatact cccaaacctt gagtgtccag ccttcccctg   1200

ttgtttttag tctcttgtgc tgtgcctagt ggcacctggg ctggggagga cactgccccg   1260

tctaggtttt tataaatgtc ttactcaagt tcaaacctcc agcctgtgaa tcaactgtgt   1320

ctctttttg acttggtaag caagtattag gctttggggt ggggggaggt ctgtaatgtg   1380

aaacaacttc ttgtcttttt ttctcccact gttgtaaata acttttaatg gccaaacccc   1440

agatttgtac tttttttttt ttctaactgc taaaaccatt ctcttccacc tggttttact   1500

gtaacatttg gaaaaggaat aaatgtcgtc cctttttaaa aaaaaaaaaa aaaaaaaaaa   1560

aa                                                                 1562


<210> SEQ ID NO 15
<211> LENGTH: 1989
<212> TYPE: DNA
<213> ORGANISM: Homo sapiens
<220> FEATURE:
<221> NAME/KEY: gene
<223> OTHER INFORMATION: Unigene: Hs.162209; GenBank Accession: AL049977
      Homo sapiens claudin 8 (CLDN8), mRNA

<400> SEQUENCE: 15

ggcacagaga accctgcttc aaagcagaag tagcagttcc ggagtccagc tggctaaaac     60

tcatcccaga ggataatggc aacccatgcc ttagaaatcg ctgggctgtt tcttggtggt    120

gttggaatgg tgggcacagt ggctgtcact gtcatgcctc agtggagagt gtcggccttc    180

attgaaaaca acatcgtggt tttgaaaac ttctgggaag gactgtggat gaattgcgtg    240

aggcaggcta acatcaggat gcagtgcaaa atctatgatt ccctgctggc tctttctccg    300

gacctacagg cagccagagg actgatgtgt gctgcttccg tgatgtcctt cttggctttc    360

atgatggcca tccttggcat gaaatgcacc aggtgcacgg gggacaatga gaaggtgaag    420
```

```
gctcacattc tgctgacggc tggaatcatc ttcatcatca cgggcatggt ggtgctcatc    480

cctgtgagct gggttgccaa tgccatcatc agagatttct ataactcaat agtgaatgtt    540

gcccaaaaac gtgagcttgg agaagctctc tacttaggat ggaccacggc actggtgctg    600

attgttggag gagctctgtt ctgctgcgtt ttttgttgca acgaaaagag cagtagctac    660

agatactcga taccttccca tcgcacaacc caaaaaagtt atcacaccgg aaagaagtca    720

ccgagcgtct actccagaag tcagtatgtg tagttgtgta tgttttttta actttactat    780

aaagccatgc aaatgacaaa aatctatatt actttctcaa aatggacccc aaagaaactt    840

tgatttactg ttcttaactg cctaatctta attacaggaa ctgtgcatca gctatttatg    900

attctataag ctatttcagc agaatgagat attaaaccca atgctttgat tgttctagaa    960

agtatagtaa tttgttttct aaggtggttc aagcatctac tctttttatc atttacttca   1020

aaatgacatt gctaaagact gcattatttt actactgtaa tttctccacg acatagcatt   1080

atgtacatag atgagtgtaa catttatatc tcacatagag acatgcttat atggttttat   1140

ttaaaatgaa atgccagtcc attacactga ataaatagaa ctcaactatt gcttttcagg   1200

gaaatcatgg atagggttga agaaggttac tattaattgt ttaaaaacag cttagggatt   1260

aatgtcctcc atttataatg aagattaaaa tgaaggcttt aatcagcatt gtaaaggaaa   1320

ttgaatggct ttctgatatg ctgtttttta gcctaggagt tagaaatcct aacttcttta   1380

tcctcttctc ccagaggctt ttttttcttt gtgtattaaa ttaacatttt taaaaagcag   1440

atattttgtc aaggggcttt gcattcaaac tgcttttcca gggctatact cagaagaaag   1500

ataaaagtgt gatctaagaa aaagtgatgg ttttaggaaa gtgaaaatat ttttgttttt   1560

gtatttgaag aagaatgatg cattttgaca agaaatcata tatgtatgga tatattttaa   1620

taagtatttg agtacagact ttgaggtttc atcaatataa ataaaagagc agaaaaatat   1680

gtcttggttt tcatttgctt accaaaaaaa caacaacaaa aaaagttgtc ctttgagaac   1740

ttcacctgct cctatgtggg tacctgagtc aaaattgtca tttttgttct gtgaaaaata   1800

aatttccttc ttgtaccatt tctgtttagt tttactaaaa tctgtaaata ctgtattttt   1860

ctgtttattc caaatttgat gaaactgaca atccaatttg aaagtttgtg tcgacgtctg   1920

tctagcttaa atgaatgtgt tctatttgct ttatacattt atattaataa attgtacatt   1980

tttctaatt                                                            1989
```

<210> SEQ ID NO 16
<211> LENGTH: 2208
<212> TYPE: DNA
<213> ORGANISM: Homo sapiens
<220> FEATURE:
<221> NAME/KEY: gene
<223> OTHER INFORMATION: Unigene: Hs.154672; GenBank Accession: NM_006636 Homo sapiens methylenetetrahydrofolate dehydrogenase (NADP+ dependent) 2, methenyltetrahydrofolate cyclohydrolase (MTHFD 2), nuclear gene encoding mitochondrial protein, transcript variant 1, mRNA

<400> SEQUENCE: 16

```
ggggcctgcc acgaggccgc agtataaccg cgtggcccgc gcgcgcgctt ccctcccggc     60

gcagtcaccg gcgcggtcta tggctgcgac ttctctaatg tctgctttgg ctgcccggct    120

gctgcagccc gcgcacagct gctcccttcg ccttcgccct ttccacctcg cggcagttcg    180

aaatgaagct gttgtcattt ctggaaggaa actggcccag cagatcaagc aggaagtgcg    240

gcaggaggta gaagagtggg tggcctcagg caacaaacgg ccacacctga gtgtgatcct    300
```

```
ggttggcgag aatcctgcaa gtcactccta tgtcctcaac aaaaccaggg cagctgcagt    360
tgtgggaatc aacagtgaga caattatgaa accagcttca atttcagagg aagaattgtt    420
gaatttaatc aataaactga ataatgatga taatgtagat ggcctccttg ttcagttgcc    480
tcttccagag catattgatg agagaaggat ctgcaatgct gtttctccag acaaggatgt    540
tgatggcttt catgtaatta atgtaggacg aatgtgtttg gatcagtatt ccatgttacc    600
ggctactcca tggggtgtgt gggaaataat caagcgaact ggcattccaa ccctagggaa    660
gaatgtggtt gtggctggaa ggtcaaaaaa cgttggaatg cccattgcaa tgttactgca    720
cacagatggg gcgcatgaac gtcccggagg tgatgccact gttacaatat ctcatcgata    780
tactcccaaa gagcagttga agaaacatac aattcttgca gatattgtaa tatctgctgc    840
aggtattcca aatctgatca cagcagatat gatcaaggaa ggagcagcag tcattgatgt    900
gggaataaat agagttcacg atcctgtaac tgccaaaccc aagttggttg gagatgtgga    960
ttttgaagga gtcagacaaa aagctgggta tatcactcca gttcctggag gtgttggccc   1020
catgacagtg gcaatgctaa tgaagaatac cattattgct gcaaaaaagg tgctgaggct   1080
tgaagagcga gaagtgctga agtctaaaga gcttggggta gccactaatt aactactgtg   1140
tcttctgtgt cacaaacagc actccaggcc agctcaagaa gcaaagcagg ccaatagaaa   1200
tgcaatattt ttaatttatt ctactgaaat ggtttaaaat gatgccttgt atttattgaa   1260
agcttaaatg ggtgggtgtt tctgcacata cctctgcagt acctcaccag ggagcattcc   1320
agtatcatgc agggtcctgt gatctagcca ggagcagcca ttaacctagt gattaatatg   1380
ggagacatta ccatatggag gatggatgct tcactttgtc aagcacctca gttacacatt   1440
cgccttttct aggattgcat ttcccaagtg ctattgcaat aacagttgat actcatttta   1500
ggtaccaaac cttttgagtt caactgatca aaccaaagga aaagtgttgc tagagaaaat   1560
tagggaaaag gtgaaaaaga aaaaatggta gtaattgagc agaaaaaaat taatttatat   1620
atgtattgat tggcaaccag atttatctaa gtagaactga attggctagg aaaaaagaaa   1680
aactgcatgt taatcatttt cctaagctgt ccttttgagg cttagtcagt ttattgggaa   1740
aatgtttagg attattcctt gctattagta ctcattttat gtatgttacc cttcagtaag   1800
ttctccccat tttagtttc taggactgaa aggattcttt tctacattat acatgtgtgt    1860
tgtcatattt ggcttttgct atatacttta acttcattgt taaatttttg tattgtatag   1920
tttctttggt gtatcttaaa acctattttt gaaaaacaaa cttggcttga taatcatttg   1980
ggcagcttgg gtaagtacgc aacttacttt tccaccaaag aactgtcagc agctgcctgc   2040
ttttctgtga tgtatgtatc ctgttgactt ttccagaaat tttttaagag tttgagttac   2100
tattgaattt aatcagactt tctgattaaa gggttttctt tctttttaa taaaacacat    2160
ctgtctggta tggtatgaat ttctgaaaaa aaaaaaaaaa aaaaaaaa                2208
```

```
<210> SEQ ID NO 17
<211> LENGTH: 2525
<212> TYPE: DNA
<213> ORGANISM: Homo sapiens
<220> FEATURE:
<221> NAME/KEY: gene
<223> OTHER INFORMATION: Unigene: Hs.18910; GenBank Accession: NM_003627
      Homo sapiens solute carrier family 43, member 1 (SLC43A1), mRNA

<400> SEQUENCE: 17
```

```
gcttcgcaga cctctggcgc ccggcgggtt cccagttccc ccgcttcttc cgaggagaca     60
gcggaggcga ggccaccggg ctgtcaggct gaagctccgt ggcggccggg tcctgcacgc    120
```

```
agagaagacc ccagcgccgg cgcggctcag ggctgggccc acgggactcc ggacgcgccg    180
cgaaagcgtt gcgctcccgg aggcgtccgc agctgctggc tgctcatttg ccggtgaccg    240
gaggctcggg gccagcatgg cccccacgct gcaacaggcg taccggaggc gctggtggat    300
ggcctgcacg gctgtgctgg agaacctctt cttctctgct gtactcctgg gctggggctc    360
cctgttgatc attctgaaga acgagggctt ctattccagc acgtgcccag ctgagagcag    420
caccaacacc acccaggatg agcagcgcag gtggccaggc tgtgaccagc aggacgagat    480
gctcaacctg ggcttcacca ttggttcctt cgtgctcagc gccaccaccc tgccactggg    540
gatcctcatg gaccgctttg gcccccgacc cgtgcggctg gttggcagtg cctgcttcac    600
tgcgtcctgc accctcatgg ccctggcctc ccgggacgtg gaagctctgt ctccgttgat    660
attcctggcg ctgtccctga atggctttgg tggcatctgc ctaacgttca cttcactcac    720
gctgcccaac atgtttggga acctgcgctc cacgttaatg gccctcatga ttggctctta    780
cgcctcttct gccattacgt tcccaggaat caagctgatc tacgatgccg gtgtggcctt    840
cgtggtcatc atgttcacct ggtctggcct ggcctgcctt atctttctga actgcaccct    900
caactggccc atcgaagcct ttcctgcccc tgaggaagtc aattacacga agaagatcaa    960
gctgagtggg ctggccctgg accacaaggt gacaggtgac ctcttctaca cccatgtgac   1020
caccatgggc cagaggctca gccagaaggc ccccagcctg gaggacggtt cggatgcctt   1080
catgtcaccc caggatgttc ggggcacctc agaaaacctt cctgagaggt ctgtcccctt   1140
acgcaagagc ctctgctccc ccactttcct gtggagcctc ctcaccatgg gcatgaccca   1200
gctgcggatc atcttctaca tggctgctgt gaacaagatg ctggagtacc ttgtgactgg   1260
tggccaggag catgagacaa atgaacagca acaaaaggtg gcagagacag ttgggttcta   1320
ctcctccgtc ttcggggcca tgcagctgtt gtgccttctc acctgccccc tcattggcta   1380
catcatggac tggcggatca aggactgcgt ggacgcccca actcagggca ctgtcctcgg   1440
agatgccagg gacggggttg ctaccaaatc catcagacca cgctactgca agatccaaaa   1500
gctcaccaat gccatcagtg ccttcaccct gaccaacctg ctgcttgtgg gttttggcat   1560
cacctgtctc atcaacaact tacacctcca gtttgtgacc tttgtcctgc acaccattgt   1620
tcgaggtttc ttccactcag cctgtgggag tctctatgct gcagtgttcc catccaacca   1680
ctttgggacg ctgacaggcc tgcagtccct catcagtgct gtgttcgcct tgcttcagca   1740
gccactttc atggcgatgg tgggacccct gaaaggagag cccttctggg tgaatctggg   1800
cctcctgcta ttctcactcc tgggattcct gttgccttcc tacctcttct attaccgtgc   1860
ccggctccag caggagtacg ccgccaatgg gatgggccca ctgaaggtgc ttagcggctc   1920
tgaggtgacc gcatagactt ctcagaccaa gggacctgga tgacaggcaa tcaaggcctg   1980
agcaaccaaa aggagtgccc catatggctt ttctacctgt aacatgcaca tagagccatg   2040
gccgtagatt tataaatacc aagagaagtt ctatttttgt aaagactgca aaaaggagga   2100
aaaaaaacct tcaaaaacgc cccctaagtc aacgctccat tgactgaaga cagtccctat   2160
cctagagggg ttgagctttc ttcctccttg ggttggagga gaccagggtg cctcttatct   2220
ccttctagcg gtctgcctcc tggtacctct tggggggatc ggcaaacagg ctacccctga   2280
ggtcccatgt gccatgagtg tgcacacatg catgtgtctg tgtatgtgtg aatgtgagag   2340
agacacagcc ctcctttcag aaggaaaggg gcctgaggtg ccagctgtgt cctgggttag   2400
gggttggggg tcggcccctt ccagggccag gagggcaggt tccctctctg gtgctgctgc   2460
```

ttgcaagtct tagaggaaat aaaaagggaa gtgagagaaa aaaaaaaaaa aaaaaaaaaa 2520
aaaaa 2525

<210> SEQ ID NO 18
<211> LENGTH: 1052
<212> TYPE: DNA
<213> ORGANISM: Homo sapiens
<220> FEATURE:
<221> NAME/KEY: gene
<223> OTHER INFORMATION: Unigene: Hs.109059; GenBank Accession: NM_002949 Homo sapiens mitochondrial ribosomal protein L12 (MRPL12), nuclear gene encoding mitochondrial protein, mRNA

<400> SEQUENCE: 18

```
gctcgaatgc ccggcagccg tggcggctag agcgttcctc cccagctcga atgcccggcg     60

gccgaggcgg ctagagcgtc gcctcctccc ggggaaccgc gtgtgacctt ccagcccgcg    120

gaccgatgct gccggcggcc gctcgccccc tgtgggggcc ttgccttggg cttcgggccg    180

ctgcgttccg ccttgccagg cgacaggtgc catgtgtctg tgccgtgcga catatgagga    240

gcagcggcca tcagaggtgt gaggccctcg ctggtgcacc cctggataac gcccccaagg    300

agtacccccc caagatacag cagctggtcc aggacatcgc cagcctcact ctcttggaaa    360

tctcagacct caacgagctc ctgaagaaaa cgttgaagat ccaggatgtc gggcttgtgc    420

cgatgggtgg tgtgatgtct ggggctgtcc ctgctgcagc agcccaggag gcggtggaag    480

aagatatccc catagcgaaa gaacggacac atttcaccgt ccgcctgacc gaggcgaagc    540

ccgtggacaa agtgaagctg atcaaggaaa tcaagaacta catccaaggc atcaacctcg    600

tccaggcaaa gaagctggtg gagtccctgc cccaggaaat caaagccaat gtcgccaaag    660

ctgaggcgga gaagatcaag gcggccctgg aggcggtggg cggcaccgtg gttctggagt    720

agcctccagc tcggaggact tgtgttcagg ggtcctgggc cccgggcgag gtcccgccct    780

cccgtggtca ctggctccgc ccccagcacc aggcgcccag tggagccgtt tgggagaatt    840

gcctgcgcca cgcagcgggg ccggacaggc cgcacagacc tactgtggcg ggagggaggg    900

gcggctgctg cctggtgacg gcacccggag gcccaccagg acgcgccacc ggtgaatgtg    960

cctctggtgg ctgctgagaa aaatacactg tgcagctcag aaaaaaaaaa aaaaaaaaaa   1020

aaaaaaaaaa aaaaaaaaaa aaaaaaaaaa aa                                 1052
```

<210> SEQ ID NO 19
<211> LENGTH: 596
<212> TYPE: PRT
<213> ORGANISM: Homo sapiens
<223> OTHER INFORMATION: GenBank Accession: NM_006457 Homo sapiens PDZ and LIM domain 5 (PDLIM5), transcript variant 1, mRNA, DKFZp564A072 (PDLIM5)

<400> SEQUENCE: 19

```
Met Ser Asn Tyr Ser Val Ser Leu Val Gly Pro Ala Pro Trp Gly Phe
1               5                   10                  15

Arg Leu Gln Gly Gly Lys Asp Phe Asn Met Pro Leu Thr Ile Ser Ser
            20                  25                  30

Leu Lys Asp Gly Gly Lys Ala Ala Gln Ala Asn Val Arg Ile Gly Asp
        35                  40                  45

Val Val Leu Ser Ile Asp Gly Ile Asn Ala Gln Gly Met Thr His Leu
    50                  55                  60

Glu Ala Gln Asn Lys Ile Lys Gly Cys Thr Gly Ser Leu Asn Met Thr
65                  70                  75                  80
```

```
Leu Gln Arg Ala Ser Ala Ala Pro Lys Pro Glu Pro Val Pro Val Gln
                85                  90                  95

Lys Gly Glu Pro Lys Glu Val Val Lys Pro Val Pro Ile Thr Ser Pro
            100                 105                 110

Ala Val Ser Lys Val Thr Ser Thr Asn Asn Met Ala Tyr Asn Lys Ala
        115                 120                 125

Pro Arg Pro Phe Gly Ser Val Ser Ser Pro Lys Val Thr Ser Ile Pro
    130                 135                 140

Ser Pro Ser Ser Ala Phe Thr Pro Ala His Ala Thr Thr Ser Ser His
145                 150                 155                 160

Ala Ser Pro Ser Pro Val Ala Ala Val Thr Pro Pro Leu Phe Ala Ala
                165                 170                 175

Ser Gly Leu His Ala Asn Ala Asn Leu Ser Ala Asp Gln Ser Pro Ser
            180                 185                 190

Ala Leu Ser Ala Gly Lys Thr Ala Val Asn Val Pro Arg Gln Pro Thr
        195                 200                 205

Val Thr Ser Val Cys Ser Glu Thr Ser Gln Glu Leu Ala Glu Gly Gln
    210                 215                 220

Arg Arg Gly Ser Gln Gly Asp Ser Lys Gln Gln Asn Gly Pro Pro Arg
225                 230                 235                 240

Lys His Ile Val Glu Arg Tyr Thr Glu Phe Tyr His Val Pro Thr His
                245                 250                 255

Ser Asp Ala Ser Lys Lys Arg Leu Ile Glu Asp Thr Glu Asp Trp Arg
            260                 265                 270

Pro Arg Thr Gly Thr Thr Gln Ser Arg Ser Phe Arg Ile Leu Ala Gln
        275                 280                 285

Ile Thr Gly Thr Glu His Leu Lys Glu Ser Glu Ala Asp Asn Thr Lys
    290                 295                 300

Lys Ala Asn Asn Ser Gln Glu Pro Ser Pro Gln Leu Ala Ser Ser Val
305                 310                 315                 320

Ala Ser Thr Arg Ser Met Pro Glu Ser Leu Asp Ser Pro Thr Ser Gly
                325                 330                 335

Arg Pro Gly Val Thr Ser Leu Thr Thr Ala Ala Ala Phe Lys Pro Val
            340                 345                 350

Gly Ser Thr Gly Val Ile Lys Ser Pro Ser Trp Gln Arg Pro Asn Gln
        355                 360                 365

Gly Val Pro Ser Thr Gly Arg Ile Ser Asn Ser Ala Thr Tyr Ser Gly
    370                 375                 380

Ser Val Ala Pro Ala Asn Ser Ala Leu Gly Gln Thr Gln Pro Ser Asp
385                 390                 395                 400

Gln Asp Thr Leu Val Gln Arg Ala Glu His Ile Pro Ala Gly Lys Arg
                405                 410                 415

Thr Pro Met Cys Ala His Cys Asn Gln Val Ile Arg Gly Pro Phe Leu
            420                 425                 430

Val Ala Leu Gly Lys Ser Trp His Pro Glu Glu Phe Asn Cys Ala His
        435                 440                 445

Cys Lys Asn Thr Met Ala Tyr Ile Gly Phe Val Glu Glu Lys Gly Ala
    450                 455                 460

Leu Tyr Cys Glu Leu Cys Tyr Glu Lys Phe Phe Ala Pro Glu Cys Gly
465                 470                 475                 480

Arg Cys Gln Arg Lys Ile Leu Gly Glu Val Ile Asn Ala Leu Lys Gln
                485                 490                 495

Thr Trp His Val Ser Cys Phe Val Cys Val Ala Cys Gly Lys Pro Ile
```

```
            500                 505                 510

Arg Asn Asn Val Phe His Leu Glu Asp Gly Glu Pro Tyr Cys Glu Thr
        515                 520                 525

Asp Tyr Tyr Ala Leu Phe Gly Thr Ile Cys His Gly Cys Glu Phe Pro
    530                 535                 540

Ile Glu Ala Gly Asp Met Phe Leu Glu Ala Leu Gly Tyr Thr Trp His
545                 550                 555                 560

Asp Thr Cys Phe Val Cys Ser Val Cys Cys Glu Ser Leu Glu Gly Gln
                565                 570                 575

Thr Phe Phe Ser Lys Lys Asp Lys Pro Leu Cys Lys Lys His Ala His
            580                 585                 590

Ser Val Asn Phe
        595


<210> SEQ ID NO 20
<211> LENGTH: 505
<212> TYPE: PRT
<213> ORGANISM: Homo sapiens
<223> OTHER INFORMATION: GenBank Accession: AAB31210
      AgX-1 antigen [Homo sapiens]

<400> SEQUENCE: 20

Met Asn Ile Asn Asp Leu Lys Leu Thr Leu Ser Lys Ala Gly Gln Glu
1               5                   10                  15

His Leu Leu Arg Phe Trp Asn Glu Leu Glu Glu Ala Gln Gln Val Glu
            20                  25                  30

Leu Tyr Ala Glu Leu Gln Ala Met Asn Phe Glu Glu Leu Asn Phe Phe
        35                  40                  45

Phe Gln Lys Ala Ile Glu Gly Phe Asn Gln Ser Ser His Gln Lys Asn
    50                  55                  60

Val Asp Ala Arg Met Glu Pro Val Pro Arg Glu Val Leu Gly Ser Ala
65                  70                  75                  80

Thr Arg Asp Gln Asp Gln Leu Gln Ala Trp Glu Ser Glu Gly Leu Phe
                85                  90                  95

Gln Ile Ser Gln Asn Lys Val Ala Val Leu Leu Leu Ala Gly Gly Gln
            100                 105                 110

Gly Thr Arg Leu Gly Val Ala Tyr Pro Lys Gly Met Tyr Asp Val Gly
        115                 120                 125

Leu Pro Ser Arg Lys Thr Leu Phe Gln Ile Gln Ala Glu Arg Ile Leu
    130                 135                 140

Lys Leu Gln Gln Val Ala Glu Lys Tyr Tyr Gly Asn Lys Cys Ile Ile
145                 150                 155                 160

Pro Trp Tyr Ile Met Thr Ser Gly Arg Thr Met Glu Ser Thr Lys Glu
                165                 170                 175

Phe Phe Thr Lys His Lys Tyr Phe Gly Leu Lys Lys Glu Asn Val Ile
            180                 185                 190

Phe Phe Gln Gln Gly Met Leu Pro Ala Met Ser Phe Asp Gly Lys Ile
        195                 200                 205

Ile Leu Glu Glu Lys Asn Lys Val Ser Met Ala Pro Asp Gly Asn Gly
    210                 215                 220

Gly Leu Tyr Arg Ala Leu Ala Ala Gln Asn Ile Val Glu Asp Met Glu
225                 230                 235                 240

Gln Arg Gly Ile Trp Ser Ile His Val Tyr Cys Val Asp Asn Ile Leu
                245                 250                 255

Val Lys Val Ala Asp Pro Arg Phe Ile Gly Phe Cys Ile Gln Lys Gly
```

```
            260                 265                 270

Ala Asp Cys Gly Ala Lys Val Val Glu Lys Thr Asn Pro Thr Glu Pro
        275                 280                 285

Val Gly Val Val Cys Arg Val Asp Gly Val Tyr Gln Val Val Glu Tyr
    290                 295                 300

Ser Glu Ile Ser Leu Ala Thr Ala Gln Lys Arg Ser Ser Asp Gly Arg
305                 310                 315                 320

Leu Leu Phe Asn Ala Gly Asn Ile Ala Asn His Phe Phe Thr Val Pro
                325                 330                 335

Phe Leu Arg Asp Val Val Asn Val Tyr Glu Pro Gln Leu Gln His His
            340                 345                 350

Val Ala Gln Lys Lys Ile Pro Tyr Val Asp Thr Gln Gly Gln Leu Ile
        355                 360                 365

Lys Pro Asp Lys Pro Asn Gly Ile Lys Met Glu Lys Phe Val Phe Asp
    370                 375                 380

Ile Phe Gln Phe Ala Lys Lys Phe Val Val Tyr Glu Val Leu Arg Glu
385                 390                 395                 400

Asp Glu Phe Ser Pro Leu Lys Asn Ala Asp Ser Gln Asn Gly Lys Asp
                405                 410                 415

Asn Pro Thr Thr Ala Arg His Ala Leu Met Ser Leu His His Cys Trp
            420                 425                 430

Val Leu Asn Ala Gly Gly His Phe Ile Asp Glu Asn Ser Ser Arg Leu
        435                 440                 445

Pro Ala Ile Pro Arg Leu Lys Asp Ala Asn Asp Val Pro Ile Gln Cys
    450                 455                 460

Glu Ile Ser Pro Leu Ile Ser Tyr Ala Gly Glu Gly Leu Glu Ser Tyr
465                 470                 475                 480

Val Ala Asp Lys Glu Phe His Ala Pro Leu Ile Ile Asp Glu Asn Gly
                485                 490                 495

Val His Glu Leu Val Lys Asn Gly Ile
            500                 505


<210> SEQ ID NO 21
<211> LENGTH: 573
<212> TYPE: PRT
<213> ORGANISM: Homo sapiens
<223> OTHER INFORMATION: GenBank Accession: NP_002147
      chaperonin [Homo sapiens]

<400> SEQUENCE: 21

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
```

```
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Val
    530                 535                 540
```

```
Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570


<210> SEQ ID NO 22
<211> LENGTH: 2224
<212> TYPE: PRT
<213> ORGANISM: Homo sapiens
<223> OTHER INFORMATION: GenBank Accession: NP_00121
      coagulation factor V precursor [Homo sapiens]

<400> SEQUENCE: 22

Met Phe Pro Gly Cys Pro Arg Leu Trp Val Leu Val Val Leu Gly Thr
1               5                   10                  15

Ser Trp Val Gly Trp Gly Ser Gln Gly Thr Glu Ala Ala Gln Leu Arg
            20                  25                  30

Gln Phe Tyr Val Ala Ala Gln Gly Ile Ser Trp Ser Tyr Arg Pro Glu
        35                  40                  45

Pro Thr Asn Ser Ser Leu Asn Leu Ser Val Thr Ser Phe Lys Lys Ile
    50                  55                  60

Val Tyr Arg Glu Tyr Glu Pro Tyr Phe Lys Lys Glu Lys Pro Gln Ser
65                  70                  75                  80

Thr Ile Ser Gly Leu Leu Gly Pro Thr Leu Tyr Ala Glu Val Gly Asp
                85                  90                  95

Ile Ile Lys Val His Phe Lys Asn Lys Ala Asp Lys Pro Leu Ser Ile
            100                 105                 110

His Pro Gln Gly Ile Arg Tyr Ser Lys Leu Ser Glu Gly Ala Ser Tyr
        115                 120                 125

Leu Asp His Thr Phe Pro Ala Glu Lys Met Asp Asp Ala Val Ala Pro
    130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
                165                 170                 175

Asn Leu Ile Glu Asp Phe Asn Ser Gly Leu Ile Gly Pro Leu Leu Ile
            180                 185                 190

Cys Lys Lys Gly Thr Leu Thr Glu Gly Gly Thr Gln Lys Thr Phe Asp
        195                 200                 205

Lys Gln Ile Val Leu Leu Phe Ala Val Phe Asp Glu Ser Lys Ser Trp
    210                 215                 220

Ser Gln Ser Ser Ser Leu Met Tyr Thr Val Asn Gly Tyr Val Asn Gly
225                 230                 235                 240

Thr Met Pro Asp Ile Thr Val Cys Ala His Asp His Ile Ser Trp His
                245                 250                 255

Leu Leu Gly Met Ser Ser Gly Pro Glu Leu Phe Ser Ile His Phe Asn
            260                 265                 270

Gly Gln Val Leu Glu Gln Asn His His Lys Val Ser Ala Ile Thr Leu
        275                 280                 285

Val Ser Ala Thr Ser Thr Thr Ala Asn Met Thr Val Gly Pro Glu Gly
    290                 295                 300

Lys Trp Ile Ile Ser Ser Leu Thr Pro Lys His Leu Gln Ala Gly Met
305                 310                 315                 320

Gln Ala Tyr Ile Asp Ile Lys Asn Cys Pro Lys Lys Thr Arg Asn Leu
                325                 330                 335
```

```
Lys Lys Ile Thr Arg Glu Gln Arg Arg His Met Lys Arg Trp Glu Tyr
            340                 345                 350

Phe Ile Ala Ala Glu Glu Val Ile Trp Asp Tyr Ala Pro Val Ile Pro
        355                 360                 365

Ala Asn Met Asp Lys Lys Tyr Arg Ser Gln His Leu Asp Asn Phe Ser
    370                 375                 380

Asn Gln Ile Gly Lys His Tyr Lys Lys Val Met Tyr Thr Gln Tyr Glu
385                 390                 395                 400

Asp Glu Ser Phe Thr Lys His Thr Val Asn Pro Asn Met Lys Glu Asp
                405                 410                 415

Gly Ile Leu Gly Pro Ile Ile Arg Ala Gln Val Arg Asp Thr Leu Lys
            420                 425                 430

Ile Val Phe Lys Asn Met Ala Ser Arg Pro Tyr Ser Ile Tyr Pro His
        435                 440                 445

Gly Val Thr Phe Ser Pro Tyr Glu Asp Glu Val Asn Ser Ser Phe Thr
    450                 455                 460

Ser Gly Arg Asn Asn Thr Met Ile Arg Ala Val Gln Pro Gly Glu Thr
465                 470                 475                 480

Tyr Thr Tyr Lys Trp Asn Ile Leu Glu Phe Asp Glu Pro Thr Glu Asn
                485                 490                 495

Asp Ala Gln Cys Leu Thr Arg Pro Tyr Tyr Ser Asp Val Asp Ile Met
            500                 505                 510

Arg Asp Ile Ala Ser Gly Leu Ile Gly Leu Leu Leu Ile Cys Lys Ser
        515                 520                 525

Arg Ser Leu Asp Arg Arg Gly Ile Gln Arg Ala Ala Asp Ile Glu Gln
    530                 535                 540

Gln Ala Val Phe Ala Val Phe Asp Glu Asn Lys Ser Trp Tyr Leu Glu
545                 550                 555                 560

Asp Asn Ile Asn Lys Phe Cys Glu Asn Pro Asp Glu Val Lys Arg Asp
                565                 570                 575

Asp Pro Lys Phe Tyr Glu Ser Asn Ile Met Ser Thr Ile Asn Gly Tyr
            580                 585                 590

Val Pro Glu Ser Ile Thr Thr Leu Gly Phe Cys Phe Asp Asp Thr Val
        595                 600                 605

Gln Trp His Phe Cys Ser Val Gly Thr Gln Asn Glu Ile Leu Thr Ile
    610                 615                 620

His Phe Thr Gly His Ser Phe Ile Tyr Gly Lys Arg His Glu Asp Thr
625                 630                 635                 640

Leu Thr Leu Phe Pro Met Arg Gly Glu Ser Val Thr Val Thr Met Asp
                645                 650                 655

Asn Val Gly Thr Trp Met Leu Thr Ser Met Asn Ser Ser Pro Arg Ser
            660                 665                 670

Lys Lys Leu Arg Leu Lys Phe Arg Asp Val Lys Cys Ile Pro Asp Asp
        675                 680                 685

Asp Glu Asp Ser Tyr Glu Ile Phe Glu Pro Pro Glu Ser Thr Val Met
    690                 695                 700

Ala Thr Arg Lys Met His Asp Arg Leu Glu Pro Glu Asp Glu Glu Ser
705                 710                 715                 720

Asp Ala Asp Tyr Asp Tyr Gln Asn Arg Leu Ala Ala Ala Leu Gly Ile
                725                 730                 735

Arg Ser Phe Arg Asn Ser Ser Leu Asn Gln Glu Glu Glu Glu Phe Asn
            740                 745                 750
```

```
Leu Thr Ala Leu Ala Leu Glu Asn Gly Thr Glu Phe Val Ser Ser Asn
        755                 760                 765

Thr Asp Ile Ile Val Gly Ser Asn Tyr Ser Ser Pro Ser Asn Ile Ser
    770                 775                 780

Lys Phe Thr Val Asn Asn Leu Ala Glu Pro Gln Lys Ala Pro Ser His
785                 790                 795                 800

Gln Gln Ala Thr Thr Ala Gly Ser Pro Leu Arg His Leu Ile Gly Lys
                805                 810                 815

Asn Ser Val Leu Asn Ser Ser Thr Ala Glu His Ser Ser Pro Tyr Ser
            820                 825                 830

Glu Asp Pro Ile Glu Asp Pro Leu Gln Pro Asp Val Thr Gly Ile Arg
        835                 840                 845

Leu Leu Ser Leu Gly Ala Gly Glu Phe Lys Ser Gln Glu His Ala Lys
    850                 855                 860

His Lys Gly Pro Lys Val Glu Arg Asp Gln Ala Ala Lys His Arg Phe
865                 870                 875                 880

Ser Trp Met Lys Leu Leu Ala His Lys Val Gly Arg His Leu Ser Gln
                885                 890                 895

Asp Thr Gly Ser Pro Ser Gly Met Arg Pro Trp Glu Asp Leu Pro Ser
            900                 905                 910

Gln Asp Thr Gly Ser Pro Ser Arg Met Arg Pro Trp Lys Asp Pro Pro
        915                 920                 925

Ser Asp Leu Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Glu Ser Thr Pro Leu Ala Asn Lys Pro
            980                 985                 990

Gly Lys Gln Ser Gly His Pro Lys  Phe Pro Arg Val Arg  His Lys Ser
        995                 1000                1005

Leu Gln  Val Arg Gln Asp Gly  Gly Lys Ser Arg Leu  Lys Lys Ser
    1010                 1015                 1020

Gln Phe  Leu Ile Lys Thr Arg  Lys Lys Lys Lys Glu  Lys His Thr
    1025                 1030                 1035

His His  Ala Pro Leu Ser Pro  Arg Thr Phe His Pro  Leu Arg Ser
    1040                 1045                 1050

Glu Ala  Tyr Asn Thr Phe Ser  Glu Arg Arg Leu Lys  His Ser Leu
    1055                 1060                 1065

Val Leu  His Lys Ser Asn Glu  Thr Ser Leu Pro Thr  Asp Leu Asn
    1070                 1075                 1080

Gln Thr  Leu Pro Ser Met Asp  Phe Gly Trp Ile Ala  Ser Leu Pro
    1085                 1090                 1095

Asp His  Asn Gln Asn Ser Ser  Asn Asp Thr Gly Gln  Ala Ser Cys
    1100                 1105                 1110

Pro Pro  Gly Leu Tyr Gln Thr  Val Pro Pro Glu Glu  His Tyr Gln
    1115                 1120                 1125

Thr Phe  Pro Ile Gln Asp Pro  Asp Gln Met His Ser  Thr Ser Asp
    1130                 1135                 1140

Pro Ser  His Arg Ser Ser Ser  Pro Glu Leu Ser Glu  Met Leu Glu
    1145                 1150                 1155

Tyr Asp  Arg Ser His Lys Ser  Phe Pro Thr Asp Ile  Ser Gln Met
```

```
    1160                1165                1170

Ser Pro  Ser Ser Glu His Glu  Val Trp Gln Thr Val  Ile Ser Pro
    1175                1180                1185

Asp Leu  Ser Gln Val Thr Leu  Ser Pro Glu Leu Ser  Gln Thr Asn
    1190                1195                1200

Leu Ser  Pro Asp Leu Ser His  Thr Thr Leu Ser Pro  Glu Leu Ile
    1205                1210                1215

Gln Arg  Asn Leu Ser Pro Ala  Leu Gly Gln Met Pro  Ile Ser Pro
    1220                1225                1230

Asp Leu  Ser His Thr Thr Leu  Ser Pro Asp Leu Ser  His Thr Thr
    1235                1240                1245

Leu Ser  Leu Asp Leu Ser Gln  Thr Asn Leu Ser Pro  Glu Leu Ser
    1250                1255                1260

Gln Thr  Asn Leu Ser Pro Ala  Leu Gly Gln Met Pro  Leu Ser Pro
    1265                1270                1275

Asp Leu  Ser His Thr Thr Leu  Ser Leu Asp Phe Ser  Gln Thr Asn
    1280                1285                1290

Leu Ser  Pro Glu Leu Ser His  Met Thr Leu Ser Pro  Glu Leu Ser
    1295                1300                1305

Gln Thr  Asn Leu Ser Pro Ala  Leu Gly Gln Met Pro  Ile Ser Pro
    1310                1315                1320

Asp Leu  Ser His Thr Thr Leu  Ser Leu Asp Phe Ser  Gln Thr Asn
    1325                1330                1335

Leu Ser  Pro Glu Leu Ser Gln  Thr Asn Leu Ser Pro  Ala Leu Gly
    1340                1345                1350

Gln Met  Pro Leu Ser Pro Asp  Pro Ser His Thr Thr  Leu Ser Leu
    1355                1360                1365

Asp Leu  Ser Gln Thr Asn Leu  Ser Pro Glu Leu Ser  Gln Thr Asn
    1370                1375                1380

Leu Ser  Pro Asp Leu Ser Glu  Met Pro Leu Phe Ala  Asp Leu Ser
    1385                1390                1395

Gln Ile  Pro Leu Thr Pro Asp  Leu Asp Gln Met Thr  Leu Ser Pro
    1400                1405                1410

Asp Leu  Gly Glu Thr Asp Leu  Ser Pro Asn Phe Gly  Gln Met Ser
    1415                1420                1425

Leu Ser  Pro Asp Leu Ser Gln  Val Thr Leu Ser Pro  Asp Ile Ser
    1430                1435                1440

Asp Thr  Thr Leu Leu Pro Asp  Leu Ser Gln Ile Ser  Pro Pro Pro
    1445                1450                1455

Asp Leu  Asp Gln Ile Phe Tyr  Pro Ser Glu Ser Ser  Gln Ser Leu
    1460                1465                1470

Leu Leu  Gln Glu Phe Asn Glu  Ser Phe Pro Tyr Pro  Asp Leu Gly
    1475                1480                1485

Gln Met  Pro Ser Pro Ser Ser  Pro Thr Leu Asn Asp  Thr Phe Leu
    1490                1495                1500

Ser Lys  Glu Phe Asn Pro Leu  Val Ile Val Gly Leu  Ser Lys Asp
    1505                1510                1515

Gly Thr  Asp Tyr Ile Glu Ile  Ile Pro Lys Glu Glu  Val Gln Ser
    1520                1525                1530

Ser Glu  Asp Asp Tyr Ala Glu  Ile Asp Tyr Val Pro  Tyr Asp Asp
    1535                1540                1545

Pro Tyr  Lys Thr Asp Val Arg  Thr Asn Ile Asn Ser  Ser Arg Asp
    1550                1555                1560
```

```
Pro Asp  Asn Ile Ala Ala Trp  Tyr Leu Arg Ser Asn  Asn Gly Asn
    1565                 1570                 1575

Arg Arg  Asn Tyr Tyr Ile Ala  Ala Glu Glu Ile Ser  Trp Asp Tyr
    1580                 1585                 1590

Ser Glu  Phe Val Gln Arg Glu  Thr Asp Ile Glu Asp  Ser Asp Asp
    1595                 1600                 1605

Ile Pro  Glu Asp Thr Thr Tyr  Lys Lys Val Val Phe  Arg Lys Tyr
    1610                 1615                 1620

Leu Asp  Ser Thr Phe Thr Lys  Arg Asp Pro Arg Gly  Glu Tyr Glu
    1625                 1630                 1635

Glu His  Leu Gly Ile Leu Gly  Pro Ile Ile Arg Ala  Glu Val Asp
    1640                 1645                 1650

Asp Val  Ile Gln Val Arg Phe  Lys Asn Leu Ala Ser  Arg Pro Tyr
    1655                 1660                 1665

Ser Leu  His Ala His Gly Leu  Ser Tyr Glu Lys Ser  Ser Glu Gly
    1670                 1675                 1680

Lys Thr  Tyr Glu Asp Asp Ser  Pro Glu Trp Phe Lys  Glu Asp Asn
    1685                 1690                 1695

Ala Val  Gln Pro Asn Ser Ser  Tyr Thr Tyr Val Trp  His Ala Thr
    1700                 1705                 1710

Glu Arg  Ser Gly Pro Glu Ser  Pro Gly Ser Ala Cys  Arg Ala Trp
    1715                 1720                 1725

Ala Tyr  Tyr Ser Ala Val Asn  Pro Glu Lys Asp Ile  His Ser Gly
    1730                 1735                 1740

Leu Ile  Gly Pro Leu Leu Ile  Cys Gln Lys Gly Ile  Leu His Lys
    1745                 1750                 1755

Asp Ser  Asn Met Pro Met Asp  Met Arg Glu Phe Val  Leu Leu Phe
    1760                 1765                 1770

Met Thr  Phe Asp Glu Lys Lys  Ser Trp Tyr Tyr Glu  Lys Lys Ser
    1775                 1780                 1785

Arg Ser  Ser Trp Arg Leu Thr  Ser Ser Glu Met Lys  Lys Ser His
    1790                 1795                 1800

Glu Phe  His Ala Ile Asn Gly  Met Ile Tyr Ser Leu  Pro Gly Leu
    1805                 1810                 1815

Lys Met  Tyr Glu Gln Glu Trp  Val Arg Leu His Leu  Leu Asn Ile
    1820                 1825                 1830

Gly Gly  Ser Gln Asp Ile His  Val Val His Phe His  Gly Gln Thr
    1835                 1840                 1845

Leu Leu  Glu Asn Gly Asn Lys  Gln His Gln Leu Gly  Val Trp Pro
    1850                 1855                 1860

Leu Leu  Pro Gly Ser Phe Lys  Thr Leu Glu Met Lys  Ala Ser Lys
    1865                 1870                 1875

Pro Gly  Trp Trp Leu Leu Asn  Thr Glu Val Gly Glu  Asn Gln Arg
    1880                 1885                 1890

Ala Gly  Met Gln Thr Pro Phe  Leu Ile Met Asp Arg  Asp Cys Arg
    1895                 1900                 1905

Met Pro  Met Gly Leu Ser Thr  Gly Ile Ile Ser Asp  Ser Gln Ile
    1910                 1915                 1920

Lys Ala  Ser Glu Phe Leu Gly  Tyr Trp Glu Pro Arg  Leu Ala Arg
    1925                 1930                 1935

Leu Asn  Asn Gly Gly Ser Tyr  Asn Ala Trp Ser Val  Glu Lys Leu
    1940                 1945                 1950
```

```
Ala Ala  Glu Phe Ala Ser Lys  Pro Trp Ile Gln Val  Asp Met Gln
    1955                 1960                 1965

Lys Glu  Val Ile Ile Thr Gly  Ile Gln Thr Gln Gly  Ala Lys His
    1970                 1975                 1980

Tyr Leu  Lys Ser Cys Tyr Thr  Thr Glu Phe Tyr Val  Ala Tyr Ser
    1985                 1990                 1995

Ser Asn  Gln Ile Asn Trp Gln  Ile Phe Lys Gly Asn  Ser Thr Arg
    2000                 2005                 2010

Asn Val  Met Tyr Phe Asn Gly  Asn Ser Asp Ala Ser  Thr Ile Lys
    2015                 2020                 2025

Glu Asn  Gln Phe Asp Pro Pro  Ile Val Ala Arg Tyr  Ile Arg Ile
    2030                 2035                 2040

Ser Pro  Thr Arg Ala Tyr Asn  Arg Pro Thr Leu Arg  Leu Glu Leu
    2045                 2050                 2055

Gln Gly  Cys Glu Val Asn Gly  Cys Ser Thr Pro Leu  Gly Met Glu
    2060                 2065                 2070

Asn Gly  Lys Ile Glu Asn Lys  Gln Ile Thr Ala Ser  Ser Phe Lys
    2075                 2080                 2085

Lys Ser  Trp Trp Gly Asp Tyr  Trp Glu Pro Phe Arg  Ala Arg Leu
    2090                 2095                 2100

Asn Ala  Gln Gly Arg Val Asn  Ala Trp Gln Ala Lys  Ala Asn Asn
    2105                 2110                 2115

Asn Lys  Gln Trp Leu Glu Ile  Asp Leu Leu Lys Ile  Lys Lys Ile
    2120                 2125                 2130

Thr Ala  Ile Ile Thr Gln Gly  Cys Lys Ser Leu Ser  Ser Glu Met
    2135                 2140                 2145

Tyr Val  Lys Ser Tyr Thr Ile  His Tyr Ser Glu Gln  Gly Val Glu
    2150                 2155                 2160

Trp Lys  Pro Tyr Arg Leu Lys  Ser Ser Met Val Asp  Lys Ile Phe
    2165                 2170                 2175

Glu Gly  Asn Thr Asn Thr Lys  Gly His Val Lys Asn  Phe Phe Asn
    2180                 2185                 2190

Pro Pro  Ile Ile Ser Arg Phe  Ile Arg Val Ile Pro  Lys Thr Trp
    2195                 2200                 2205

Asn Gln  Ser Ile Ala Leu Arg  Leu Glu Leu Phe Gly  Cys Asp Ile
    2210                 2215                 2220

Tyr


<210> SEQ ID NO 23
<211> LENGTH: 514
<212> TYPE: PRT
<213> ORGANISM: Homo sapiens
<223> OTHER INFORMATION: GenBank Accession: NP_000875
      inosine monophosphate dehydrogenase 2 [Homo sapiens]

<400> SEQUENCE: 23

Met Ala Asp Tyr Leu Ile Ser Gly Gly Thr Ser Tyr Val Pro Asp Asp
1               5                   10                  15

Gly Leu Thr Ala Gln Gln Leu Phe Asn Cys Gly Asp Gly Leu Thr Tyr
            20                  25                  30

Asn Asp Phe Leu Ile Leu Pro Gly Tyr Ile Asp Phe Thr Ala Asp Gln
        35                  40                  45

Val Asp Leu Thr Ser Ala Leu Thr Lys Lys Ile Thr Leu Lys Thr Pro
    50                  55                  60

Leu Val Ser Ser Pro Met Asp Thr Val Thr Glu Ala Gly Met Ala Ile
```

```
65                  70                  75                  80

Ala Met Ala Leu Thr Gly Gly Ile Gly Phe Ile His His Asn Cys Thr
                85                  90                  95

Pro Glu Phe Gln Ala Asn Glu Val Arg Lys Val Lys Lys Tyr Glu Gln
            100                 105                 110

Gly Phe Ile Thr Asp Pro Val Val Leu Ser Pro Lys Asp Arg Val Arg
        115                 120                 125

Asp Val Phe Glu Ala Lys Ala Arg His Gly Phe Cys Gly Ile Pro Ile
    130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu Glu His Asp Cys Phe Leu Glu
                165                 170                 175

Glu Ile Met Thr Lys Arg Glu Asp Leu Val Val Ala Pro Ala Gly Ile
            180                 185                 190

Thr Leu Lys Glu Ala Asn Glu Ile Leu Gln Arg Ser Lys Lys Gly Lys
        195                 200                 205

Leu Pro Ile Val Asn Glu Asp Asp Glu Leu Val Ala Ile Ile Ala Arg
    210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
                245                 250                 255

Lys Tyr Arg Leu Asp Leu Leu Ala Gln Ala Gly Val Asp Val Val Val
            260                 265                 270

Leu Asp Ser Ser Gln Gly Asn Ser Ile Phe Gln Ile Asn Met Ile Lys
        275                 280                 285

Tyr Ile Lys Asp Lys Tyr Pro Asn Leu Gln Val Ile Gly Gly Asn Val
    290                 295                 300

Val Thr Ala Ala Gln Ala Lys Asn Leu Ile Asp Ala Gly Val Asp Ala
305                 310                 315                 320

Leu Arg Val Gly Met Gly Ser Gly Ser Ile Cys Ile Thr Gln Glu Val
                325                 330                 335

Leu Ala Cys Gly Arg Pro Gln Ala Thr Ala Val Tyr Lys Val Ser Glu
            340                 345                 350

Tyr Ala Arg Arg Phe Gly Val Pro Val Ile Ala Asp Gly Gly Ile Gln
        355                 360                 365

Asn Val Gly His Ile Ala Lys Ala Leu Ala Leu Gly Ala Ser Thr Val
    370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
                405                 410                 415

Leu Asp Ala Met Asp Lys His Leu Ser Ser Gln Asn Arg Tyr Phe Ser
            420                 425                 430

Glu Ala Asp Lys Ile Lys Val Ala Gln Gly Val Ser Gly Ala Val Gln
        435                 440                 445

Asp Lys Gly Ser Ile His Lys Phe Val Pro Tyr Leu Ile Ala Gly Ile
    450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
                485                 490                 495
```

```
Ala Gln Val Glu Gly Gly Val His Ser Leu His Ser Tyr Glu Lys Arg
            500                 505                 510

Leu Phe


<210> SEQ ID NO 24
<211> LENGTH: 216
<212> TYPE: PRT
<213> ORGANISM: Homo sapiens
<223> OTHER INFORMATION: GenBank Accession: NP_000933
      peptidylprolyl isomerase B precursor [Homo sapiens]

<400> SEQUENCE: 24

Met Leu Arg Leu Ser Glu Arg Asn Met Lys Val Leu Leu Ala Ala Ala
1               5                   10                  15

Leu Ile Ala Gly Ser Val Phe Phe Leu Leu Leu Pro Gly Pro Ser Ala
            20                  25                  30

Ala Asp Glu Lys Lys Lys Gly Pro Lys Val Thr Val Lys Val Tyr Phe
        35                  40                  45

Asp Leu Arg Ile Gly Asp Glu Asp Val Gly Arg Val Ile Phe Gly Leu
    50                  55                  60

Phe Gly Lys Thr Val Pro Lys Thr Val Asp Asn Phe Val Ala Leu Ala
65                  70                  75                  80

Thr Gly Glu Lys Gly Phe Gly Tyr Lys Asn Ser Lys Phe His Arg Val
                85                  90                  95

Ile Lys Asp Phe Met Ile Gln Gly Gly Asp Phe Thr Arg Gly Asp Gly
            100                 105                 110

Thr Gly Gly Lys Ser Ile Tyr Gly Glu Arg Phe Pro Asp Glu Asn Phe
        115                 120                 125

Lys Leu Lys His Tyr Gly Pro Gly Trp Val Ser Met Ala Asn Ala Gly
    130                 135                 140

Lys Asp Thr Asn Gly Ser Gln Phe Phe Ile Thr Thr Val Lys Thr Ala
145                 150                 155                 160

Trp Leu Asp Gly Lys His Val Val Phe Gly Lys Val Leu Glu Gly Met
                165                 170                 175

Glu Val Val Arg Lys Val Glu Ser Thr Lys Thr Asp Ser Arg Asp Lys
            180                 185                 190

Pro Leu Lys Asp Val Ile Ile Ala Asp Cys Gly Lys Ile Glu Val Glu
        195                 200                 205

Lys Pro Phe Ala Ile Ala Lys Glu
    210                 215


<210> SEQ ID NO 25
<211> LENGTH: 545
<212> TYPE: PRT
<213> ORGANISM: Homo sapiens
<223> OTHER INFORMATION: GenBank Accession: NP_005989
      chaperonin containing TCP1, subunit 3 isoform a [Homo sapiens]

<400> SEQUENCE: 25

Met Met Gly His Arg Pro Val Leu Val Leu Ser Gln Asn Thr Lys Arg
1               5                   10                  15

Glu Ser Gly Arg Lys Val Gln Ser Gly Asn Ile Asn Ala Ala Lys Thr
            20                  25                  30

Ile Ala Asp Ile Ile Arg Thr Cys Leu Gly Pro Lys Ser Met Met Lys
        35                  40                  45

Met Leu Leu Asp Pro Met Gly Gly Ile Val Met Thr Asn Asp Gly Asn
    50                  55                  60
```

```
Ala Ile Leu Arg Glu Ile Gln Val Gln His Pro Ala Ala Lys Ser Met
65                  70                  75                  80

Ile Glu Ile Ser Arg Thr Gln Asp Glu Glu Val Gly Asp Gly Thr Thr
                85                  90                  95

Ser Val Ile Ile Leu Ala Gly Glu Met Leu Ser Val Ala Glu His Phe
            100                 105                 110

Leu Glu Gln Gln Met His Pro Thr Val Val Ile Ser Ala Tyr Arg Lys
        115                 120                 125

Ala Leu Asp Asp Met Ile Ser Thr Leu Lys Lys Ile Ser Ile Pro Val
    130                 135                 140

Asp Ile Ser Asp Ser Asp Met Met Leu Asn Ile Ile Asn Ser Ser Ile
145                 150                 155                 160

Thr Thr Lys Ala Ile Ser Arg Trp Ser Ser Leu Ala Cys Asn Ile Ala
                165                 170                 175

Leu Asp Ala Val Lys Met Val Gln Phe Glu Glu Asn Gly Arg Lys Glu
            180                 185                 190

Ile Asp Ile Lys Lys Tyr Ala Arg Val Glu Lys Ile Pro Gly Gly Ile
        195                 200                 205

Ile Glu Asp Ser Cys Val Leu Arg Gly Val Met Ile Asn Lys Asp Val
    210                 215                 220

Thr His Pro Arg Met Arg Arg Tyr Ile Lys Asn Pro Arg Ile Val Leu
225                 230                 235                 240

Leu Asp Ser Ser Leu Glu Tyr Lys Lys Gly Glu Ser Gln Thr Asp Ile
                245                 250                 255

Glu Ile Thr Arg Glu Glu Asp Phe Thr Arg Ile Leu Gln Met Glu Glu
            260                 265                 270

Glu Tyr Ile Gln Gln Leu Cys Glu Asp Ile Ile Gln Leu Lys Pro Asp
        275                 280                 285

Val Val Ile Thr Glu Lys Gly Ile Ser Asp Leu Ala Gln His Tyr Leu
    290                 295                 300

Met Arg Ala Asn Ile Thr Ala Ile Arg Arg Val Arg Lys Thr Asp Asn
305                 310                 315                 320

Asn Arg Ile Ala Arg Ala Cys Gly Ala Arg Ile Val Ser Arg Pro Glu
                325                 330                 335

Glu Leu Arg Glu Asp Asp Val Gly Thr Gly Ala Gly Leu Leu Glu Ile
            340                 345                 350

Lys Lys Ile Gly Asp Glu Tyr Phe Thr Phe Ile Thr Asp Cys Lys Asp
        355                 360                 365

Pro Lys Ala Cys Thr Ile Leu Leu Arg Gly Ala Ser Lys Glu Ile Leu
    370                 375                 380

Ser Glu Val Glu Arg Asn Leu Gln Asp Ala Met Gln Val Cys Arg Asn
385                 390                 395                 400

Val Leu Leu Asp Pro Gln Leu Val Pro Gly Gly Gly Ala Ser Glu Met
                405                 410                 415

Ala Val Ala His Ala Leu Thr Glu Lys Ser Lys Ala Met Thr Gly Val
            420                 425                 430

Glu Gln Trp Pro Tyr Arg Ala Val Ala Gln Ala Leu Glu Val Ile Pro
        435                 440                 445

Arg Thr Leu Ile Gln Asn Cys Gly Ala Ser Thr Ile Arg Leu Leu Thr
    450                 455                 460

Ser Leu Arg Ala Lys His Thr Gln Glu Asn Cys Glu Thr Trp Gly Val
465                 470                 475                 480
```

```
Asn Gly Glu Thr Gly Thr Leu Val Asp Met Lys Glu Leu Gly Ile Trp
                485                 490                 495

Glu Pro Leu Ala Val Lys Leu Gln Thr Tyr Lys Thr Ala Val Glu Thr
            500                 505                 510

Ala Val Leu Leu Leu Arg Ile Asp Asp Ile Val Ser Gly His Lys Lys
        515                 520                 525

Lys Gly Asp Asp Gln Ser Arg Gln Gly Gly Ala Pro Asp Ala Gly Gln
    530                 535                 540

Glu
545


<210> SEQ ID NO 26
<211> LENGTH: 374
<212> TYPE: PRT
<213> ORGANISM: Homo sapiens
<223> OTHER INFORMATION: GenBank Accession: NP_006351
      eukaryotic translation initiation factor 3, subunit M [Homo
      sapiens]

<400> SEQUENCE: 26

Met Ser Val Pro Ala Phe Ile Asp Ile Ser Glu Glu Asp Gln Ala Ala
1               5                   10                  15

Glu Leu Arg Ala Tyr Leu Lys Ser Lys Gly Ala Glu Ile Ser Glu Glu
            20                  25                  30

Asn Ser Glu Gly Gly Leu His Val Asp Leu Ala Gln Ile Ile Glu Ala
        35                  40                  45

Cys Asp Val Cys Leu Lys Glu Asp Asp Lys Asp Val Glu Ser Val Met
    50                  55                  60

Asn Ser Val Val Ser Leu Leu Leu Ile Leu Glu Pro Asp Lys Gln Glu
65                  70                  75                  80

Ala Leu Ile Glu Ser Leu Cys Glu Lys Leu Val Lys Phe Arg Glu Gly
                85                  90                  95

Glu Arg Pro Ser Leu Arg Leu Gln Leu Leu Ser Asn Leu Phe His Gly
            100                 105                 110

Met Asp Lys Asn Thr Pro Val Arg Tyr Thr Val Tyr Cys Ser Leu Ile
        115                 120                 125

Lys Val Ala Ala Ser Cys Gly Ala Ile Gln Tyr Ile Pro Thr Glu Leu
    130                 135                 140

Asp Gln Val Arg Lys Trp Ile Ser Asp Trp Asn Leu Thr Thr Glu Lys
145                 150                 155                 160

Lys His Thr Leu Leu Arg Leu Leu Tyr Glu Ala Leu Val Asp Cys Lys
                165                 170                 175

Lys Ser Asp Ala Ala Ser Lys Val Met Val Glu Leu Leu Gly Ser Tyr
            180                 185                 190

Thr Glu Asp Asn Ala Ser Gln Ala Arg Val Asp Ala His Arg Cys Ile
        195                 200                 205

Val Arg Ala Leu Lys Asp Pro Asn Ala Phe Leu Phe Asp His Leu Leu
    210                 215                 220

Thr Leu Lys Pro Val Lys Phe Leu Glu Gly Glu Leu Ile His Asp Leu
225                 230                 235                 240

Leu Thr Ile Phe Val Ser Ala Lys Leu Ala Ser Tyr Val Lys Phe Tyr
                245                 250                 255

Gln Asn Asn Lys Asp Phe Ile Asp Ser Leu Gly Leu Leu His Glu Gln
            260                 265                 270

Asn Met Ala Lys Met Arg Leu Leu Thr Phe Met Gly Met Ala Val Glu
        275                 280                 285
```

```
Asn Lys Glu Ile Ser Phe Asp Thr Met Gln Gln Glu Leu Gln Ile Gly
    290                 295                 300

Ala Asp Asp Val Glu Ala Phe Val Ile Asp Ala Val Arg Thr Lys Met
305                 310                 315                 320

Val Tyr Cys Lys Ile Asp Gln Thr Gln Arg Lys Val Val Val Ser His
                325                 330                 335

Ser Thr His Arg Thr Phe Gly Lys Gln Gln Trp Gln Gln Leu Tyr Asp
            340                 345                 350

Thr Leu Asn Ala Trp Lys Gln Asn Leu Asn Lys Val Lys Asn Ser Leu
        355                 360                 365

Leu Ser Leu Ser Asp Thr
    370


<210> SEQ ID NO 27
<211> LENGTH: 167
<212> TYPE: PRT
<213> ORGANISM: Homo sapiens
<223> OTHER INFORMATION: GenBank Accession: NP_002916
      regulator of G-protein signaling 10 isoform b [Homo sapiens]

<400> SEQUENCE: 27

Met Glu His Ile His Asp Ser Asp Gly Ser Ser Ser Ser Ser His Gln
1               5                   10                  15

Ser Leu Lys Ser Thr Ala Lys Trp Ala Ala Ser Leu Glu Asn Leu Leu
            20                  25                  30

Glu Asp Pro Glu Gly Val Lys Arg Phe Arg Glu Phe Leu Lys Lys Glu
        35                  40                  45

Phe Ser Glu Glu Asn Val Leu Phe Trp Leu Ala Cys Glu Asp Phe Lys
    50                  55                  60

Lys Met Gln Asp Lys Thr Gln Met Gln Glu Lys Ala Lys Glu Ile Tyr
65                  70                  75                  80

Met Thr Phe Leu Ser Ser Lys Ala Ser Ser Gln Val Asn Val Glu Gly
                85                  90                  95

Gln Ser Arg Leu Asn Glu Lys Ile Leu Glu Glu Pro His Pro Leu Met
            100                 105                 110

Phe Gln Lys Leu Gln Asp Gln Ile Phe Asn Leu Met Lys Tyr Asp Ser
        115                 120                 125

Tyr Ser Arg Phe Leu Lys Ser Asp Leu Phe Leu Lys His Lys Arg Thr
    130                 135                 140

Glu Glu Glu Glu Glu Asp Leu Pro Asp Ala Gln Thr Ala Ala Lys Arg
145                 150                 155                 160

Ala Ser Arg Ile Tyr Asn Thr
                165


<210> SEQ ID NO 28
<211> LENGTH: 319
<212> TYPE: PRT
<213> ORGANISM: Homo sapiens
<223> OTHER INFORMATION: GenBank Accession: NP_008838
      pyrroline-5-carboxylate reductase 1 isoform 1 [Homo sapiens]

<400> SEQUENCE: 28

Met Ser Val Gly Phe Ile Gly Ala Gly Gln Leu Ala Phe Ala Leu Ala
1               5                   10                  15

Lys Gly Phe Thr Ala Ala Gly Val Leu Ala Ala His Lys Ile Met Ala
            20                  25                  30

Ser Ser Pro Asp Met Asp Leu Ala Thr Val Ser Ala Leu Arg Lys Met
```

```
        35                  40                  45

Gly Val Lys Leu Thr Pro His Asn Lys Glu Thr Val Gln His Ser Asp
    50                  55                  60

Val Leu Phe Leu Ala Val Lys Pro His Ile Ile Pro Phe Ile Leu Asp
65                  70                  75                  80

Glu Ile Gly Ala Asp Ile Glu Asp Arg His Ile Val Val Ser Cys Ala
                85                  90                  95

Ala Gly Val Thr Ile Ser Ser Ile Glu Lys Lys Leu Ser Ala Phe Arg
            100                 105                 110

Pro Ala Pro Arg Val Ile Arg Cys Met Thr Asn Thr Pro Val Val Val
        115                 120                 125

Arg Glu Gly Ala Thr Val Tyr Ala Thr Gly Thr His Ala Gln Val Glu
    130                 135                 140

Asp Gly Arg Leu Met Glu Gln Leu Leu Ser Ser Val Gly Phe Cys Thr
145                 150                 155                 160

Glu Val Glu Glu Asp Leu Ile Asp Ala Val Thr Gly Leu Ser Gly Ser
                165                 170                 175

Gly Pro Ala Tyr Ala Phe Thr Ala Leu Asp Ala Leu Ala Asp Gly Gly
            180                 185                 190

Val Lys Met Gly Leu Pro Arg Arg Leu Ala Val Arg Leu Gly Ala Gln
        195                 200                 205

Ala Leu Leu Gly Ala Ala Lys Met Leu Leu His Ser Glu Gln His Pro
    210                 215                 220

Gly Gln Leu Lys Asp Asn Val Ser Ser Pro Gly Gly Ala Thr Ile His
225                 230                 235                 240

Ala Leu His Val Leu Glu Ser Gly Gly Phe Arg Ser Leu Leu Ile Asn
                245                 250                 255

Ala Val Glu Ala Ser Cys Ile Arg Thr Arg Glu Leu Gln Ser Met Ala
            260                 265                 270

Asp Gln Glu Gln Val Ser Pro Ala Ala Ile Lys Lys Thr Ile Leu Asp
        275                 280                 285

Lys Val Lys Leu Asp Ser Pro Ala Gly Thr Ala Leu Ser Pro Ser Gly
    290                 295                 300

His Thr Lys Leu Leu Pro Arg Ser Leu Ala Pro Ala Gly Lys Asp
305                 310                 315


<210> SEQ ID NO 29
<211> LENGTH: 1556
<212> TYPE: PRT
<213> ORGANISM: Homo sapiens
<223> OTHER INFORMATION: GenBank Accession: NP_038476
      bromodomain adjacent to zinc finger domain, 1A isoform a [Homo
      sapiens]

<400> SEQUENCE: 29

Met Pro Leu Leu His Arg Lys Pro Phe Val Arg Gln Lys Pro Pro Ala
1               5                   10                  15

Asp Leu Arg Pro Asp Glu Glu Val Phe Tyr Cys Lys Val Thr Asn Glu
            20                  25                  30

Ile Phe Arg His Tyr Asp Asp Phe Phe Glu Arg Thr Ile Leu Cys Asn
        35                  40                  45

Ser Leu Val Trp Ser Cys Ala Val Thr Gly Arg Pro Gly Leu Thr Tyr
    50                  55                  60

Gln Glu Ala Leu Glu Ser Glu Lys Lys Ala Arg Gln Asn Leu Gln Ser
65                  70                  75                  80
```

```
Phe Pro Glu Pro Leu Ile Ile Pro Val Leu Tyr Leu Thr Ser Leu Thr
                85                  90                  95

His Arg Ser Arg Leu His Glu Ile Cys Asp Asp Ile Phe Ala Tyr Val
            100                 105                 110

Lys Asp Arg Tyr Phe Val Glu Glu Thr Val Glu Val Ile Arg Asn Asn
        115                 120                 125

Gly Ala Arg Leu Gln Cys Arg Ile Leu Glu Val Leu Pro Pro Ser His
    130                 135                 140

Gln Asn Gly Phe Ala Asn Gly His Val Asn Ser Val Asp Gly Glu Thr
145                 150                 155                 160

Ile Ile Ile Ser Asp Ser Asp Asp Ser Glu Thr Gln Ser Cys Ser Phe
                165                 170                 175

Gln Asn Gly Lys Lys Lys Asp Ala Ile Asp Pro Leu Leu Phe Lys Tyr
            180                 185                 190

Lys Val Gln Pro Thr Lys Lys Glu Leu His Glu Ser Ala Ile Val Lys
        195                 200                 205

Ala Thr Gln Ile Ser Arg Arg Lys His Leu Phe Ser Arg Asp Lys Leu
    210                 215                 220

Lys Leu Phe Leu Lys Gln His Cys Glu Pro Gln Asp Gly Val Ile Lys
225                 230                 235                 240

Ile Lys Ala Ser Ser Leu Ser Thr Tyr Lys Ile Ala Glu Gln Asp Phe
                245                 250                 255

Ser Tyr Phe Phe Pro Asp Asp Pro Pro Thr Phe Ile Phe Ser Pro Ala
            260                 265                 270

Asn Arg Arg Arg Gly Arg Pro Pro Lys Arg Ile His Ile Ser Gln Glu
        275                 280                 285

Asp Asn Val Ala Asn Lys Gln Thr Leu Ala Ser Tyr Arg Ser Lys Ala
    290                 295                 300

Thr Lys Glu Arg Asp Lys Leu Leu Lys Gln Glu Glu Met Lys Ser Leu
305                 310                 315                 320

Ala Phe Glu Lys Ala Lys Leu Lys Arg Glu Lys Ala Asp Ala Leu Glu
                325                 330                 335

Ala Lys Lys Lys Glu Lys Glu Asp Lys Glu Lys Lys Arg Glu Glu Leu
            340                 345                 350

Lys Lys Ile Val Glu Glu Glu Arg Leu Lys Lys Lys Glu Glu Lys Glu
        355                 360                 365

Arg Leu Lys Val Glu Arg Glu Lys Glu Arg Glu Lys Leu Arg Glu Glu
    370                 375                 380

Lys Arg Lys Tyr Val Glu Tyr Leu Lys Gln Trp Ser Lys Pro Arg Glu
385                 390                 395                 400

Asp Met Glu Cys Asp Asp Leu Lys Glu Leu Pro Glu Pro Thr Pro Val
                405                 410                 415

Lys Thr Arg Leu Pro Pro Glu Ile Phe Gly Asp Ala Leu Met Val Leu
            420                 425                 430

Glu Phe Leu Asn Ala Phe Gly Glu Leu Phe Asp Leu Gln Asp Glu Phe
        435                 440                 445

Pro Asp Gly Val Thr Leu Glu Val Leu Glu Glu Ala Leu Val Gly Asn
    450                 455                 460

Asp Ser Glu Gly Pro Leu Cys Glu Leu Leu Phe Phe Phe Leu Thr Ala
465                 470                 475                 480

Ile Phe Gln Ala Ile Ala Glu Glu Glu Glu Glu Val Ala Lys Glu Gln
                485                 490                 495

Leu Thr Asp Ala Asp Thr Lys Asp Leu Thr Glu Ala Leu Asp Glu Asp
```

```
            500                 505                 510

Ala Asp Pro Thr Lys Ser Ala Leu Ser Ala Val Ala Ser Leu Ala Ala
        515                 520                 525

Ala Trp Pro Gln Leu His Gln Gly Cys Ser Leu Lys Ser Leu Asp Leu
    530                 535                 540

Asp Ser Cys Thr Leu Ser Glu Ile Leu Arg Leu His Ile Leu Ala Ser
545                 550                 555                 560

Gly Ala Asp Val Thr Ser Ala Asn Ala Lys Tyr Arg Tyr Gln Lys Arg
                565                 570                 575

Gly Gly Phe Asp Ala Thr Asp Asp Ala Cys Met Glu Leu Arg Leu Ser
            580                 585                 590

Asn Pro Ser Leu Val Lys Lys Leu Ser Ser Thr Ser Val Tyr Asp Leu
        595                 600                 605

Thr Pro Gly Glu Lys Met Lys Ile Leu His Ala Leu Cys Gly Lys Leu
    610                 615                 620

Leu Thr Leu Val Ser Thr Arg Asp Phe Ile Glu Asp Tyr Val Asp Ile
625                 630                 635                 640

Leu Arg Gln Ala Lys Gln Glu Phe Arg Glu Leu Lys Ala Glu Gln His
                645                 650                 655

Arg Lys Glu Arg Glu Glu Ala Ala Ala Arg Ile Arg Lys Arg Lys Glu
            660                 665                 670

Glu Lys Leu Lys Glu Gln Glu Gln Lys Met Lys Glu Lys Gln Glu Lys
        675                 680                 685

Leu Lys Glu Asp Glu Gln Arg Asn Ser Thr Ala Asp Ile Ser Ile Gly
    690                 695                 700

Glu Glu Glu Arg Glu Asp Phe Asp Thr Ser Ile Glu Ser Lys Asp Thr
705                 710                 715                 720

Glu Gln Lys Glu Leu Asp Gln Asp Met Val Thr Glu Asp Glu Asp Asp
                725                 730                 735

Pro Gly Ser His Lys Arg Gly Arg Arg Gly Lys Arg Gly Gln Asn Gly
            740                 745                 750

Phe Lys Glu Phe Thr Arg Gln Glu Gln Ile Asn Cys Val Thr Arg Glu
        755                 760                 765

Pro Leu Thr Ala Asp Glu Glu Glu Ala Leu Lys Gln Glu His Gln Arg
    770                 775                 780

Lys Glu Lys Glu Leu Leu Glu Lys Ile Gln Ser Ala Ile Ala Cys Thr
785                 790                 795                 800

Asn Ile Phe Pro Leu Gly Arg Asp Arg Met Tyr Arg Arg Tyr Trp Ile
                805                 810                 815

Phe Pro Ser Ile Pro Gly Leu Phe Ile Glu Glu Asp Tyr Ser Gly Leu
            820                 825                 830

Thr Glu Asp Met Leu Leu Pro Arg Pro Ser Ser Phe Gln Asn Asn Val
        835                 840                 845

Gln Ser Gln Asp Pro Gln Val Ser Thr Lys Thr Gly Glu Pro Leu Met
    850                 855                 860

Ser Glu Ser Thr Ser Asn Ile Asp Gln Gly Pro Arg Asp His Ser Val
865                 870                 875                 880

Gln Leu Pro Lys Pro Val His Lys Pro Asn Arg Trp Cys Phe Tyr Ser
                885                 890                 895

Ser Cys Glu Gln Leu Asp Gln Leu Ile Glu Ala Leu Asn Ser Arg Gly
            900                 905                 910

His Arg Glu Ser Ala Leu Lys Glu Thr Leu Leu Gln Glu Lys Ser Arg
        915                 920                 925
```

```
Ile Cys Ala Gln Leu Ala Arg Phe Ser Glu Glu Lys Phe His Phe Ser
    930                 935                 940

Asp Lys Pro Gln Pro Asp Ser Lys Pro Thr Tyr Ser Arg Gly Arg Ser
945                 950                 955                 960

Ser Asn Ala Tyr Asp Pro Ser Gln Met Cys Ala Glu Lys Gln Leu Glu
                965                 970                 975

Leu Arg Leu Arg Asp Phe Leu Leu Asp Ile Glu Asp Arg Ile Tyr Gln
            980                 985                 990

Gly Thr Leu Gly Ala Ile Lys Val  Thr Asp Arg His Ile  Trp Arg Ser
        995                 1000                1005

Ala Leu  Glu Ser Gly Arg Tyr  Glu Leu Leu Ser Glu  Glu Asn Lys
    1010                 1015                 1020

Glu Asn  Gly Ile Ile Lys Thr  Val Asn Glu Asp Val  Glu Glu Met
    1025                 1030                 1035

Glu Ile  Asp Glu Gln Thr Lys  Val Ile Val Lys Asp  Arg Leu Leu
    1040                 1045                 1050

Gly Ile  Lys Thr Glu Thr Pro  Ser Thr Val Ser Thr  Asn Ala Ser
    1055                 1060                 1065

Thr Pro  Gln Ser Val Ser Ser  Val Val His Tyr Leu  Ala Met Ala
    1070                 1075                 1080

Leu Phe  Gln Ile Glu Gln Gly  Ile Glu Arg Arg Phe  Leu Lys Ala
    1085                 1090                 1095

Pro Leu  Asp Ala Ser Asp Ser  Gly Arg Ser Tyr Lys  Thr Val Leu
    1100                 1105                 1110

Asp Arg  Trp Arg Glu Ser Leu  Leu Ser Ser Ala Ser  Leu Ser Gln
    1115                 1120                 1125

Val Phe  Leu His Leu Ser Thr  Leu Asp Arg Ser Val  Ile Trp Ser
    1130                 1135                 1140

Lys Ser  Ile Leu Asn Ala Arg  Cys Lys Ile Cys Arg  Lys Lys Gly
    1145                 1150                 1155

Asp Ala  Glu Asn Met Val Leu  Cys Asp Gly Cys Asp  Arg Gly His
    1160                 1165                 1170

His Thr  Tyr Cys Val Arg Pro  Lys Leu Lys Thr Val  Pro Glu Gly
    1175                 1180                 1185

Asp Trp  Phe Cys Pro Glu Cys  Arg Pro Lys Gln Arg  Ser Arg Arg
    1190                 1195                 1200

Leu Ser  Ser Arg Gln Arg Pro  Ser Leu Glu Ser Asp  Glu Asp Val
    1205                 1210                 1215

Glu Asp  Ser Met Gly Gly Glu  Asp Asp Glu Val Asp  Gly Asp Glu
    1220                 1225                 1230

Glu Glu  Gly Gln Ser Glu Glu  Glu Glu Tyr Glu Val  Glu Gln Asp
    1235                 1240                 1245

Glu Asp  Asp Ser Gln Glu Glu  Glu Glu Val Ser Leu  Pro Lys Arg
    1250                 1255                 1260

Gly Arg  Pro Gln Val Arg Leu  Pro Val Lys Thr Arg  Gly Lys Leu
    1265                 1270                 1275

Ser Ser  Ser Phe Ser Ser Arg  Gly Gln Gln Gln Glu  Pro Gly Arg
    1280                 1285                 1290

Tyr Pro  Ser Arg Ser Gln Gln  Ser Thr Pro Lys Thr  Thr Val Ser
    1295                 1300                 1305

Ser Lys  Thr Gly Arg Ser Leu  Arg Lys Ile Asn Ser  Ala Pro Pro
    1310                 1315                 1320
```

```
Thr Glu  Thr Lys Ser Leu Arg  Ile Ala Ser Arg Ser  Thr Arg His
    1325                 1330                 1335

Ser His  Gly Pro Leu Gln Ala  Asp Val Phe Val Glu  Leu Leu Ser
    1340                 1345                 1350

Pro Arg  Arg Lys Arg Arg Gly  Arg Lys Ser Ala Asn  Asn Thr Pro
    1355                 1360                 1365

Glu Asn  Ser Pro Asn Phe Pro  Asn Phe Arg Val Ile  Ala Thr Lys
    1370                 1375                 1380

Ser Ser  Glu Gln Ser Arg Ser  Val Asn Ile Ala Ser  Lys Leu Ser
    1385                 1390                 1395

Leu Gln  Glu Ser Glu Ser Lys  Arg Arg Cys Arg Lys  Arg Gln Ser
    1400                 1405                 1410

Pro Glu  Pro Ser Pro Val Thr  Leu Gly Arg Arg Ser  Ser Gly Arg
    1415                 1420                 1425

Gln Gly  Gly Val His Glu Leu  Ser Ala Phe Glu Gln  Leu Val Val
    1430                 1435                 1440

Glu Leu  Val Arg His Asp Asp  Ser Trp Pro Phe Leu  Lys Leu Val
    1445                 1450                 1455

Ser Lys  Ile Gln Val Pro Asp  Tyr Tyr Asp Ile Ile  Lys Lys Pro
    1460                 1465                 1470

Ile Ala  Leu Asn Ile Ile Arg  Glu Lys Val Asn Lys  Cys Glu Tyr
    1475                 1480                 1485

Lys Leu  Ala Ser Glu Phe Ile  Asp Asp Ile Glu Leu  Met Phe Ser
    1490                 1495                 1500

Asn Cys  Phe Glu Tyr Asn Pro  Arg Asn Thr Ser Glu  Ala Lys Ala
    1505                 1510                 1515

Gly Thr  Arg Leu Gln Ala Phe  Phe His Ile Gln Ala  Gln Lys Leu
    1520                 1525                 1530

Gly Leu  His Val Thr Pro Ser  Asn Val Asp Gln Val  Ser Thr Pro
    1535                 1540                 1545

Pro Ala  Ala Lys Lys Ser Arg  Ile
    1550                 1555


<210> SEQ ID NO 30
<211> LENGTH: 195
<212> TYPE: PRT
<213> ORGANISM: Homo sapiens
<223> OTHER INFORMATION: GenBank Accession: NP_075385
      MARCKS-like 1 [Homo sapiens]

<400> SEQUENCE: 30

Met Gly Ser Gln Ser Ser Lys Ala Pro Arg Gly Asp Val Thr Ala Glu
1               5                   10                  15

Glu Ala Ala Gly Ala Ser Pro Ala Lys Ala Asn Gly Gln Glu Asn Gly
            20                  25                  30

His Val Lys Ser Asn Gly Asp Leu Ser Pro Lys Gly Glu Gly Glu Ser
        35                  40                  45

Pro Pro Val Asn Gly Thr Asp Glu Ala Ala Gly Ala Thr Gly Asp Ala
    50                  55                  60

Ile Glu Pro Ala Pro Pro Ser Gln Gly Ala Glu Ala Lys Gly Glu Val
65                  70                  75                  80

Pro Pro Lys Glu Thr Pro Lys Lys Lys Lys Lys Phe Ser Phe Lys Lys
                85                  90                  95

Pro Phe Lys Leu Ser Gly Leu Ser Phe Lys Arg Asn Arg Lys Glu Gly
            100                 105                 110
```

```
Gly Gly Asp Ser Ser Ala Ser Ser Pro Thr Glu Glu Glu Gln Glu Gln
        115                 120                 125

Gly Glu Ile Gly Ala Cys Ser Asp Glu Gly Thr Ala Gln Glu Gly Lys
    130                 135                 140

Ala Ala Ala Thr Pro Glu Ser Gln Glu Pro Gln Ala Lys Gly Ala Glu
145                 150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195


<210> SEQ ID NO 31
<211> LENGTH: 350
<212> TYPE: PRT
<213> ORGANISM: Homo sapiens
<223> OTHER INFORMATION: GenBank Accession: NP_006627
      methylene tetrahydrofolate dehydrogenase 2 isoform A precursor
      [Homo sapiens]

<400> SEQUENCE: 31

Met Ala Ala Thr Ser Leu Met Ser Ala Leu Ala Ala Arg Leu Leu Gln
1               5                   10                  15

Pro Ala His Ser Cys Ser Leu Arg Leu Arg Pro Phe His Leu Ala Ala
            20                  25                  30

Val Arg Asn Glu Ala Val Val Ile Ser Gly Arg Lys Leu Ala Gln Gln
        35                  40                  45

Ile Lys Gln Glu Val Arg Gln Glu Val Glu Glu Trp Val Ala Ser Gly
    50                  55                  60

Asn Lys Arg Pro His Leu Ser Val Ile Leu Val Gly Glu Asn Pro Ala
65                  70                  75                  80

Ser His Ser Tyr Val Leu Asn Lys Thr Arg Ala Ala Ala Val Val Gly
                85                  90                  95

Ile Asn Ser Glu Thr Ile Met Lys Pro Ala Ser Ile Ser Glu Glu Glu
            100                 105                 110

Leu Leu Asn Leu Ile Asn Lys Leu Asn Asn Asp Asp Asn Val Asp Gly
        115                 120                 125

Leu Leu Val Gln Leu Pro Leu Pro Glu His Ile Asp Glu Arg Arg Ile
    130                 135                 140

Cys Asn Ala Val Ser Pro Asp Lys Asp Val Asp Gly Phe His Val Ile
145                 150                 155                 160

Asn Val Gly Arg Met Cys Leu Asp Gln Tyr Ser Met Leu Pro Ala Thr
                165                 170                 175

Pro Trp Gly Val Trp Glu Ile Ile Lys Arg Thr Gly Ile Pro Thr Leu
            180                 185                 190

Gly Lys Asn Val Val Val Ala Gly Arg Ser Lys Asn Val Gly Met Pro
        195                 200                 205

Ile Ala Met Leu Leu His Thr Asp Gly Ala His Glu Arg Pro Gly Gly
    210                 215                 220

Asp Ala Thr Val Thr Ile Ser His Arg Tyr Thr Pro Lys Glu Gln Leu
225                 230                 235                 240

Lys Lys His Thr Ile Leu Ala Asp Ile Val Ile Ser Ala Ala Gly Ile
                245                 250                 255

Pro Asn Leu Ile Thr Ala Asp Met Ile Lys Glu Gly Ala Ala Val Ile
            260                 265                 270
```

```
Asp Val Gly Ile Asn Arg Val His Asp Pro Val Thr Ala Lys Pro Lys
        275                 280                 285

Leu Val Gly Asp Val Asp Phe Glu Gly Val Arg Gln Lys Ala Gly Tyr
    290                 295                 300

Ile Thr Pro Val Pro Gly Gly Val Gly Pro Met Thr Val Ala Met Leu
305                 310                 315                 320

Met Lys Asn Thr Ile Ile Ala Ala Lys Lys Val Leu Arg Leu Glu Glu
                325                 330                 335

Arg Glu Val Leu Lys Ser Lys Glu Leu Gly Val Ala Thr Asn
            340                 345                 350


<210> SEQ ID NO 32
<211> LENGTH: 559
<212> TYPE: PRT
<213> ORGANISM: Homo sapiens
<223> OTHER INFORMATION: GenBank Accession: NP_003618
      solute carrier family 43, member 1 [Homo sapiens]

<400> SEQUENCE: 32

Met Ala Pro Thr Leu Gln Gln Ala Tyr Arg Arg Arg Trp Trp Met Ala
1               5                   10                  15

Cys Thr Ala Val Leu Glu Asn Leu Phe Phe Ser Ala Val Leu Leu Gly
            20                  25                  30

Trp Gly Ser Leu Leu Ile Ile Leu Lys Asn Glu Gly Phe Tyr Ser Ser
        35                  40                  45

Thr Cys Pro Ala Glu Ser Ser Thr Asn Thr Thr Gln Asp Glu Gln Arg
    50                  55                  60

Arg Trp Pro Gly Cys Asp Gln Gln Asp Glu Met Leu Asn Leu Gly Phe
65                  70                  75                  80

Thr Ile Gly Ser Phe Val Leu Ser Ala Thr Thr Leu Pro Leu Gly Ile
                85                  90                  95

Leu Met Asp Arg Phe Gly Pro Arg Pro Val Arg Leu Val Gly Ser Ala
            100                 105                 110

Cys Phe Thr Ala Ser Cys Thr Leu Met Ala Leu Ala Ser Arg Asp Val
        115                 120                 125

Glu Ala Leu Ser Pro Leu Ile Phe Leu Ala Leu Ser Leu Asn Gly Phe
    130                 135                 140

Gly Gly Ile Cys Leu Thr Phe Thr Ser Leu Thr Leu Pro Asn Met Phe
145                 150                 155                 160

Gly Asn Leu Arg Ser Thr Leu Met Ala Leu Met Ile Gly Ser Tyr Ala
                165                 170                 175

Ser Ser Ala Ile Thr Phe Pro Gly Ile Lys Leu Ile Tyr Asp Ala Gly
            180                 185                 190

Val Ala Phe Val Val Ile Met Phe Thr Trp Ser Gly Leu Ala Cys Leu
        195                 200                 205

Ile Phe Leu Asn Cys Thr Leu Asn Trp Pro Ile Glu Ala Phe Pro Ala
    210                 215                 220

Pro Glu Glu Val Asn Tyr Thr Lys Lys Ile Lys Leu Ser Gly Leu Ala
225                 230                 235                 240

Leu Asp His Lys Val Thr Gly Asp Leu Phe Tyr Thr His Val Thr Thr
                245                 250                 255

Met Gly Gln Arg Leu Ser Gln Lys Ala Pro Ser Leu Glu Asp Gly Ser
            260                 265                 270

Asp Ala Phe Met Ser Pro Gln Asp Val Arg Gly Thr Ser Glu Asn Leu
        275                 280                 285
```

```
Pro Glu Arg Ser Val Pro Leu Arg Lys Ser Leu Cys Ser Pro Thr Phe
    290                 295                 300

Leu Trp Ser Leu Leu Thr Met Gly Met Thr Gln Leu Arg Ile Ile Phe
305                 310                 315                 320

Tyr Met Ala Ala Val Asn Lys Met Leu Glu Tyr Leu Val Thr Gly Gly
                325                 330                 335

Gln Glu His Glu Thr Asn Glu Gln Gln Gln Lys Val Ala Glu Thr Val
            340                 345                 350

Gly Phe Tyr Ser Ser Val Phe Gly Ala Met Gln Leu Leu Cys Leu Leu
        355                 360                 365

Thr Cys Pro Leu Ile Gly Tyr Ile Met Asp Trp Arg Ile Lys Asp Cys
    370                 375                 380

Val Asp Ala Pro Thr Gln Gly Thr Val Leu Gly Asp Ala Arg Asp Gly
385                 390                 395                 400

Val Ala Thr Lys Ser Ile Arg Pro Arg Tyr Cys Lys Ile Gln Lys Leu
                405                 410                 415

Thr Asn Ala Ile Ser Ala Phe Thr Leu Thr Asn Leu Leu Leu Val Gly
            420                 425                 430

Phe Gly Ile Thr Cys Leu Ile Asn Asn Leu His Leu Gln Phe Val Thr
        435                 440                 445

Phe Val Leu His Thr Ile Val Arg Gly Phe Phe His Ser Ala Cys Gly
    450                 455                 460

Ser Leu Tyr Ala Ala Val Phe Pro Ser Asn His Phe Gly Thr Leu Thr
465                 470                 475                 480

Gly Leu Gln Ser Leu Ile Ser Ala Val Phe Ala Leu Leu Gln Gln Pro
                485                 490                 495

Leu Phe Met Ala Met Val Gly Pro Leu Lys Gly Glu Pro Phe Trp Val
            500                 505                 510

Asn Leu Gly Leu Leu Leu Phe Ser Leu Leu Gly Phe Leu Leu Pro Ser
        515                 520                 525

Tyr Leu Phe Tyr Tyr Arg Ala Arg Leu Gln Gln Glu Tyr Ala Ala Asn
    530                 535                 540

Gly Met Gly Pro Leu Lys Val Leu Ser Gly Ser Glu Val Thr Ala
545                 550                 555


<210> SEQ ID NO 33
<211> LENGTH: 198
<212> TYPE: PRT
<213> ORGANISM: Homo sapiens
<223> OTHER INFORMATION: GenBank Accession: NP_002940
      mitochondrial ribosomal protein L12 [Homo sapiens]

<400> SEQUENCE: 33

Met Leu Pro Ala Ala Ala Arg Pro Leu Trp Gly Pro Cys Leu Gly Leu
1               5                   10                  15

Arg Ala Ala Ala Phe Arg Leu Ala Arg Arg Gln Val Pro Cys Val Cys
            20                  25                  30

Ala Val Arg His Met Arg Ser Ser Gly His Gln Arg Cys Glu Ala Leu
        35                  40                  45

Ala Gly Ala Pro Leu Asp Asn Ala Pro Lys Glu Tyr Pro Pro Lys Ile
    50                  55                  60

Gln Gln Leu Val Gln Asp Ile Ala Ser Leu Thr Leu Leu Glu Ile Ser
65                  70                  75                  80

Asp Leu Asn Glu Leu Leu Lys Lys Thr Leu Lys Ile Gln Asp Val Gly
                85                  90                  95
```

```
Leu Val Pro Met Gly Gly Val Met Ser Gly Ala Val Pro Ala Ala Ala
            100                 105                 110

Ala Gln Glu Ala Val Glu Glu Asp Ile Pro Ile Ala Lys Glu Arg Thr
        115                 120                 125

His Phe Thr Val Arg Leu Thr Glu Ala Lys Pro Val Asp Lys Val Lys
    130                 135                 140

Leu Ile Lys Glu Ile Lys Asn Tyr Ile Gln Gly Ile Asn Leu Val Gln
145                 150                 155                 160

Ala Lys Lys Leu Val Glu Ser Leu Pro Gln Glu Ile Lys Ala Asn Val
                165                 170                 175

Ala Lys Ala Glu Ala Glu Lys Ile Lys Ala Ala Leu Glu Ala Val Gly
            180                 185                 190

Gly Thr Val Val Leu Glu
        195


<210> SEQ ID NO 34
<211> LENGTH: 20
<212> TYPE: DNA
<213> ORGANISM: Homo sapiens

<400> SEQUENCE: 34

aacctgtgac cacccctgaa                                              20


<210> SEQ ID NO 35
<211> LENGTH: 22
<212> TYPE: DNA
<213> ORGANISM: Homo sapiens

<400> SEQUENCE: 35

tctttgtctc cgtttgcaga aa                                           22


<210> SEQ ID NO 36
<211> LENGTH: 17
<212> TYPE: DNA
<213> ORGANISM: Homo sapiens

<400> SEQUENCE: 36

attgcacagg ttgctac                                                 17


<210> SEQ ID NO 37
<211> LENGTH: 23
<212> TYPE: DNA
<213> ORGANISM: Homo sapiens

<400> SEQUENCE: 37

ttgcattcag aaaggagcag act                                          23


<210> SEQ ID NO 38
<211> LENGTH: 24
<212> TYPE: DNA
<213> ORGANISM: Homo sapiens

<400> SEQUENCE: 38

caactggttc tgtagggttc gttt                                         24


<210> SEQ ID NO 39
<211> LENGTH: 18
<212> TYPE: DNA
<213> ORGANISM: Homo sapiens
```

<400> SEQUENCE: 39
tggagcaaag gtggtaga 18